United States Patent [19]
Nakagawa et al.

[11] Patent Number: 5,707,987
[45] Date of Patent: Jan. 13, 1998

[54] CARBAPENEM DERIVATIVES

[75] Inventors: Susumu Nakagawa; Hiroshi Fukatsu; Ryosuke Ushijima, all of Tsukuba, Japan

[73] Assignee: Banyu Pharmaceutical Co., Ltd., Tokyo, Japan

[21] Appl. No.: 696,910

[22] PCT Filed: Feb. 24, 1995

[86] PCT No.: PCT/JP95/00280

§ 371 Date: Aug. 23, 1996

§ 102(e) Date: Aug. 23, 1996

[87] PCT Pub. No.: WO95/23150

PCT Pub. Date: Aug. 31, 1995

[30] Foreign Application Priority Data

Feb. 25, 1994 [JP] Japan ..... 6-052686
Mar. 8, 1994 [JP] Japan ..... 6-064606
Apr. 22, 1994 [JP] Japan ..... 6-107568
Apr. 26, 1994 [JP] Japan ..... 6-110289
Apr. 28, 1994 [JP] Japan ..... 6-114288

[51] Int. Cl.$^6$ ............... A61K 31/40; C07D 487/04
[52] U.S. Cl. ............... 514/210; 540/350; 540/302
[58] Field of Search ............... 540/302, 350; 514/210

[56] References Cited

U.S. PATENT DOCUMENTS 5,571,805 11/1996 Jung et al. ............... 514/210
5,583,218 12/1996 Takemura et al. ............... 540/111

Primary Examiner—Mukund J. Shah
Assistant Examiner—Pavanaram K. Sripada
Attorney, Agent, or Firm—Oblon, Spivak, McClelland, Maier & Neustadt, P.C.

[57] ABSTRACT

A compound of the formula:

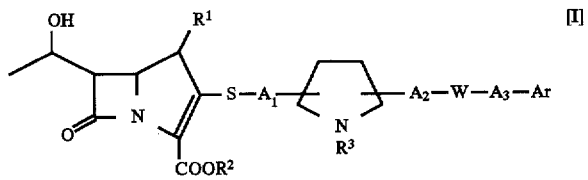

wherein $R^1$ is a hydrogen atom or a lower alkyl group, $R^2$ is a hydrogen atom or a negative charge, $R^3$ is a hydrogen atom or a lower alkyl group, Ar is a phenyl group, a naphthyl group or a group of:

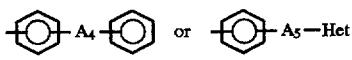

(wherein each of $A_4$ and $A_5$ is a single bond, —NHSO$_2$— or the like, and Het is a pyrrolinyl group, a 1,4-diazabicyclo[2.2.2]octanyl group or the like which may be substituted with a hydroxyl group, a carbamoyl lower alkyl group or the like) which may be substituted with a lower alkyl group, a lower alkylsulfamoyl group or the like which may be substituted with a hydroxyl group, a di-lower alkylsulfonyl group or the like; a hydroxyl group; a di-lower alkylsulfamoyl group or the like, each of $A_1$, $A_2$ and $A_3$ is a single bond or a lower alkylene group which may be substituted with a lower alkyl group, a lower alkylsulfamoyl group or the like which may be substituted with a hydroxyl group, a di-lower alkylsulfamoyl group or the like; a pyridyl group or a pyridino group; and W is a sulfur atom, a single bond; or a pharmaceutically acceptable salt or ester; a process for its production and an antibacterial agent containing it as an active ingredient.

30 Claims, No Drawings

CARBAPENEM DERIVATIVES

TECHNICAL FIELD

This application is a 371 of PCT/JP95/00280 Feb. 24, 1995.

The present invention relates to novel carbapenem (7-oxo-1-azabicyclo[3.2.0]hept-2-en-2-carboxylic acid) compounds, antibacterial agents containing such compounds as active ingredients, and a process for producing such compounds.

BACKGROUND ART

In recent years, new β-lactam antibiotic substances have been found in nature which have the same β-lactam rings as penicillin derivatives and as cephalosporin derivatives, but which have different basic structures.

For example, naturally derived carbapenem compounds such as thienamycin isolated from the fermentation of *Streptomyces Cattleya* (J. Am. Chem. Soc., vol. 100, p.6491 (1978)), may be mentioned. Thienamycin has an excellent antibacterial spectrum and strong antibacterial activities over a wide range against gram positive bacteria and gram negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p.62 (1982); ditto, vol. 23, p.300 (1983)).

Merck & Co., Inc. have synthesized many thienamycin analogues with an aim to maintain the excellent antibacterial activities of thienamycin and to secure chemical stability. As a result, imipenem, (5R,6S)-3-[2-(formimidoylamino) ethylthie]-6-[(R)-1-hydroxyethyl]-7-oxo-1-azabicyclo [3.2.0]hept-2-en-2-carboxylic acid monohydrate, obtained by formimidation of the amino group of thienamycin, has been practically developed as a pharmaceutical product (J. Med. Chem., vol. 22, p. 1435 (1979)).

Imipenem has antibacterial activities of an equal or higher level than thienamycin against various types of bacteria and has β-lactamase resistance. Especially against *Pseudomonas aeruginosa*, its antibacterial activities are superior to thienamycin by from 2 to 4 times. Further, the stability of imipenem in the solid form or in an aqueous solution is remarkably improved over thienamycin.

However, like thienamycin, imipenem is likely to be decomposed by DHP-I in the human kidney. Therefore, it can not be used for treatment of the urinary-tract infection. Further, it presents toxicity against the kidney due to the decomposition products. Therefore, imipenem can not be administered alone and is required to be used in combination with a DEP-I inhibitor like cilastatin (J. Antimicrob. Chemother., vol. 12 (Suppl. D), p. 1 (1983)). In recent years, imipenem has been frequently used for the treatment and prevention of infectious diseases. Consequently, highly methicillin-resistant *Staphylococcus aureus* which is resistant to imipenem and imipenem-resistant *Pseudomonas aeruginosa* are increasing in the clinical field. Imipenem does not show adequate treating effects against these resistant bacteria.

As the prior arts closest to the present invention, Japanese Unexamined Patent Publication No. 179876/1988 (hereinafter referred to as publication A) and Japanese Unexamined Patent Publication No. 204490/1990 (hereinafter referred to as publication B) may be mentioned. Publication A describes carbapenem compounds having at the 2-position of the carbapenem structure a pyrrolidinylthio group substituted with a group of A—X—$R^4$. Publication B describes carbapenem compounds having at the 2-position of the carbapenem structure a pyrrolidinylthio group substituted with a group of A—O—$R^4$.

However, according to publication A, the definition of $R^4$ in the substituent is restricted to an optionally substituted lower alkyl group, a heterocyclic group which may be optionally substituted or a-lower alkylsulfonyl group. Similarly, publication B mentions that the definition of $R^4$ in the substituent is restricted to a substituted lower alkyl group such as a monohalo(lower)alkyl group, a mono- or di-(lower)alkylamino(lower)alkyl group, a protected mono (lower)alkylamino(lower)alkyl group, a mono- or di-(lower) alkylcarbamoyl(lower)alkyl group or a protected or unprotected carboxy(lower)alkyl group.

The above-mentioned publications A and B as the prior arts disclose as the utility of their inventions that these compounds have antibacterial activities, but present only data obtained by using *Staphylococcus aureus* and *Pseudomonas aeruginosa* as test bacteria.

Namely, these prior arts do not disclose or suggest the compounds of the present invention characterized by having a substituent presented by the formula:

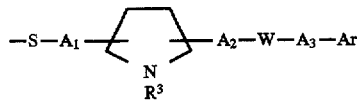

wherein $R^3$ is a hydrogen atom or a lower alkyl group, Ar is a phenyl group, a naphthyl group or a group of:

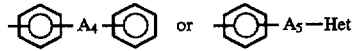

(wherein each of $A_4$ and $A_5$, which may be the same or different, is a single bond, a methylene group, an ethylene group, an oxygen atom, an imino group, a sulfur atom, a sulfonyl group, —CONH— or —$NHSO_2$—, and Het is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents, selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonylamino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group, each of $A_1$, $A_2$ and $A_3$, which may be same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and W is a sulfur atom, a group of N—X (wherein X is a hydrogen atom, a lower alkyl group, a formal group, a lower alkanoyl group or a sulfamoyl group), an oxygen atom, a group of CH(OH) or a single bond, much less the marked effects of the compounds on methycillin resistant *Staphylococcus aureus*.

β-Lactam antibiotics exhibit selective toxicity against bacteria and show no substantial effects against animal cells. Therefore, they are widely used for treatment of infectious diseases caused by bacteria, as antibiotics having little side effects, and thus are highly useful drugs.

However, in recent years, methicillin-resistant *Staphylococcus aureus* (hereinafter referred to simply as MRSA), methicillin-resistant coagulase negative Staphylococci (hereinafter referred to simply as MRCNS) and resistant *Pseudomonas aeruginosa* have been isolated frequently from patients with the immunity decreased, as bacteria causing hardly curable infectious diseases, and are raising a series social problem. Further, recently, the strong toxicity of vancomycin, which is selectively used against MRSA, to the kidney, and the increasing resistance of pathogenic bacteria such as MRSA and MRCNS are becoming clinically serious problems. Accordingly, it is strongly desired to develop an antibacterial agent having excellent antibacterial activities against such resistant bacteria. However, no β-lactam antibacterial agents which meet such desire have not been developed yet. With respect to carbapenem compounds, such drugs are strongly desired to be developed as have improved antibacterial activities against bacteria causing hardly curable infectious diseases, especially against MRSA and MRCNS, improved stability against DHP-I, reduced toxicity against the kidney and no side effects against the central nervous system.

DISCLOSURE OF INVENTION

The present inventors have made extensive researches with an aim to provide novel carbapenem compounds which have excellent antibacterial activities and which are resistant to DHP-I. As a result, they have found that carbapenem compounds of the present invention having, at the 2-position of the carbapenem structure, a group of the formula:

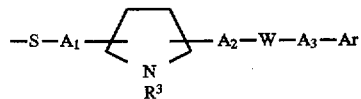

wherein $R^3$, Ar, $A_1$, $A_2$, $A_3$ and W are as defined above, are novel compounds not disclosed in any literatures, and that such compounds have strong antibacterial activities against gram positive bacteria including MRSA and against gram negative bacteria including *Pseudomonas aeruginosa* and further exhibit excellent stability against DHP-I. The present invention has been accomplished on the basis of this discovery.

The present invention provides a compound of the formula:

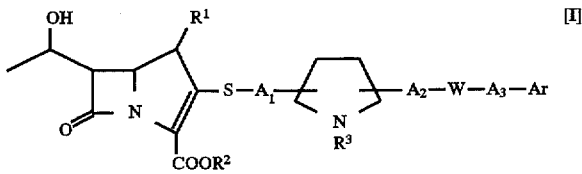

wherein $R^1$ is a hydrogen atom or a lower alkyl group, $R^2$ is a hydrogen atom or a negative charge, $R^3$ is a hydrogen atom or a lower alkyl group, Ar is a phenyl group, a naphthyl group or a group of:

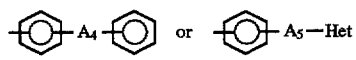

(wherein each of $A_4$ and $A_5$, which may be the same or different, is a single bond, a methylene group, an ethylene group, an oxygen atom, an imino group, a sulfur atom, a sulfonyl group, —CONH— or —NHSO$_2$—, and Het is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents, selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonylamino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group, each of $A_1, A_2$ and $A_3$, which may be same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and W is a sulfur atom, a group of N—X (wherein X is a hydrogen atom, a lower alkyl group, a formyl group, a lower alkanoyl group or a sulfamoyl group), an oxygen atom, a group of CH(OH) or a single bond; or a pharmaceutically acceptable salt or ester thereof, a process for its production and its use as an antibacterial agent.

Now, the present invention will be described in detail with reference to the preferred embodiments. Firstly, the symbols and terms used in this specification will be explained.

The compound of the present invention has a basic structure of the formula:

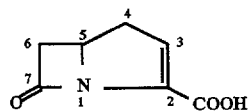

which is systematically referred to as a 7-oxo-1-azabicyclo [3.2.0]hept-2-en-2-carboxylic acid. For the convenience sake, in this specification, this basic structure will be referred to as a 1-carbapen-2-em-3-carboxylic acid by putting the numbers based on a commonly widely used carbapenem of the formula:

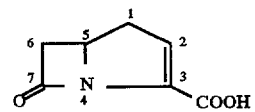

The present invention includes optical isomers and stereoisomers based on the asymmetric carbon atoms at the 1-position, 5-position, 6-position and 8-position of the carbapenem structure. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

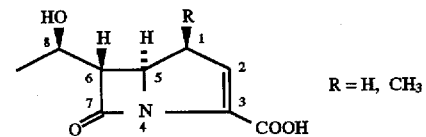

Also with respect to the substituted pyrrolidinylthio group at the 2-position of the carbapenem nuclei, the present invention includes isomers based on the asymmetric carbon atoms on the substituted pyrrolidine nucleus. Among these isomers, preferred are compounds of a (2'S,4'S) configuration and of a (2'R,4'R) configuration.

The mode of the substitution of the pyrrolidine ring in the side chain at the 2-position of the carbapenem structure is not particularly restricted, and the pyrrolidine ring may be substituted at any positions.

Preferred modes of substitution are

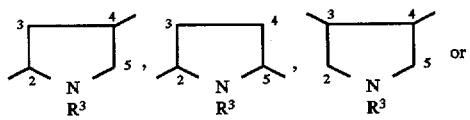

-continued

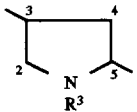

and the like, and the mode of substitution represented by

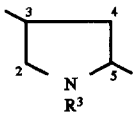

is particularly preferred.

The lower alkyl group means a linear or branched alkyl group having from 1 to 6 carbon atoms, such as a methyl group, an ethyl group, a propyl group, an isopropyl group, a butyl group, a sec-butyl group, a t-butyl group, a pentyl group or a hexyl group, preferably a methyl group, an ethyl group or a tert-butyl group.

The lower alkanoyl group means an alkanoyl group having from 2 to 7 carbon atoms, such as an acetyl group, a propenyl group or a butyryl group, preferably an acetyl group.

The halogen atom means a fluorine atom, a chlorine atom, a bromine atom or an iodine atom, preferably a fluorine atom, a chlorine atom or a bromine atom.

The lower alkoxy group means a linear or branched alkoxy group having from 1 to 6 carbon atoms with the above lower alkyl group substituted on an oxygen atom, such as a methoxy group, an ethoxy group, a propoxy group, an isopropoxy group, a butoxy group, a sec-butoxy group, a tert-butoxy group, a pentoxy group or a hetoxy group, preferably a methoxy group, an ethoxy group or a t-butoxy group.

The lower alkylthio group means a linear or branched alkylthio group having from 1 to 6 carbon atoms with the above lower alkyl group substituted on a sulfur atom, such as a methylthio group, an ethylthio group, a propylthio group, an isopropylthio group, a butylthio group, a sec-butylthio group, a t-butylthio group, a pentylthio group or a hexylthio group, preferably a methylthio group, an ethylthio group or a t-butylthio group.

The lower alkylcarbamoyl group means an alkylcarbamoyl group having from 2 to 7 carbon atoms with the above lower alkyl group substituted on a carbamoyl group, such as a methylcarbamoyl group, an ethylcarbamoyl group, a propylcarbamoyl group, an isopropylcarbamoyl group, a butylcarbamoyl group, a sec-butylcarbamoyl group, a t-butylcarbamoyl group, a pentylcarbamoyl group or a hexylcarbamoyl group, preferably a methylcarbamoyl group, an ethylcarbamoyl group or a t-butylcarbamoyl group.

The di-lower alkylcarbamoyl group means a dialkylcarbamoyl group having from 3 to 13 carbon atoms with the above-mentioned two lower alkyl groups substituted on a carbamoyl group, such as a dimethylcarbamoyl group, a diethylcarbamoyl group, a dipropylcarbamoyl group, a diisopropylcarbamoyl group, a dibutylcarbamoyl group, a di-sec-butylcarbamoyl group, a di-t-butylcarbamoyl group, a dipentylcarbamoyl group, a dihexylcarbamoyl group, an ethylmethylcarbamoyl group, a methylpropylcarbamoyl group or a t-butylmethylcarbamoyl group, preferably a dimethylcarbamoyl group, a diethylcarbamoyl group or a di-t-butylcarbamoyl group.

The lower alkylamino group means an alkylamino group having from 1 to 6 carbon atoms with the above lower alkyl group substituted on an amino group, such as a methylamino group, an ethylamino group, a propylamino group, an isopropylamino group, a butylamino group, a sec-butylamino group, a t-butylamino group, a pentylamino group or a hexylamino group, preferably a methylamino group, an ethylamino group or a t-butylamino group.

The di-lower alkylamino group means a dialkylamino group having from 2 to 12 carbon atoms with the above-mentioned two lower alkyl groups substituted on an amino group, such as a dimethylamino group, a diethylamino group, a dipropylamino group, a diisopropylamino group, a dibutylamino group, a di-sec-butylamino group, a di-t-butylamino group, a dipentylamino group, a dihexylamino group, an ethylmethylamino group, a methylpropylamino group, a butylmethylamino group or a t-butylmethylamino group, preferably a dimethylamino group, a diethylamino group or a di-t-butylamino group.

The tri-lower alkylammonio group means a trialkylammonio group having from 3 to 18 carbon atoms with the above-mentioned three lower alkyl groups substituted on an amino group, such as a trimethylammonio group, a triethylammonio group, a tripropylammonio group, a triisopropylammonio group, a tributylammonio group, a tri-sec-butylammonio group, a tri-t-butylammonio group, a tripentylammonio group or a trihexylammonio group, preferably a trimethylammonio group, a triethylammonio group or a tri-t-butylammonio group.

The lower alkanoylamino group means an alkanoylamino group having from 2 to 7 carbon atoms with the above-mentioned lower alkanoyl group substituted on an amino group, such as an acetylamino group, a propionylamino group or a butyrylamino group, preferably an acetylamino group or a propionylamino group.

The lower alkoxycarbonyl group means an alkoxycarbonyl group having from 2 to 7 carbon atoms with the above lower alkoxy groups substituted on a carbonyl group, such as a methoxycarbonyl group, an ethoxycarbonyl group, a propoxycarbonyl group, an isopropoxycarbonyl group, a butoxycarbonyl group, a sec-butoxycarbonyl group, a t-butoxycarbonyl group, a pentoxycarbonyl group or a hetoxycarbonyl group, preferably a methoxycarbonyl group, an ethoxycarbonyl group or a t-butoxycarbonyl group.

The carbamoyl lower alkylamino group means a carbamoylalkylamino group having from 2 to 7 carbon atoms with a carbamoyl group substituted on the above lower alkylamino group, such as a carbamoylmethylamino group, a 1-carbamoylethylamino group, a 2-carbamoylethylamino group, a 1-carbamoylpropylamino group, a 2-carbamoylpropylamino group, a 3-carbamoylpropylamino group, a 2-carbamoyl-1-methylethylamino group, a 1-carbamoylbutylamino group, a 2-carbamoylbutylamino group, a 3-carbamoylbutylamino group, a 4-carbamoylbutylamino group, a 2-carbamoyl-1,1-dimethylamino group, a 1-carbamoylpentylamino group, a 2-carbamoylpentylamino group, a 3-carbamoylpentylamino group, a 4-carbamoylpentylamino group, a 5-carbamoylpentylamino group, a 1-carbamoylhexylamino group, a 2-carbamoylhexylamino group, a 3-carbamoylhexylamino group, a 4-carbamoylhexylamino group, a 5-carbamoylhexylamino group or a 6-carbamoylhexylamino group, preferably a carbamoylmethylamino group, a 2-carbamoylethylamino group or a 2-carbamoyl-1,1-dimethylamino group.

The amino lower alkyl group means an aminoalkyl group having from 1 to 6 carbon atoms with an amino group substituted on the above lower alkyl group, such as an aminomethyl group, a 1-aminoethyl group, a 2-aminoethyl group, a 1-aminopropyl group, a 2-aminopropyl group, a 3-aminopropyl group, a 2-amino-1-methylethyl group, a 1-aminobutyl group, a 2-aminobutyl group, a 3-aminobutyl group, a 4-aminobutyl group, a 2-amino-1,1-dimethyl group, a 1-aminopentyl group, a 2-aminopentyl group, a 3-aminopentyl group, a 4-aminopentyl group, a 5-aminopentyl group, a 1-aminohexyl group, a 2-aminohexyl group, 3-aminohexyl group, a 4-aminohexyl group, a 5-aminohexyl group or a 6-aminohexyl group, preferably an aminomethyl group, a 2-aminoethyl group or a 2-amino-1,1-dimethyl group.

The carboxy lower alkyl group means a carboxyalkyl group having from 1 to 6 carbon atoms with a carboxyl group substituted on the above lower alkyl group, such as a carboxymethyl group, a 1-carboxyethyl group, a 2-carboxyethyl group, a 1-carboxypropyl group, a 2-carboxypropyl group, a 3-carboxypropyl group, a 2-carboxy-1-methylethyl group, a 1-carboxybutyl group a 2-carboxybutyl group, a 3-carboxybutyl group, a 4-carboxybutyl group, a 2-carboxy-1,1-dimethyl group, a 1-carboxypentyl group, a 2-carboxypentyl group, a 3-carboxypentyl group, a 4-carboxypentyl group, a 5-carboxypentyl group, a 1-carboxyhexyl group, a 2-carboxyhexyl group, a 3-carboxyhexyl group, a 4-carboxyhexyl group, a 5-carboxyhexyl group or a 6-carboxyhexyl group, preferably a carboxymethyl group, a 2-carboxyethyl group or a 2-carboxy-1,1-dimethyl group.

The carbamoyl lower alkyl group means a carbamoylalkyl group having from 1 to 6 carbon atoms with a carbamoyl group substituted on the above lower alkyl group, such as a carbamoylmethyl group, a 1-carbamoylethyl group, a 2-carbamoylethyl group, a 1-carbamoyl propyl group, a 2-carbamoylpropyl group, a 3-carbamoylpropyl group, a 2-carbamoyl-1-methylethyl group, a 1-carbamoylbutyl group, a 2-carbamoylbutyl group, a 3-carbamoylbutyl group, a 4-carbamoylbutyl group, a 2-carbamoyl-1,1-dimethyl group, a 1-carbamoylpentyl group, a 2-carbamoylpentyl group, a 3-carbamoylpentyl group, a 4-carbamoylpentyl group, a 5-carbamoylpentyl group, a 1-carbamoylhexyl group, a 2-carbamoylhexyl group, a 3-carbamoylhexyl group, a 4-carbamoylhexyl group, a 5-carbamoylhexyl group or a 6-carbamoylhexyl group, preferably a carbamoylmethyl group, a 2-carbamoylethyl group or a 2-carbamoyl-1,1-dimethyl group.

The hydroxy lower alkyl group means a hydroxyalkyl group having from 1 to 6 carbon atoms with a hydroxy group substituted on the above lower alkyl group, such as a hydroxymethyl group, a 1-hydroxyethyl group, a 2-hydroxyethyl group, a 1-hydroxypropyl group, a 2-hydroxypropyl group, a 3-hydroxypropyl group, a 2-hydroxy-1-methylethyl group, a 1-hydroxybutyl group, a 2-hydroxybutyl group, a 3-hydroxybutyl group, a 4-hydroxybutyl group, a 2-hydroxy-1,1-dimethyl group, a 1-hydroxypentyl group, a 2-hydroxypentyl group, a 3-hydroxypentyl group, a 4-hydroxypentyl group, a 5-hydroxypentyl group, a 1-hydroxyhexyl group, a 2-hydroxyhexyl group, a 3-hydroxyhexyl group, a 4-hydroxyhexyl group, a 5-hydroxyhexyl group or a 6-hydroxyhexyl group, preferably a hydroxymethyl group, a 2-hydroxyethyl group or a 2-hydroxy-1,1-dimethyl group.

The amino lower alkylcarbonylamino group means an aminoalkylcarbonylamino group having from 2 to 7 carbon atoms with the above amino lower alkyl group substituted on a carbonylamino group, such as an aminomethylcarbonylamino group, a 1-aminoethylcarbonylamino group, a 2-aminoethylcarbonylamino group, a 1-aminopropylcarbonylamino group, a 2-aminopropylcarbonylamino group, a 3-aminopropylcarbonylamino group, a 2-amino-1-methylethylcarbonylamino group, a 1-aminobutylcarbonylamino group, a 2-aminobutylcarbonylamino group, a 3-aminobutylcarbonylamino group, a 4-aminobutylcarbonylamino group, a 2-amino-1,1-dimethylcarbonylamino group, a 1-aminopentylcarbonylamino group, a 2-aminopentylcarbonylamino group, a 3-aminopentylcarbonylamino group, a 4-aminopentylcarbonylamino group, a 5-aminopentylcarbonylamino group, a 1-aminohexylcarbonylamino group, a 2-aminohexylcarbonylamino group, a 3-aminohexylcarbonylamino group, a 4-aminohexylcarbonylamino group, a 5-aminohexylcarbonylamino group or a 6-aminohexylcarbonylamino group, preferably an aminomethylcarbonylamino group, a 2-aminoethylcarbonylamino group or a 2-amino-1,1-dimethylcarbonylamino group.

The lower alkylsulfonyl group means a linear or branched alkylsulfonyl group having from 1 to 6 carbon atoms with the above lower alkyl group substituted on a sulfonyl group, such as a methylsulfonyl group, an ethylsulfonyl group, a propylsulfonyl group, an isopropylsulfonyl group, a butylsulfonyl group, a sec-butylsulfonyl group, a t-butylsulfonyl group, a pentylsulfonyl group or a hexylsulfonyl group, preferably a methylsulfonyl group, an ethylsulfonyl group or a t-butylsulfonyl group.

The di-lower alkylsulfonyl group means a dialkylsulfonyl group having from 2 to 12 carbon atoms with the above-mentioned two lower alkyl groups substituted on a sulfonyl group, such as a dimethylsulfonyl group, a diethylsulfonyl group, a dipropylsulfonyl group, a diisopropylsulfonyl group, a dibutylsulfonyl group, a di-sec-butylsulfonyl group, a di-t-butylsulfonyl group, a dipentylsulfonyl group, a dihexylsulfonyl group, an ethylmethylsulfonyl group, a methylpropylsulfonyl group or a t-butylmethylsulfonyl group, preferably a dimethylsulfonyl group, a diethylsulfonyl group or a di-t-butylsulfonyl group.

The lower alkylsulfamoyl group means a linear or branched alkylsulfamoyl group having from 1 to 6 carbon atoms with the above lower alkyl group substituted on a sulfamoyl group, such as a methylsulfamoyl group, an ethylsulfamoyl group, a propylsulfamoyl group, an isoproylsulfamoyl group, a butylsulfamoyl group, a sec-butylsulfamoyl group, a t-butylsulfamoyl group, a pentylsulfamoyl group or a hexylsulfamoyl group, preferably a methylsulfamoyl group, an ethylsulfamoyl group or a t-butylsulfamoyl group.

The di-lower alkylsulfamoyl group means a dialkylsulfamoyl group having from 2 to 12 carbon atoms with the above two lower alkyl groups substituted on a sulfamoyl group, such as a dimethylsulfamoyl group, a diethylsulfamoyl group, a dipropylsulfamoyl group, a diisopropylsulfamoyl group, a dibutylsulfamoyl group, a di-sec-butylsulfamoyl group, a di-t-butylsulfamoyl group, a dipentylsulfamoyl group, a di-hexylsulfamoyl group, an ethylmethylsulfamoyl group, a methylpropylsulfamoyl group or a t-butylmethylsulfamoyl group, preferably a dimethylsulfamoyl group, a diethylsulfamoyl group or a di-t-butylsulfamoyl group.

The lower alkylsulfonylamino group means a linear or branched alkylsulfonylamino group having from 1 to 6 carbon atoms with the above lower alkyl sulfonyl group substituted on an amino group, such as a methylsulfonylamino group, an ethylsulfonylamino group, a propylsulfonylamino group, an isopropylsulfonylamino group, a butylsulfonylamino group, a sec-butylsulfonylamino group, a t-butylsulfonylamino group, a pentylsulfonylamino group or a hexylsulfonylamino group, preferably a methylsulfonylamino group, an ethylsulfonylamino group or a t-butylsulfonylamino group.

The aryl group means an aryl group having from 6 to 12 carbon atoms, such as a phenyl group or an naphthyl group, preferably a phenyl group.

The aryloxy group means an aryloxy group having from 6 to 12 carbon atoms with the above aryl group substituted on an oxygen atom, such as a phenoxy group or a naphthoxy group, preferably a phenoxy group.

The arylthio group means an arylthio group having from 6 to 12 carbon atoms with the above aryl group substituted on a sulfur atom, such as a phenylthio group or a naphthylthio group, preferably a phenylthio group.

The arylcarbamoyl group means an arylcarbamoyl group having from 7 to 13 carbon atoms with the above aryl group substituted on a carbamoyl group, such as a phenylcarbamoyl group or a naphthylcarbamoyl group, preferably a phenylcarbamoyl group.

The arylsulfonyl group means an arylsulfonyl group having from 6 to 12 carbon atoms with the above aryl group substituted on a sulfonyl group, such as a phenylsulfonyl group or a naphthylsulfonyl group, preferably a phenylsulfonyl group.

The aryloxycarbonyl group means an aryloxycarbonyl group having from 6 to 12 carbon atoms with the aryloxy group substituted on a carbonyl group, such as a phenoxycarbonyl group or a naphthoxycarbonyl group, preferably a phenoxycarbonyl group.

The arylsulfonylamino group means an arylsulfonylamino group having from 6 to 12 carbon atoms with the above arylsulfonyl group substituted on an amino group, such as a phenylsulfonylamino group or a naphthylsulfonylamino group, preferably a phenylsulfonylamino group.

The aralkyl group means an aralkyl group having from 7 to 14 carbon atoms, such as a benzyl group, a phenethyl group, a phenylpropyl group, a phenylbutyl group, a naphthylmethyl group, a naphthylethyl group, a naphthylpropyl group or a naphthylbutyl group, preferably a benzyl group, a phenethyl group, a naphthylmethyl group or a naphthylethyl group.

The aralkylamino group means an aralkylamino group having from 7 to 14 carbon atoms with the above aralkyl group substituted on an amino group, such as a benzylamino group, a phenethylamino group, a phenylpropylamino group, a phenylbutylamino group, a naphthylmethylamino group, a naphthylethylamino group, a naphthylpropylamino group or a naphthylbutylamino group, preferably a benzylamino group, a phenethylamino group, a naphthylmethylamino group or a naphthylethylamino group.

The aroyl group means an aroyl group having from 7 to 11 carbon atoms, such as a benzoyl group, toluoyl group or a naphthylcarbonyl group.

The aroylamino group means an aroylamino group having from 7 to 14 carbon atoms with the above aroyl group substituted on an amino group, such as a benzoylamino group, a toluoylamino group or a naphthylcarbonylamino group, preferably a benzoylamino group.

The lower alkylene group means a linear or branched alkylene group having from 1 to 6 carbon atoms, such as a methylene group, an ethylene group, a propylene group, a butylene group, a methylmethylene group or a dimethylmethylene group, preferably a methylene group, an ethylene group or a propylene group.

The carboxyl-protecting group may, for example, be a lower alkyl group such as a methyl group, an ethyl group, a propyl group, an isopropyl group or a t-butyl group; a halogenated lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted-2-oxo-1,3-dioxol-4-yl)methyl group such as a (5-methyl-2-oxo-1,3-dioxol-4-yl)methyl group; a lower alkylsilyl group such as a trimethylsilyl group or a t-butyldimethylsilyl group; an indanyl group, a phthalidyl group or a methoxymethyl group. Particularly preferred are a 2-propenyl group, a p-nitrobenzyl group, a p-methoxybenzyl group, a benzhydryl group and a t-butyldimethylsilyl group.

The hydroxyl-protecting group may, for example, be a lower alkylsilyl group such as a trimethylsilyl group or a t-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a t-butoxycarbonyl group, an 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; or an aralkyloxycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred are a 2-propenyloxycarbonyl group, a p-nitrobenzyloxycarbonyl group and a t-butyldimethylsilyl group.

The amino-protecting group may, for example, be an aralkylidene group such as a benzylidene group, a p-chlorobenzylidene group, a p-nitrobenzylidene group, a salicylidene group, an α-naphthylidene group or a β-naphthylidene group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)methyl group or a trityl group; a lower alkanoyl group such as a formyl group, an acetyl group, a propionyl group, a butyryl group, an oxalyl group, a succinyl group or a pivaloyl group; a halogenated lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a t-butoxycarbonyl group; a halogenated lower alkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenethyloxycarbonyl group; or a lower alkylsilyl group such as a trimethylsilyl group or a t-butyldimethylsilyl group. Particularly preferred are a 2-propenyloxycarbonyl group, a t-butoxycarbonyl group and a p-nitrobenzyloxycarbonyl group.

$R^1$ is a hydrogen atom or a lower alkyl group.
$R^2$ is a hydrogen atom or a negative charge.
$R^3$ is a hydrogen atom or a lower alkyl group.
Ar is a phenyl group, a naphthyl group or a group of:

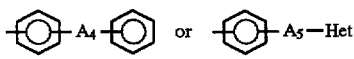

(wherein each of $A_4$ and $A_5$, which may be the same or different, is a single bond, a methylene group, an ethylene group, an oxygen atom, an imino group, a sulfur atom, a sulfonyl group, —CONH— or —NHSO$_2$—, and Het is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents, selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group and a carbamoyl lower alkyl group).

The above-mentioned phenyl group, the above-mentioned naphthyl group or the aryl group in the group of:

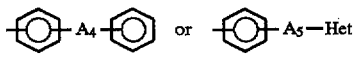

(wherein $A^4$, $A^5$ and Het are as defined above) may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group, a lower alkylsulfamoyl group, a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group. Among this group of substituents, the lower alkyl group, the lower alkylcarbamoyl group, the lower alkylsulfonylamino group, the lower alkylamino group, the lower alkoxy group, the aryloxy group, the lower alkylthio group, the lower alkylsulfonyl group and the lower alkylsulfamoyl group may be substituted with the same or different one to three substituents, selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonylamino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group.

Among the substituents for the aryl group, preferred are a lower alkyl group, a lower alkylcarbamoyl group, a lower alkylsulfonylamino group, a lower alkylamino group, a lower alkoxy group, a lower alkylthio group, a lower alkylsulfonyl group, a lower alkylsulfamoyl group, a hydroxyl group, a halogen atom, a carboxyl group, a carbamoyl group, an amino group and a sulfamoyl group. Particularly preferred are an amino group and a lower alkyl group.

Among the substituents for the substituents for the aryl group, preferred are a hydroxyl group, a carboxyl group, a carbamoyl group, an amino group and a lower alkylamino group. Particularly preferred are an amino group and a lower alkylamino group.

As Ar, preferred is $Ar_a$, which is a phenyl group, a naphthyl group or a group of:

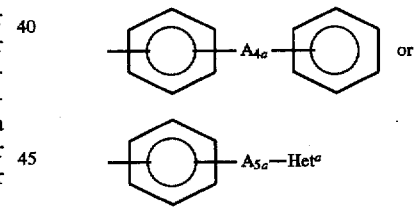

(wherein each of $A_{4a}$ and $A_{5a}$, which may be the same or different, is a single bond, a methylene group or an ethylene group, and Het$^a$ is an imidazolio group, a pyridinio group, a morpholinyl group, a quinuclidinio group or a 1,4-diazabicyclo[2.2.2]octanyl group which may be substituted with the same or different one to three substituents selected from the group consisting of a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, a lower alkylthio group, a lower alkylsulfonyl group and a lower alkylsulfamoyl group which may be substituted with the same or different one to three substituents selected from the group consisting of a hydroxyl group, a carboxyl group, a carbamoyl group, an amino group and a lower alkylamino group, and a hydroxyl group, a halogen atom, a carboxyl group, a carbamoyl group, an amino group and a sulfamoyl group. Particularly preferred is $Ar_b$, which is a phenyl group, a naphthyl group or a group of:

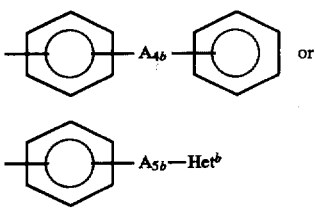

(wherein each of $A_{4b}$ and $A_{5b}$, which may be the same or different, is a single bond, a methylene group or an ethylene group, and $Het^b$ is an imidazolio group or a 1,4-diazabicyclo [2.2.2]octanyl group which may be substituted with the same or different one to three substituents selected from the group consisting of a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylthio group, a lower alkylsulfonyl group and a lower alkylsulfamoyl group which may be substituted with the same or different one to three substituents selected from the group consisting of an amino group and a lower alkylamino group, and a halogen atom, a carbamoyl group and a sulfamoyl group.

Each of $A_4$ and $A_5$, which may be the same or different, is a single bond, a methylene group, an ethylene group, an oxygen atom, an imino group, a sulfur atom, a sulfonyl group, —CONH— or —NHSO$_2$—.

As $A_4$ and $A_5$, preferred are $A_{4a}$ and $A_{5a}$, and $A_{4b}$ and $A_{5b}$, which may be the same or different, and each of which is a single bond, a methylene group or an ethylene group. When $A_4$ or $A_5$ is —CONH— or —NHSO$_2$—, $A_4$ and $A_5$ may be linked to the benzene ring or the heterocyclic group in the order of —CONH— or —NHCO— via the carbon atom or the nitrogen atom, or in the order of —NHSO$_2$— or —SO$_2$NH— via the nitrogen atom or the sulfur atom.

Het is a heterocyclic group such as a pyrrolinyl group, a pyrrolyl group, an imidazoyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group.

The heterocyclic group may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group and a carbamoyl lower alkyl group.

As the heterocyclic group, preferred are an imidazolio group, a pyridinio group, a morpholinyl group, a quinuclidinio group and a 1,4-diazabicyclo[2.2.2]octanyl group. Particularly preferred are an imidazolio group and a 1,4-diazabicyclo[2.2.2]octanyl group.

As the substituents for the heterocyclic group, preferred are a lower alkyl group, a hydroxy lower alkyl group and a carbamoyl lower alkyl group, and particularly preferred are a hydroxy lower alkyl group and a carbamoyl lower alkyl group. The heterocyclic group may be substituted with the same or different one to three substituents selected from these substituents.

Accordingly, as Het, preferred is $Het^a$, which is an imidazolio group, a pyridinio group, a morpholinyl group, a quinuclidinio group or a 1,4-diazabicyclo[2.2.2]octanyl group which may be substituted with the same or different one to three substituents selected from the group consisting of a lower alkyl group, a hydroxy lower alkyl group and a carbamoyl lower alkyl group. Particularly preferred is $Het^b$, which is an imidazolio group or a 1,4-diazabicyclo[2.2.2] octanyl group which may be substituted with the same or different one to three substituents selected from the group consisting of a hydroxy lower alkyl group and a carbamoyl lower alkyl group.

Each of $A_1$, $A_2$ and $A_3$, which may be the same or different, is a single bond or a lower alkylene group.

The lower alkylene group may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group, a lower alkylsulfamoyl group, a pyridyl group and a pyridinio group. Among these substituents, the lower alkyl group, the lower alkylcarbamoyl group, the lower alkylamino group, the lower alkoxy group, the lower alkylthio group, the lower alkylsulfonyl group, the lower alkylsulfonylamino group and the lower alkylsulfamoyl group (hereinafter referred to as substituent group A) may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group (hereinafter referred to simply as substituent group B).

Among substituent group A, preferred are a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group. Particularly preferred is a lower alkyl group.

Among substituent group B, preferred are a hydroxyl group, a carbamoyl group, an amino group, a lower alkylamino group and a lower alkylthio group. Particularly preferred are a carbamoyl group, an amino group and a lower alkylamino group.

The pyridyl group and the pyridinio group may be substituted with a substituent selected from the group consisting of a lower alkyl group, a carboxy lower alkyl group and a carbamoyl lower alkyl group.

Therefore, as $A_1$, $A_2$ and $A_3$, preferred are $A_{1a}$, $A_{2a}$ and $A_{3a}$, which may be the same or different, and each of which is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents, selected from the group consisting of a hydroxyl group, a carbamoyl group, an amino group, a lower alkylamino group and a lower alkylthio group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group). Particularly preferred are $A_{1b}$, $A_{2b}$ and $A_{3b}$, which may be the same or different, and each of which is a single bond or a lower alkylene group which may be substituted with a substituent selected from the group consisting of a lower alkyl group which may be substituted with the same or different one to three substituents selected from the group consisting of a carbamoyl group, an amino group and a lower alkylamino group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group).

W is a sulfur atom, a group of N—X (wherein X is a hydrogen atom, a lower alkyl group, a formyl group, a lower alkanoyl group or a sulfamoyl group), an oxygen atom, a group of CH(OH) or a single bond. Particularly preferred is a sulfur atom. However, compounds of the present invention wherein W is a group of N—X (wherein X is a hydrogen atom, a lower alkyl group, a formyl group, a lower alkanoyl group or a sulfamoyl group), an oxygen atom, a group of CH(OH) or a single bond, also exhibit good antibacterial activities.

Now, the compounds of the formula [I] will be described in detail.

Among the compounds of the formula [I], preferred are compounds represented by the formula:

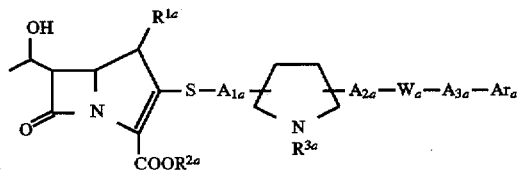

[I-a]

wherein $R^{1a}$ is a lower alkyl group, $R^{2a}$ is a hydrogen atom or a negative charge, $R^{3a}$ is a hydrogen atom, $Ar_a$ is a phenyl group, a naphthyl group or a group of:

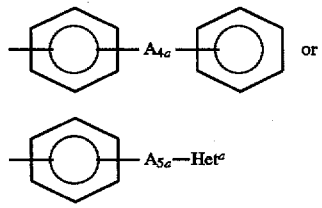

(wherein each of $A_{4a}$ and $A_{5a}$, which may be the same or different, is a single bond, a methylene group or an ethylene group, and $Het^a$ is an imidazolio group, a pyridinio group, a morpholinyl group, a quinuclidinio group or a 1,4-diazabicyclo[2.2.2]octanyl group which may be substituted with the same or different one to three substituents selected from the group consisting of a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkyl-sulfonylamino group, a lower alkylamino group, a lower alkoxy group, a lower alkylthio group, a lower alkylsulfonyl group and a lower alkylsulfamoyl group which may be substituted with the same or different one to three substituents selected from the group consisting of a hydroxyl group, a carboxyl group, a carbamoyl group, an amino group and a lower alkylamino group, and a hydroxyl group, a halogen atom, a carboxyl group, a carbamoyl group, an amino group and a sulfamoyl group, each of $A_{1a}$, $A_{2a}$ and $A_{3a}$, which may be the same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a carbamoyl group, an amino group, a lower alkylamino group and a lower alkylthio group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and $W_a$ is a sulfur atom, a group of N—$X_a$ (wherein $X_a$ is a hydrogen atom, a lower alkyl group, a formyl group, a lower alkanoyl group or a sulfamoyl group), an oxygen atom, a group of CH(OH) or a single bond. Particularly preferred are those wherein $W_a$ is a sulfur atom. However, compounds wherein $W_a$ is a group of N—$X_a$ (wherein $X_a$ is a hydrogen atom, a lower alkyl group, a formyl group, a lower alkanoyl group or a sulfamoyl group), an oxygen atom, a group of CH(OH) or a single bond, compounds wherein $W_a$ is a group of N—$X_a$ (wherein $X_a$ is a hydrogen atom, a lower alkyl group, a formyl group, a lower alkanoyl group or a sulfamoyl group), compounds wherein $W_a$ is an oxygen atom, compounds wherein $W_a$ is a group of CH(OH) and compounds wherein $W_a$ is a single bond also have good antibacterial activities.

Among the compounds of the formula [I-a], more preferred are compounds represented by the formula:

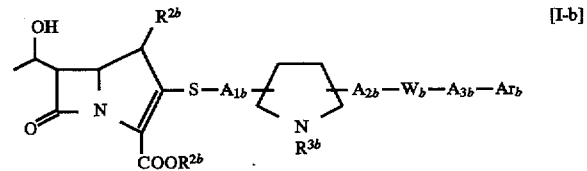

[I-b]

wherein $R^{1b}$ is a lower alkyl group, $R^{2b}$ is a hydrogen atom or a negative charge, $R^{3b}$ is a hydrogen atom, $Ar_b$ is a phenyl group, a naphthyl group or a group of:

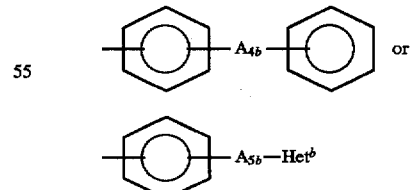

(wherein each of $A_{4b}$ and $A_{5b}$, which may be the same or different, is a single bond, a methylene group or an ethylene group, and $Het^b$ is an imidazolio group or a 1,4-diazabicyclo [2.2.2]octanyl group which may be substituted with the same or different one to three substituents selected from the group consisting of a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylthio group, a lower alkylsulfonyl group and a lower alkylsulfamoyl group which may be substituted with the same or different one to three substituents selected from the group consisting of an amino group and a lower alkylamino group, and a halogen atom, a carbamoyl group and a sulfamoyl group, each of $A_{1b}$, $A_{2b}$ and $A_{3b}$, which may be the same or different, is a single bond or a lower alkylene group which may be substituted with a substituent selected from the group consisting of a lower alkyl group which may be substituted with the same or different one to three substituents selected from the group consisting of a carbamoyl group, an amino group and a lower alkylamino group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and $W_b$ is a sulfur atom, a group of N—$X_b$ (wherein $X_b$ is a hydrogen atom, a lower alkyl group, a formyl group, a lower alkanoyl group or a sulfamoyl group), an oxygen atom, a group of CH(OH) or a single bond. Thereamong, particularly preferred are those wherein $W_b$ is a sulfur atom. However, compounds wherein $W_b$ is a group of N—$X_b$ (wherein $X_b$ is a hydrogen atom, a lower alkyl group, a formyl group, a lower alkanoyl group or a sulfamoyl group), an oxygen atom, a group of CH(OH) or a single bond, compounds wherein $W_b$ is a group of N—$X_b$ (wherein $W_b$ is a hydrogen atom, a lower alkyl group, a formyl group, a lower alkanoyl group or a sulfamoyl group), compounds wherein $W_b$ is an oxygen atom, compounds wherein $W_b$ is a group of CH(OH) or compounds wherein $W_b$ is a single bond, also have good antibacterial activities.

Specifically, among the compounds of the formula [I], preferred are, for example, (1R,5S,6S)-2-[(3S,5S)-5-[4-(2-aminoethylthio)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(3-aminomethyl-4-chlorophenyl)thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethyl-2-sulfamoylphenyl)thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylcarbamoyl)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[[4-(2-aminoethylcarbamoyl)-2-sulfamoylphenyl]thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethyloxy)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(3-aminopropionylamino)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfonylamino)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-aminomethylphenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfamoyl)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(8-aminomethyl-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(3-aminomethyl-5-glycylamino-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-[(3-aminoethylsulfonylaminoethyl)-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(3-aminomethyl-5-glycylaminomethyl-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-[6-(4-carbamoylmethyl-1,4-diazabicyclo[2.2.2]octanedium-1-ylmethyl)-2-naphthylmethylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[3-(4-carbamoylmethyl-1,4-diazabicyclo[2.2.2]octanedium-1-ylmethyl)-2naphthylmethylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenylaminomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethyl-1-naphthylaminomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenoxymethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenylethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylbenzyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethyl-1-naphthylmethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenyl)pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethyl-5-phenylphenyl)hydroxymethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethyl-1-naphthylmethyl)hydroxymethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethylphenyl)hydroxymethyl]pyrrolidin-3-ylthio]-6-[(1R)-hydroxyethyl]-1-methyl-1-carbapen-2-em-3-carboxylic acid and (1R,5S,6S)-2-[(3S,5S)-5-[(5-aminomethyl-2-fluorophenyl)hydroxymethyl]pyrrolidin-3-ylthio]-6-[(1R)-hydroxyethyl]-1-methyl-1-carbapen-2-em-3-carboxylic acid.

Particularly preferred are (1R,5S,6S)-2-[(3S,5S)-5-[4-(2-aminoethylthio)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-aminomethyl-2-sulfamoylphenyl)thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylcarbamoyl)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[[4-(2-aminoethylcarbamoyl)-2-sulfamoylphenyl]thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(3-aminopropionylamino)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfonylamino)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-aminomethylphenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfamoyl)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(8-aminomethyl-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-[6-(4-carbamoylmethyl-1,4-diazobicyclo[2.2.2]octanedium-1-ylmethyl)-2-naphthylmethylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenylaminomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylbenzyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenyl)pyrrolidin-3-ylthio]-6-[(1R)-hydroxyethyl]-1-methyl-1-carbapen-2-em-3-carboxylic acid and (1R,5S,6S)-2-[(3S,5S)-5-(4-aminomethylphenyl)hydroxymethyl]pyrrolidin-3-ylthio]-6-[(1R)-hydroxyethyl]-1-methyl-1-carbapen-2-em-3-carboxylic acid.

The compounds of the formula [I] have been created, as a result of extensive researches by the present inventors, from compounds represented by the formula:

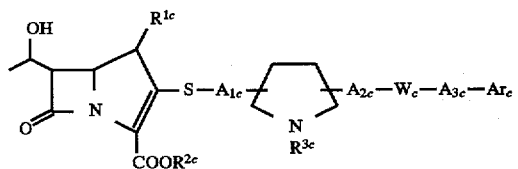

[I-c]

wherein $R^{1c}$ is a hydrogen atom or a lower alkyl group, $R^{2c}$ is a hydrogen atom or a negative charge, $R^{3c}$ is a hydrogen atom or a lower alkyl group, $Ar_c$ is a phenyl group, a naphthyl group or a group of:

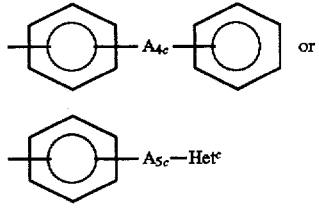

(wherein each of $A_{4c}$ and $A_{5c}$, which may be the same or different, is a single bond, a methylene group, an oxygen atom, an imino group, a sulfur atom, a sulfonyl group, —CONH— or —NHSO$_2$—, and $Het^c$ is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group) which may be substituted with the same or different one to five substituents selected from the group consisting of a lower alkyl group, a lower alkylcarbamoyl group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonylamino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group, each of $A_{1c}$, $A_{2c}$ and $A_{3c}$, which may be same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group (wherein the pyridyl group may be substituted with a substituent selected from the group consisting of a lower alkyl group, a carboxy lower alkyl group and a carbamoyl lower alkyl group), and $W_c$ is a sulfur atom; compounds represented by the formula:

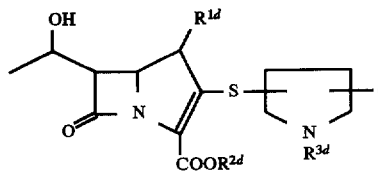

wherein $R^{1d}$ is a hydrogen atom or a lower alkyl group, $R^{2d}$ is a hydrogen atom, $R^{3d}$ is a hydrogen atom or a lower alkyl group, each of $R^{4d}$ and $R^{5d}$, which may be the same or different, is a hydrogen atom, a halogen atom, a hydroxyl group, a carbamoyl group or a sulfamoyl group, $X_d$ is a hydrogen atom, a lower alkyl group, a formyl group or a lower alkanoyl group, either $Y_d$ or $Z_d$ is a hydrogen atom, the other is a group (d):

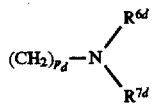 (d)

(wherein each of $R^{6d}$ and $R^{7d}$, which may be the same or different, is a hydrogen atom or a lower alkyl group, or $R^{6d}$ and $R^{7d}$ form a $C_{2-6}$ alkylene group, and $p_d$ is an integer of from 0 to 3), each of $A_d$ and $B_d$, which may be the same or different, is a phenyl group or a naphthyl group (provided that $R^{5d}$, $B_d$ and $Z_d$ may form a hydrogen atom), $m_d$ is 1 or 2, and $n_d$ is 0 or 1 (provided that when $Y_d$ or $Z_d$ is a hydrogen atom, $Z_d$ and $R^{5d}$, or $Y_d$ and $R^{4d}$ may form a nitrogen-containing 5 to 7-membered heterocyclic ring); compounds represented by the formula:

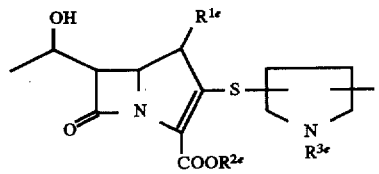

wherein $R^{1e}$ is a hydrogen atom or a lower alkyl group, $R^{2e}$ is a hydrogen atom, $R^{3e}$ is a hydrogen atom or a lower alkyl group, each of $R^{4e}$ and $R^{5e}$, which may be the same or different, is a hydrogen atom, a carbamoyl group or a sulfamoyl group, either $Y_e$ or $Z_e$ is a hydrogen atom, the other is a group (e):

 (e)

(wherein each of $R^{6e}$ and $R^{7e}$, which may be the same or different, is a hydrogen atom or a lower alkyl group, or $R^{6e}$ and $R^{7e}$ form a $C_{2-6}$ alkylene group, and $p_e$ is an integer of from 0 to 3), each of $A_e$ and $B_e$, which may be the same or different, is a phenyl group or a naphthyl group (provided that $R^{5e}$, $B_e$ and $Z_e$ may form a hydrogen atom), $m_e$ is 1 or 2, and $n_e$ is 0 or 1 (provided that when $Y_e$ or $Z_e$ is a hydrogen atom, $Z_e$ and $R^{5e}$, or $Y_e$ and $R^{4e}$ may form a nitrogen-containing 5 to 7-membered heterocyclic ring); compounds represented by the formula:

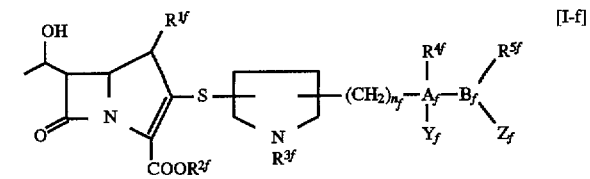

wherein $R^{1f}$ is a hydrogen atom or a lower alkyl group, $R^{2f}$ is a hydrogen atom, $R^{3f}$ is a hydrogen atom, a lower alkyl group or a lower alkenyl group, each of $R^{4f}$ and $R^{5f}$, which may be the same or different, is a hydrogen atom, a halogen atom, a hydroxyl group, a lower alkyl group, a carbamoyl group or a sulfamoyl group, either $Y_f$ or $Z_f$ is a hydrogen atom, the other is a group (f):

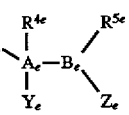 (f)

(wherein each of $R^{6f}$ and $R^{7f}$ which may be the same or different, is a hydrogen atom or a lower alkyl group, or $R^{6f}$ and $R^{7f}$ form a $C_{2-6}$ alkylene group, and $p_f$ is an integer of from 0 to 3), each of $A_f$ and $B_f$, which may be the same or different, is a phenyl group or a naphthyl group (provided that $R^{5f}$, $B_f$ and $Z_f$ may form a hydrogen atom), and $n_f$ is an integer of from 1 to 3 (provided that when $Y_f$ or $Z_f$ is a hydrogen atom, $Z_f$ and $R^{5f}$, or $Y_f$ and $R^{4f}$ may form a nitrogen-containing 5 to 7-membered heterocyclic ring); and compounds represented by the formula:

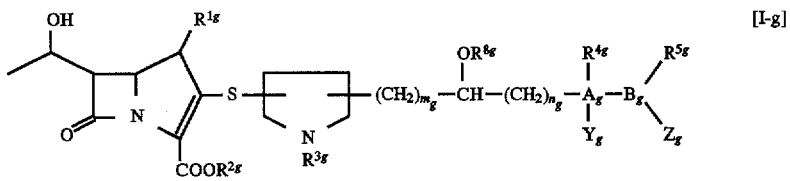
[I-g]

wherein $R^{1g}$ is a hydrogen atom or a lower alkyl group, $R^{2g}$ is a hydrogen atom, $R^{3g}$ is a hydrogen atom or a lower alkyl group, each of $R^{4g}$ and $R^{5g}$, which may be the same or different, is a hydrogen atom, a halogen atom, a hydroxyl group, a lower alkyl group, a carbamoyl group or a sulfamoyl group, either $Y_g$ or $Z_g$ is a hydrogen atom, the other is a group (g):

(g)

(wherein each of $R^{6g}$ and $R^{7g}$, which may be the same or different, is a hydrogen atom or a lower alkyl group, or $R^{6g}$ and $R^{7g}$ may form a $C_{2-6}$ alkylene group, and $p_g$ is an integer of from 0 to 3), $R^{8g}$ is a hydrogen atom, each of $A_g$ and $B_g$, which may be the same or different, is a phenyl group or a naphthyl group (provided that $R^{5g}$, $B_g$ and $Z_g$ may form a hydrogen atom), $m_g$ is an integer of 1 or 2, and $n_g$ is an integer of 0 or 1 (provided that when $Y_g$ or $Z_g$ is a hydrogen atom, $Z_g$ and $R^{5g}$, or $Y_g$ and $R^{4g}$ may form a nitrogen-containing 5 to 7-membered heterocyclic ring). The compounds of the formula [I] naturally include the compounds of the formula [I-c], the compounds of the formula [I-d], the compounds of the formula [I-e], the compounds of the formula [I-f] and the compounds of the formula [I-g].

In the compounds of the formula [I], the mode of the substitution of the pyrrolidine ring in the side chain at the 2-position of the carbapenem structure is not particularly restricted, and the pyrrolidine ring may be substituted at any positions.

Therefore, the compounds of the formula [I] include compounds of the formulae:

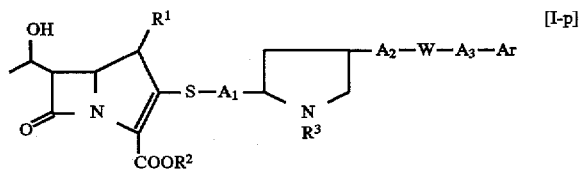
[I-p]

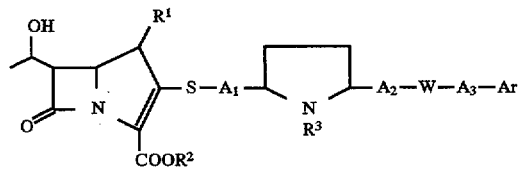
[I-q]

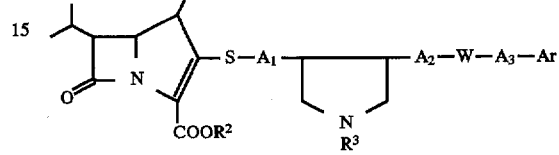
[I-r]

and

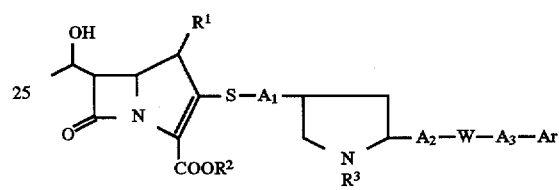
[I-s]

wherein $R^1$, $R^2$, $R^3$, Ar, $A_1$, $A_2$, $A_3$ and W are as defined above. Particularly preferred are compounds of the formula [I-s].

The salt of the compound of the formula (I) is a common pharmaceutically acceptable salt and may, for example, be a salt at the carboxyl group at the 3-position of the carbapenem structure, or at the pyrrolidine base or the base on the side chain substituted on the pyrrolidine ring.

The basic addition salt at said carboxyl group includes, for example, an alkali metal salt such as a sodium salt or a potassium salt; an alkaline earth metal salt such as a calcium salt or a magnesium salt; an ammonium salt; an aliphatic amine salt such as a trimethylamine salt, a triethylamine salt, a dicyclohexylamine salt, an ethanolamine salt, a diethanolamine salt, a triethanolamine salt or a procaine salt; an aralkylamine salt such as an N,N'-dibenzylethylenediamine salt; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; and a basic amino acid salt such as an arginine salt or a lysine salt.

The acid addition salt at the pyrrolidine base or at the base on the side chain substituted on the pyrrolidine ring includes, for example, an inorganic salt such as a hydrochloride, a sulfate, a nitrate, a phosphate, a carbonate, a hydrogencarbonate or a perchlorate; an organic salt such as an acetate, a propionate, a lactate, a maleate, a fumarate, a tartrate, a malate, a succinate or an ascorbate; a sulfonate such as a methanesulfonate, an isethionate, a benzenesulfonate or a p-toluenesulfonate; and an acidic amino acid salt such as an aspartate or a glutamate.

The non-toxic ester of the compound of the formula (I) means a common pharmaceutically acceptable ester at the carboxyl group at the 3-position of the carbapenem structure. For example, it includes an ester with an alkanoyloxymethyl group such as an acetoxymethyl group or a pivaloyloxymethyl group, an ester with an alkoxycarbonyloxyalkyl group such as a 1-(ethoxycarbonyloxy)ethyl group, an ester with a phthalidyl group and an ester with a (5-substituted-2-oxo-1,3-dioxol-4-yl)methyl group such as a (5-methyl-2-oxo-1,3-dioxol-4-yl)methyl group.

Now, the process for producing the compound of the present invention will be described.

The compound of the formula [I] can be obtained by reacting a compound of the formula:

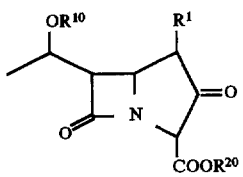 [II]

wherein $R^1$ is a hydrogen atom or a lower alkyl group, $R^{10}$ is a hydrogen atom or a hydroxyl-protecting group, and $R^{20}$ is a hydrogen atom or a carboxyl-protecting group, or a reactive derivative thereof, with a compound of the formula:

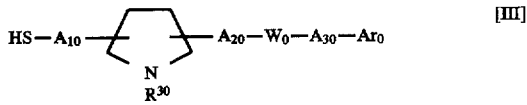 [III]

wherein $R^{30}$ is a hydrogen atom, a lower alkyl group or an imino-protecting group, $Ar_0$ is a phenyl group, a naphthyl group or a group of:

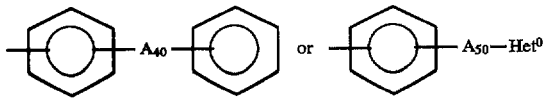

(wherein each of $A_{40}$ and $A_{50}$, which may be the same or different, is a single bond, a methylene group, an ethylene group, an oxygen atom, an imino group which may be protected, a sulfur atom, a sulfonyl group, —CONH— or —NHSO$_2$—, and $Het^0$ is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, piperazinyl group, a morpholinyl group, a benzothiazolyl group, an isoindolyl group, a quinuclidinyl group, a quinuclidinio group, a benzthiazol-1,1-dioxo-6-yl group or a 1,4-diazabicyclo[2.2.2]octanyl group which may be substituted with the same or different one to three substituents selected from the group consisting of a hydroxyl group which may be protected, a halogen atom, a cyano group, a carboxyl group which may be protected, a lower alkoxycarbonyl group, a carbamoyl group, a lower alkylcarbamoyl group, a di-lower alkylcarbamoyl group, a carbamoyloxy group, an amino group which may be protected, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group which may be protected and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group which may be protected, a halogen atom, a cyano group, a carboxyl group which may be protected, a lower alkoxycarbonyl group, a carbamoyl group, a lower alkylcarbamoyl group, a di-lower alkylcarbamoyl group, a carbamoyloxy group, an amino group which may be protected, a lower alkylamino group, a di-lower alkylamino group, a tri-lower alkylammonio group, a carbamoyl lower alkylamino group, an aroylamino group, an amino lower alkyl group which may be protected, an amino lower alkylcarbonylamino group which may be protected, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group which may be protected, a halogen atom, a cyano group, a carboxyl group which may be protected, a lower alkoxycarbonyl group, a carbamoyl group, a di-lower alkylcarbamoyl group, an arylcarbamoyl group, a piperazinocarbonyl group, an amino group which may be protected, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group which may be protected, a sulfamoyl group and a di-lower alkylsulfamoyl group, each of $A_{10}$, $A_{20}$ and $A_{30}$, which may be the same or different, is a single bond or a lower alkylene group which may be substituted with a substituent selected from the group consisting a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxy group which may be protected, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group which may be protected, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group and pyridinio group (wherein the pyridyl group and the pyridinio group may be substituted with a substituent selected from the group consisting of a lower alkyl group, a carboxy lower alkyl group which may be protected and a carbamoyl lower alkyl group), and $W_0$ is a sulfur atom, a group of N—$X_0$ (wherein $X_0$ is a hydrogen atom, an amino-protecting group, a lower alkyl group, a formyl group, a lower alkanoyl group or a sulfamoyl group), an oxygen atom, a group of CH(OR$^8$) (wherein $R^8$ is a hydrogen atom or a hydroxyl-protecting group) or a single bond, to obtain a compound of the formula:

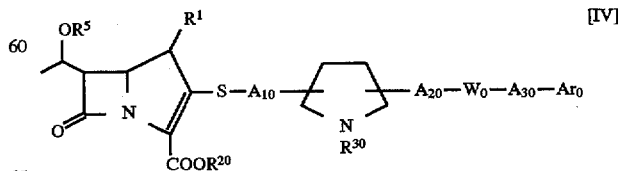 [IV]

wherein $R^1$, $R^5$, $R^{20}$, $R^{30}$, $A_{10}$, $A_{20}$, $A_{30}$, $Ar_0$ and $W_0$ are as defined above, then if necessary, removing any protecting groups of the compound of the formula [IV], and if necessary, converting the compound thus obtained into a pharmaceutically acceptable salt or non-toxic ester thereof.

A compound of the formula:

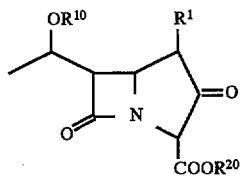

wherein $R^1$, $R^{10}$ and $R^{20}$ are as defined above, is reacted with an activating reagent in an inert organic solvent in the presence of a base to form a reactive derivative [II'] represented by the formula:

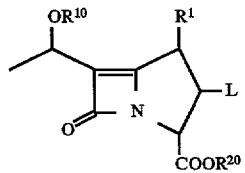

wherein $R^1$, $R^{10}$ and $R^{20}$ are as defined above, and L is a leaving group.

The inert organic solvent to be used for the reaction may, for example, be diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric triamide or a mixture of such solvents. Particularly preferred are acetonitrile and benzene.

The base to be used for the reaction may, for example, be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-dimethylaminopyridine, picoline, lutidine, guinoline or isoguinoline. Particularly preferred are N,N-diisopropylethylamine and triethylamine.

The activating reagent to be used for the reaction may, for example, be an acid anhydride such as trifluoroacetic anhydride, methanesulfonic anhydride, trifluoromethanesulfonic anhydride or p-toluenesulfonic anhydride; or an acid chloride such as methanesulfonyl chloride, p-toluenesulfonyl chloride or diphenyl chlorophosphate. Particularly preferred is diphenyl chlorophosphate.

In the formula [II'], L is a leaving group such as a trifluoroacetoxy group, a methanesulfonyloxy group, a trifluoromethanesulfonyloxy group, a p-toluenesulfonyloxy group or a diphenoxyphosphoryloxy group. Particularly preferred is a diphenoxyphosphoryloxy group.

For the reaction, from 1 to 3 mols, preferably from 1 to 1.5 mols, of the base and from 1 to 1.2 mols of the activating reagent are used per mol of the compound of the formula [II].

The reaction is conducted usually within a temperature range of from −40° to 50° C., preferably from −20° to 20° C., and usually completed quantitatively in from 0.5 to 3 hours.

After completion of the reaction, the reaction product is treated in accordance with a usual method to obtain the reactive derivative [II'] of the compound of the formula [II] quantitatively.

The reaction of the reactive derivative of the formula [II'] with a compound of the formula:

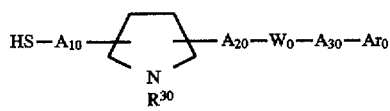

wherein $R^{30}$, $Ar_0$, $A_{10}$, $A_{20}$, $A_{30}$ and $W_0$ are as defined above, is conducted using the above-mentioned inert organic solvent and base to form a compound of the formula:

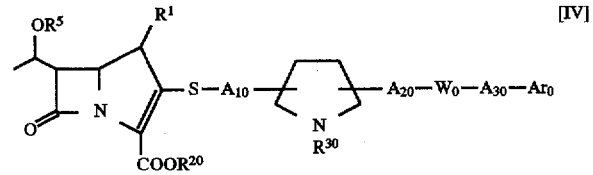

wherein $R^1$, $R^5$, $R^{20}$, $R^{30}$, $A_{10}$, $A_{20}$, $A_{30}$, $Ar_0$ and $W_0$ are as defined above.

The reaction is conducted using from 1 to 2 mols, preferably from 1 to 1.5 mols, of the base and from 1 to 1.2 mols of the compound of the formula [III], per mol of the reactive derivative of the formula [II']. The reaction is conducted usually within a temperature range of from −40° to 50° C., preferably from −20° to 20° C., and the reaction is completed usually in from 0.5 to 3 hours.

Further, the compound of the formula [IV] can be prepared in one step from the compound of the formula [II]. Namely, without isolating the reactive derivative of the formula [II'] prepared from the compound of the formula [II], the compound of the formula [III] is reacted thereto in the same reaction system to prepare the compound of the formula [IV] efficiently. To conduct the production in one step, from 2 to 4 mols, preferably from 2.5 to 3.5 mols, of the base is employed per mol of the compound of the formula [II].

After completion of the reaction, usual treatment is conducted to obtain a crude product of the formula [IV], which may be subjected to a reaction for removing a protecting group without purification. However, it is preferred to purify the crude product [IV] by crystallization or by column chromatography by means of e.g. silica gel.

From the compound of the formula [IV] thus obtained, a compound of the formula [I] can be obtained, if necessary, by conducting a reaction for removing a protecting group for a hydroxyl group, an amino group and a carboxyl group, and if necessary by converting the compound thus obtained into a pharmaceutically acceptable salt or non-toxic ester thereof.

For the removal of the protecting groups, the method varies depending upon the type of the protecting groups. However, the removal can be conducted in accordance with conventional methods, for example, by solvolysis, by chemical reduction or by hydrogenation.

For example, when in the above formula [IV], the protecting group for the hydroxyl group and/or for the amino group is an aralkyloxycarbonyl group such as a benzyloxycarbonyl group or a p-nitrobenzyloxycarbonyl group, and the protecting group for the carboxyl group is an aralkyl group such as a benzyl group, a p-nitrobenzyl group or a benzhydryl group, such protecting groups can be removed by catalytic hydrogenation by means of a platinum catalyst such as platinum oxide, platinum wire or platinum black, or a palladium catalyst such as palladium black, palladium oxide, palladium-carbon or palladium hydroxide-carbon.

As a solvent to be used for such a catalytic hydrogenation reaction, methanol, ethanol, tetrahydrofuran, dioxane, acetic acid or a solvent mixture of such an organic solvent with water or with a buffer solution of e.g. a phosphate, may be used.

The reaction can be completed in from 0.5 to 4 hours at a temperature within a range of from 0° to 50° C. under hydrogen gas stream of from 1 to 4 atm.

When in the above formula [IV], the protecting group for the hydroxyl group and/or the amino group is an allyloxycarbonyl group, and the protecting group for the carboxyl group is an allyl group, such protecting groups can be removed by reacting an organo-soluble palladium complex catalyst in an inert organic solvent containing an allyl group-capturing agent (method by W. McCombie et al., J. Org. Chem., vol. 47, pp. 587–590 (1982) and method by F. Guibé et al., the same literature, vol. 52, pp. 4984–4993 (1987)).

The solvent useful for the reaction includes, for example, water, acetone, diethyl ether, tetrahydrofuran, dioxane, ethyl acetate, acetonitrile, methylene chloride, chloroform and a solvent mixture thereof.

The palladium compound complex useful for this reaction includes, for example, palladium-carbon, palladium hydroxide-carbon, palladium(II) chloride, palladium(II) acetate, tetrakis(triphenylphosphine)palladium (O), tetrakis (triphenoxyphosphine)palladium (O), tetrakis (triethoxyphosphine)palladium (O), bis[ethylenebis (diphenylphosphine)]palladium (O), tetrakis[tri(2-furyl) phosphine]palladium (O), bis(triphenylphosphine) palladium(II) chloride and bis(triphenylphosphine) palladium(II) acetate.

The allyl group-capturing agent may, for example, be dimedone, formic acid, acetic acid, ammonium formate, sodium formate, sodium 2-ethylhexanoate, potassium 2-ethylhexanoate, pyrrolidine, piperidine and tributyltin hydride.

The reaction is conducted usually within a temperature range of from −10° to 50° C., preferably from 0° to 30° C. using from 0.01 to 0.5 mol of the catalyst and from 1 to 6 mols of the nuclophilic agent relative to 1 mol of the compound of the formula [IV], and the reaction is completed usually in from 0.5 to 3 hours.

Further, when in the above formula [IV], the protecting group for the hydroxyl group and/or the amino group is an o-nitrobenzyloxycarbonyl group, and the protecting group for the carboxyl group is an o-nitrobenzyl group, such protecting groups can be removed by a photo reaction (method by Amit et al., J. Org. Chem., vol. 39, pp. 192–196 (1974)).

After completion of the reactions for removing the protecting groups, the compound of the formula [I] can be isolated by usual treatment such as column chromatography using silica gel or adsorptive resin, freeze-drying or crystallization.

Further, when the protecting group for the carboxyl group at the 3-position of the compound of the formula [IV] is a lower alkanoyloxyalkyl group such as an acetoxymethyl group or a pivaloyloxymethyl group, a methoxymethyl group, an indanyl group or a phthalidyl group, such an ester will be physiologically hydrolyzed in vivo. Therefore, such a compound can directly be administered to a human being or to an animal without preliminarily removing the protecting group.

The compound of the formula [I] can be converted to a pharmaceutically acceptable salt or ester by a conventional method.

The starting material represented by the formula [II] can be prepared, for example, by a method by Salzmann et al.  when $R^1$ is a hydrogen atom (J. Am. Chem. Soc., vol. 102, pp.6161–6163 (1981)) or by a method by Shih et al. when $R^1$ is a methyl group (Heterocycles, vol. 21, pp.29–40 (1984)).

The starting material represented by the formula [III] can be synthesized in accordance with the methods described in the Reference Examples.

The compounds of the present invention exhibit strong antibacterial activities against various gram positive bacteria including MRSA and gram negative bacteria.

To demonstrate the usefulness of the compounds of the present invention, the in vitro antibacterial activities against bacteria were measured by the following agar plate dilution method (standard method by Japan Chemotherapy Society, Chemotherapy, vol. 29, pp. 76–79 (1981)). One platinum loopful of each test microorganism incubated overnight in Mueller Hinton broth, was inoculated to Mueller Hinton agar (inoculum size: $10^6$ CFU/ml). Such culture media contained antibacterial agents in various concentrations. After incubation at 37° C. for 16 hours, the minimum inhibitory concentrations (MIC: μg/ml) were measured. The minimum inhibitory concentrations of the compounds of the present invention were compared with imipenem. The results are shown in Table 1.

TABLE 1

| Minimum Inhibitory Concentration (MIC: μg/ml) | | | | | | |
|---|---|---|---|---|---|---|
| | Example 1 | Example 121 | Example 127 | Example 131 | Example 140 | Imipenem |
| S. aureus BB5939* | 0.39 | 0.39 | 0.78 | 0.78 | 0.78 | 6.25 |
| S. aureus pMS520/Smith | 1.56 | 1.56 | 3.13 | 3.13 | 1.56 | >25 |

*β-Latamase-producing bacterium

Further, the DHP-I susceptibility was quantitatively analyzed by the method by Kropp et al., Antimicrob. Agents Chemother., vol. 22, pp. 62–70 (1982), whereby the smaller the numerical value representing the ratio to imipenem (=1.0), the higher the stability.

The DHP-1 susceptibility of the compounds of the present invention were compared with imipenem. The results are shown in Table 2.

TABLE 2

| DHP-I Susceptibility | | | | | | | |
|---|---|---|---|---|---|---|---|
| | Example 1 | Example 121 | Example 127 | Example 128 | Example 131 | Example 137 | Example 140 | Imipenem |
| DHP-I susceptibility | 0.15 | 0.15 | 0.15 | 0.16 | <0.05 | <0.05 | <0.05 | 1.0 |

The compounds of the present invention have excellent antibacterial activities particularly, against gram positive bacteria including MRSA and are useful as antibacterial agents for the treatment and prevention of the human infectious diseases caused by such bacteria. Typical pathogens sensitive to the antibacterial agents of the present invention include, for example, species of genus Staphylococcus, genus Enterococcus, genus Escherichia, genus Enterobacter, genus Klebsiella, genus Serratia, genus Proteus and genus Pseudomonas.

The compounds of the present invention are markedly improved in side effects against the central nervous system and in the toxicity against the kidney, as compared with imipenem.

The compounds of the present invention are very stable against DHP-I although the stability varies depending upon the individual compounds, and they are excellent also in the physicochemical stability and in the solubility in water.

The compounds of the present invention may be used in the form of drug formulations suitable for parenteral administration, oral administration or external administration, by mixing them with carriers of solid or liquid excipients known in this field. The main administration route is parenteral (intravenous or intramuscular injection) administration by injection or local administration. Drug formulations include liquid formulations such as injection solutions, syrups or emulsions, solid formulations such as tablets, capsules or granules, and external application formulations such as ointments or suppositories. These formulations may contain additives such as a base, an assisting agent, a stabilizer, a wetting agent, an emulsifier, an absorption-promoting agent, a surfactant, etc. which are commonly employed, as the case requires.

The additives include, for example, distilled water for injection, Ringer's solution, glucose, sucrose syrup, gelatin, edible oil, cacao butter, ethylene glycol, sucrose, corn starch, magnesium stearate and talc.

The dose varies depending upon the condition, the weight, the age and the sex of the patient, the type of formulation, the number of administration times, etc. Usually, however, a preferred daily dose of the active ingredient to an adult is from about 5 to 50 mg/kg, and a preferred daily dose to a child is within a range of from about 5 to 25 mg/kg, which is preferably administered once a day or in a few times a day.

The compound of the present invention may be administered in combination with a DEP-I inhibiting agent such as cilastatin [sodium (Z)-7-(L-amino-2-carboxyethylthio)-2-(2,2-dimethylcyclopropanecarboxamide)-2-heptenoate] (Japanese Unexamined Patent Publication No. 81518/1981; European Patent No. 28,778; J. Med. Chem., vol. 30, p. 1074 (1987)).

EXAMPLES AND REFERENCE EXAMPLES

The present invention is now illustrated in greater detail by way of EXAMPLES and REFERENCE EXAMPLES, but it should not be understood that the present invention is deemed to be limited thereto.

In Examples and Reference Examples, for thin layer chromatography, Silicagel 60F$_{245}$ (Merck) was used as plates, and a UV detector was used as a means for detection. Silica gel for column chromatography used herein was Wakogel™ C-300 (Wakojunyaku), and the silica gel for reverse phase column chromatography was LC-SORB™ SP-B-ODS (Chemco) or YMC-GEL™ ODS-AQ120-S50 (Yamamura Kagaku Kenkyujo). As the high pressure liquid chromatography, JASCO 800 series (Japan Spectroscopic Co., Ltd.) was used. When the NMR spectrum was measured using dimethyl sulfoxide-d$_6$ or chloroform-d solution, tetramethylsilane (TMS) was used as the internal standard, and when measured using a deuterium oxide solution, 2,2-dimethyl-2-silapentane-5-sulfonate (DSS) was used as the internal standard, and the measurement was conducted by means of XL-200 (200 MHz; Varian) model spectrometer. All δ values are shown by ppm.

The meanings of the abbreviations used for the NMR measurement are as follows:
s: singlet
d: doublet
dd: double doublet
m: multiplet
br: broad
J: coupling constant
Hz: hertz
CDCl$_3$: chloroform-d
D$_2$O: deuterium oxide Abbreviations used in reaction schemes have the following meanings.
Ac: acetyl group
All: allyl group
Alloc: allyloxycarbonyl group
$^t$Bu: t-butyl group
Boc: t-butoxycarbonyl group
Me: methyl group
Ms: methanesulfonyl group (mesyl group)
MOM: methoxymethoxy group
Ph: phenyl group
PNB: p-nitrobenzyl group
PNZ: p-nitrobenzyloxycarbonyl group
Tr: trityl group
TBS: t-butyldimethylsilyl group
TBDPS: t-butyldiphenylsilyl group
THP: tetrahydropyranyl group

EXAMPLE 1

Sodium (1R,5S,6S)-6-[(1R)-1-hydroxyethyl]-1-methyl-2-[(3S,5S)-5-(phenylthiomethyl)pyrrolidin-3-ylthio]-1-carbapen-2-em-3-carboxylate

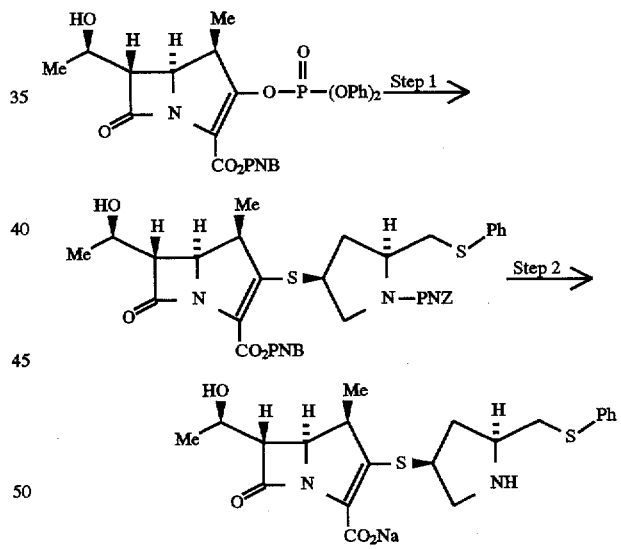

(Step 1)

To a solution of p-nitrobenzyl (1R,5S,6S)-2-diphenoxyphosphoryloxy-6-[(1R)-1-hydroxyethyl]-1-methyl-1-carbapen-2-em-3-carboxylate (2.24 g, 3.78 mmol) in acetonitrile (70 ml), DIPA (0.9 ml, 5.16 mmol) was added under cooling with ice, and then a solution of (3S,5S)-3-mercapto-1-p-nitrobenzyloxycarbonyl-5-(phenylthiomethyl)pyrrolidine (1.39 g, 3.42 mmol) in acetonitrile (15 ml) was dropwise added thereto. The reaction solution was stirred at 5° C. overnight, and ethyl acetate (300 ml) was added to the reaction solution. The organic layer was washed with water and saturated aqueous sodium chloride, dried over anhydrous sodium sulfate and concentrated in vacuo. The residue was purified by silica gel column chromatography (dichloromethane-ethyl acetate), to give p-nitrobenzyl (1R,5S,6S)-6-[(1R)-1-hydroxyethyl]-1-methyl-2-[(3S,5S)-1-p-nitrobenzyloxycarbonyl-5-(phenylthiomethyl)pyrrolidin-3-ylthio]-1-carbapen-2-em-3-carboxylate (1.55 g, yield: 60%).

IR(KBr)cm$^{-1}$: 3469,2969,1770,1704,1606,1519,1346, 1209, 1139,852,738.

$^1$H-NMR(CDCl$_3$)δ:1.24(3H,d,J=7.4 Hz),1.36(3H,d,J=6.0 Hz), 2.50–2.70(1H,m),2.90–3.20(1H,m),3.20–3.70(5H,m), 4.10–4.30(4H,m),5.10–5.30(3H,m),5.50–5.60(1H,m), 7.20–7.30(6H,m),7.40–7.50(3H,m),7.60–7.70(2H,m), 8.10–8.30(4H,m)

(Step 2)

To a solution of the compound (1.29 g, 1.70 mmol) obtained in Step 1 in a mixture of 0.2M MOPS buffer (pH 7.0, 45 ml), THF (45 ml) and ethanol (9 ml), 10% palladium-carbon (1.3 g) was added, and catalytic reduction was conducted at room temperature under a pressure of 3 atom of hydrogen for 8 hours. The catalyst was filtered off, and the filtrate was concentrated in vacuo. The resulting aqueous solution was adjusted to pH 8 with aqueous sodium hydrogencarbonate, washed with ethyl acetate and concentrated in vacuo. The insolubles formed in small amounts were filtered off, and the filtrate was purified by reverse phase column chromatography (eluted with 50 ml of 15% water-containing THF). The desired fractions were Collected, and the solvent was removed in vacuo, and the residue was lyophilized to give the title compound (96 mg, yield: 12%).

IR(KBr)cm$^{-1}$: 3415,2965,1750,1590,1390,1285,1145, 1085, 745,605.

$^1$H-NMR(D$_2$O)δ:1.17(3H,d,J=7.3 Hz),1.27(3H,d,J=6.3 Hz), 1.50–1.70(1H,m),2.50–2.70(1H,m),3.10–3.50(7H,m), 3.50–3.60(1H,m),3.80–3.90(1H,m),4.10–4.30(2H,m),4.80 (1H,s),7.30–7.50(6H,m).

UVλ$_{max}$(0.1M MOPS buffer, pH7.0): 297 nm (ε=6470).

EXAMPLE 2

Sodium (1R,5S,6S)-6-[(1R)-1-hydroxyethyl]-1-methyl-2-[(3S,5S)-5-(4-sulfonamidephenylthiomethyl)pyrrolidin-3-ylthio]-1-carbapen-2-em-3-carboxylate

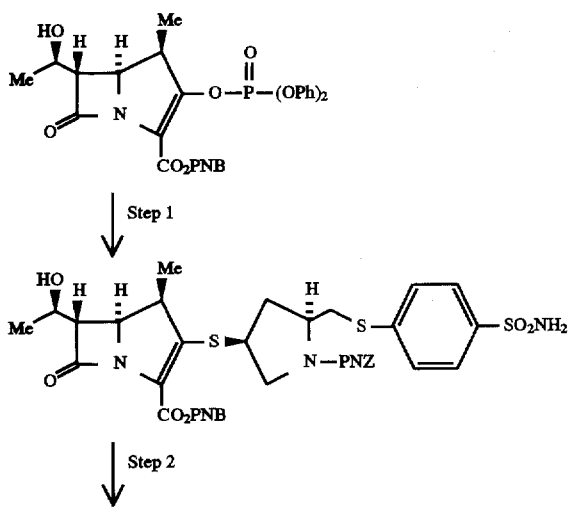

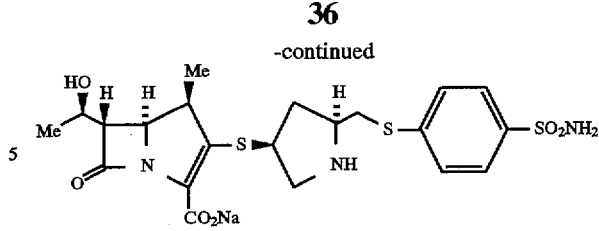

(Step 1)

To a solution of (2S,4S)-4-acetylthio-1-p-nitrobenzyloxycarbonyl-2-(4-sulfamoylphenyl)thiomethylpyrrolidine (1.48 g, 2.82 mmol) in a mixture of methanol (30 ml) with chloroform (30 ml), 1N aqueous NaOH (3.11 ml, 3.11 mmol) was added in a nitrogen stream at 5° C., and the resulting reaction solution was stirred at the same temperature for 1 hour. The reaction solution was neutralized with 1N aqueous HCl (3.11 ml, 3.11 mmol), and the solvent was distilled off in vacuo. To a solution of the residue and p-nitrobenzyl (1R,5S,6S)-2-diphenylphosphoryloxy-6-[(1R)-1-hydroxyethyl]-1-methyl-1-carbapen-2-em-3-carboxylate (2.24 g, 3.78 mmol) in acetonitrile (50 ml), DIPA (0.78 ml, 4.48 mmol) was added, and the reaction solution was stirred at 5° C. overnight. To the reaction solution, ethyl acetate was added. The solution was washed successively with water, 10% aqueous citric acid, saturated aqueous sodium hydrogencarbonate and saturated aqueous sodium chloride. Then, it was dried over anhydrous sodium sulfate, and the solvent was distilled off in vacuo. The resulting residue was purified by silica gel column chromatography (heptane-ethyl acetate) to give p-nitrobenzyl (1R,5S,6S)-6-[(1R)-1-hydroxyethyl]-1-methyl-2-[(3S,5S)-1-p-nitrobenzyloxycarbonyl-5-(4-sulfamoylphenylthiomethyl)pyrrolidin-3-ylthio]-1-carbapen-2-em-3-carboxylate (1.57 g, yield: 67%).

IR(KBr)cm$^{-1}$: 3392,1770,1699,1606,1519,1346,1209, 1162,1139,1106.

$^1$H-NMR(DMSO-d$_6$)δ: 1.14(6H,d,J=7.1 Hz),1.75–1.94 (1H,m), 2.44–2.74(1H,m),3.00–3.70(5H,m),3.88–4.30(5H, m), 5.07(1H,d,J=5.3 Hz),5.15–5.53(1H,m),7.32(2H,br s),7.35–7.77(8H,m),8.22(4H,d,J=8.6 Hz).

(Step 2)

To a solution of the compound (0.5 g, 0.62 mmol) obtained in Step 1 in a mixture of 0.5M MOPS buffer (pH 7.0, 9.8 mol), THF (27 ml) and ethanol (14 ml), 10% palladium-carbon (0.50 g) was added and catalytic reduction was conducted at room temperature at an ordinary temperature under the atmospheric pressure of hydrogen overnight. The catalyst was filtered off, and the filtrated was concentrated in vacuo. The resulting aqueous solution was washed with methylene chloride and then concentrated again. The insolubles formed in small amounts were filtered off and the filtrate was purified by reverse phase column chromatography (eluted with 50 ml of 6–12% water-containing THF). The desired fractions were collected, the solvent was distilled off, and then the residue was lyophilized to give the title compound (21 mg, yield: 64%).

IR(KBr)cm$^{-1}$: 3382,2967,1745,1589,1392,1326,1159, 1079,923.

$^1$H-NMR(D$_2$O)δ: 1.13(3H,d,J=7.2 Hz),1.24(3H,d,J=6.4 Hz),1.40–1.55(1H,m),2.45–2.63(1H,m),2.93–3.04(1H,m), 3.17–3.56(6H,m),3.67–3.83(1H,m),4.08–4.26(2H,m), 7.51 (2H,dd,J=2.1&6.8 Hz),7.78(2H,dd,J=2.1&6.8 Hz).

UVλ$_{max}$ (0.1M MOPS buffer, pH7.0):300 nm (ε=10800).

EXAMPLE 3

(1R,5S,6S)-2-[(3S,5S)-5-[4-(2-Aminoethylthio)-phenylthiomethyl]pyrrolidin-3-ylthio]-6-[(1R)-1-hydroxyethyl]-1-methyl-1-carbapen-2-em-3-carboxylic acid monohydrochloride IR(KBr)cm$^{-1}$: 3390,2960,1770,1704,1540,1405,1324, 1274, 1207,1139,1106,1045,983,933,813,769,719.

$^1$H-NMR(CDCl$_3$)δ: 1.24(3H,d,J=5.1 Hz), 1.35(3H,d,J= 6.3 Hz), 1.99(1H,m),2.56(1H,m),3.02(3H,m),3.20–3.40(5H, m),3.58(2H,m),3.90–4.30(4H,m),4.60–4.90(2H,m), 5.10–5.50(7H,m),5.80–6.10(3H,m),7.29(4H,s).

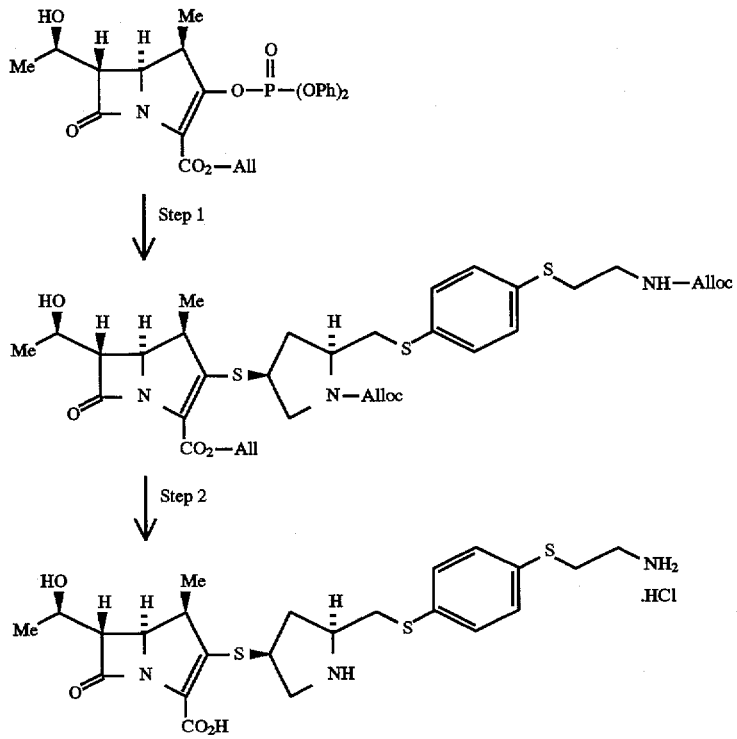

(Step 1)

To a solution of (2S,4S)-4-tritylthio-1-(4-allyloxycarbonyl)-2-[4-(2-allyloxycarbonylaminoethylthio) phenylthiomethyl]-pyrrolidine (1.53 g, 2.14 mmol) in methylene chloride (30 ml), triethylsilane (0.41 ml) and trifluoroacetic acid (5 ml) were added at 5° C., and the resulting reaction solution was stirred at the same temperature for 1 hour. The solvent was distilled off in vacuo, and the resulting residue was dissolved in ethyl acetate. The organic layer was washed successively with water, phosphate buffer (pH 5.5) and saturated aqueous sodium chloride and dried over anhydrous sodium sulfate, and the solvent was distilled off in vacuo. The resulting residue was purified by silica gel column chromatography (ethyl acetate-heptane) to give 0.71 g of an oily thiol derivative. To a solution of the thiol derivative and ally (1R,5S,6S)-2-diphenylphosphoryloxy-6-[(1R)-1-hydroxyethyl]-1-methyl-1-carbapen-2-em-3-carboxylate (756 mg, 1.52 mmol) in acetonitrile (28 ml), DIPA (0.317 ml, 1.80 mmol) was added under cooling with ice, and the reaction solution was stirred at 5° C. overnight. To the reaction solution, ethyl acetate (100 ml) was added, and the resulting mixture was washed successively with water and saturated aqueous sodium chloride. The organic layer was dried over anhydrous sodium sulfate, and the solvent was distilled off in vacuo. The resulting residue was purified by silica gel column chromatography (heptane-ethyl acetate) to give allyl (1R,5S,6S)-2-[(3S,5S)-1-N-(allyloxycarbonyl)-5-[4-(2-aminoethylthio) phenylthiomethyl]pyrrolidin-3-ylthio]-6-[(1R)-1-hydroxyethyl]-1-methyl-1-carbapen-2-em-3-carboxylate (590 mg, yield: 54%).

(Step 2)

To a solution of the compound (590 mg, 0.82 mmol) obtained in Step 1 in methylene chloride (15 ml), water (0.1 ml), bis(triphenylphosphine)palladium(II) chloride (21 mg, 0.03 mmol) and tributyltin hydride (1.1 ml, 4.1 mmol) were added in a nitrogen stream under cooling with ice. The resulting mixture was stirred at the same temperature for 30 minutes and then extracted with phosphate buffer (0.3M, pH 5.6, 100 ml×3). The extract was concentrated in vacuo, adjusted to pH 8.9 with 1N aqueous NaOH, and purified by reverse phase chromatography (eluted with 14 ml of 4–15% water-containing THF). The desired fractions were collected, adjusted to pH 6.6 with 1N HCl, and then concentrated in vacuo. The residue was lyophilized to give the title compound (211 mg, yield: 47%).

IR(KBr)cm$^{-1}$: 3384,2967,1751,1581,1392,1286,1265, 1182, 1149,1105,813.

$^1$H-NMR(D$_2$O)δ: 1.18(3H,d,J=7.2 Hz),1.28(3H,d,J=6.3 Hz), 1.69(1H,m),2.69(1H,m),3.15–3.65(10H,m),3.80(1H, m), 3.95(1H,m),4.25(2H,m),7.48(4H,s).

UVλ$_{max}$ (0.1M MOPS buffer, pH 7.0):300 nm (ε=10700).

EXAMPLE 4

(1R,5S,6S)-2-[(3S,5S)-5-(3-Aminomethyl-4-chlorophenylthiomethyl)pyrrolidin-3-ylthio]-6-[(1R)-1-hydroxyethyl]-1-methyl-1-carbapen-2-em-3-carboxylic acid

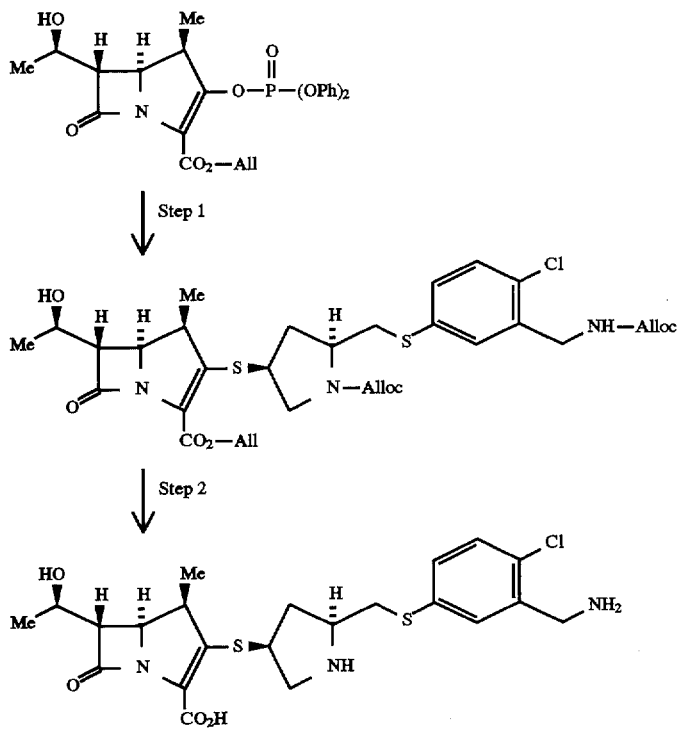

(Step 1)

To a mixed solution of (2S,4S)-4-acetylthio-1-allyloxycarbonyl-2-(3-allyloxycarbonylaminomethyl-4-chlorophenyl)thiomethylpyrrolidine (481 mg, 0.87 mmol) in a mixture of methanol (4 ml) and THF (2 ml), 1N aqueous NaOH (0.95 ml, 0.95 mmol) was added in a nitrogen stream. The reaction solution was stirred at the same temperature for 20 minutes. The mixture was neutralized with 1N aqueous HCl (1.04 ml, 1.04 mmol) and then ethyl acetate and water were added thereto. The organic layer was washed successively with water and saturated aqueous sodium chloride. The solvent was distilled off in vacuo to obtain a crude thiol derivative. To a solution of allyl (1R,5S,6S)-2-diphenoxyphosphoryloxy-6-[(1R)-1-hydroxyethyl]-1-methyl-1-carbapen-2-em-3-carboxylate (478 mg, 0.96 mmol) in acetonitrile (7 ml), a solution of the thiol derivative obtained as above in acetonitrile (7 ml) and DIPA (0.227 ml, 1.31 mmol) were added in a nitrogen stream. The reaction solution was stirred at a temperature from −20° C. to −30° C. overnight. To the reaction solution, ethyl acetate was added and the organic layer was washed successively with water and saturated aqueous sodium chloride, dried over anhydrous sodium sulfate, and then concentrated in vacuo. The resulting residue was purified by silica gel column chromatography (heptane-ethyl acetate) to give allyl (1R,5S,6S)-6-[(1R)-1-hydroxyethyl]-2-[(3S,5S)-1-allyloxycarbonyl-5-(3-allyloxycarbonylaminoethyl-4-chlorophenyl)thiomethylpyrrolidin-3-ylthio]-1-methyl-carbapen-2-em-3-carboxylate (242 mg, yield: 39.4%).

IR(KBr)cm$^{-1}$: 3420,1693,1549,1408,1340,1107,797,606.

$^1$H-NMR(CDCl$_3$)δ: 1.20–1.30(3H,m),1.40–1.50(3H,m), 1.90–2.10(1H,m),2.50–2.60(1H,m),3.20–4.30(9H,m), 4.40–4.60(8H,m),5.20–5.50(6H,m),5.81–6.10(3H,m), 7.20–7.40(3H,m).

(Step 2)

To a solution of the compound (242 mg, 0.34 mmol) obtained in Step 1 in methylene chloride (6 ml), water (0.03 ml), bis(triphenylphosphine)palladium(II) chloride (4.8 mg, 0.0068 mmol) and tributyltin hydride (0.302 ml, 1.12 mmol) were added in a nitrogen stream under cooling with ice. The resulting mixture was stirred at 0° C. for 10 minutes and then at room temperature for 30 minutes. The solvent was distilled off in vacuo and the residue was dissolved in 1N aqueous sodium hydrogencarbonate. The resulting solution was washed with heptane three times, concentrated in vacuo and then purified by reverse phase column chromatography (eluted with 14 ml of 9–15% water-containing tetrahydrofuran). The desired fractions were collected and the solvent was distilled off in vacuo. The resulting residue was lyophilized to give the title compound (84 mg, yield: 50%).

IR(KBr)cm$^{-1}$: 3417,2968,1745,1585,1392,1281,1103, 1047, 770,606.

$^1$H-NMR(D$_2$O)δ: 1.18(3H,d,J=7.0 Hz), 1.28(3H,d,J=6.3 Hz), 1.60–1.70(1H,m),2.60–2.70(1H,m),3.20–3.50(7H,m), 3.70–3.80(1H,m),3.80–3.90(1H,m),4.20–4.30(3H,m), 7.50–7.60(3H,m).

UVλ$_{max}$ (0.1M MOPS buffer, pH7.0): 300 nm (ε=7950).

EXAMPLE 5

(1R,5S,6S)-2-[(3S,5S)-5-[(4-Aminomethyl-2-sulfamoyl)phenylthiomethyl]pyrrolidin-3-ylthio]-6-[(1R)-1-hydroxyethyl]-1-methyl-carbapen-2-em-3-carboxylic acid monohydrochloride

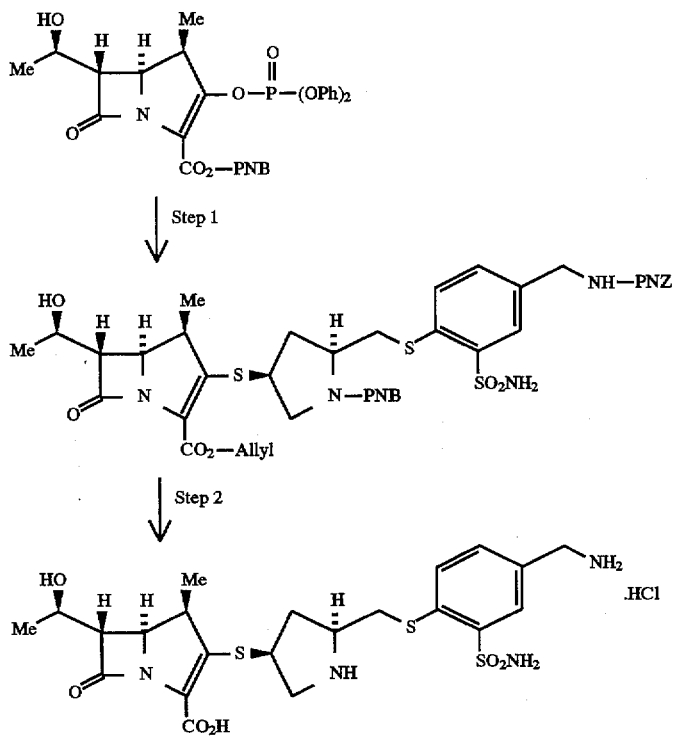

(Step 1)

To a solution of (2S,4S)-4-acetyltylthio-2-[(4-p-nitrobenzyloxycarbonylaminomethyl-2-sulfamoyl)phenylthiomethyl]-1-p-nitrobenzyloxycarbonylpyrrolidin (540 mg, 0.74 mmol) in methanol (10 ml) and THF (2 ml), 1N aqueous NaOH (0.809 ml, 0.81 mmol) was added at 0° C. in a nitrogen stream and the resulting reaction solution was stirred at the same temperature for 45 minutes. The reaction solution was neutralized with 1N aqueous HCl (0.883 ml, 0.88 mmol) and then ethyl acetate was added thereto. The organic layer was washed with water and concentrated in vacuo. To a solution of the resulting residue and p-nitrobenzyl (1R,5S,6S)-2-diphenylphosphoryloxy-6-[(1R)-1-hydroxyethyl]-1-methyl-1-carbapen-2-em-3-carboxylate (438 mg, 0.74 mmol) in acetonitrile (16 ml), DIPA (0.192 ml, 1.1 mmol) was added. The resulting reaction solution was stirred at 5° C. overnight. To the reaction solution, ethyl acetate was added, and the organic layer was washed successively with water, 10% aqueous citric acid, saturated aqueous sodium hydrogencarbonate, and saturated aqueous sodium chloride.. After drying over anhydrous sodium sulfate, the solvent was distilled off in vacuo. The resulting residue was purified by silica gel column chromatography (chloroform-methanol) to give p-nitrobenzyl (1R,5S,6S)-2-[(3S,5S)-5-[(4-p-nitrogenzyloxycarbonylaminomethyl-2-sulfamoyl)phenylthiomethyl]pyrrolidin-3-ylthio]-6-[(1R)-1-hydroxyethyl]-1-methyl-1-carbapen-2-em-3-carboxylate (190 mg, yield: 25%).

IR(KBr)cm$^{-1}$: 3396,1768,1702,1521,1346,1110.

(Step 2)

A solution of the compound (250 mg, 0.24 mmol) obtained in Step 1 was dissolved in a mixture of 0.2M MOPS buffer (pH 7.0, 6 ml), THF (6 ml) and ethanol (1.2 mmol). To the mixture, 10% palladium-carbon (0.2 g) was added and catalytic reduction was conducted at room temperature under the atmospheric pressure of hydrogen overnight. The catalyst was filtered off, then the filtrate was concentrated in vacuo, and the resulting aqueous solution was washed with chloroform and concentrated again. The insolubles formed in small amounts were filtered off, and the filtrate was purified by reverse phase column chromatography (eluted with 14 ml of 6–9% water-containing THF). The fractions containing the desired product were collected, adjusted to pH 6.2 with hydrochloric acid, concentrated in vacuo and lyophilized to give the title compound (66 mg, yield: 48%).

IR(KBr)cm$^{-1}$: 3386,2968,1749,1579,1392,1331,1157.

$^1$H-NMR(D$_2$O)δ: 1.13(3H,d,J=7.3 Hz), 1.22(3H,d,J=6.4 Hz), 1.73(1H,m),2.70(1H,m),3.25–3.45(3H,m),3.45–3.70 (3H,m),3.85–4.05(2H,m),4.10–4.30,4.68, 7.67(1H,d,J=8.0 Hz),7.77(1H,d,J=8.0 Hz),8.06(1H,s).

UVλ$_{max}$ (0.1M MOPS buffer, pH 7.0): 300 nm (ε=12200).

In the following Examples 6 to 64, compounds represented by the formula (A) which have substituents R$_1$ and R$_2$ were synthesized in the same manner as in Examples 1 to 5.

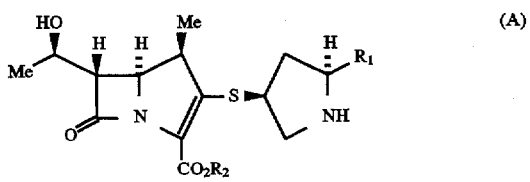

(A)

EXAMPLE 6

R$_1$= ⌒⌒SPh; R$_2$= H

IR(KBr)cm$^{-1}$: 3430,2970,1750,1590,1400,1290,1140, 1090,740.

$^1$H-NMR(D$_2$O)δ: 1.16(3H,d,J=7.0 Hz), 1.25(3H,d,J=6.0 Hz), 1.80–2.00(2H,m),2.40(1H,m),2.80–3.40(8H,m),3.70 (1H,m), 4.10–4.30(2H,m),7.20–7.50(5H,m).

UVλ$_{max}$ (0.1M MOPS buffer, pH 7.0): 300 nm (ε=7310).

EXAMPLE 7

R$_1$= ; R$_2$=H

IR(KBr)cm$^{-1}$: 3425,1750,1595,1395,1290,1080.

$^1$H-NMR(D$_2$O)δ: 1.18(3H,d,J=7.2 Hz), 1.28(3H,d,J=6.4 Hz),2.40–2.50(2H,m),2.60–2.70(2H,m),2.80–2.90(1H,m), 3.00–3.50(4H,m),3.60–3.90(3H,m),4.10–4.30(2H,m), 7.30–7.50(5H,m).

UVλ$_{max}$ (0.1M MOPS buffer, pH 7.0): 300 nm (ε=7330).

EXAMPLE 8

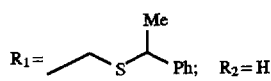
R$_1$= ; R$_2$=H

IR(KBr)cm$^{-1}$: 3438,1745,1670,1620,1350.

$^1$H-NMR(D$_2$O)δ: 1.19(3H,d,J=7.0 Hz), 1.28(3H,d,J=6.2 Hz), 1.58(3H,d,J=7.0 Hz),2.40–2.90(4H,m),3.00–3.10 (1H, m),3.20–3.50(4H,m),3.70–3.90(1H,m),4.10–4.30 (3H,m), 7.30–7.60(5H,m).

UVλ$_{max}$ (0.1M MOPS buffer, pH 7.0): 298 nm (ε=5500).

EXAMPLE 9

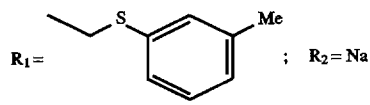
R$_1$= ; R$_2$=Na

IR(KBr)cm$^{-1}$: 3425,2965,1755,1590,1390,775,605.

$^1$H-NMR(D$_2$O)δ: 0.80–1.10(2H,m), 1.18(3H,d,J=7.1 Hz), 1.28(3H,d,J=6.3 Hz), 1.50–1.70(1H,m),2.32(3H,s), 2.50–2.70(1H,m),3.00–3.50(6H,m),3.50–3.60(1H,m), 3.80–3.90(1H,m),4.10–4.30(2H,m),4.60–5.00(1H,m), 7.10–7.20(1H,m),7.20–7.40(1H,m).

UVλ$_{max}$ (0.1M MOPS buffer, pH 7.0): 298 nm (ε=8880).

EXAMPLE 10

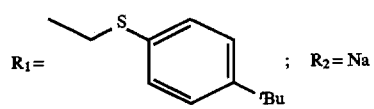
R$_1$= ; R$_2$=Na

IR(KBr)cm$^{-1}$: 3425,2964,1755,1597,1392,1266,1076, 609.

$^1$H-NMR(D$_2$O)δ: 1.14(3H,d,J=7.4 Hz), 1.24(9H,s), 1.26 (3H,d,J=9.3 Hz), 1.40(1H,m),2.40(1H,m),2.90(1H,m), 3.10–3.40(6H,m),3.63(1H,m),4.22(2H,m),7.38(4H,s).

UVλ$_{max}$ (0.1M MOPS buffer, pH 7.0): 296 nm (ε=8000).

EXAMPLE 11

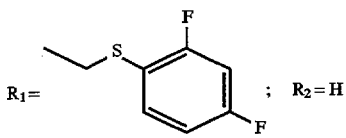
R$_1$= ; R$_2$=H

IR(KBr)cm$^{-1}$: 3432,2967,2358,1753,1593,1452,1392, 1255.

$^1$H-NMR(D$_2$O) δ: 1.21(3H,d,J=7.1 Hz), 1.31(3H,d,J=6.4 Hz), 1.47(1H,m),2.55(1H,m),2.98(1H,m),3.20–3.50(6H,m), 3.78(1H,m),4.22(2H,m),6.95(1H,m), 7.22(1H,m),7.62(1H, m).

UVλ$_{max}$ (0.1M MOPS buffer, pH 7.0): 300 nm (ε=8780).

EXAMPLE 12

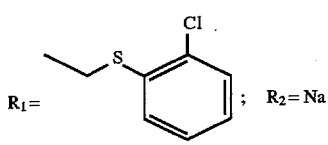
R$_1$= ; R$_2$=Na

IR(KBr)cm$^{-1}$: 3421,1749,1592,1452,1398,1284.

$^1$H-NMR(D$_2$O)δ: 0.90–1.40(1H,m), 1.05(3H,d,J=6.7 Hz), 1.21(3H,d,J=6.2 Hz),2.26–2.47(1H,m),2.86–2.91(1H,m), 2.96–3.32(6H,m),3.43–3.61(1H,m),4.03–4.25(2H,m), 7.04–7.46(4H,m).

UVλ$_{max}$ (0.1M MOPS buffer, pH 7.0): 300 nm (ε=8100).

EXAMPLE 13

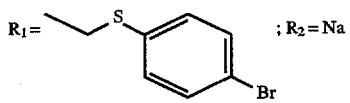
R$_1$= ; R$_2$=Na

IR(KBr)cm$^{-1}$: 3425,1750,1595,1400,1085,610.

$^1$H-NMR(D$_2$O)δ: 1.17(3H,d,J=7.5 Hz),1.27(3H,d,J=6.1 Hz), 2.30–2.50(1H,m),2.80–3.00(1H,m),3.00–3.50(6H,m), 3.60–3.70(1H,m),4.20–4.40(2H,m),7.35(2H,d,J=8.7 Hz), 7.52(2H,d,J=8.7 Hz).

UVλ$_{max}$ (0.1M MOPS buffer, pH 7.0): 300 nm (ε=6810).

EXAMPLE 14

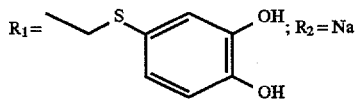
R$_1$= ; R$_2$=Na

IR(KBr)cm$^{-1}$: 3420,2970,1750,1650,1600,1520,1400, 1310,1180, 780.

$^1$H-NMR(D$_2$O)δ: 1.19(3H,d,J=7.0 Hz), 1.25(3H,d,J=6.0 Hz), 1.90(1H,m),2.50–2.80(3H,m),3.00–3.30(2H,m),3.40 (1H,m),3.50–3.80(2H,m),3.90(1H,m), 4.10–4.30(2H,m), 5.55(1,m),6.50(1H,m),7.20(1H,m).

UVλ$_{max}$(0.1M MOPS buffer, pH 7.0): 297 nm (ε=9840).

EXAMPLE 15

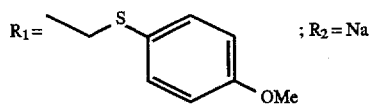 ; $R_2$=Na

IR(KBr)cm$^{-1}$: 3430,2970,1750,1590,1490,1400,1280, 1250,1080, 830,610.

$^1$H-NMR(D$_2$O)δ: 1.13(3H,d,J=7.0 Hz), 1.25(3H,d,J=6.0 Hz), 2.40(1H,m),2.85(1H,m),3.00–3.40(6H,m),3.65(1H,m), 3.79(3H,s),4.10–4.30(2H,m),6.96(2H,d,J=9.0 Hz),7.44(2H, d,J=9.0 Hz).

UVλ$_{max}$ (0.1M MOPS buffer, pH 7.0): 300 nm (ε=8110).

EXAMPLE 16

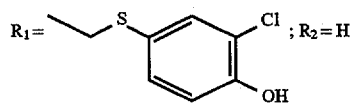 ; $R_2$=H

IR(KBr)cm$^{-1}$: 1747,1737,1649,1591,1560,1543,1398, 1290.

$^1$H-NMR(D$_2$O)δ: 1.13(3H,d,J=7.0 Hz), 1.23(3H,d,J=6.5 Hz), 1.62(1H,m),2.60(1H,m),3.00–3.34(4H,m),3.40(1H,m), 3.50(1H,m),3.62(1H,m),3.88(1H,m),4.10–4.24(2H,m), 6.76 (1H,d,J=7.4 Hz),7.22(1H,dd,J=1.6&7.4 Hz), 7.47(1H,d,J= 1.6 Hz).

UVλ$_{max}$ (0.1M MOPS buffer, pH 7.0): 296 nm (ε=7900).

EXAMPLE 17

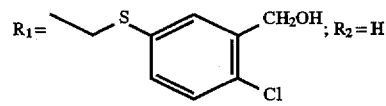 ; $R_2$=H

IR(KBr)cm$^{-1}$: 3419,1747,1593,1394,1282,1101,1065, 770,606.

$^1$H-NMR(D$_2$O)δ: 1.18(3H,d,J=7.3 Hz), 1.28(3H,d,J=6.4 Hz), 1.60–1.70(1H,m),2.60–2.70(1H,m),3.20–3.60(6H,m), 3.70–3.80(1H,m),3.90–4.00(1H,m),4.20–4.30(2H,m), 7.40–7.60(3H,m).

UVλ$_{max}$ (0.1M MOPS buffer, pH 7.0): 300 nm (ε=8130).

EXAMPLE 18

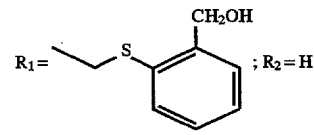 ; $R_2$=H

IR(KBr)cm$^{-1}$: 3421,3388,1751,1587,1567,1394.

$^1$H-NMR(D$_2$O)δ: 1.23(3H,d,J=7.3 Hz), 1.32(3H,d,J=6.4 Hz), 1.76–1.82(1H,m),2.72–2.77(1H,m),3.32–3.66(6H,m), 3.82–3.85(1H,m),3.98–4.03(1H,m),4.23–4.32(2H,m), 7.43–7.67(4H,m).

UVλ$_{max}$ (0.1M MOPS buffer, pH 7.0): 297 nm (ε=9360).

EXAMPLE 19

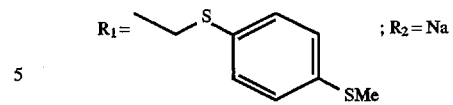 ; $R_2$=Na

IR(KBr)cm$^{-1}$: 3419,2967,1751,1594,1479,1394,1286, 1106,811.

$^1$H-NMR(D$_2$O)δ: 1.11(3H,d,J=7.1 Hz), 1.27(3H,d,J=6.2 Hz), 1.28(1H,m),2.35(1H,m),2.40(3H,s),2.85(1H,m), 3.00–3.30(5H,m),3.34(1H,dd,J=2.2&6.0 Hz),3.56(1H,m), 4.20(2H, m),7.17(2H,d,J=8.5 Hz),7.35(2H,d,J=8.5 Hz).

UVλ$_{max}$ (0.1M MOPS buffer, pH 7.0): 300 nm (ε=10800).

EXAMPLE 20

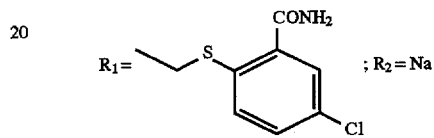 ; $R_2$=Na

IR(KBr)cm$^{-1}$: 3417,1745,1662,1591,1396,1290,1105, 606.

$^1$H-NMR(D$_2$O)δ: 1.18(3H,d,J=7.1 Hz), 1.29(3H,d,J=6.4 Hz), 1.30–1.40(1H,m),2.41–2.50(1H,m),2.80–3.00(1H,m), 3.10–3.50(6H,m),3.70–3.80(1H,m),4.10–4.30(2H,m),7.50–7.60(3H,m).

UVλ$_{max}$ (0.1M MOPS buffer, pH 7.0): 297 nm (ε=10300).

EXAMPLE 21

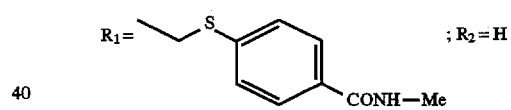 ; $R_2$=H

IR(KBr)cm$^{-1}$: 3421,2966,1765,1639,1593,1549,1396, 1317,1147, 1092,762,606.

$^1$H-NMR(D$_2$O)δ: 1.15(3H,d,J=4.9 Hz), 1.25(3H,d,J=6.3 Hz), 1.60–1.80(1H,m),2.60–2.80(1H,m),2.90(3H,s), 3.20–3.60(5H,m),3.70–3.80(1H,m),4.00–4.90(1H,m), 4.15–4.30(2H,m),7.49(2H,d,J=5.6 Hz),7.68(2H,d,J=6.0 Hz)

UVλ$_{max}$ (0.1M MOPS buffer, pH 7.0): 300 nm (ε=12600).

EXAMPLE 22

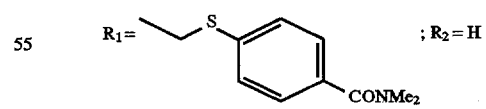 ; $R_2$=H

IR(KBr)cm$^{-1}$: 419,1747,1603,1396,1267,1099,763,606.

$^1$H-NMR(D$_2$O)δ: 1.18(3H,d,J=7.1 Hz), 1.27(3H,d,J=6.4 Hz), 1.70–1.80(1H,m),2.60–2.80(1H,m),3.00(3H,s),3,08 (3H,s), 3.30–3.40(3H,m),3.40–3.50(1H,m),3.50–3.60(2H, m), 3.70–3.80(1H,m),3.90–4.00(1H,m),4.20–4.40(2H,m), 7.41 (2H,d,J=8.3 Hz),7.54(2H,d,J=8.3 Hz).

UVλ$_{max}$ (0.1M MOPS buffer, pH 7.0): 300 nm (ε=9630).

EXAMPLE 23

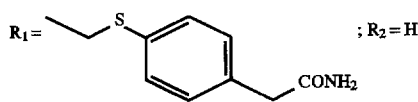

IR(KBr)cm$^{-1}$: 3394,2968,1045,1660,1593,1394,1282, 1146,1088, 804,770,606.

$^1$H-NMR(D$_2$O)δ: 1.17(3H,d,J=7.4 Hz), 1.27(3H,d,J=6.4 Hz), 1.70–1.80(1H,m),2.70–2.80(1H,m),3.20–3.70(8H,m), 3.70–3.80(1H,m),3.90–4.00(1H,m),4.20–4.30 (2H,m),7.30 (2H,d,J=8.1 Hz),7.47(2H,d,J=6.2 Hz).

UVλ$_{max}$ (0.1M MOPS buffer, pH 7.0): 300 nm (ε=8190).

EXAMPLE 24

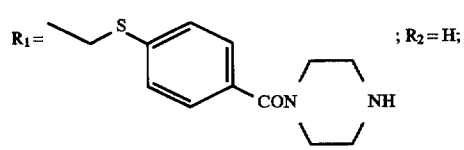

Monohydrochloride

IR(KBr) cm$^{-1}$: 3743,3490,1751,1743,1706,1597,1463, 1394,1286.

$^1$H-NMR(D$_2$O)δ: 1.08 (3H,d,J=7.0 Hz) ,1.17 (3H,d,J=6.4 Hz ), 1.50–1.60 (1H,m), 2.50–2.65 (1H,m), 2.90–3.87 (23H, m), 4.05–4.20(2H,m) ,7.33(2H,d,J=8.3 Hz),7.45(2H,d,J=8.3 Hz).

UVλ$_{max}$ (0.1M MOPS buffer, pH 7.0): 300 nm (ε=9940).

EXAMPLE 25

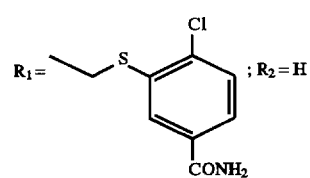

IR(KBr)cm$^{-2}$: 3394,2968,1745,1670,1595,1398,1290, 1103,606.

$^1$H-NMR(D$_2$O)δ: 1.19 (3H, d, J=7.1 Hz ), 1.28 (3H, d,J=6.4 Hz ), 1.40–1.50 (1H,m), 2.41–2.60 (1H).

UVλ$_{max}$(0.1M MOPS buffer, pH 7.0): 299 nm (ε=10300).

EXAMPLE 26

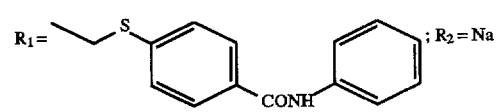

IR(KBr)cm$^{-1}$: 3453,1741,1646,1596,1538,1394,1344.

$^1$H-NMR(D$_2$O)δ: 1.20 (3H,d,J=7.0 Hz), 1.27 (4H, d,J=4.8 Hz), 1.80– 2.00(1H,m),2.30–2.60(3H,m),2.80–3.00(2H,m), 3.00–3.40(4H,m),3.70–3.80(2H,m),4.10–4.30(2H,m), 7.20–7.60(7H,m),7.70–7.80(2H,m).

UVλ$_{max}$ (0.1M MOPS buffer, pH 7.0): 300 nm (ε=12900).

EXAMPLE 27

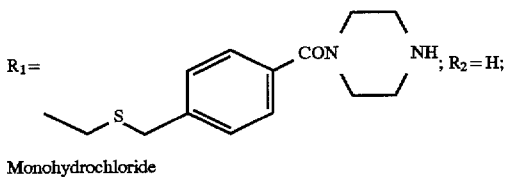

Monohydrochloride

IR(KBr)cm$^{-1}$: 3421,1745,1587,1386,1108,763,605.

$^1$H-NMR(D$_2$O)δ: 0.80(3H,d,J=7.4 Hz),0.89(3H,d,J=6.4 Hz), 1.21–1.24(1H,m),2.26–2.31(1H,m),2.49(2H,d,J=7.3 Hz),2.80–2.97(6H,m),3.04–3.07(1H,m),3.16–3.38(4H,m), 3.40–3.58(5H,m),3.80–3.87(2H,m),7.06–7.14(4H,m).

UVλ$_{max}$ (0.1M MOPS buffer, pH 7.0): 298 nm (ε=9080).

EXAMPLE 28

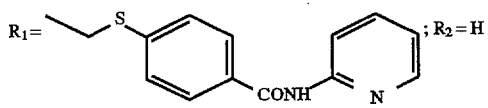

IR(KBr)cm$^{-1}$: 2360,2333,1751,1741,1691,1675,1643, 1593,1562, 1549,1514.

$^1$H-NMR(D$_2$O)δ: 1.07–1.21(6H,m), 1.27–1.45(1H,m), 2.72–2.82(1H,m),3.89–4.00(1H,m),4.09–4.12(1H,m), 7.39–7.49(1H,m),7.52–7.77(1H,m),7.88–7.91(1H,m), 8.44–8.46(1H,m).

UVλ$_{max}$ (0.1M MOPS buffer, pH 7.0): 296 nm (ε=26200).

EXAMPLE 29

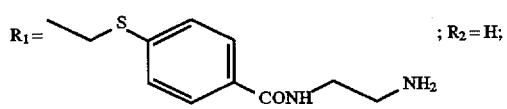

Monohydrochloride

IR(KBr)cm$^{-1}$: 1755,1633,1597,1550,1533,1394,1092.

$^1$H-NMR(D$_2$O)δ: 1.15(3H,d,J=7.3 Hz), 1.24(3H,d,J=6.3 Hz), 1.77(1H,m),2.74(1H,m),3.23(2H,t,J=5.9 Hz),3.30–3.45 (4H,m),3.53–3.63(2H,m),3.68(2H,t,J=5.9 Hz),3.83–4.04 (2H,m),4.15–4.25(2H,m),7.53(2H,d,J=8.3 Hz), 7.75 (2H,d, J=8.3 Hz).

UVλ$_{max}$ (0.1M MOPS buffer, pH 7.0): 300 nm (ε=13700).

EXAMPLE 30

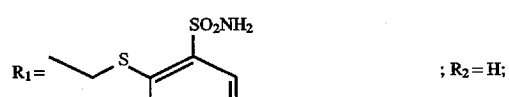

Monohydrochloride

IR(KBr)cm$^{-1}$: 3429,2927,1747,1684,1653,1541,1398.

$^1$H-NMR(D$_2$O)δ: 1.13(3H,d,J=7.0 Hz), 1.23(3H,d,J=6.2 Hz), 1.75(1H,m),2.70(1H,m),3.20–3.45(5H,m),3.55–3.75 (5H,m),3.95(2H,m),4.19(2H,m),7.77(1H,d,J=7.9 Hz), 7.98 (1H,d,J=7.9 Hz),8.37(1H,s).

UVλ$_{max}$ (0.1M MOPS buffer, pH 7.0): 300 nm (ε=18100).

EXAMPLE 31

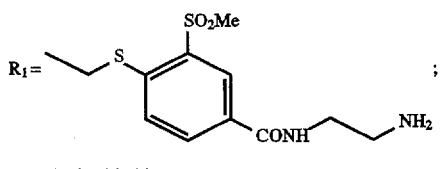

Monohydrochloride

IR(KBr)cm$^{-1}$: 1755,1641,1628,1595,1550,1460,1389, 1302, 1250,1140.

$^1$H-NMR(D$_2$O)δ: 1.15(3H,d,J=7.3 Hz), 1.25(3H,d,J=6.3 Hz), 1.82(1H,m),2.79(1H,m),3.25(2H,t,J=5.9 Hz),3.30–3.45 (3H,m),3.41(3H,s),3.55–3.75(3H,m),3.71(2H,t, J=5.9 Hz), 3.90–4.05(2H,m),7.73(1H,d,J=8.2 Hz), 8.05(1H,d,J=8.2 Hz),8.37(1H,s).

UVλ$_{max}$ (0.1M MOPS buffer, pH 7.0): 301 nm (ε=17300).

EXAMPLE 32

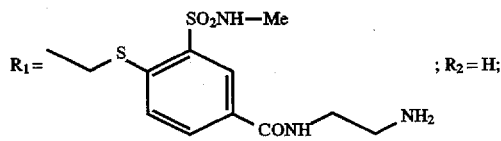

Monohydrochloride

IR(KBr)cm$^{-1}$: 3429,2968,1753,1643,1595,1541,1456, 1394,1317, 1153,1092.

$^1$H-NMR(D$_2$O)δ: 1.13(3H,d,J=7.2 Hz), 1.23(3H,d,J=6.4 Hz), 1.79(1H,m),2.55(3H,s),2.76(1H,m),3.20–3.43(5H,m), 3.60–3.84(5H,m),3.93–4.03(2H,m),4.13–4.22(2H,m),7.73 (1H,d,J=8.4 Hz),7.99(1H,dd, J=2.1&8.4 Hz),8.32(1H,d,J= 2.1 Hz).

UVλ$_{max}$ (0.1M MOPS buffer, pH 7.0): 298 nm (ε=15900).

EXAMPLE 33

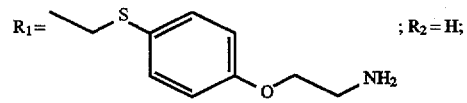

Monohydrochloride

IR(KBr)cm$^{-1}$: 3421,1747,1589,1408,1394,1282,1243.

$^1$H-NMR(D$_2$O)δ: 1.14(3H,d,J=7.1 Hz), 1.24(3H,d,J=6.4 Hz),3.18–3.42(8H,m),3.55–3.62(1H,m),3.70–3.78(1H,m), 3.88–3.95(2H,m),4.15–4.27(4H,m),7.01(2H,d,J=4.0 Hz), 7.49(2H,d,J=8.7 Hz).

UVλ$_{max}$ (0.1M MOPS buffer, pH 7.0): 297 nm (ε=7660).

EXAMPLE 34

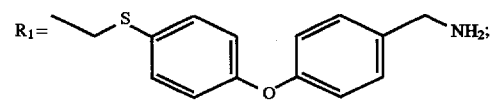

R$_2$ = H; Monohydrochloride

IR(KBr)cm$^{-1}$: 2966,1749,1587,1394,1242.

$^1$H-NMR(D$_2$O)δ: 1.12(3H,d,J=7.4 Hz), 1.23(3H,d,J=6.4 Hz), 1.67(1H,m),2.64(1H,m),3.20–3.40(5H,m),3.57(1H,m), 3.78(1H,m),3.92(1H,m),4.12(2H,s),4.10–4.20(2H,m),7.04 (2H,d,J=8.8 Hz),7.06(2H,d,=8.4 Hz),7.41 (2H,d,J=8.4 Hz)7.51(2H,d,J=8.8Hz).

UVλ$_{max}$ (0.1M MOPS buffer, pH 7.0): 300nm (ε=10000).

EXAMPLE 35

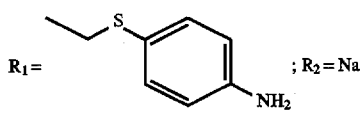

IR(KBr)cm$^{-1}$: 3446,1629,1392,1089,1051.

$^1$H-NMR(D$_2$O)δ: 0.80–1.00(2H,m), 1.17(3H,d,J=6.8 Hz), 1.27(3H,d,J=6.6 Hz), 1.40–1.80(2H,m), 1.80–2.00(3H,m), 2.80–2.90(5H,m),3.60–3.80(4H,m),6.80(2H,d,J=8.5 Hz), 7.34(2H,d,J=7.2 Hz).

UVλ$_{max}$ (0.1M MOPS buffer, pH 7.0): 300 nm (ε=3610).

EXAMPLE 36

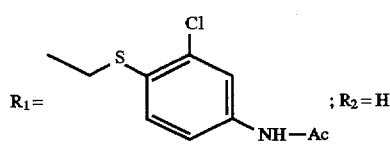

IR(KBr)cm$^{-1}$: 1749,1668,1650,1589,1522,1471,1390, 1308.

$^1$H-NMR(D$_2$O)δ: 1.12(3H,d,J=7.0 Hz), 1.23(3H,d,J=6.2 Hz), 1.48(1H,m),2.10(3H,s),2.45(1H,m),2.90(1H,m), 3.10–3.22(3H,m),3.22–3.40(3H,m),3.70(1H,m),4.08–4.24 (2H,m),7.27(1H,dd,J=1.5&8.8 Hz), 7.42(1H,d,J=8.5 Hz), 7.58(1H,d,J=1.5 Hz).

UVλ$_{max}$ (0.1M MOPS buffer, pH 7.0): 300 nm (ε=10900).

EXAMPLE 37

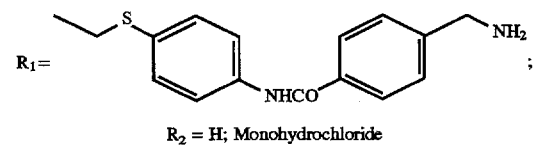

R$_2$ = H; Monohydrochloride

IR (KBr) cm$^{-1}$: 3423,2967,1751,1646,1589,1527,1396, 1319.

$^1$H-NMR(D$_2$O)δ: 1.16 (3H,d,J=7.3 Hz),1.26 (3H,d,J=6.2 Hz),1.60–1.80 (1H,m), 2.50–2.80 (1H,m), 3.20–3.70 (6H, m), 3.70–4.10 (2H,m), 4.10–4.30 (3H,m), 4.60–5.40 (7H, m), 7.50–7.70 (6H,m),7.80–8.00 (2H,m).

UVλ$_{max}$ (0.1M MOPS buffer, pH 7.0): 300 nm (ε=19200).

EXAMPLE 38

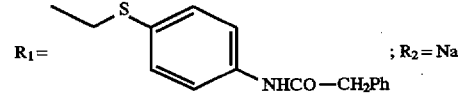

IR (KBr)cm$^{-1}$: 3421,1747,1668,1591,1527,1494,1396, 1344, 727,698.

$^1$H-NMR(D$_2$O)δ: 1.10 (3H,d, J=3.8 Hz), 1.26 (3E, d, J=5.9 Hz), 2.20–2.50 (1H,m), 2.70–3.00 (2H,m), 3.00–3.40 (6H,m), 3.50–3.80(3H,m),4.00–4.30(3H,m),4.50–5.00(1H, m),7.10–7.50 (10H,m).

UVλ$_{max}$ (0.1M MOPS buffer, pH 7.0): 300 nm (ε=9610).

EXAMPLE 39

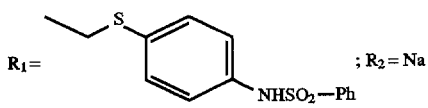

$R_1=$ ; $R_2 = Na$

IR(KBr)cm$^{-1}$: 3432,1741,1646,1585,1396,1124,1089, 601.

$^1$H-NMR(D$_2$O)δ: 1.16 (3H,d,J=7.1 Hz), 1.29 (4H,d,J=6.4 Hz), 2.70–3.80 (11H,m), 4.10–4.40 (3H,m), 6.80–6.90 (2H, m), 7.20–7.40 (2H,m), 7.50–7.60 (3H,m), 7.80–7.90 (2H, m).

UVλ$_{max}$ (0.1M MOPS buffer, pH 7.0): 300 nm (ε=6590).

EXAMPLE 40

$R_1=$ ; $R_2 = H$; Monohydrochloride

IR(KBr)cm$^{-1}$: 3421,2967,1751,1683,1591,1538,1496, 1398,1288.

$^1$H-NMR(D$_2$O)δ: 1.20(3H,d,J=7.4 Hz), 1.30(3H,d,J=6.3 Hz), 1.70–1.90(1H,m),2.60–3.00(4H,m),3.20–3.50(9H,m), 3.60–4.10(4H,m),4.20–4.30(3H,m),7.49(2H,d,J=8.5 Hz), 7.55(2H,d,J=8.6 Hz).

UVλ$_{max}$ (0.1M MOPS buffer, pH 7.0): 300 nm (ε=10800).

EXAMPLE 41

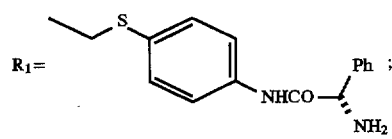

$R_1=$ ; $R_2 = H$; Monohydrochloride

IR(KBr)cm$^{-1}$: 3417,2360,1751,1695,1592,1394.

$^1$H-NMR(D$_2$O)δ: 1.19(3H,d,J=7.4 Hz), 1.32(3H,d,J=6.3 Hz), 1.70–1.80(1H,m),2.70–2.80(1H,m),3.30–4.10(9H,m), 4.20–4.30(2H,m),4.60–5.00(4H,m),5.20(1H,s),7.30–7.70 (10H,m).

UVλ$_{max}$ (0.1M MOPS buffer, pH 7.0): 300 nm (ε=11800).

EXAMPLE 42

$R_1=$ ; $R_2 = H$; Monohydrochloride

IR(KBr)cm$^{-1}$: 3486,1731,1621,1151.

$^1$H-NMR(D$_2$O)δ: 1.12(3H,d,J=7.3 Hz), 1.26(3H,d,J=6.2 Hz), 1.67–1.70(1H,m),2.15–2.20(1H,m),2.64–2.71 (1H,m), 3.01(1H,t,J=7.2 Hz),3.27–3.48(9H,m),3.50–3.64 (3H,m), 3.72–3.81(1H,m),3.91–4.00(2H,m),4.16–4.23 (2H,m),7.27 (2H,d,J=9.3 Hz),7.52(2H,d,J=9.2 Hz).

UVλ$_{max}$ (0.1M MOPS buffer, pH 7.0): 300 nm (ε=9720).

EXAMPLE 43

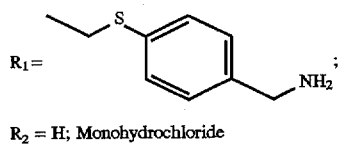

$R_1=$ ;
$R_2 = H$; Monohydrochloride

IR(KBr)cm$^{-1}$: 1749,1558,1396,1089.

$^1$H-NMR(D$_2$O)δ: 1.18(3H,d,J=7.3 Hz), 1.28(3H,d,J=6.3 Hz), 1.60–1.70(1H,m),2.60–2.70(1H,m),3.20–3.40(3H,m), 3.40–3.50 (3H,m),3.60–4.00(2H,m),4.16(2H,s),4.15–4.30 (2H,m), 7.43 (2H,d,J=8.6 Hz), 7.54 (2H,d,J=8.6 Hz).

UVλ$_{max}$ (0.1M MOPS buffer, pH 7.0): 297 nm (ε=8290).

EXAMPLE 44

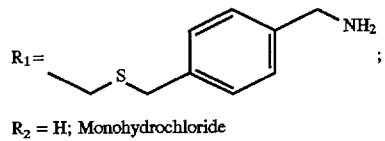

$R_1=$ ;
$R_2 = H$; Monohydrochloride

IR(KBr)cm$^{-1}$: 3359,2964,1745,1583,1641,1388,1346, 1103,765.

$^1$H-NMR(D$_2$O)δ: 0.81(3H,d,J=7.3 Hz),0.90(3H,d,J=6.3 Hz), 1.15–1.19(1H,m),2.25–2.31(1H,m),2.47–2.49(2H,m), 2.85–2.98(2H,m),3.05–3.08(1H,m),3.12–3.20(1H,m), 3.22–3.40(1H,m),3.49(2H,s),3.50–3.59(1H,m),3.79–3.89 (4H,m),7.07(4H, s).

UVλ$_{max}$ (0.1M MOPS buffer, pH 7.0): 298 nm (ε=8840).

EXAMPLE 45

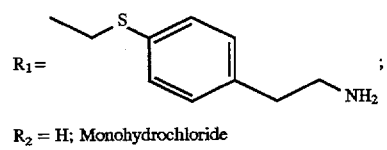

$R_1=$ ;
$R_2 = H$; Monohydrochloride

IR(KBr)cm$^{-1}$: 1749,1585,1390.

$^1$H-NMR(D$_2$O)δ: 1.15(3H,d,J=7.0 Hz), 1.25(3H,d,J=6.4 Hz), 1.64–1.78(1H,m),2.61–2.73(1H,m),2.96(2H,t,J=7.3 Hz), 3.24 (2H,t,J=7.3 Hz),3.20–3.50(5H,m), 3.58 (1H,dd,J= 6.5&12.5 Hz),3.71–3.86(1H,m),3.89–4.00 (1H,m), 4.14–4.25(2H,m),7.30(2H,d,J=8.3 Hz), 7.47 (2H,d,J=8.3 Hz).

UVλ$_{max}$ (0.1M MOPS buffer, pH 7.0): 297 nm (ε=8820).

EXAMPLE 46

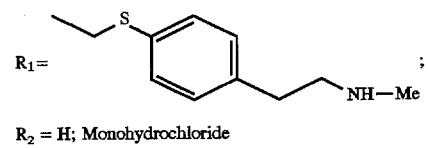

$R_1=$ ;
$R_2 = H$; Monohydrochloride

IR(KBr)cm$^{-1}$: 1755,1587,1390.

$^1$H-NMR(D$_2$O)δ: 1.16(3H,d,J=7.1 Hz), 1.26(3H,d,J=6.4 Hz), 1.67–1.80(1H,m),2.62–2.78(1H,m),2.68(3H,s), 3.00 (2H,t,J=7.4 Hz),3.29(2H,t,J=7.0 Hz),3.22–3.50(5H,m),3.60 (1H,dd,J=6.4&12.3 Hz),3.75–3.89(1H,m),3.89–4.00(1H, m), 4.14–4.26(2H,m),7.30(2H,d,J=8.0 Hz),7.49(2H,d,J=8.0 Hz).

UVλ$_{max}$ (0.1M MOPS buffer, pH 7.0): 297 nm (ε=9140).

EXAMPLE 47

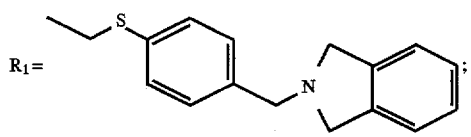

R₂ = H; Monohydrochloride

IR(KBr)cm⁻¹: 1753,1593,1390.

¹H-NMR(D₂O)δ: 1.15(3H,d,J=7.4 Hz), 1.27(3H,d,J=6.4 Hz), 1.75(1H,m),2.70(1H,m),3.20–3.80(7H,m),3.80–4.05 (2H,m),4.25(1H,m),4.60(2H,s),4.70(4H,br s),7.30–7.68(8H, m).

UVλ$_{max}$ (0.1M MOPS buffer, pH 7.0): 300 nm (ε=8810).

EXAMPLE 48

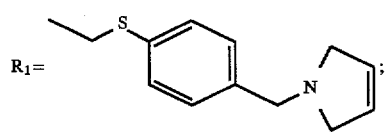

R₂ = H; Monohydrochloride

IR(KBr)cm⁻¹: 3421,1751,1589,1392.

¹H-NMR(D₂O)δ: 1.18(3H,d,J=7.2 Hz), 1.27(3H,d,J=6.4 Hz), 1.73(1H,m),2.72(1H,m),3.25–4.30(6H,m),4.11(4H,s), 4.48(2H,s),5.92(2H,s),7.50(2H,d,J=8.4 Hz), 7.58 (2H,d,J=8.4 Hz).

UVλ$_{max}$ (0.1M MOPS buffer, pH 7.0): 300 nm (ε=9360).

EXAMPLE 49

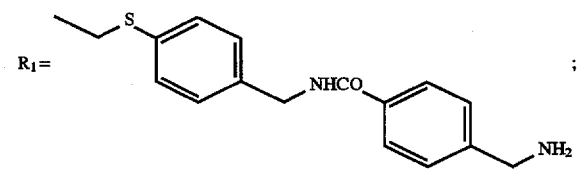

R₂ = H; Monohydrochloride

IR(KBr)cm⁻¹: 1755,1581,1387,1296.

¹H-NMR(D₂O)δ: 1.05(3H,d,J=7.0 Hz), 1.26(3H,d,J=6.4 Hz), 1.56–1.69 (1H,m),2.55–2.68(1H,m),3.20–3.50(5H,m), 3.56–3.67 (1H,m),3.77–3.96(2H,m),4.11–4.30(2H,m), 4.25 (2H,s),4.5–5.0,7.40(2H,d,J=8.3 Hz),7.50–7.60 (4H,m),7.82 (2H,d,J=6.6 Hz).

UVλ$_{max}$ (0.1M MOPS buffer, pH 7.0): 300 nm (ε=8950).

EXAMPLE 50

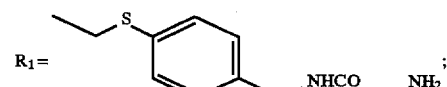

R₂ = H; Monohydrochloride

IR(KBr)cm⁻¹: 3423,2967,1751,1679,1587,1454,1396.

¹H-NMR(D₂O)δ: 1.22(3H,d,J=6.7 Hz), 1.32(3H,d,J=6.3 Hz), 1.70–1.80(1H,m),2.68–2.77(1H,m),3.30–3.55(2H,m), 3.60–4.11(4H,m),4.20–4.30(3H,m),7.37(2H,d,J=9.3 Hz), 7.54(2H,d,J=9.3 Hz).

EXAMPLE 51

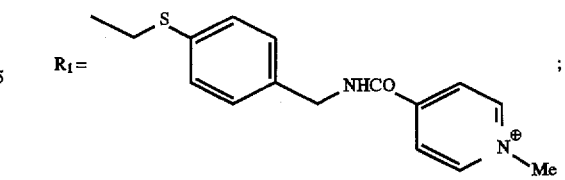

R₂ = H; Anion; ⊖Cl

IR(KBr)cm⁻¹: 1753,1664,1595,1390,1288,1149.

¹H-NMR(D₂O)δ: 1.11(3H,d,J=7.1 Hz), 1.25(3H,d,J=6.1 Hz), 1.56– 1.70(1H,m),2.54–2.70(1H,m),3.20–4.80(12H, m), 4.42(3H,s),7.24–7.51(5H,m),8.40(2H,d,J=6.4 Hz), 8.90 (2H,d,J=6.4 Hz).

UVλ$_{max}$ (0.1M MOPS buffer, pH 7.0): 300 nm (ε=10600).

EXAMPLE 52

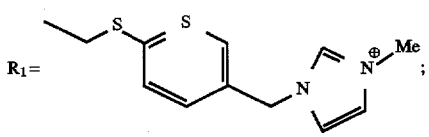

R₂ = H; Anion; ⊖Cl

IR(KBr)cm⁻¹: 1749,1589,1387.

¹H-NMR(D₂O)δ: 1.11(3H,d,J=7.1 Hz), 1.21(3H,d,J=6.4 Hz), 1.59–1.60 (1H,m),2.56–2.70(1H,m),3.20–3.32(3H,m), 3.35–3.56 (3H,m),3.68–3.80(1H,m),3.81(3H,s),3.84–3.93 (1H,m),4.11–4.21(2H,m),5.31(2H, s), 7.33 (2H,d,J=8.6 Hz), 7.36–7.43(2H,m), 7.48 (2H,d,J=8.6 Hz),8.69(1H,s).

UVλ$_{max}$ (0.1M MOPS buffer, pH 7.0): 300 nm (ε=9520).

EXAMPLE 53

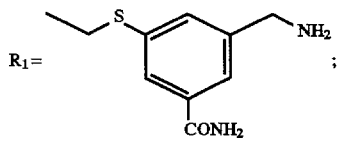

R₂= H; Monohydrochloride

IR(KBr)cm⁻¹: 1749,1668,1576,1394.

¹H-NMR(D₂O)δ: 1.16(3H,d,J=7.1 Hz), 1.26(3H,d,J=6.1 Hz), 1.67–1.81(1H,m),2.64–2.80(1H,m),3.26–3.50(4H,m), 3.50–3.62(2H,m),3.78–3.91(1H,m),3.92–4.02(1H,m), 4.17–4.23(2H,m),4.23(2H,s),7.74(2H,s),7.91(1H,s).

UVλ$_{max}$ (0.1M MOPS buffer, pH 7.0): 298 nm (ε=10000).

EXAMPLE 54

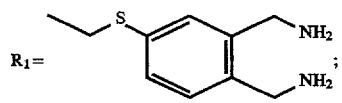

R₂ = H; Monohydrochloride

IR(KBr)cm⁻¹: 1753,1599,1390.

¹H-NMR(D₂O)δ: 1.20(3H,d,J=7.0 Hz), 1.28(3H,d,J=6.0 Hz), 1.75(1H,m),2.73(1H,m),7.40–7.65(3H,m).

UVλ$_{max}$ (0.1M MOPS buffer, pH 7.0): 300 nm (ε=6130).

EXAMPLE 55

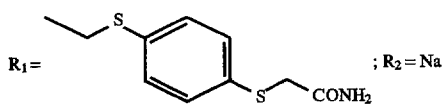
R₁ = [structure]; R₂ = Na

IR(KBr)cm⁻¹: 3421,1749,1670,1589,1394,1288,1107, 813.

$^1$H-NMR(D$_2$O)δ: 1.18(3H,d,J=7.3 Hz), 1.28(3H,d,J=6.4 Hz), 1.38(1H,m),2.47(1H,m),2.92(1H,dd,J=3.7&12.3 Hz), 3.10–4.30(6H,m),3.67(2H,s),3.72(1H,m),4.20(2H,m), 7.41 (4H,s).

UVλ$_{max}$(0.1M MOPS buffer, pH7.0): 300 nm (ε=10300).

EXAMPLE 56

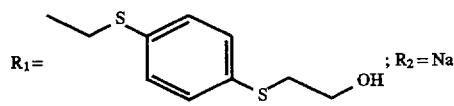
R₁ = [structure]; R₂ = Na

IR(KBr)cm⁻¹: 3386,1751,1591,1394,1288,1106,813.

$^1$H-NMR(D$_2$O)δ: 1.18(3H,d,J=6.9 Hz), 1.29(3H,d,J=6.4 Hz), 1.39(1H,m),2.43(1H,m),2.93(1H,dd,J=3.6&12.0 Hz), 3.13(2H,t,J=6.2 Hz),3.10–3.40(6H,m),3.70(1H,m), 3.74 (2H,t,J=6.2 Hz),4.10–4.30(2H,m),7.41(4H,s)

UVλ$_{max}$(0.1M MOPS buffer, pH 7.0): 300 nm (ε=11100).

EXAMPLE 57

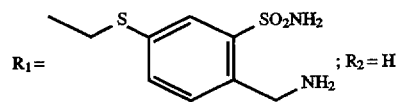
R₁ = [structure]; R₂ = H

IR(KBr)cm⁻¹: 1747,1718,1649,1633,1591,1560,1543, 1394,1153.

$^1$H-NMR(D$_2$O)δ: 1.16(3H,d,J=7.0 Hz), 1.25(3H,d,J=6.4 Hz), 1.78(1H,m),2.75(1H,m),3.25–3.50(4H,m),3.56–3.70 (2H,m),3.85–4.04(2H,m),4.15–4.26(2H,m), 4.48(2H,s),7.61 (1H,d,J=7.9 Hz),7.76(1H,d,J=7.9 Hz), 8.05 (1H,m).

UVλ$_{max}$(0.1M MOPS buffer, pH 7.0): 300 nm (ε=10800).

EXAMPLE 58

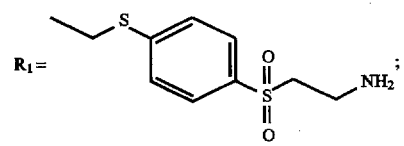
R₁ = [structure];
R₂ = H; Monohydrochloride

IR(KBr)cm⁻¹: 3409,2967,1754,1579,1394,1309,1280, 1151,1095, 1078,763.

$^1$H-NMR(D$_2$O)δ: 1.19(3H,d,J=7.3 Hz), 1.27(3H,d,J=6.4 Hz), 1.81(1H,m),2.79(1H,m),3.30–3.80(10H,m),3.95(2H, m), 4.23(2H,m),7.67(2H,d,J=8.4 Hz),7.92(2H,d,J=8.4 Hz).

UVλ$_{max}$(0.1M MOPS buffer, pH 7.0): 300 nm (ε=13910).

EXAMPLE 59

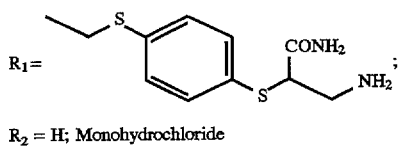
R₁ = [structure];
R₂ = H; Monohydrochloride

IR(KBr)cm⁻¹: 3425,2968,2364,1753,1672,1605,1392, 1284,1101.

$^1$H-NMR(D$_2$O)δ: 1.19(3H,d,J=7.3 Hz), 1.29(3H,d,J=6.3 Hz), 1.70–1.80(1H,m),2.71–2.80(1H,m),3.20–3.70(8H,m), 3.90–4.10(3H,m),4.20–4.30(2H,m),7.50–7.60(4H,m).

UVλmax(0.1M MOPS buffer, pH 7.0): 300 nm (ε=10800).

EXAMPLE 60

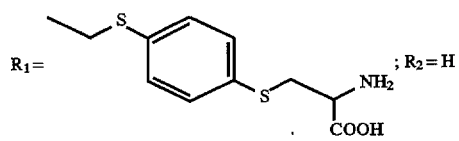
R₁ = [structure]; R₂ = H

IR(KBr)cm⁻¹: 3421,2970,1749,1633,1597,1487,1394, 1290, 1255,1097.

$^1$H-NMR(D$_2$O)δ: 1.19(3H,d,J=7.0 Hz), 1.29(3H,d,J=6.5 Hz), 1.70–1.80(1H,m),2.70–2.80(1H,m),3.30–3.70(8H,m), 3.80–3.90(2H,m),3.95–4.05(1H,m),4.20–4.30(2H,m),7.50 (4H,m) UVλ$_{max}$ (0.1M MOPS buffer, pH 7.0): 300 nm (ε=10100).

EXAMPLE 61

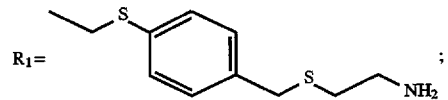
R₁ = [structure];
R₂ = H; Monohydrochloride

IR(KBr)cm⁻¹: 3421,2966,1753,1587,1390,1255,1145, 1085,765.

$^1$H-NMR(D$_2$O)δ: 1.13(3H,d,J=5.8 Hz), 1.23(3H,d,J=4.8 Hz), 1.67(1H,m),2.67–2.70(3H,m),3.11–3.89(12H,m), 4.10–4.20(2H,m),7.33(2H,d),7.44(2H,d).

UVλ$_{max}$ (0.1M MOPS buffer, pH 7.0): 296 nm (ε=7330).

EXAMPLE 62

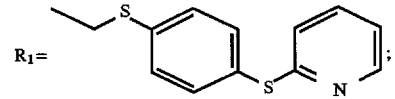
R₁ = [structure];
R₂ = H; Monohydrochloride

IR(KBr)cm⁻¹: 1753,1577,1392.

$^1$H-NMR(D$_2$O)δ: 1.08(3H,d,J=9.3 Hz), 1.12(3H,d,J=6.0 Hz), 1.20–1.65(2H,m),3.80–4.10(2H,m),4.90–5.05(1H,br), 6.92(1H,d,J=8.1 Hz),7.09–7.17(1H,m),7.40–7.57(4H,m), 7.60–7.70(1H,m),8.36–8.40(1H,m).

UVλmax(0.1M MOPS buffer, pH 7.0): 300 nm (ε=18300).

EXAMPLE 63

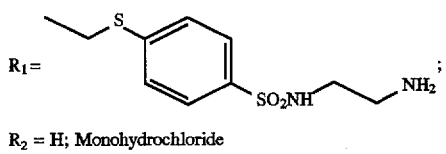

R₂ = H; Monohydrochloride

IR(KBr)cm⁻¹: 3421,2970,1745,1583,1390,1336,1157, 1099.

¹H-NMR(D₂O)δ: 1.14(3H,d,J=7.2 Hz), 1.23(3H,d,J=6.3 Hz),3.05– 3.15(4H,m),3.30–3.45(4H,m),3.50–3.65(2H,m), 3.80–4.00(2H,m),4.10–4.25(2H,m),7.60(2H,d,J=8.7 Hz), 7.80(2H,d,J=8.7 Hz).

UVλ$_{max}$ (0.1M MOPS buffer, pH 7.0): 300 nm (ε=11700).

EXAMPLE 64

R₂ = H; Monohydrochloride

IR(KBr)cm⁻¹: 3375,2966,1751,1662,1600,1577,1394, 1284,1261.

¹H-NMR(D₂O)δ: 1.14(3H,d,J=7.2 Hz), 1.24(3H,d,J=6.4 Hz), 1.63–1.73(1H,m),2.62–2.70(1H,m),3.15–3.19(2H,m), 3.26–3.36(5H,m),3.40–3.47(2H,m),3.58(1H,m),3.78(1H, m), 3.93(1H,m),4.15–4.22(2H,m),7.53–7.59(3H,m).

UVλ$_{max}$ (0.1M MOPS buffer, pH 7.0): 300 nm (ε=12700).

In the following Example 65 to 68, compounds represented by the formula (B) which have substituents R₃ and R₄ were synthesized in the same manner as in Examples 1 to5.

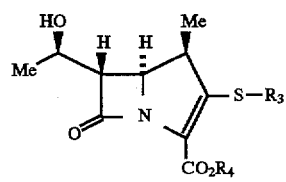

EXAMPLE 65

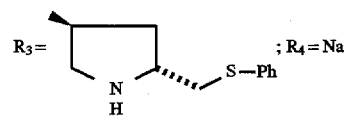

IR(KBr)cm⁻¹: 3420,2970,1750,1590,1390,1290,1150, 740.

¹H-NMR(D₂O)δ: 1.12(3H,d,J=7.0 Hz), 1.22(3H,d,J=6.0 Hz),2.00–2.20(2H,m),3.00–3.20(2H,m),3.20–3.30(2H,m), 3.40(1H,m),3.55(1H,m),3.75(1H,m),3.90(1H,m), 4.20(2H, m),7.20–7.50(5H,m).

UVλ$_{max}$ (0.1M MOPS buffer, pH 7.0): 297 nm (ε=9970).

EXAMPLE 66

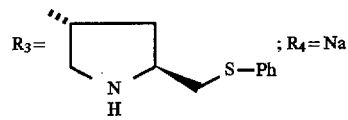

IR(KBr)cm⁻¹: 3420,2970,1750,1590,1400.

¹H-NMR(D₂O)δ: 1.11(3H,d,J=7.0 Hz), 1.26(3H,d,J=6.0 Hz), 1.80–2.00(2H,m),2.50(1H,m),2.70(1H,m),3.05(1H,m), 3.15–3.50(4H,m),3.60–3.80(2H,m),4.00–4.25(2H,m), 7.20–7.50(5H,m).

UVλ$_{max}$ (0.1M MOPS buffer, pH 7.0): 299 nm (ε=7450).

EXAMPLE 67

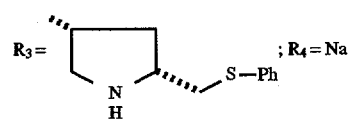

IR(KBr)cm⁻¹: 3420,2970,1750,1590,1390,1280,1180, 1150, 1070,740.

¹H-NMR(D₂O)δ: 1.09(3H,d,J=7.0 Hz), 1.23(3H,d,J=6.0 Hz), 1.70(1H,m),2.50(1H,m),3.10–3.50(6H,m),3.60(1H,m), 3.80(1H,m),4.05(1H,m), 4.20(1H,m),7.20–7.50(5H,m).

UVλ$_{max}$ (0.1M MOPS buffer, pH 7.0): 298 nm (ε=9150).

EXAMPLE 68

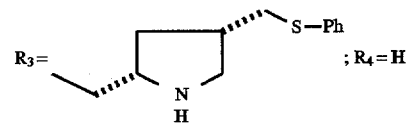

IR(KBr)cm⁻¹: 3390,1753,1587,1390.

¹H-NMR(D₂O)δ: 1.10(3H,d,J=6.0 Hz), 1.15(3H,d,J=6.0 Hz), 1.45(1H,m),2.45(1H,m),2.70–3.30(6H,m),3.60(1H,m), 3.70(1H,m),4.00(2H,m),7.30(5H,m).

UVλ$_{max}$(0.1M MOPS buffer, pH 7.0): 298 nm (ε=7780).

In the following Examples 69 to 123, compounds represented by the formula (A) which have substituents R₁ and R₂ were synthesized in the same manner as in Examples to 5.

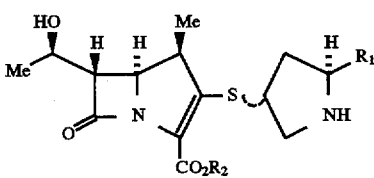

EXAMPLE 69

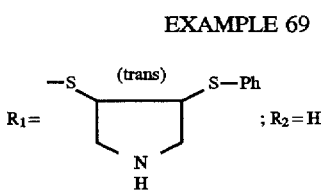

Diastereomer A
IR(KBr)cm⁻¹: 1755,1597,1394.

¹-NMR(D₂O)δ: 1.13(3H,d,J=7.0 Hz), 1.26(3H,d,J=6.0 Hz), 3.22(1H,m),3.36(1H,m),4.43(1H,m),7.41(3H,m), 7.62 (2H,m).
UVλ$_{max}$ (0.1M MOPS buffer, pH 7.0): 300 nm (ε=7040).
Diastereomer B
IR(KBr)cm⁻¹: 1755,1597,1394.
¹H-NMR(D₂O)δ: 1.05(3H,d,J=7.0 Hz), 1.27(3H,d,J=6.0 Hz), 4.40(1H,m),7.43(3H,m),7.62(2H,m).
UVλ$_{max}$ (0.1M MOPS buffer, pH 7.0): 297 nm (ε=6530).

EXAMPLE 70

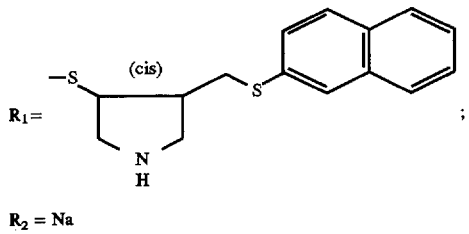

Diastereomer A
IR(KBr)cm⁻¹: 3047,1754,1594,1390.
¹-NMR(D₂O)δ: 1.10–1.30(6H,m),2.80–4.30(m), 7.40–7.55(3H,m),7.70–7.85(4H,m).
UVλ$_{max}$ (0.1M MOPS buffer, pH 7.0): 300 nm (ε=8100).
Diastereomer B
IR(KBr)cm⁻¹: 3444,1756,1594,1392.
¹H-NMR(D₂O)δ: 1.10–1.40(6H,m),2.80–4.30(m), 7.40–7.55(3H,m),7.70–7.90(4H,m).
UVλ$_{max}$ (0.1M MOPS buffer, pH 7.0): 300 nm (ε=9220).

EXAMPLE 71

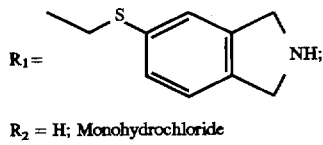

IR(KBr)cm⁻¹: 1759,1600,1390.
¹H-NMR(D₂O)δ: 1.21(3H,d,J=7.0 Hz), 1.31(3H,d,J=6.0 Hz), 1.77(1H,m),2.74(1H,m),3.65(1H,dd,J=3.0&8.0 Hz), 3.89(1H,m),4.00(1H,m),4.20–4.30(2H,m), 7.44(1H,d,J=8.0 Hz),7.55(2H,m).
UVλ$_{max}$ (0.1M MOPS buffer, pH 7.0): 300 nm (ε=10400).

EXAMPLE 72

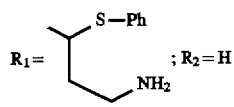

Diastereomer A
IR(KBr)cm⁻¹: 3425,2930,1750,1580,1460,1390,1280.
¹H-NMR(D₂O)δ: 1.21(3H,d,J=7.4 Hz), 1.30(3H,d,J=6.3 Hz), 1.60–2.10(3H,m),2.50–2.70(1H,m),3.10–3.80(9H,m), 3.80–4.00(1H,m),4.10–4.30(2H,m),4.80(2H,s),7.40–7.50 (3H,m),7.50–7.60(3H,m).
UVλ$_{max}$ (0.1M MOPS buffer, pH 7.0): 299 nm (ε=9100).
Diastereomer B
IR(KBr)cm⁻¹: 3420,2970,1755,1580,1390.
¹H-NMR(D₂O)δ: 1.22(3H,d,J=6.7 Hz), 1.30(3H,d,J=6.3 Hz), 1.80–2.10(2H,m),2.70–2.90(1H,m),3.10–3.60(8H,m), 3.70–3.80(1H,m),3.90–4.10(1H,br),4.20–4.30(2H,m),4.80 (3H,s),7.40–7.50(3H,m),7.50–7.60(3H,m).
UVλ$_{max}$ (0.1M MOPS buffer, pH 7.0): 299 nm (ε=8690).

EXAMPLE 73

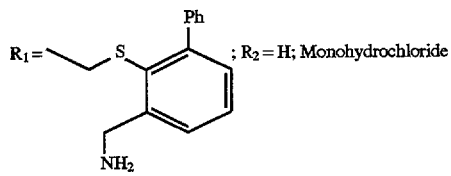

IR(KBr)cm⁻¹: 1751,1583.
¹H-NMR(D₂O)δ: 1.29(3H,d), 1.31(3H,d),2.19(1H,m), 2.80(2H,m), 3.30(5H,m),3.74(1H,m),4.23(2H,m),7.60(8H, m).
UVλ$_{max}$ (0.1M MOPS buffer, pH 7.0): 300 nm (ε=11200).

EXAMPLE 74

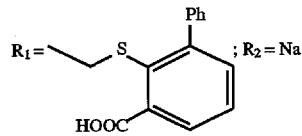

IR(KBr)cm⁻¹: 1745,1585.
¹H-NMR(D₂O)δ: 1.13(3H,d), 1.28(3H,d), 1.38(1H,m), 2.20(1H,m), 2.34(1H,m),2.59(2H,m),2.98(1H,m),3.45(4H, m), 3.83(1H,m),4.22(2H,m),7.34(2H,m),7.56(6H,m).
UVλ$_{max}$ (0.1M MOPS buffer, pH 7.0): 300 nm (ε=8000).

EXAMPLE 75

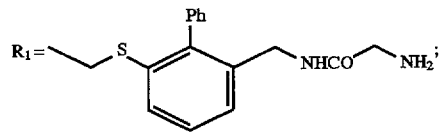

IR(KBr)cm⁻¹: 1753,1677,1581.
¹H-NMR(D₂O)δ: 1.80(3H,d), 1.31(3H,d), 1.66(1H,m), 2.63(1H,m), 3.29(4H,m),3.46(1H,m),3.67(3H,m),3.79(1H, m), 3.92(1H,m),4.21(4H,m),7.31(2H,m),7.52(6H,m).
UVλ$_{max}$ (0.1M MOPS buffer, pH 7.0): 300 nm (ε=8010).

EXAMPLE 76

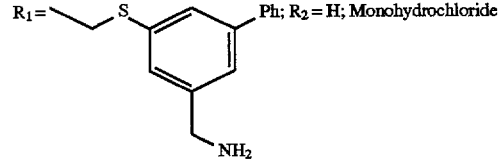

IR(KBr)cm⁻¹: 3421,2966,1750,1580,1392.
¹H-NMR(D₂O)δ: 1.02(3H,d,J=6.8 Hz), 1.10(3H,d,J=6.3 Hz), 1.50–1.60(1H,m),2.25–2.41(3H,m),2.55–2.90(3H,m), 3.08–3.48(5H,m),3.51–3.95(2H,m),4.95–5.04(1H,m), 7.39–7.70(8H,m).
UVλ$_{max}$ (0.1M MOPS buffer, pH 7.0): 300 nm (ε=9810).

EXAMPLE 77

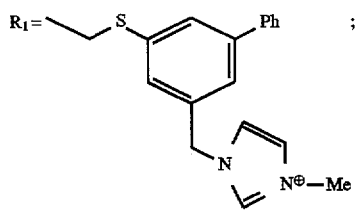

$R_2$ = Negative charge; Monohydrochloride

EXAMPLE 78

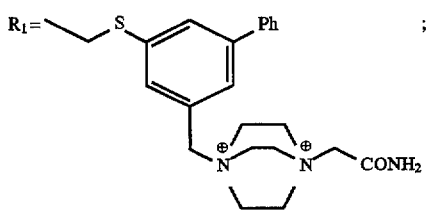

$R_2$= H; Anion: 2Cl$^\ominus$

IR(KBr)cm$^{-1}$: 3435,1755,1699,1587,1390,1259,1171,1030.

$^1$H-NMR(D$_2$O)δ: 1.10(3H,d,J=7.3 Hz),1.22(3H,d,J=6.5 Hz), 1.65–1.71(1H,m),2.10–2.16(1H,m),2.64–2.70(1H,m), 2.92–2.98(1H,m),3.18–3.61(8H,m),3.86–4.38(16H,m), 4.84 (2H,br s),7.45–7.68(7H,m),7.95(1H,br s).

UVλ$_{max}$ (0.1M MOPS buffer, pH 7.0): 300 nm (ε=8020).

EXAMPLE 79

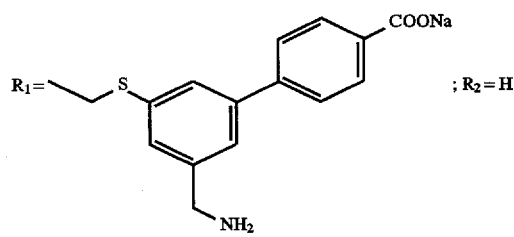

; $R_2$ = H

IR(KRr)cm$^{-1}$: 3405,2968,1749,1593,1541,1388.

$^1$H-NMR(D$_2$O)δ: 1.10(3H,d),1.20(3H,d),1.75(1H,m), 2.70(1H,m), 3.20–4.30(12,m),7.40–8.10(7H,m).

UV$_{max}$ (0.1M MOPS buffer, pH 7.0): 300 nm (ε=7480).

EXAMPLE 80

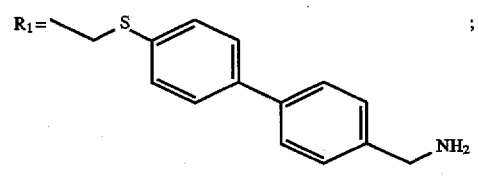

$R_2$ = H

IR(KBr)cm$^{-1}$: 3419,1749,1594,1394.

$^1$H-NMR(D$_2$O)δ: 1.10(6H,m),7.48(2H,m),7.54(2H,m), 7.62(2H,m), 7.72(2H,m).

UVλ$_{max}$(0.1M MOPS buffer, pH 7.0): 300 nm (ε=18400).

EXAMPLE 81

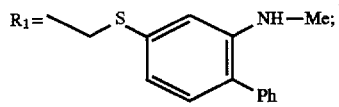

$R_2$ = H; Monohydrochloride

IR(KBr)cm$^{-1}$: 1753,1581.

$^1$H-NMR(D$_2$O)δ: 1.81(3H,d), 1.29(3H,d), 1.78(1H,m), 1.90(1H,m), 2.52(3H,s),2.76(1H,m),3.42(3H,m),3.63(2H,m), 3.76(2H,m),3.98(2H,m),4.26(3H,m),7.59(8H,m).

UVλ$_{max}$ (0.1M MOPS buffer, pH 7.0): 300 nm (ε=11100).

EXAMPLE 82

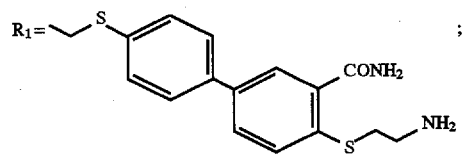

$R_2$ = H; Monohydrochloride

IR(KBr)cm$^{-1}$: 3433,2968,1753,1659,1605,1390.

$^1$H-NMR(D$_2$O)δ: 1.09(3H,d,J=7.0 Hz), 1.22(3H,d,J=6.3 Hz), 1.71(1H,m),2.67(1H,m),3.15(2H,t),3.20–3.40(6H,m), 3.48(1H,m),3.56(1H,m),3.84(1H,m),3.92(1H,m), 4.15(2H, m),7.54(2H,d,J=8.0 Hz),7.63(2H,d,J=8.0 Hz), 7.75(2H,d).

UVλ$_{max}$ (0.1M MOPS buffer, pH 7.0): 297 nm (ε=33500).

EXAMPLE 83

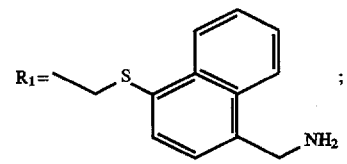

$R_2$ = H; Monohydrochloride

IR(KBr)cm$^{-1}$: 3417,3386,2966,1753,1577,1452,1388, 1263.

$^1$H-NMR(D$_2$O)δ: 1.07(3H,d,J=7.2 Hz), 1.21(3H,d,J=6.4 Hz), 1.57–1.75(1H,m),2.50–2.70(1H,m),3.13–3.66(6H,m), 3.76–3.97(2H,m),4.02–4.23(2H,m),4.63(2H,s),7.52– 7.55(1 H,m),7.68–7.74(3 H,m),8.04–8.09(1 H,m),8.43–8.48(1 H,m)

UVλ$_{max}$(0.1M MOPS buffer, pH7.0): 302 nm(ε=16800)

Example 84

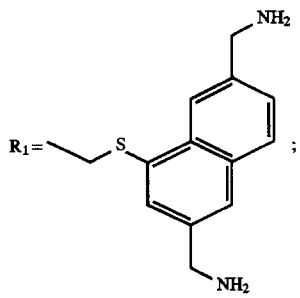

R$_2$ = H; Monohydrochloride

IR(KBr)cm$^{-1}$: 3430,2970,1750,1580,1450,1390,1280, 1150,890

$^1$H-NMR(D$_2$O)δ: 1.09(3 H,d,J=7.0 Hz),1.23(3 H,d,J=6.0 Hz), 1.70(1 H,m),2.60(1 H,m),3.20–3.45(3 H,m), 3.45–3.65(3 H,m),3.85–4.00(2 H,m),4.10–4.30(2 H,m), 4.35(2 H,s),4.41(2 H,s),7.66(1 H,d,J=8.0 Hz), 7.84(1 H,s), 7.97(1 H,s),8.06(1 H,d,J=9.0 Hz),8.47(1 H,s)

UVλ$_{max}$(0.1M MOPS buffer, pH7.0): 300 nm(ε=14000)

Example 85

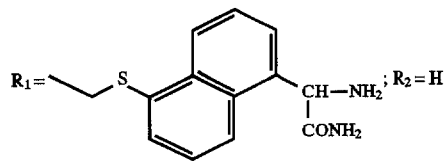

IR(KBr)cm$^{-1}$: 3430,1754,1672,1592,1388

$^1$H-NMR(D$_2$O)δ: 1.09–1.11(3 H,m),1.23–1.25(3 H,m), 1.64–1.69(1 H,m),2.53–2.60(1 H,m),3.22–3.56(6 H,m), 3.67–3.73(1 H,m),3.83–3.88(1 H,m),4.13–4.21(2 H,m), 5.80–5.81(1 H,m),7.54–7.67(3 H,m),7.81(1 H,d,J=7.0 Hz), 8.19(1 H,d,J=8.8 Hz),8.49–8.52(1 H,m)

UVλ$_{max}$(0.1M MOPS buffer, pH7.0): 301 nm(ε=17900)

Example 86

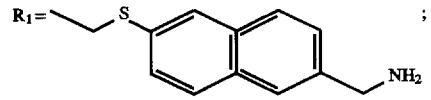

R$_2$ = H; Monohydrochloride

IR(KBr)cm$^{-1}$: 3390,2970,1750,1590,1390,1090

$^1$H-NMR(D$_2$O)δ: 1.08(3 H,d,J=7.4 Hz),1.22(3 H,d,J=6.5 Hz),1.70–1.82(1 H,m),2.65–2.75(1 H,m),3.20–3.45(4 H,m), 3.55–3.65(2 H,m),3.80–4.00(2 H,m),4.10–4.20(2 H,m), 4.31(2 H,s),7.50–7.60(2 H,m),7.85–7.95(3 H,m),7.99(1 H,s)

UVλ$_{max}$(0.1M MOPS buffer, pH7.0): 300 nm(ε=14700)

Example 87

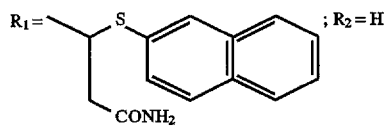

Diastereomer A

IR(KBr)cm$^{-1}$: 3425,1747,1670,1585,1395

$^1$H-NMR(D$_2$O)δ: 1.01(3 H,d,J=6.1 Hz),1.25(3 H,d,J=6.5 Hz),1.40–1.60(1 H,m),2.10–2.80(3 H,m),2.90–3.90(7 H,m), 4.00–4.30(2 H,m),7.30–7.60(3 H,m),7.70–8.10(4 H,m)

UVλ$_{max}$(0.1M MOPS buffer, pH7.0): 300 nm(ε=11600)

Diastereomer B

IR(KBr)cm$^{-1}$: 3425,1747,1670,1590,1395

$^1$-NMR(D$_2$O)δ: 0.88(3 H,d,J=6.8 Hz),1.23(3 H,d,J=6.1 Hz),1.30–1.50(1 H,m),2.20–2.70(3 H,m),2.70–3.60(6 H,m), 3.60–3.80(1 H,m),4.00–4.30(2 H,m),7.20–7.70(6 H,m), 7.80–7.90(1 H,m)

UVλ$_{max}$(0.1M MOPS buffer, pH7.0): 300 nm(ε=11800)

Example 88

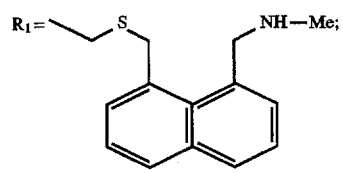

R$_2$ = H; Monohydrochloride

IR(KBr)cm$^{-1}$: 3415,2967,1750,1580,1450,1390,1285, 1267,775

$^1$H-NMR(D$_2$O)δ: 1.14(3 H,d,J=7.1 Hz),1.27(3 H,d,J=6.4 Hz),2.30–2.40(2 H,m),2.80–2.90(2 H,m),3.10–3.60(6 H,m), 3.70–3.80(2 H,m),4.10–4.40(4 H,m),7.50–7.70(4 H,m), 8.00–8.10(2 H,m)

UVλ$_{max}$(0.1M MOPS buffer, pH7.0): 300 nm(ε=14200)

Example 89

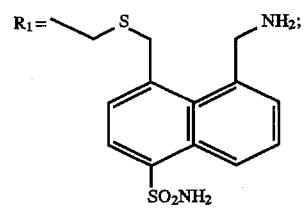

R$_2$ = H; Monohydrochloride

IR(KBr)cm$^{-1}$: 3421,2969,1749,1585,1392,1317,1149

$^1$H-NMR(D$_2$O)δ: 1.03(3 H,d,J=7.1 Hz),1.20(3 H,d,J=6.2 Hz),2.20–2.30(2 H,m),2.70–2.90(2 H,m),3.10–3.50(6 H,m), 3.70 3.80(1 H,m),4.00–4.20(2 H,m),4.30–4.40(2 H,m), 7.60(1 H,d,J=8.0 Hz),7.70–7.80(2 H,m),8.20(1 H,d,J=7.8 Hz),8.70(1 H,m)

UVλ$_{max}$(0.1M MOPS buffer, pH7.0): 300 nm(ε=17710)

Example 90

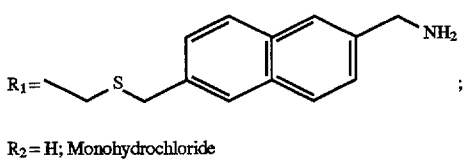

R₂ = H; Monohydrochloride

IR(KBr)cm⁻¹: 3428,2969,2362,1753,1606,1392

¹H-NMR(D₂O)δ: 1.12(3 H,d,J=7.2 Hz),1.27(3 H,d,J=6.2 Hz),1.40–1.50(1 H,m),2.50–2.60(1 H,m),2.80–3.00(2 H,m), 3.20–3.30(2 H,m),3.40–3.50(1 H,m),3.50–3.60(1 H,m), 3.70–3.80(1 H,m),3.80–3.90(1 H,m),4.01(2 H,s), 4.10–4.30(2 H,m),4.35(2 H,s),4.20–4.80(5 H,m), 7.50–7.70(2 H,m),7.80–8.00(4 H,m)

UVλ$_{max}$(0.1M MOPS buffer, pH7.0): 300 nm(ε=9040)

Example 91

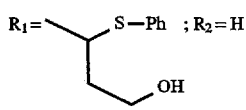

6Diastereomer A

IR(KBr)cm⁻¹: 3390,2930,1755,1590,1385,1260

¹H-NMR(D₂O)δ: 1.17(3 H,d,J=7.4 Hz),1.28(3 H,d,J=6.3 Hz),1.60–2.00(3 H,m),2.60–4.30(15 H,m),4.80(1 H,s), 7.30–7.60(5 H,m)

UVλ$_{max}$(0.1M MOPS buffer, pH7.0): 298 nm(ε=10140)

Diastereomer B

IR(KBr)cm⁻¹: 3400,2965,1750,1590,1390,1075,750,610

¹H-NMR(D₂O)δ: 1.18(3 H,d,J=7.5 Hz),1.28(3 H,d,J=6.3 Hz),1.40–1.50(1 H,m),2.40–2.60(1 H,m),2.90–3.00(1 H,m), 3.20–3.50(6 H,m),3.70–3.90(3 H,m),4.10–4.30(2 H,m), 4.60–4.90(3 H,m),7.30–7.50(3 H,m),7.50–7.60(2 H,m)

UVλ$_{max}$(0.1M MOPS buffer, pH7.0): 298 nm(ε=9070)

Example 92

R₂ = H; Monohydrochloride

Diastereomer A

IR(KBr)cm⁻¹: 3340,2950,1750,1585,1385,1280,1140,1065,775

¹H-NMR(D₂O)δ: 0.98(3 H,d,J=6.6 Hz),1.30(3 H,d,J=6.3 Hz),1.60–1.80(2 H,m),1.90–2.10(1 H,m),2.10–2.20(1 H,m), 2.50–2.70(1 H,m),3.00–3.50(4 H,m),3.50–3.70(2 H,m), 3.70–3.90(1 H,m),4.10–4.30(1 H,m),7.40–8.00(6 H,m), 8.30–8.40(1 H,m)

UVλ$_{max}$(0.1M MOPS buffer, pH7.0): 300 nm(ε=14700)

Diastereomer B

IR(KBr)cm⁻¹: 3410,2965,1755,1585,1390,1280,1145,1085,775

¹H-NMR(D₂O)δ: 1.17(3 H,d,J=7.0 Hz),1.29(3 H,d,J=6.3 Hz),1.70–2.20(3 H,m),2.70–2.80(1 H,m),3.20–3.50(5 H,m), 3.60–3.70(2 H,m),3.90–4.10(1 H,m),4.20–4.30(2 H,m), 7.50–7.80(3 H,m),7.90(1 H,m),8.00–8.10(2 H,m), 8.50–8.60(1 H,m)

UVλ$_{max}$(0.1M MOPS buffer, pH7.0): 299 nm(ε=14200)

Example 93

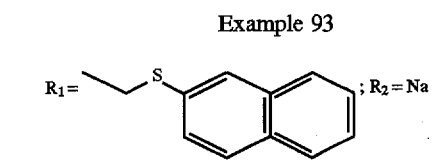

IR(KBr)cm⁻¹: 3430,2970,1750,1590,1400,1070

¹H-NMR(D₂O)δ: 0.99(3 H,d,J=6.0 Hz),1.20(3 H,d,J=6.0 Hz), 2.25(1 H,m),2.70–3.60(9 H,m),4.00–4.20(2 H,m), 7.20–7.90(7 H,m)

UVλ$_{max}$(0.1M MOPS buffer, pH7.0): 300 nm(ε=10860)

Example 94

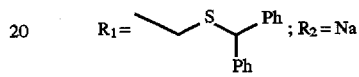

IR(KBr)cm⁻¹: 3425,2967,1753,1596,1390,1079,754,703,605

¹H-NMR(D₂O)δ: 1.03(1 H,m),1.20(3 H,d,J=7.4 Hz), 1.25(3 H,d,J=6.0 Hz),3.65(2 H,m),4.13(1 H,m),7.18–7.49 (10 H,m)

UVλmax(0.1M MOPS buffer, pH7.0): 300 nm(ε=8780)

Example 95

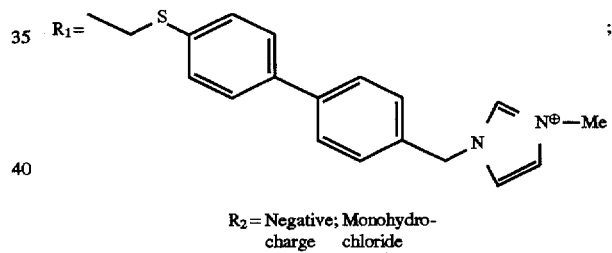

R₂ = Negative; Monohydrocharge chloride

IR(KBr)cm⁻¹: 3419,1749,1595,1394

¹H-NMR(D₂O)δ: 1.10(3 H,br d),1.25(3 H,br d),1.75(1 H,m), 2.70(1 H,m),3.40(6 H,m),3.60(1 H,m),3.85(3 H,br s),3.90(1 H,m),4.20(2 H,m),5.42(2 H,br s),7.40–7.80(10 H,m),8.80(1 H,br s)

UVλ$_{max}$(0.1M MOPS buffer, pH7.0): 300 nm(ε=19500)

Example 96

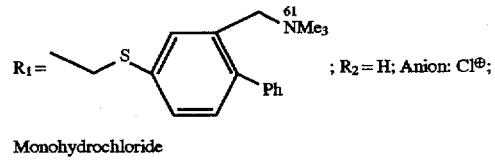

Monohydrochloride

IR(KBr)cm⁻¹: 1743,1585

¹H-NMR(D₂O)δ: 1.25(6 H,m),1.79(1 H,m),2.83(1 H,m), 2.85(6 H,s), 3.40(3 H,s),3.80(12 H,m),7.53(8 H,m)

UVλ$_{max}$(0.1M MOPS buffer, pH7.0): 300 nm(ε=10300)

Example 97

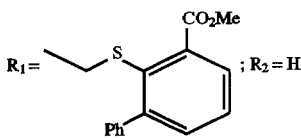

IR(KBr)cm$^{-1}$: 1743,1585

$^1$H-NMR(DMSO-d$_6$)δ: 0.89(1 H,m),1.05(3 H,d,J=6.9 Hz), 1.13(3 H,d,J=6.3 Hz),1.92(1 H,m),2.31(1 H,m), 2.48(1 H,m),2.78(1 H,m),3.37(5 H,m),3.84(3 H,s), 3.89(1 H,m), 4.06(1 H,m),7.43(6H,m),7.49(2 H,m)

UVλ$_{max}$(0.1M MOPS buffer, pH7.0): 300 nm(ε=10600)

Example 98

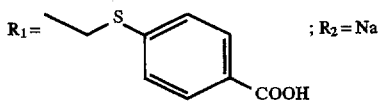

IR(KBr)cm$^{-1}$: 3421,2964,1747,1591,1386,1103,763,605

$^1$H-NMR(D$_2$O)δ: 0.78(3 H,d,J=7.0 Hz),0.87(3 H,d,J=6.3 Hz),1.27–1.30(1 H,m),2.26–2.31(1 H,m),2.31–2.53(2 H,m), 2.90–2.95(2 H,m),3.03–3.06(1 H,m),3.18–3.34(2 H,m), 3.48(2 H,s),3.52–3.57(1 H,m),3.78–3.85(2 H,m), 7.03–7.45(4 H,m)

UVλ$_{max}$(0.1M MOPS buffer, pH7.0): 297 nm(ε=8880)

Example 99

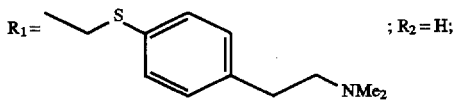

Monohydrochloride

IR(KBr)cm$^{-1}$: 1751,1587,1384

$^1$H-NMR(D$_2$O)δ: 1.16(3 H,d,J=7.4 Hz),1.26(3 H,d,J=6.3 Hz),1.68–1.80(1 H,m),2.63–2.78(1 H,m),2.90(6 H,s), 3.06(2 H,t,J=7.4 Hz),3.25–3.52(7 H,m), 3.61(1 H,dd,J=6.6 & 12.5 Hz),3.77–3.89(1 H,m), 3.90–4.00(1 H,m),4.16–4.27(2 H,m), 7.32(2 H,d,J=8.0 Hz), 7.49(2 H,d,J=8.0 Hz)

UVλ$_{max}$(0–1M MOPS buffer, pH7.0): 297 nm(ε=9580)

Example 100

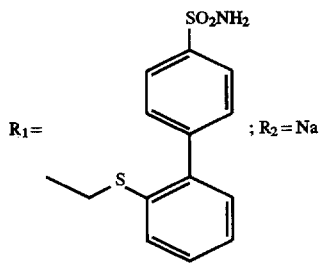

IR(KBr)cm$^{-1}$: 3421,1741,1585,1461,1390,1340

$^1$H-NMR(D$_2$O)δ: 1.01(3 H,d),1.24(3 H,d,J=6.1 Hz), 2.70–3.40(7 H,m),4.00–4.30(2 H,m),7.00–7.60(6 H,m), 7.86(2 H,d,J=8.1 Hz)

UVλ$_{max}$(0.1M MOPS buffer, pH7.0): 300 nm(ε=8610)

Example 101

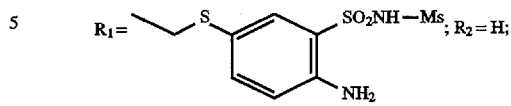

Monohydrochloride

IR(KBr)cm$^{-1}$: 1768,1749,1649,1616,1595,1579,1562, 1540,1105

$^1$H-NMR(D$_2$O)δ: 1.18(3 H,d,J=7.1 Hz),1.27(3 H,d,J=6.4 Hz), 1.77(1 H,m),2.74(1 H,m),3.07(3 H,s),3.29–3.47(4 H,m),3.52–3.66(2 H,m),3.83(1 H,m),3.96(1 H,m), 4.17–4.27(2 H,m),4.53(2 H,s),7.57(1 H,d,J=8.0 Hz), 7.72(1 H,dd,J=1.9 & 8.0 Hz),8.02(1 H,d,J=1.9 Hz)

UVλ$_{max}$(0.1M MOPS buffer, pH7.0 ): 300 nm(ε=10400)

Example 102

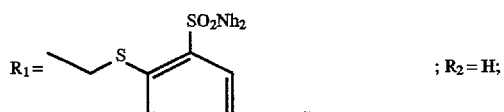

Monohydrochloride

IR(KBr)cm$^{-1}$: 3423,2966,1755,1603,1458,1390,1327, 1155

$^1$H-NMR(D$_2$O)δ: 1.13(3 H,d,J=6.9 Hz),1.23(3 H,d,J=6.4 Hz), 1.68(1 H,m),2.63(1 H,m),2.70(2 H,t,J=6.7 Hz), 3.12(2 H,t,J=6.7 Hz),3.25–3.70(6 H,m),3.84(2 H,s),3.91(2 H,m), 4.19(2 H,m), 7.62(1 H,d,J=8.0 Hz),7.70(1 H,d,J=8.0 Hz), 8.00(1 H,s)

UVλ$_{max}$(0.1M MOPS buffer, pH7.0): 298 nm(ε=13100)

Example 103

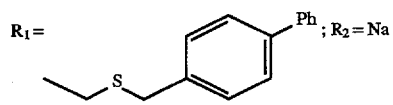

IR(KBr)cm$^{-1}$: 3419,2964,2925,1749,1733,1600,1540, 1519, 1506,1488

$^1$H-NMR(D$_2$O)δ: 1.07(3 H,d,J=7.1 Hz),1.18(3 H,d,J=6.3 Hz), 7.42–7.72(m)

UVλ$_{max}$(0.1M MOPS buffer, pH7.0): 300 nm(ε=8000)

Example 104

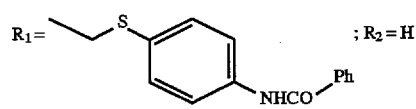

IR(KBr)cm$^{-1}$: 3388,1741,1646,1587,1396,1072,765,607

$^1$H-NMR(D$_2$O)δ: 1.17(3 H,d,J=6.6 Hz),1.28(3 H,d,J=6.3 Hz),2.30–2.60(3 H,m),3.10–3.50(6 H,m),4.10–4.30(3 H,m), 7.30–7.40(7 H,m),7.88(2 H,d,J=7.7 Hz)

UVλ$_{max}$(0.1M MOPS buffer, pH7.0): 300 nm(ε=14200)

Example 165

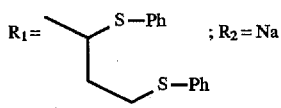

Diastereomer A
IR(KBr)cm$^{-1}$: 3442,1750,1590,1400,1065
$^1$H-NMR(D$_2$O)δ: 0.80–1.30(m),1.50–4.30(m),7.00–7.60 (m)
UVλ$_{max}$(0.1M MOPS buffer, pH7.0): 300 nm(ε=5000)
Diastereomer B
IR(KBr)cm$^{-1}$: 3410,1740,1665,1621,1400
$^1$H-NMR(D$_2$O)δ: 0.90–1.30(m),1.60–4.30(m),6.90–7.50 (m)
UVλ$_{max}$(0.1M MOPS buffer, pH7.0): 300 nm(ε=3080)

Example 106

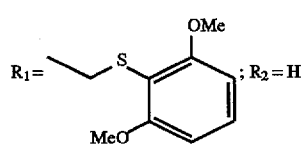

IR(KBr)cm$^{-1}$: 1756,1594,1257,1099
$^1$H-NMR(D$_2$O)δ: 1.18(3 H,d,J=6.3 Hz),1.28(3 H,d,J=6.4 Hz), 1.60(1 H,m),2.55–2.90(3 H,m),3.20–3.45(2 H,m), 3.50–4.00(12 H,m),4.15–4.30(2 H,m),6.70–6.80(2 H,m), 7.30(1 H,m)
UVλ$_{max}$(0.1M MOPS buffer, pH7.0): 298 nm(ε=7930)

Example 107

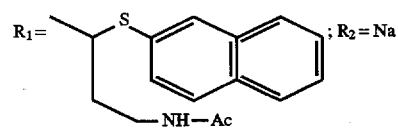

Diastereomer A
IR(KBr)cm$^{-1}$: 3415,1750,1640,1590,1395,1290
$^1$H-NMR(D$_2$O)δ: 1.08(3 H,d,J=7.0 Hz),1.27(3 H,d,J=6.2 Hz),1.40–1.70(2 H,m),1.81(3 H,s),2.20–2.40(1 H,m), 2.80–3.00(1 H,m),3.10–3.70(9 H,m),4.10–4.30(2 H,m), 7.40–7.60(3 H,m),7.80–7.90(3 H,m),7.90(1 H,s)
UVλ$_{max}$(0.1M MOPS buffer, pH7.0): 300 nm(ε=11100)
Diastereomer B
$^1$H-NMR(D$_2$O)δ: 1.00–4.50(m),7.40–7.60(m),7.70–8.00 (m)
UVλ$_{max}$(0.1M MOPS buffer, pH7.0): 300 nm(ε=7370)

Example 108

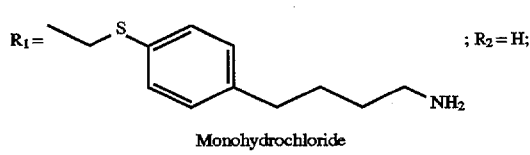

Monohydrochloride

IR(KBr)cm$^{-1}$: 1753,1579,1390
$^1$H-NMR(D$_2$O)δ: 1.09(3 H,d,J=7.0 Hz),1.19(3 H,d,J=6.4 Hz),1.50–1.67(5 H,m),2.51–2.65(3 H,m),2.82–2.95(2 H,m), 3.15–3.38(3 H,m),3.44–3.53(1 H,m),3.62–3.76(1H,m), 3.80–3.90(1 H,m),4.09–4.18(2 H,m),7.20(2 H,d,J=7.8 Hz), 7.37(2 H,d,J=7.8 Hz)

UVλ$_{max}$(0.1M MOPS buffer, pH7.0): 297 nm(ε=3470)

Example 109

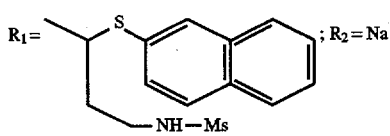

Diastereomer A
IR(KBr)cm$^{-1}$: 3420,2970,1750,1590,1395,1310,1150
$^1$H-NMR(D$_2$O)δ: 0.96(3 H,d,J=5.0 Hz),1.24(3 H,d,J=6.1 Hz),1.30–2.10(4 H,m),2.92(3 H,s),3.00–3.50(9 H,m), 4.00–4.20(2 H,m),7.00–8.00(7 H,m)
UVλ$_{max}$(0.1M MOPS buffer, pH7.0): 300 nm(ε=11300)
Diastereomer B
IR(KBr)cm$^{-1}$: 3490,1745,1641,1590,1390,1310,1150
$^1$H-NMR(D$_2$O)δ: 0.93(3 H,d,J=6.3 Hz),1.24(3 H,d,J=6.3 Hz),1.10–2.30(4 H,m),2.92(3 H,s),2.90–3.10(4 H,m), 3.20–3.50(5 H,m),4.00–4.30(2 H,m),7.20–7.90(7 H,m)
UVλ$_{max}$(0.1M MOPS buffer, pH7.0): 300 nm(ε=8940)

Example 110

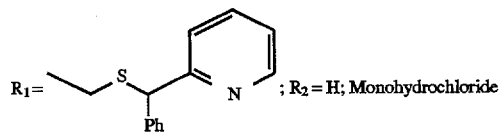

IR(KBr)cm$^{-1}$: 3421,1741,1645,1587,1566,1516,761,607
$^1$H-NMR(D$_2$O)δ: 1.13(3 H,d,J=7.0 Hz),1.22(3 H,d,J=6.4 Hz),1.50–1.65(1 H,m),2.00–2.12(1 H,m),2.52–2.70(1 H,m), 2.80–3.15(2 H,m),3.21–3.44(2 H,m),3.50–3.96(3 H,m), 4.12–4.22(1 H,m),5.45(1 H,s),7.26–7.60(6 H,m), 7.75–7.85(1 H,m),8.40–8.48(1 H,m),9.88(1 H,s)
UVλ$_{max}$(0.1M MOPS buffer, pH7.0): 298 nm(ε=8190)

Example 111

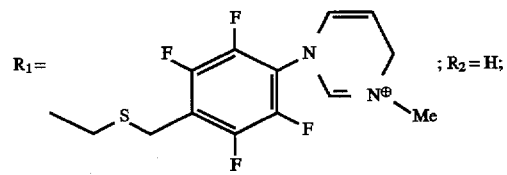

Anion; Cl$^\ominus$; Monohydrochloride

IR(KBr)cm$^{-1}$: 3421,1749,1589,1509
$^1$H-NMR(D$_2$O)δ: 1.20(3 H,d,J=7.0 Hz),1.28(3 H,d,J=6.4 Hz), 1.65(1 H,m),2.65–3.10(3 H,m),3.25–3.65(4 H,m), 4.05(3 H,s),3.75–4.30(6 H,m),7.76(1 H,d,J=1.2 Hz), 7.84(1 H,s)
UVλ$_{max}$(0.1M MOPS buffer, pH7.0): 297 nm(ε=9430)

Example 112

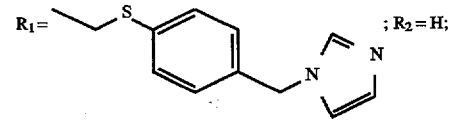

Monohydrochloride

IR(KBr)cm⁻¹: 1749,1560,1394

¹H-NMR(D₂O)δ: 1.11(3 H,d,J=7.3 Hz),1.22(3 H,d,J=6.4 Hz),1.63–1.74(1 H,m),2.59–2.72(1 H,m),3.22–3.36(2 H,m), 3.37–3.49(2 H,m),3.51–3.60(1 H,m),3.72–3.85(1 H,m), 3.86–3.97(1 H,m),4.12–4.23(2 H,m),5.29(2 H,s), 7.23–7.41(4 H,m),7.45(2 H,d,J=8.7 Hz),8.33(1 H,s)

Example 113

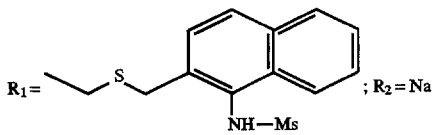

; R₂ = Na

IR(KBr)cm⁻¹: 3420,2970,1740,1645,1590,1515,1400, 1340, 1315,1150,1080

¹H-NMR(D₂O)δ: 1.09(3 H,d,J=7.0 Hz),1.23(3 H,d,J=6.0 Hz),2.30–2.70(3 H,m),2.92(3 H,s),3.10–3.40(3 H,m),3.65(1 H,m), 4.00–4.20(4 H,m),7.40–7.60(3 H,m),7.70(1 H,m), 7.85(1 H,m),8.25(1 H,m)

UVλ$_{max}$(0.1M MOPS buffer, pH7.0): 300 nm(ε=11100)

Example 114

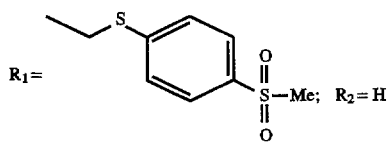

IR(KBr)cm⁻¹: 3384,1749,1581,1396,1301,1151,1097, 1079,777

¹H-NMR(D₂O)δ: 1.15–1.29(6 H,m),1.45(1 H,m),2.50(1 H,m), 2.95(1 H,dd,J=3.8 & 12.8 Hz),3.24(3 H,s), 3.15–3.45(5 H,m),3.73(1 H,m),4.07–4.25(3 H,m), 7.56(2 H,d,J=8.6 Hz),7.84(2 H,d,J=8.6 Hz)

UVλ$_{max}$(0.1M MOPS buffer, pH7.0): 300 nm(ε=11800)

Example 115

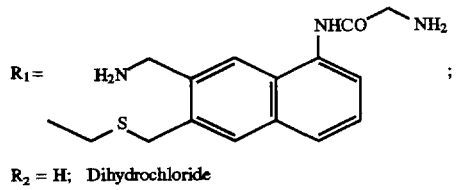

R₂ = H; Dihydrochloride

IR(KBr)cm⁻¹: 3430,2970,1750,1690,1550,1450,1390, 1270, 1150,900

¹H-NMR(D₂O)δ: 1.04(3 H,d,J=7 Hz),1.24(3 H,d,J=7 Hz), 1.34(1 H,m),2.47(1 H,m),2.88(2 H,d,J=7 Hz),3.15–3.25(2 H,m),3.37(1 H,m),3.53(1 H,m),3.75–3.9(2 H,m),4.0–4.2(4 H,m),4.21(2 H,s),4.53(2 H,s),7.5–7.7(2 H,m),7.9–8.0(2 H,m),8.02(1 H,s)

UVλ$_{max}$(0.1M MOPS buffer, pH7.0): 294 nm(ε=12700)

Example 116

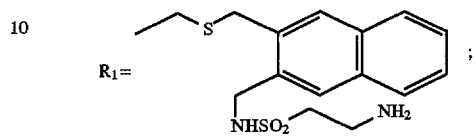

;

R₂ = H; Monohydrochloride

IR(KBr) cm⁻¹: 3841,3426,2967,1749,1635,1542,1456, 1394,1147

¹H-NMR(D₂O)δ: 1.09(3 H,d,J=7.1 Hz),1.25(3 H,d,J=6.4 Hz),1.41–1.51(1H,m),2.43–2.55(1H,m),2.91–3.98(2H,m), 3.16–3.27(2 H,m),3.38–3.65(6 H,m),3.70–3.88(2 H,m), 4.09–4.25(4 H,m),4.66(2 H,s),7.50–7.61(2 H,m),7.86(1 H,s), 7.90–7.98(2 H,m),7.99(1 H,s)

UVλ$_{max}$(0.1M MOPS buffer, pH7.0): 300 nm(ε=9130)

Example 117

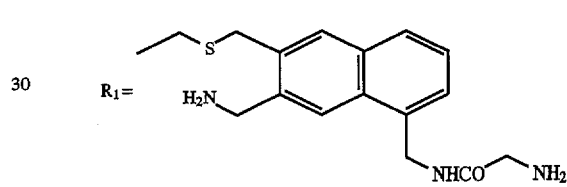

;

R₂ = H; Monohydrochloride

IR(KBr)cm⁻¹: 3425,2967,1749,1679,1560,1456,1394, 1267

¹H-NMR(D₂O)δ: 1.07(3 H,d,J=7.25 Hz),1.24(3 H,d,J= 6.4 Hz), 1.35(1 H,m),2.50(1 H,m),2.90(2 H,d),3.16–3.31(2 H,m),3.39(1 H,dd),3.55(1 H,m),3.78–3.90(4 H,m), 4.05–4.25(4 H,m),4.55(2 H,s),4.91(2 H,s), 7.51–7.60(2 H,m),7.87–7.91(2 H,m),8.13(1 H,s)

UVλ$_{max}$(0.1M MOPS buffer, pH7.0): 300 nm(ε=11500)

Example 118

(1R,5S,6S)-2-[(3S,5S)-5-[6-(4-Carbamoylmethyl-1,4-diazabicyclo[2.2.2]octanedium-1-ylmethyl)naphthalen-2-ylmethylthiomethyl]pyrrolidin-3-ylthio]-6-[(1R)-1-hydroxyethyl]- 1-methyl-1-carbapen-2-em-3-carboxylic acid dichloride

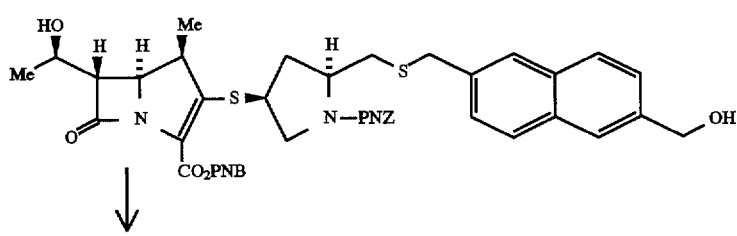

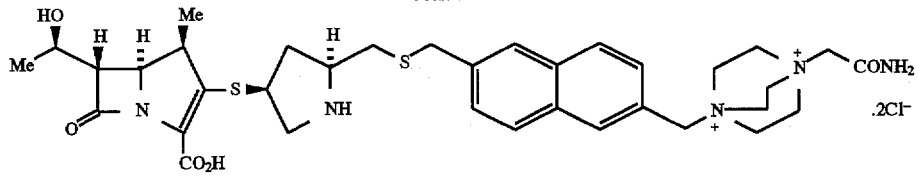

-continued

To a solution of p-nitrobenzyl (1R,5S,6S)-6-[(1R)-1-hydroxyethyl]-1-methyl-2-[(3S,5S)-1-p-nitrobenzyloxycarbonyl-5-[6-hydroxymethyl-2-ylmethylthiomethyl]pyrrolidin-3-ylthio]-1-carbapen-2-em-3-carboxylate (1.81 g, 2.14 mmol) obtained in accordance with the method described in Examples 1 to 5 in a mixture of THF (20 ml) and DMF (2 ml), TEA (0.36 ml, 2.57 mmol) and then propanesulfonic acid chloride (0.33 ml, 2.57 mmol) was added dropwise under cooling with ice. The resulting reaction solution was stirred under cooling with ice for 30 minutes and poured into a liquid mixture of ethyl acetate and water. The organic layer was washed successively with 1N aqueous potassium hydrogensulfate and saturated aqueous sodium chloride, dried over anhydrous sodium sulfate, and concentrated in vacuo. To the solution of the resulting yellow oil in acetone (10 ml), sodium iodide (630 mg, 4.20 mmol) was added under cooling with ice. The resulting reaction solution was stirred at the same temperature for 20 minutes, concentrated in vacuo, and poured into a liquid mixture of ethyl acetate with water. The organic layer was separated, washed successively with 2% aqueous sodium thiosulfate and saturated aqueous sodium chloride, dried over anhydrous sodium sulfate, and concentrated in vacuo. To a solution of the resulting yellow oil in acetonitrile (30 ml), 1-carbamoylmethyl-1,4-diazabicyclo[2.2.2]octanedium trifluoromethanesulfonate (3.2 g, 10 mmol) was added thereto. The resulting mixture was stirred at room temperature overnight and then the solvent was distilled off. To a solution of the residue in a mixture of 0.25 mol MOPS buffer (pH 7.0, 80 ml), THF (80 ml) and ethanol (4 ml), 10% palladium carbon (2.0 g) was added. Catalytic reduction was conducted at room temperature under the atmospheric pressure of hydrogen for 4 hours. After the catalyst was filtered off, the filtrate was concentrated in vacuo. The resulting aqueous solution was washed with ethyl acetate and then concentrated in vacuo. To the solution, sodium chloride was added and it was stirred for 10 minutes, and then the excess sodium chloride and the insolubles formed in small amounts were filtered off. The filtrate was purified by reverse phase column chromatography (14 ml, 1–2% aqueous THF solution) and lyophilized to give the title compound (209 mg, yield: 13%).

IR(KBr)cm$^{-1}$: 3444,2362,1747,1690,1651,1568,1541,1400

$^1$H-NMR(D$_2$O)δ: 1.11(3 H,d,J=7.3 Hz),1.27(3 H,d,J=6.7 Hz), 1.47(1 H,m),2.60(1 H,m),2.88(2 H,m),3.27(2 H,m), 3.41(1 H,dd,J=2.7 & 6.0 Hz),3.60(1 H,dd,J=6.6 & 12.5 Hz), 3.83(1 H,m),3.90(1 H,m),4.04(2 H,s),4.11–4.30(14 H,m), 4.41(2 H,s),5.00(2 H,s),7.64(2 H,dd,J=8.2 & 10.2 Hz), 7.94(1 H,s),8.07(2 H,dd,J=5.7 & 8.6 Hz),8.15(1 H,s)

UVλ$_{max}$(0.1M MOPS buffer, pH7.0): 290 nm(ε=12000)

In the following Examples 119 and 120, compounds represented by the formula (A) which have substituents R$_1$ and R$_2$ were synthesized in the same manner as in Example 118.

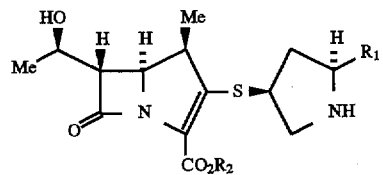

(A)

Example 119

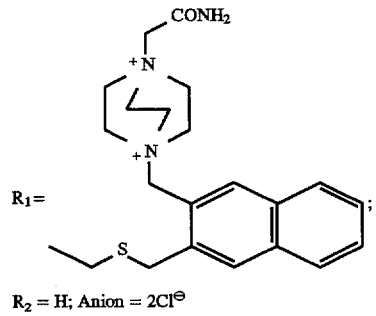

R$_2$ = H; Anion = 2Cl$^\ominus$

IR(KBr)cm$^{-1}$: 3361,1749,1697,1392,858,763

$^1$H-NMR(D$_2$O)δ: 1.06(3 H,d,J=7.0 Hz),1.23(3 H,d,J=6.4 Hz), 1.30(1 H,m),2.38(1 H,m),2.82(2 H,m),3.18(2 H,m), 3.36(1 H,m),3.50(1 H,dd,J=6.5 & 12.4 Hz),3.62(1 H,m), 3.78(1 H,m),4.10–4.21(14 H,m),4.37(2 H,s),5.15(2 H,s), 7.67(2 H,m),7.97(3 H,m),8.19(1 H,s)

UVλ$_{max}$(0.1M MOPS buffer, pH7.0): 300 nm(ε=8640)

Example 120

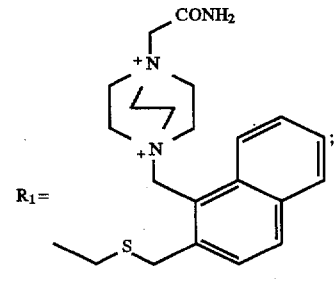

R$_2$ = H; Anion = 2Cl$^\ominus$

IR(KBr)cm$^{-1}$: 3403,1743,1693,1647,1549,1407,1267

$^1$H-NMR(D$_2$O)δ: 0.93(3 H,d,J=7.3 Hz),1.12(3 H,d,J=7.0 Hz), 2.62(1 H,m),3.20(2 H,m),3.39(2 H,m),3.66(2 H,m), 4.15(12 H,m),4.33(2 H,m),4.57(2 H,s),7.64–8.20(6 H,m), 1.20(1 H,m),2.90(2 H,m)

UVλ$_{max}$(0.1M MOPS buffer, pH7.0): 295 nm(ε=9620)

Example 121

(1R,5S,6S)-2-[(3S,5S)-5-[4-(Aminomethyl)anilinomethyl]-pyrrolidin-3-ylthio]-6-[(R)-1-hydroxyethyl]-1-methyl-1-carbapen-2-em-3-carboxylic acid monohydrochloride

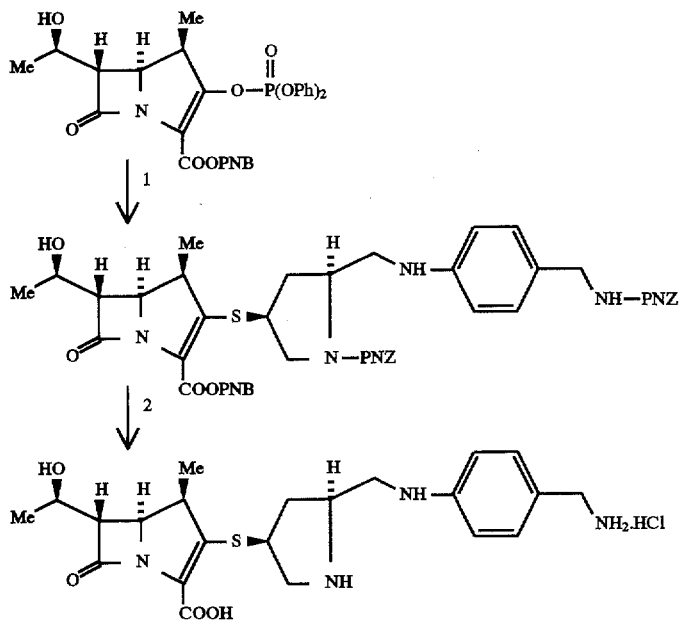

(Step 1)

To a solution of (2S,4S)-N-(p-nitrobenzyloxycarbonyl)-2-[4-[N-(p-nitrobenxyloxycarbonyl)aminomethyl]anilinomethyl]-4-tritylthiopyrrolidine (1.55 g, 1.85 mmol) in methylene chloride (15 ml), trifluoroacetic acid (1.37 ml, 1.85 mmol) and triethylsilane (0.443 ml, 2.78 mmol) were successviely added dropwise at 0° C. in a nitrogen steam. The reaction solution was stirred for 3 hours, then diluted with water and chloroform, and adjusted to pH 6.7 with potassium carbonate. The organic layer was washed with saturated aqueous sodium chloride, dried over anhydrous magnesium sulfate, and then concentrated in vacuo to give a crude product of (2S,4S)-4-mercapto-N-(p-nitrobenzyloxycarbonyl)-2-[4-[N-(p-nitrobenzyloxycarbonyl)aminomethyl]anilinomethyl]-pyrrolidine.

To a solution of p-nitrobenzyl (1R,5S,6S)-2-diphenoxyphosphoryloxy-6-[(R)-1-hydroxyethyl]-1-methyl-1-carbapen-2-em-3-carboxylate (1.10 g, 1.85 mmol) and the above crude product in acetonitrile (30 ml), N,N-diisopropylethylamine (0.644 ml, 3.70 mmol) was added dropwise in a nitrogen stream under cooling with ice. The resulting reaction solution was stirred at the same temperature for 24 hours. Then, water was added to terminate the reaction, and the mixed solution was extracted with ethyl acetate. The organic layer was washed with saturated aqueous sodium chloride and dried over anhydrous magnesium sulfate, and concentrated in vacuo. The resulting residue was Subjected to silica gel column chromatography (Wakogel™ C-300, ethyl acetate) to give p-nitrobenzyl (1R,5S,6S)-6-[(R)-1-hydroxyethyl]-1-methyl-2-[(3S,5S)-5-[4-[N-(p-nitrobenzyloxycarbonyl)aminomethyl]-anilinomethyl] pyrrolidin-3-ylthio]-1-carbapen-2-em-3-carboxylate (913 mg, yield: 52.5%).

$^1$H NMR(CDCl$_3$)δ: 1.28(3 H,d,J=6.8 Hz),1.37(3 H,d,J=6.2 Hz), 1.80–2.01(1 H,m),2.54–2.69(1 H,m),3.25–3.41(4 H,m),3.43–3.73(2 H,m),3.80–4.60(6 H,m),5.04–5.14(1 H,m),5.19–5.30(5 H,m),5.51(1 H,d,J=13.8 Hz),6.40–6.65(2 H,m),6.94– 7.11(2 H,m),7.51(2 H,d,J=8.7 Hz),7.65(2 H,d, J=8.8 Hz), 8.21(2 H,d,J=8.7 Hz),8.21(2 H,d,J=8.8 Hz)

(Step 2)

To a solution of the compound (400 mg, 0.426 mmol) obtained in Step 1 in tetrahydrofuran (30 ml), 0.2N sodium 3-morpholinopropanesulfonate buffer (15 ml, pH 6.5) and 10% palladium-carbon (400 mg) were added. The resulting mixed solution was stirred vigorously in a hydrogen stream at room temperature for 20 hours. After the catalyst was filtered off, the organic solvent was concentrated in vacuo to obtain an aqueous solution. The insolubles were filtered off and then the filtrate was adjusted to pH 7.0 with 1N aqueous sodium hydroxide. The solution was subjected to reverse phase column chromatography (YMC.GEL™ODS-AQ-120-S50, 14 ml, methanol-water 25:75). The fractions containing the desired product were concentrated and lyophilized to give the title compound (78.6 mg, yield: 38.2%).

IR(KBr) cm$^{-1}$: 1751,1614,1531,1389,1265

$^1$H NMR(D$_2$O)δ: 1.17(3 H,d,J=7.1 Hz),1.24(3 H,d,J=6.5 Hz), 1.69–1–82(1 H,m),2.65–2.79(1 H,m),3.15–3.45(3 H,m),3.48–3.70(3 H,m),3.84–4.13(2 H,m),4.02(2 H,s), 4.14–4.23(2 H,m),6.79(2 H,d,J=8.6 Hz),7.26(2 H,d,J=8.6 Hz)

In the following Examples 122 to 124, compounds represented by the formula (C) which have substituents R$_5$ and R$_6$ were synthesized in the same manner as in Example 121.

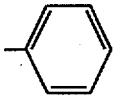

| Ex. No. | $R_5$ | $R_6$ | IR (KBr) cm$^{-1}$ | $^1$H NMR (D$_2$O) δ | Remarks |
|---|---|---|---|---|---|
| 122 | (phenyl) | H | 1755, 1600 | 1.21(3H, d, J=7.0Hz), 1.28(3H, d, J=6.3Hz), 1.70–2.00(1H, m), 3.30–3.50(4H, m), 3.50–3.60(2H, m), 3.70–3.80(4H, m), 3.90–4.10(1H, m), 4.20–4.30(1H, m), 6.70–6.90 (3H, m), 7.20–7.40(2H, m), | Mono-hydrochloride |
| 123 | (3-COOH-phenyl) | H | 1749, 1589 | 0.80–1.00(1H, m), 1.21(3H, d, J=7.1Hz), 1.28(3H, d, J=6.3Hz), 1.50–2.50(3H, m), 2.70–3.10.(1H, m), 3.20–3.50(4H, m), 3.50–3.70 (3H, m), 3.80–4.10(3H, m), 4.20–4.30 (2H, m), 6.8–7.0(1H, m), 7.2–7.4 (3H, m), | — |
| 124 | (3-COOMe-phenyl) | H | 1754, 1716, 1591 | 1.21(3H, d, J=7.4Hz), 1.28(3H, d, J=6.4Hz), 1.70–1.90(1H, m), 2.70–2.90(1H, m), 3.20–3.50 (4H, m), 3.50–3.70(3H, m), 3.90(3H, s), 4.00–4.10(2H, m), 4.20–4.30(2H, m), 4.60–5.00(3H, m), 7.00–7.10 (1H, m), 7.30–7.50(3H, m), | — |

In the following Example 125, compounds represented by the formula (B) which have substituents $R_3$ and $R_4$ were synthesized in the same manner as in Example 121.

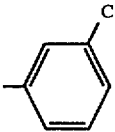

Example 125

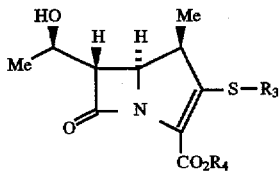

$R_4 = H$

Diastereomer A

IR(KBr)cm$^{-1}$: 1741,1565,1340

$^1$H-NMR(D$_2$O)δ: 0.97(3 H,d,J=7 Hz),1.15(3 H,d,J=6 Hz), 4.05(2 H,m),4.41(1 H,m),6.75–6.92(3 H,m),7.20–7.32(2 H,m)

UVλ$_{max}$(0.1M MOPS buffer, pH7.0 ): 300 nm(ε=8630 )

Diastereomer B

IR(KBr)cm$^{-1}$: 1739,1533,1402

$^1$H-NMR(D$_2$O)δ: 0.94(3 H,d,J=7 Hz),1.25(3 H,d,J=6 Hz), 4.20(2 H,m),6.80–6.95(3 H,m),7.20–7.35(2 H,m)

UVλ$_{max}$(0.1M MOPS buffer, pH7.0): 300 nm(ε=5080)

In the following Example 126, a compound represented by the formula (A) which has substituents $R_1$ and $R_2$ was synthesized in the same manner as in Example 121.

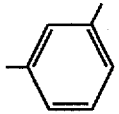

Example 126

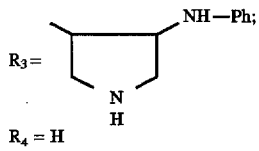

$R_2$ = H; Monohydrochloride

IR(KBr)cm$^{-1}$: 3382,2967,1751,1583,1537,1446,1390

$^1$H-NMR(D$_2$O)δ: 1.13(3 H,d,J=6.3 Hz),1.22(3 H,d,J=6.3 Hz),1.75– 1.89(1 H,m),2.67–2.84(1 H,m),3.20–3.44(3 H,m) ,3.58–3.77(3 H,m),3.95–4.23(4 H,m),4.50(2 H,s), 6.71(1 H,d,J=7.9 Hz),7.46(1 H,d,J=7.8 Hz),7.57–7.68(2 H,m), 7.97(1 H,d,J=8.3 Hz),8.08(1 H,d,J=8.2 Hz)

UVλ$_{max}$(0.1M MOPS buffer, pH7.0): 300 nm(ε=13400)

Example 127

(1R,5S,6S)-2-[(3S,5S)-5-[4-(Aminomethyl) phenoxymethyl]-pyrrolidin-3-ylthio]-6-[(R)-1-hydroxyethyl]-1-methyl-1-carbapen-2-em-3-carboxylic acid monohydrochloride

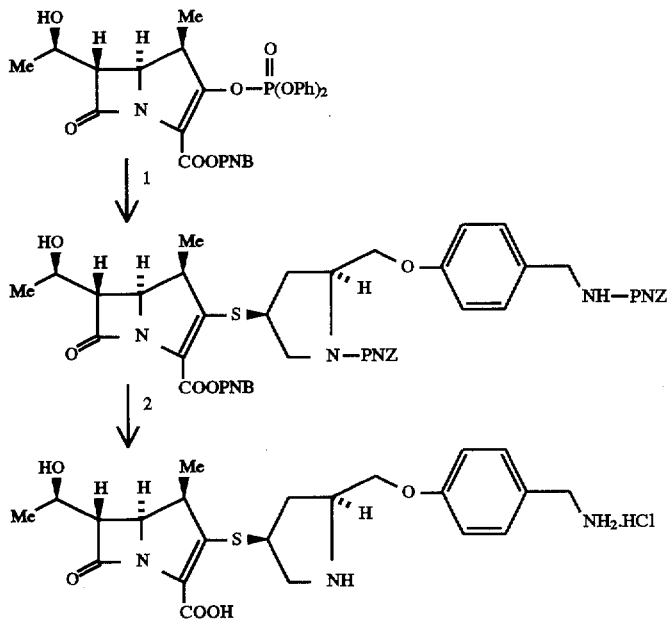

(Step 1)

To a solution of (2S,4S)-4-acetylthio-N-(p-nitrobenzyloxycarbonyl)-2-[4-[N-(p-nitrobenzyloxycarbonyl)aminomethyl]phenoxymethyl]-pyrrolidine (786 mg, 1.23 mmol) in tetrahydrofuranmethanol (1:1, 20 ml), 1N aqueous sodium hydroxide (1.48 ml, 1.48 mmol) was added in a nitrogen stream under cooling with ice. The reaction solution was stirred at 2 hours, and 1N hydrochloric acid (1.6 ml, 1.6 mmol) was added thereto. The resulting mixed solution was extracted with ethyl acetate. The extract was washed with saturated aqueous sodium chloride and dried over anhydrous sodium sulfate. The solvent was distilled off in vacuo to obtain a crude product of (2S,4S)-4-mercapto-N-(p-nitrobenzyloxycarbonyl)-2-[4-[N-(p-nitrobenzyloxycarbonyl)aminomethyl]phenoxymethyl]-pyrrolidine.

To a solution of the above crude product and p-nitrobenzyl (1R,5S,6S)-2-diphenoxyphosphoryloxy-6-[(1R)-1-hydroxyethyl]-1-methyl-1-carbapen-2-em-3-carboxylate (731 mg, 1.23 mmol) in acetonitrile (20 ml), N,N-diisopropylethylamine (0.257 ml, 1.48 mmol) was added dropwise in a nitrogen stream under cooling with ice. The resulting mixed solution was stirred at the same temperature for 14 hours. To the reaction solution, water was added to terminate the reaction. And the mixed solution was extracted with ethyl acetate. The extract was washed with saturated aqueous sodium chloride and then dried over anhydrous magnesium sulfate. The solvent was distilled off in vacuo and the resulting residue was subjected to silica gel chromatography (Wakogel™ C-300, heptane-ethyl acetate= 1:9) to give p-nitrobenzyl (1R,5S,6S)-6-[(R)-1-hydroxyethyl]-1-methyl-2-[(3S,5S)-N-(p-nitrobenzyloxycarbonyl)-5-[4-[N-(p-nitrobenzyloxycarbonyl)aminomethyl]phenoxymethyl]-pyrrolidin-3-ylthio]-1-carbapen-2-em-3-carboxylate (947 mg, yield: 81.8%).

$^1$H-NMR(CDCl$_3$)δ: 1.28(3 H,d,J=7.1 Hz),1.38(3 H,d,J= 6.3 Hz), 2.10–2.27(1 H,m),2.55–2.70(1 H,m),3.25–3.46(3 H,m),3.62–3.78(1 H,m),4.00–4.22(2 H,m),4.23–4.36(2 H,m), 4.33(2 H,d,J=5.9 Hz),5.12–5.37(5 H,m), 5.51(1 H,d, J=14.0 Hz),6.71–6.91(2 H,m),7.13–7.24(2 H,m), 7.42–7.57(4 H,m),7.66(2 H,d,J=8.8 Hz),8.07–8.30(4 H,m), 8.21(2 H,d,J=8.8 Hz)

(Step 2)

To a solution of the compound (420 mg, 0.446 mmol) obtained in the preceding step in tetrahydrofuran (30 ml), 0.2N sodium 3-morpholinopropanesulfonate buffer (15 ml, pH 6.5) and 10% palladium-carbon catalyst (400 mg) were added. The resulting mixed solution was stirred vigorously in a hydrogen stream at room temperature for 16 hours. The catalyst was separated from the reaction mixture by filtration and the filtrate was concentrated in vacuo to obtain an aqueous solution. The insolubles were filtered off and the filtrate was adjusted to pH 7.0 with 1N aqueous sodium hydroxide and then subjected to reverse phase column chromatography (YMC.GEL™ODS-AQ-120-S50, 14 ml; methanol-water 3:7). The fractions containing the desired product were concentrated and lyophilized to give the title compound (109 mg, yield: 54.4%).

IR(KBr)cm$^{-1}$: 1753,1610,1516,1392,1248

$^1$H-NMR(D$_2$O)δ: 1.19(3 H,d,J=7.2 Hz),1.25(3 H,d,J=6.5 Hz), 1.85–1.97(1 H,m),2.70–2.83(1 H,m),3.30–3.46(3 H,m), 3.68(1 H,dd,J1=12.0 Hz,J2=6.0 Hz),4.00–4.30(5 H,m),4.10(2 H,s),4.35–4.41(1 H,m), 7.06(2 H,d,J=8.7 Hz), 7.39(2 H,d,J=8.7 Hz)

Example 128

(1R,5S,6S)-6-[(R)-1-Hydroxyethyl]-1-methyl-2-[(3S,5S)-5-(phenoxymethyl)pyrrolidin-3-ylthio]-1-carbapen-2-em-3-carboxylic acid

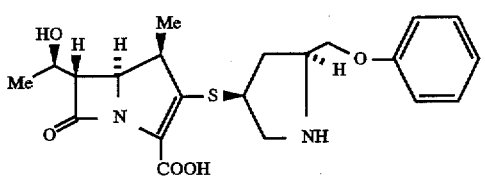

The title compound was prepared in the same manner as in Example 127.

IR(KBr)cm$^{-1}$: 3400,1750,1590

$^1$H-NMR(DMSO-d$_6$)δ: 1.09(3 H,d,J=6.7 Hz), 1.13(3 H,d, J=6.1 Hz),2.35–2.53(2 H,m),2.78–2.85(1 H,m),3.10–3.25(2 H,m),3.30–3.80(3 H,m),3.85–4.05(3 H,m),4.05–4.12(1 H,m),6.87–6.95(3 H,m),7.22–7.30(2 H,m)

UVλ$_{max}$(0.1M MOPS buffer, pH7.0): 296 nm(ε=6310)

Example 130

(1R,5S,6S)-2-[(3S,5R)-5-(4-Aminomethylphenethyl) pyrrolidin-3-ylthio]-6-[(R)-1-hydroxyethyl]-1-methyl-1-carbapen-2-em-3-carboxylic acid monohydrochloride

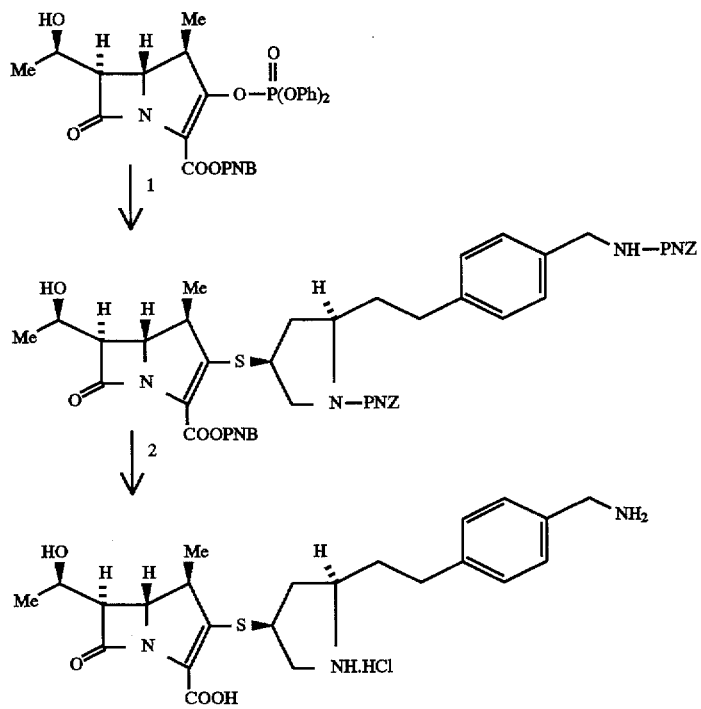

In the following Example 129, compounds represented by the formula (B) which have substituents R$_3$ and R$_4$ were synthesized in the same manner as in Example 127.

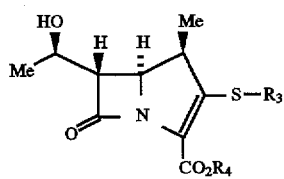

(B)

Example 129

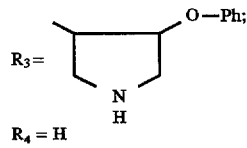

R$_4$ = H

Diastereomer A

IR(KBr)cm$^{-1}$: 1751,1597,1394

$^1$H-NMR(D$_2$O)δ: 1.15(3 H,d,J=7 Hz),1.26(3 H,d,J=6 Hz), 3.77(1 H,m),4.20(1 H,m),5.30(1 H,m),7.08(7 H,m), 7.38(2 H,m)

UVλ$_{max}$(0.1M MOPS buffer, pH7.0): 299 nm(ε=6790)

Diastereomer B

IR(KBr)cm$^{-1}$: 1751,1596,1394

$^1$H-NMR(D$_2$O)δ: 1.00(3 H,d,J=7 Hz),1.08(3 H,d,J=6 Hz), 5.13(1 H,m),6.97(3 H,m),7.31(2 H,m)

(Step 1)

To a solution of (2S,4S)-4-acetylthio-N-(p-nitrobenzyloxycarbonyl)-2-[4-[N-(p-nitrobenzyloxycarbonyl)aminomethyl]phenethyl] pyrrolidine (495 mg, 0.777 mmol) in tetrahydrofuran-methanol (2:1, 15 ml), 1N aqueous sodium hydroxide (1.5 ml, 1.5 mmol) was added in a nitrogen stream under cooling with ice. After this reaction solution was stirred at the same temperature for 2 hours, 1N aqueous hydrochloric acid (2.0 ml, 2.0 mmol) was added thereto, and this mixed solution was extracted with ethyl acetate. The organic layer was washed with saturated aqueous sodium chloride and dried over anhydrous magnesium sulfate. The solvent was distilled off in vacuo to give a crude product of (2R,4S)-4-mercapto-N-(p-nitrobenzyloxycarbonyl)-2-[4-[N-(p-nitrobenzyloxycarbonyl)aminomethyl]phenethyl]-pyrrolidine.

To a solution of the above crude product and p-nitrobenzyl (1R,5S,6S)-2-diphenoxyphosphoryloxy-6-[(R)-1-hydroxyethyl]-1-methyl-1-carbapen-2-em-3-carboxylate (460 mg, 0.777 mmol) in acetonitrile (10 ml), N,N-diisopropylethylamine (0.176 ml, 1.01 mmol) was added in a nitrogen stream under cooling with ice. The reaction solution was stirred for 12 hours, brought together with water to terminate the reaction, and then extracted with ethyl acetate. The organic layer was washed with saturated aqueous sodium chloride and dried over anhydrous magnesium sulfate. The solvent was distilled off in vacuo and the residue was subjected to silica gel chromatography (Wakogel™ C-300, heptane-ethyl acetate=1:4) to give p-nitrobenzyl (1R,5S,6S)-6-[(R)-1-hydroxyethyl]-1-methyl-2-[(3S,5R)-N-(p-nitrobenzyloxycarbonyl)-5-[4-[N-(p-nitrobenzyloxycarbonyl)aminomethyl]phenethyl] pyrrolidin-3-ylthio]-1-carbapen-2-em-3-carboxylate (512 mg, yield: 70.1%).

$^1$H-NMR(CDCl$_3$)δ: 1.27(3 H,d,J=6.8 Hz),1.38(3E,d,J=6.0 Hz), 1.60–1.90(2 H,m),2.10–2.70(4 H,m),3.20–3.45(3 H,m),3.50–3.66(1 H,m),3.89–4.50(4 H,m),4.36(2 H,d,J=5.9 Hz),5.10–5.40(5 H,m),5.50(1 H,d,J=14 Hz),7.00–7.30(4 H,m),7.40– 7.60(4 H,m),7.65(2 H,d,J=8.6 Hz),8.10–8.40(6 H,m)

(Step 2)

To a solution of the compound (306 mg, 0.326 mmol) obtained in the preceding step in tetrahydrofuran (20 ml), 0.2M sodium 3-morpholinopropanesulfonate buffer (10 ml, pH 6.5) and 10% palladium-carbon catalyst (300 mg) were added. This reaction solution was stirred vigorously in a hydrogen stream at room temperature for 16 hours. The catalyst was separated from the reaction solution by filtration and the filtrate was concentrated in vacuo to obtain an aqueous solution. The insolubles were filtered off and the filtrate was subjected to reverse phase column chromatography (YMC.GEL™ODS-AQ-120-S50, 14 ml; methanol-water 35:75). The fractions containing the desired product were concentrated and lyophilized to give the title compound (80.2 mg, yield: 51.1%).

IR(KBr)cm$^{-1}$: 1751,1579,1392

$^1$H-NMR(D$_2$O)δ: 1.15(3 H,d,J=7.1 Hz),1.24(3 H,d,J=6.3 Hz), 1.56–1.70(1 H,m),1.99–2.22(2 H,m),2.62–2.73(3 H,m), 3.25–3.44(3 H,m),3.55–3.75(2 H,m),3.90–4.00(1 H,m),4.12(2 H,s),4.10–4.26(2 H,m), 7.32(2 H,d,J=8.2 Hz), 7.37(2 H,d,J=8.2 Hz)

In the following Example 131 to 134, compounds represented by the formula (D) which have substituents R$_7$ and R$_8$ were synthesized in the same manner as in Example 130.

| Ex. No. | R$_7$ | R$_8$ | IR (KBr) cm$^{-1}$ | $^1$H NMR (D$_2$O) δ | Remarks |
|---|---|---|---|---|---|
| 131 | (4-ethylbenzyl-NH$_2$) | H | 1756, 1585, 1388 | 1.20(3H, d, J=7.3Hz), 1.28(3H, d, J=6.4Hz), 1.80(1H, m), 2.20 (1H, m), 2.70(1H, m), 3.00(1H, t, J=7.3Hz), 3.20(1H, m), 3.22–3.50(3H, m), 3.65(1H, m), 3.85–4.10(2H, m), 4.19(2H, s), 4.22(1H, m), 7.36–7.52(4H, m) | Mono-hydro-chloride |
| 132 | (3-ethylbenzyl-NH$_2$) | H | 1753, 1612, 1571, 1390 | 1.21(3H, d, J=7.3Hz), 1.29(3H, d, J=6.3Hz), 1.80(1H, m), 2.70 (1H, m), 3.12–3.52(6H, m), 3.65(1H, m), 3.90–4.10(2H, m), 4.20(2H, s), 4.25(1H, m), 7.35–7.55(4H, m) | Mono-hydro-chloride |
| 133 | (ethylbenzene) | H | 1753, 1593 | 1.22(3H, d, J=7.1Hz), 1.29(3H, d, J=6.6Hz), 1.79(1H, m), 2.71 (1H, m), 3.18(2H, m), 3.40(4H, m), 3.63(2H, m), 3.98(2H, m), 4.22(2H, m), 7.37(15H, m) | — |
| 134 | (propylbenzene) | H | 1750, 1590, 1450 | 1.20(3H, d, J=7.3Hz), 1.29(3H, d, J=6.4Hz), 1.70–1.80(1H, m), 2.00–2.20(2H, m), 2.70–2.80(3H, m), 3.30–3.40(2H, m), 3.50(1H, m), 3.60–3.70 (2H, m), 3.90–4.00(1H, m), 4.20–4.30(2H, m), 7.20–7.50 (5H, m) | — |

Example 135

(1R,5S,6S)-2-[(3S,5R)-5-(4-Aminomethyl-1-naphthylmethyl)-pyrrolidin-3-ylthio]-6-[(R)-1-hydroxyethyl]-1-methyl-1-carbapen-2-em-3-carboxylic acid monohydrochloride

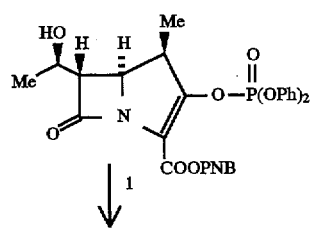

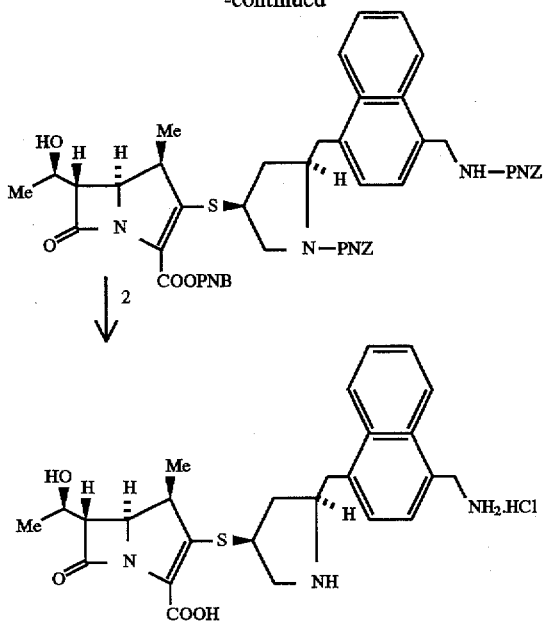

(Step 1)

To a solution of (2R,4S)-4-acetylthio-N-(p-nitrobenzyloxycarbonyl)-2-[4-(p-nitrobenzyloxycarbonylaminomethyl)-1-naphthylmethyl]pyrrolidine (144 mg, 0.21 mmol) in methanol-tetrahydrofuran (3:1) (4 ml), 1N aqueous sodium hydroxide (0.24 ml, 0.24 mmol) was added in a nitrogen stream under cooling with ice. This reaction solution was stirred for 10 minutes and then 1N hydrochloric acid (0.24 ml, 0.24 mmol) was added thereto. Then the resulting solution was concentrated in vacuo. The resulting residue was poured into a liquid mixture of ethyl acetate with water. The organic layer was washed with saturated aqueous sodium chloride, dried over anhydrous sodium sulfate, and concentrated in vacuo to give a crude product of (2R,4S)-4-mercapto-N-(p-nitrobenzyloxycarbonyl)-2-[4-(p-nitrobenzyloxycarbonylaminomethyl)-1-naphthylmethyl]-pyrrolidine as a yellow oily substance.

To a solution of p-nitrobenzyl (1R,5S,6S)-2-diphenoxyphosphoryloxy-6-[(1R)-1-hydroxyethyl]-1-methyl-1-carbapen-2-em-3-carboxylate (127 mg, 0.21 mmol) in acetonitrile (3 ml), a solution of the above crude product in acetonitrile (2 ml) and N,N-diisopropylethylamine (45 μl, 0.26 mmol) were successively added dropwise in a nitrogen stream under cooling with ice. The reaction solution was stirred at the same temperature for 18 hours and then concentrated in vacuo. The resulting residue was poured into a liquid mixture of ethyl acetate with water. The organic layer was washed with saturated aqueous sodium chloride, dried over anhydrous sodium sulfate, and concentrated in vacuo. The resulting residue was subjected to silica gel column chromatography (Wakogel™ C-300, heptane-ethyl acetate 1:2) to give p-nitrobenzyl (1R,5S,6S)-6-[(1R)-1-hydroxyethyl]-1-methyl-2-[(3S,5R)-N-(p-nitrobenzyloxycarbonyl)-5-[4-(p-nitrobenzyloxycarbonylaminomethyl)-1-naphthylmethyl]pyrrolidin-3-ylthio]-1-carbapen-2-em-3-carboxylate (173 mg, yield: 82.9%) as a yellow powder.

¹H-NMR(CDCl₃)δ: 1.23(3 H,m),1.37(3 H,d,J=7.1 Hz), 1.84(1 H,m), 2.16(1 H,m),3.27(1 H,m),3.34(1 H,m),3.49(1 H,m), 3.63(1 H,m),3.81–4.10(2 H,m),4.26(2 H,m),4.39(1 H,m), 4.82(2 H,m),5.24(4 H,m),5.32(1 H,m),5.51(1 H,m), 7.22(2 H,m),7.33(1 H,m),7.51(5 H,m),7.64(2 H,m), 8.01(2 H,m),8.19(5 H,m),8.51(1 H,m)

(Step 2)

To a solution of the compound (171 mg, 0.18 mmol) obtained in Step 1 in tetrahydrofuran (15 ml), 0.2N sodium 3-morpholinopropanesulfonate buffer (5 ml, pH 6.4) and 10% palladium-carbon catalyst (60 mg) were added. This reaction solution was stirred vigorously at room temperature at atmospheric pressure in a hydrogen stream for 21 hours. The catalyst was separated from the reaction solution by filtration and the filtrate was concentrated in vacuo to an aqueous solution. After the insolubles were filtered off, the filtrate was adjusted to pH 6.4 with 1N aqueous sodium hydroxide and subjected to reverse phase column chromatography (YMC.GEL™ODS-AQ-20-S50, 14 ml methanol-water 2:8). The fractions containing the desired product were concentrated and lyophilized to give the title compound (2.9 mg, yield: 3.4%).

IR(KBr)cm⁻¹: 3386,1753,1591

¹H-NMR(D₂O)δ: 0.98(3 H,d,J=7.1 Hz),1.10(3 H,d,J=7.0 Hz), 1.62(1 H,m),2.40(1 H,m),3.16(4 H,m),3.44(4 H,m), 3.73(1 H,m),3.79(1 H,m),3.99(2 H,m),7.42(2 H,m), 7.59(2 H,m),8.02(2 H,m)

Example 136

(5S,6S)-6-[(R)-1-Hydroxyethyl]-2-[(3S,5R)-5-(1-naphthylmethyl)pyrrolidin-3-ylthio]-1-carbapen-2-em-3-carboxylic acid

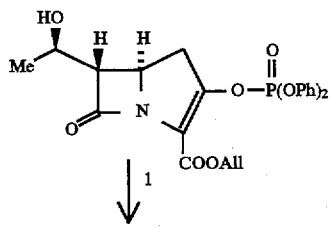

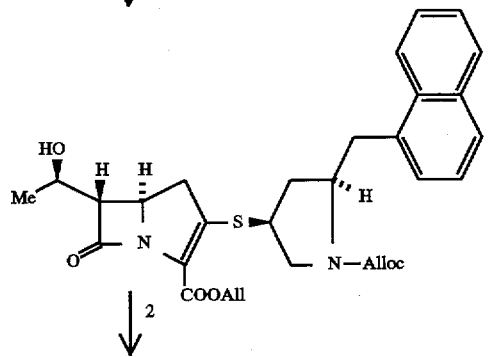

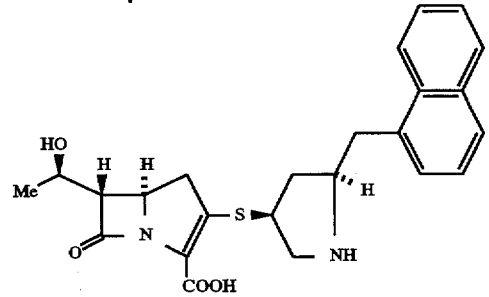

(Step 1)

Allyl (5R,6S)-2-[(3S,5S)-N-(allyloxycarbonyl)-5-(1-naphthylmethyl)pyrrolidin-3-ylthio]-6-[(1R)-1-hydroxyethyl]-1-carbapen-2-em-3-carboxylate (633 mg, yield: 70.1%) was prepared as a yellow powder, from (2R,4S)-4-acetylthio-N-allyloxycarbonyl-2-(1-naphthylmethyl)pyrrolidine (610 mg, 1.53 mmol), allyl (5R, 6S)-2-diphenoxyphosphoryloxy-6-[(1R)-1-hydroxyethyl]-1-carbapen-2-em-3-carboxylate (743 mg, 1.53 mmol), 1N aqueous sodium hydroxide (1.8 ml, 1.8 mmol), 1N aqueous hydrochloric acid (1.8 ml, 1.8 mmol) and N,N-diisopropylethylamine (800 μl, 4.59 mmol), in the same manner as in Example 135-1.

$^1$H-NMR(CDCl$_3$)δ: 1.32(3 H,d,J=7.2 Hz),1.81(1 H,m), 2.14(1 H,m), 3.03(4 H,m),3.49(2 H,m),4.26(5 H,m),4.72(4 H,m), 5.36(4 H,m),6.01(2 H,m),7.46(4 H,m),7.80(2 H,m), 8.36(1 H,m)

(Step 2)

To a solution of the compound (310 mg, 0.53 mmol) obtained in Step 1 in dichloromethane (10 ml), water (47 μl), bis(triphenylphosphine)palladium(II) chloride (18 mg, 0.026 mmol) and tributyltin hydride (352 μl, 1.31 mmol) were added in a nitrogen stream under cooling with ice. The resulting solution was stirred at the same temperature for 20 minutes. The reaction mixture was extracted with water (80 ml) and the aqueous layer was washed with chloroform twice. Then, the insolubles were filtered off. The filtrate was concentrated in vacuo to about 30 ml and the resulting residue was subjected to reverse phase column chromatography (YMC.GEL™ODS-AQ-120-S50 14 ml methanol-water 1:1). The fractions containing the desired product were concentrated and lyophilized to give the title compound (15.0 mg, yield: 5.6%).

IR(KBr)cm$^{-1}$: 1756,1592,1081

$^1$H-NMR(DMSO-d$_6$)δ: 1.10(3 H,m),1.51(1 H,m),2.22(1 H,m), 2.88–4.09(11 H,m),7.46(4 H,m),7.84(2 H,m),8.21(1 H,m)

Example 137

(1R,5S,6S)-2-[(3S,5R)-N-Allyl-5-(1-naphthylmethyl) pyrrolidin-3-ylthio]-6-[(R)-1-hydroxyethyl]-1-methyl-1-carbapen-2-em-3-carboxylic acid

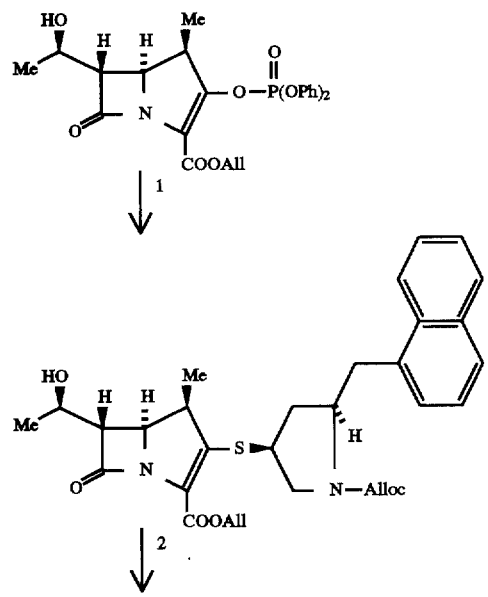

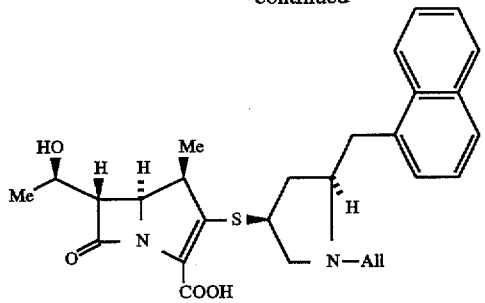

(Step 1)

Allyl (1R,5S,6S)-6-[(1R)-1-hydroxyethyl]-2-[(3S,5R)-N-(allyloxycarbonyl)-5-(1-naphthylmethyl)pyrrolidin-3-ylthio]-1-methyl-1-carbapen-2-em-3-carboxylate (564 mg, yield: 69.3%) was obtained from (2R,4S)-4-acetylthio-N-(allyloxycarbonyl)-2-(1-naphthylmethyl)pyrrolidine (536 mg, 1.34 mmol) and allyl (1R,5S,6S)-2-diphenoxyphosphoryloxy-6-[(1R)-1-hydroxyethyl]-1-carbapen-2-em-3-carboxylate (670 mg, 1.34 mmol) in the same manner as in Example 135-1.

$^1$H-NMR(CDCl$_3$)δ: 1.22(3 H,d,J=7.0 Hz),1.37(3 H,d,J= 6.6 Hz), 2.12(1 H,m),2.90(1 H,m),3.19–3.61(4 H,m), 3.96–4.44(6 H,m),4.62–4.91(4 H,m),5.21–5.50(4 H,m), 5.98(2 H,m),7.43(4 H,m),7.80(2 H,m),8.36(1 H,m)

(Step 2)

To a solution of the compound (564 mg, 0.93 mmol) obtained in Step 1 in dichloromethane (20 ml), water (84 μl), bis(triphenylphosphine)palladium(II) chloride (35 mg, 0.05 mmol) and tributyltin hydride (576 μl, 2.14 mmol) were added in a nitrogen stream under cooling with ice. The resulting solution was stirred at the same temperature for 20 minutes and concentrated in vacuo. To the resulting residue, 2.00 ml of water was added and the resulting aqueous solution was adjusted to pH 5.0 with 1N aqueous hydrochloric acid. This solution was subjected to reverse phase phase column chromatography (YMC.GEL™ODS-AQ-120-S50 methanol-water 1:1), and the fractions containing the desired product were concentrated and lyophilized to give the title compound (104 mg, yield: 23%).

IR(KBr)cm$^{-1}$: 1754,1592

$^1$H-NMR(DMSO-d$_6$)δ: 1.03(3 H,d,J=6.8 Hz),1.14(3 H,d, J=6.6 Hz), 1.40(1 H,m),1.96(1 H,m),2.40–4.10(12 H,m), 5.20(2 H,m), 5.90(1 H,m),7.46(4 H,m),7.82(2 H,m),8.06(1 H,m)

Example 138

(1R,5S,6S)-2-[5-(4'-Aminomethyl-4-biphenylmethyl) pyrrolidin-3-ylthio]-6-[(R)-1-hydroxyethyl]-1-methyl-1-carbapen-2-em-3-carboxylic acid monohydrochloride

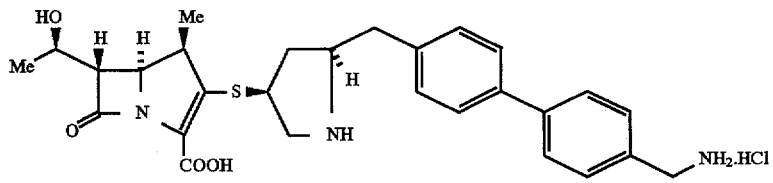

The title compound was prepared in the same manner as in Example 135.

IR(KBr)cm$^{-1}$: 1755,1628

$^1$H-NMR(DMSO-d$_6$)δ: 0.80(3 H,d,J=6.6 Hz),0.87(3 H,d, J=6.0 Hz), 1.40–1.43(1 H,m),2.29–2.34(1 H,m),2.79–3.06(5 H,m),3.22–3.29(1 H,m),3.58–3.61(2 H,m),3.79–3.85(4 H,m),7.04–7.38(8 H,m)

In the following Example 139, compounds represented by the formula (B) which have substituents R$_3$ and R$_4$ were synthesized in the same manner as in Example 135.

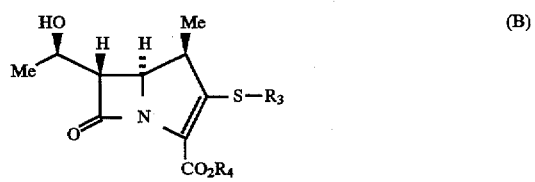

Example 139

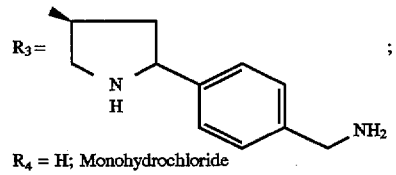

R$_4$ = H; Monohydrochloride

Diastereomer A
IR(KBr)cm$^{-1}$: 1749,1652,1558

$^1$H-NMR(D$_2$O)δ: 1.22(3 H,d,J=7 Hz),1.27(3 H,d,J=6 Hz), 2.14(1 H,m),3.00(1 H,m),3.39(1 H,m),3.46(2 H,m), 3.80(1 H,m),4.14(1 H,m),4.20(2 H,s),4.24(1 H,m), 7.52(2 H,d,J=8 Hz),7.55(2 H,d,J=8 Hz)

UVλ$_{max}$(0.1M MOPS buffer, pH7.0): 298 nm(ε=9910)

Diastereomer B

IR(KBr)cm$^{-1}$: 1749,1646,1558

$^1$H-NMR(D$_2$O)δ: 1.22(3 H,d,J=7 Hz),1.27(3 H,d,J=6.5 Hz), 2.51(1 H,m),2.73(1 H,m),3.30–3.50(3 H,m), 3.86(1 H,dd,J=12.5 & 6 Hz),4.20–4.30(5 H,m), 5.03(1 H,dd,J=10.5 & 7 Hz),7.52(4 H,br s)

UVλ$_{max}$(0.1M MOPS buffer, pH7.0): 298 nm(ε=9520)

Example 140

(1R,5S,6S)-2-[(3S,5S)-5-[[4'-Aminomethyl-4-biphenyl] hydroxymethyl]pyrrolidin-3-ylthio]-6-[(R)-1-hydroxyethyl] -1-methyl-1-carbapen-2-em-3-carboxylic acid monohydrochloride diastereomer I

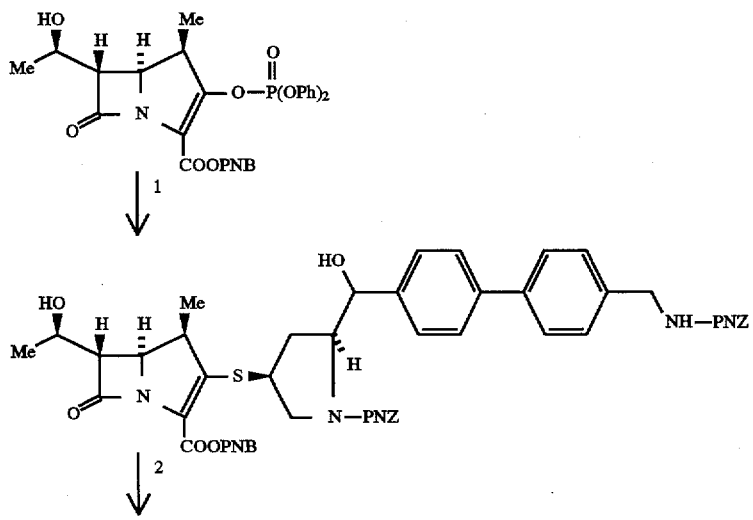

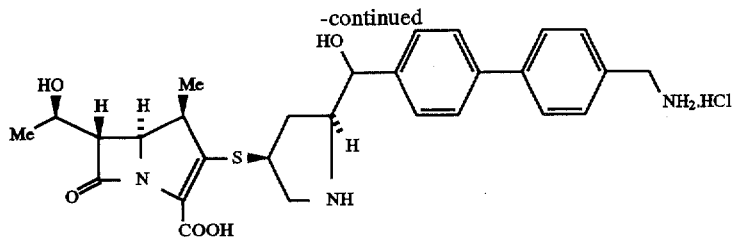

(Step 1)

To a solution of (2S,4S)-4-acetylthio-2-[hydroxy[4'-[(p-nitrobenzyloxycarbonylamino)methyl]-4-biphenyl]methyl]-N-(p-nitrobenzyloxycarbonyl)pyrrolidine diastereomer I (385 mg, 0.57 mmol) in methanol:dichloromethane (1:1, 20 ml), 1N aqueous sodium hydroxide (0.63 ml, 0.63 mmol) was added in a nitrogen stream under cooling with ice. This reaction solution was stirred for 30 minutes and then 1N aqueous hydrochloric acid (0.63 ml, 0.63 mmol) was added thereto. This reaction solution was poured into a liquid mixture of ethyl acetate with water. The organic layer was washed with saturated aqueous sodium chloride, dried over anhydrous sodium sulfate, and concentrated in vacuo to give a crude product of (2S,4S)-2-[hydroxy[4'-[(p-nitrobenzyloxycarbonylamino)methyl]-4-biphenyl]methyl]-4-mercapto-N-(p-nitrobenzyloxycarbonyl)pyrrolidine diastereomer I. To a solution of the crude product in acetonitrile (13 ml), p-nitrobenzyl (1R,5S,6S)-2-dipheonoxyphosphoryloxy-6-[(R)-1-hydroxyethyl]-1-methyl-1-carbapen-2-em-3-carboxylate (373.1 mg, 0.63 mmol) and then N,N-diisopropylamine (0.13 ml, 0.74 mmol) was added in a nitrogen stream under cooling with ice. The resulting reaction solution was stirred at the same temperature for 18 hours and then concentrated in vacuo. The resulting residue was poured into a liquid mixture of ethyl acetate with water. The organic layer was washed with saturated aqueous sodium chloride, dried over anhydrous sodium sulfate, and then concentrated in vacuo. The resulting oily residue was subjected to silica gel column chromatography (Wakogel™ C-300, 60 ml; ethyl acetate) to give p-nitrobenzyl (1R,5S,6S)-6-[(R)-1-hydroxyethyl]-2-[(3S,5S)-5-[hydroxy[4'-[(p-nitrobenzyloxycarbonylamino) methyl]-4-biphenyl]methyl]-N-(p-nitrobenzyloxycarbonyl) pyrrolidin-3-ylthio]-1-methyl-1-carbapen-2-em-3-carboxylate diastereomer I (434 mg, yield: 74.8%) as a pale yellow oily substance.

IR(KBr)cm$^{-1}$: 2969,2362,1770,1704,1521

$^1$H-NMR(CDCl$_3$)δ: 1.22–1.25(3 H,m),1.38(3 H,d,J=6.3 Hz),1.71– 1.75(1 H,m),2.09–2.26(2 H,m),3.12–3.51(4 H,m), 4.22–4.46(5 H,m),5.20–5.62(8 H,m),7.35–7.69(14 H,m),8.20–8.27(6 H,m)

(Step 2)

To a solution of the compound (430 mg, 0.42 mmol) obtained in Step 1 in tetrahydrofuran (40 ml), ethanol (20 ml), 0.1N sodium 3-morpholinopropanesulfonate buffer (20 ml, pH 6.5) and then 10% palladium carbon catalyst (150 mg) were added. Then, the reaction mixture was stirred vigorously in a hydrogen stream under pressure (45 psi) for 16 hours. The catalyst was separated from the reaction mixture by filtration. The filtrate was adjusted to pH 5.0 with 0.1N aqueous hydrochloric acid and then concentrated in vacuo to obtain an aqueous solution. The insolubles were filtered off and the filtrate was subjected to reverse phase column chromatography (YMC.GEL™ODS-AQ-120-S50, 14 ml acetonitrile-water=1:9). The fractions containing the desired compound were concentrated and lyophilized to give the title compound (137 mg, yield: 57.9%).

IR(KBr)cm$^{-1}$: 3781,2973,1751,1735,1491

$^1$H-NMR(D$_2$O)δ: 0.79(3 H,d,J=7.3 Hz),0.88(3 H,d,J=6.3 Hz),1.57–1.65(1 H,m),2.08–2.15(1 H,m),2.91–3.07(3 H,m), 3.28–3.35(1 H,m),3.57–3.85(6 H,m),4.78–4.80(2 H,m), 7.16–7.41(8 H,m)

In the following Examples 141 to 148, compounds represented by the formula (D) which have substituents $R_7$ and $R_8$ were synthesized in the same manner as in Example 140.

| Ex. No. | $R_7$ | $R_8$ | IR (nujol) | $^1$H-NMR (D$_2$O) δ | Remarks |
|---|---|---|---|---|---|
| 141 | (OH-CH(CH$_3$)-C$_6$H$_3$(Ph)-CH$_2$-NH$_2$) | H | 1749, 1583 | 1.21(3H, d, J=7.2Hz), 1.29 (3H, d, J=6.6Hz), 1.96(1H, m), 2.51(1H, m), 3.35(2H, m), 3.48(1H, m), 3.64(2H, m), 4.04(2H, m), 4.23(4H, m), 7.53(8H, m) | Monohydrochloride |

| Ex. No. | R₇ | R₈ | IR (nujol) | ¹H-NMR (D₂O) δ | Remarks |
|---|---|---|---|---|---|
| 142 | OH-CH(CH₃)- on naphthalen-1-yl with 4-CH₂NH₂ | H | 1751, 1587 | 1.16(3H, d, J=7.1Hz), 1.29 (3H, d, J=6.6Hz), 2.21(1H, m), 3.40(3H, m), 3.62(3H, m), 3.91 (3H, m), 4.21(3H, m), 7.74(4H, m), 8.20(2H, m) | Single substance Monohydrochloride |
| 143 | OH-CH(CH₃)- on naphthalen-2-yl | H | 1755, 1593 | 1.21 (6H, m), 1.97(1H, m), 2.34(1H, m), 3.01–4.30(9H, m), 5.20(1H, m), 7.66(3H, m), 8.02(4H, m) | — |
| 144A | OH-CH(CH₃)- on 3-(CH₂NH₂)phenyl | H | 1756, 1571, 1390 | 1.21(3H, d, J=6.0Hz), 1.30(3H, d, J=4.6Hz), 2.00(1H, m), 2.50(1H, m), 3.30–3.45(2H, m), 3.48(1H, m), 3.72(1H, m), 4.00(1H, m), 4.12 (1H, m), 4.20–4.35(4H, m), 5.19 (1H, d, J=6.0Hz), 7.45–7.60(4H, m) | Diastereomer A polar substance Monohydrochloride |
| 144B | OH-CH(CH₃)- on 3-(CH₂NH₂)phenyl | H | 1749, 1675, 1392 | 1.20(3H, d, J=7.2Hz), 1.30(3H, d, J=6.6Hz), 1.75(1H, m), 2.40(1H, m), 3.36(1H, m), 3.40–3.55(2H, m), 3.74(1H, m), 3.95–4.20(2H, m), 4.20–4.30(4H, m), 7.48–7.60 (4H, m) | Diastereomer B less polar substance Monohydrochloride |
| 145A | 2-(CH₂NH₂)phenyl-CH(OH)(CH₃)- | H | 1749, 1577, 1392 | 1.27(3H, d, J=7.4Hz), 1.33(3H, d, J=6.4Hz), 2.10(1H, m), 2.75(1H, m), 3.20(1H, m), 3.40–3.60(3H, m), 3.80–4.10(2H, m), 4.20–4.35 (3H, m), 4.45(1H, d, J=13.7Hz), 5.12(1H, d, J=8.0Hz), 7.52(2H, d, J=4.0Hz), 7.55–7.70(2H, m) | Diastereomer A polar substance Monohydrochloride |
| 145B | 2-(CH₂NH₂)phenyl-CH(OH)(CH₃)- | H | 1749, 1589, 1386 | 1.23(3H, d, J=7.1Hz), 1.33(3H, d, J=6.3Hz), 1.65(1H, m), 2.50(1H, m), 3.30–3.55(3H, m), 3.75(1H, m), 4.05(1H, m), 4.20–4.35(3H, m), 4.42(2H, s), 5.22(1H, d, J=9.3 Hz), 7.50–7.65(4H, m) | Diastereomer B less polar substance |
| 146 | OH-CH(CH₃)- on 4-(CH₂NH₂)phenyl | H | 1751, 1587, 1145 | 1.10(3H, d, J=7.4Hz), 1.20(3H, d, J=6.3Hz), 1.60(0.3H, m), 1.85 (0.7H, m), 2.35(1H, m), 3.28–3.40 (3H, m), 3.60(1H, m), 3.80–4.05 (2H, m), 4.08–4.25(4H, m), 4.90 (0.3H, d, J=8.7Hz), 5.08(0.7H, d, J= 5.4Hz), 9.83(4H, s) | Monohydrochloride Diastereomer A (polar substance): Diastereomer B (less polar substance) = 3:7 |

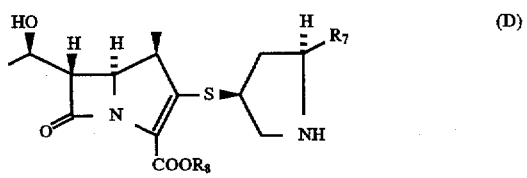

(D)

| 146A | OH-CH(CH₃)- on 4-(CH₂NH₂)phenyl | H | 1747, 1648, 1548 | 1.14(3H, d, J=6.6Hz), 1.23(3H, d, J=6.0Hz), 1.88–1.92(1H, m), 2.43–2.48(1H, m), 3.26–3.41 (3H, m), 3.60–4.05(3H, m), 4.15–4.21(4H, m), 5.11(1H, d, J=4.8Hz), 7.48(4H, s) | Diastereomer A polar substance Monohydrochloride |

| Ex. No. | R$_7$ | R$_8$ | IR (nujol) | $^1$H-NMR (D$_2$O) δ | Remarks |
|---|---|---|---|---|---|
| 146B | 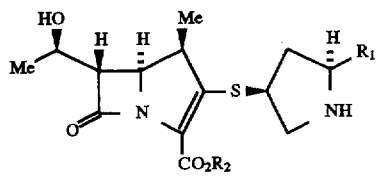 | H | 1753, 1599, 1392 | 1.19(3H, d, J=7.3Hz), 1.30(3H, d, J=6.3Hz), 1.73(1H, m), 2.39(1H, m), 3.25–3.50(3H, m), 3.60–3.80(1H, m), 3.90–4.13(2H, m), 4.14–4.35(4H, m), 5.00(1H, d, J= 8.5Hz), 7.54(4H, br) | Diastereomer B less polar substance Monohydrochloride |
| 147 | 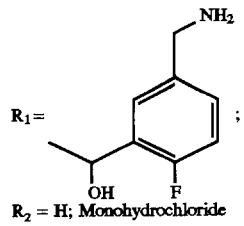 | H | 3460, 1755, 1593 | 1.20(3H, m), 1.29(3H, d, J=7.4Hz), 1.70–2.04(1H, m), 2.20–2.62 (1H, m), 3.40(4H, m), 3.69(1H, m), 4.00(2H, m), 4.23(2H, m), 7.46 (5H, m), 5.01(1H, m) | — |

In the following Example 148, a compound represented by the formula (A) which have substituents R$_1$ and R$_2$ was synthesized in the same manner as in Example 140.

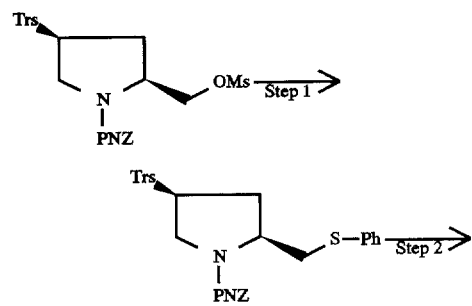

Example 148

R$_1$ =

R$_2$ = H; Monohydrochloride

IR(KBr)cm$^{-1}$: 1755,1582,1392

$^1$H-NMR(D$_2$O)δ: 1.21(3 H,d,J=7 Hz),1.31(3 H,d,J=6.5 Hz), 1.77(1 H,m),2.57(1 H,m),3.39(1 H,m),3.46(2 H,m), 3.73(1 H,dd,J=12 & 6.5 Hz),4.03(1 H,m),4.15–4.30(5 H,m), 5.26(1 H,d,J=8 Hz),7.29(1 H,t,J=9 Hz),7.55(1 H,m), 7.62(1 H,m)

UVλ$_{max}$(0.1M MOPS buffer, pH7.0): 299 nm(ε=9460)

Reference Example 1

(2S,4S)-4-Mercapto-N-(p-nitrobenzyloxycarbonyl)-2-(phenylthiomethyl)pyrrolidine

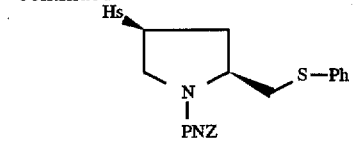

(Step 1)

To a solution of (2S,4S)-2-mesyloxymethyl-N-(p-nitrobenzyloxycarbonyl)-4-tritylthiopyrrolidine (9.6 g, 15.2 mmol) in THF (190 ml), thiophenol (2.34 ml, 22.8 mmol) and 1,8-diazabicyclo[5.4.0]-7-undecene (3.4 ml, 22.8 mmol) were successively added dropwise in a nitrogen stream under cooling with ice. The reaction solution was stirred at room temperature for 15 minutes and the solvent was distilled off. To the residue, ethyl acetate was added. The organic layer was washed with 1N aqueous potassium hydrogensulfate and saturated aqueous sodium chloride, dried over anhydrous sodium sulfate, and concentrated in vacuo. The resulting residue was subjected to silica gel column chromatography (Wakogel™ C-300 heptane-ethyl acetate 3:1) to give (2S,4S)-N-(p-nitrobenzyloxycarbonyl)-2-phenylthiomethyl-4-tritylthiopyrrolidine (9.24 mg, yield: 94%) as a yellow oily substance.

$^1$H-NMR(CDCl$_3$)δ: 1.58(1 H,s),1.65–1.95(1 H,m), 2.00–2.15(1 H,m),2.65–3.17(3 H,m),3.20–3.55(1 H,m), 4.90–5.10(2 H,m),7.05–7.55(22 H,m),8.07–8.30(2 H,m)

IR(KBr)cm$^{-1}$: 3056,1702,1604,1521,1440,1346,1103, 742

(Step 2)

To a solution of the compound (1.8 g, 2.78 mmol) obtained in Step 1 in dichloromethane (18 ml), trifluoroacetic acid (18 ml) was added dropwise in a nitrogen stream under cooling with ice, and then triethylsilane (0.32 ml, 3.06 mmol) was added thereto. The reaction solution was stirred for 1 hour. The solvent was distilled off and then ethyl acetate was added to the residue. The resulting solution was washed with 1M phosphate buffer (pH 5.5) and saturated aqueous sodium chloride, dried over anhydrous sodium sulfate, and concentrated in vacuo. The residue was subjected to silica gel column chromatography (Wakogel™ C-300 heptane-ethyl acetate 5:1) to give the title compound (1.07 g, yield: 95%) as a yellow oily substance.

$^1$H-NMR(CDCl$_3$)δ: 1.50–2.00(3 H,m),3.05–3.65(3 H,m) ,3.90–4.20(2 H,m),5.05–5.20(2 H,m),7.05–7.50(7 H,m), 8.10–8.25(2 H,m)

Reference Example 2

(2S,4S)-4-Acetylthio-1-p-nitrobenzyloxycarbonyl-2-(4-sulfamoylphenyl)thiomethlpyrrolidine

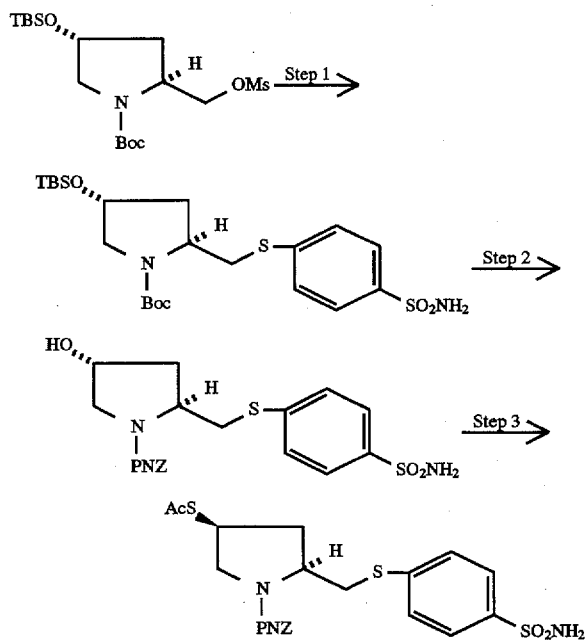

(Step 1)

To a liquid mixture of a solution of (2S,4R)-N-t-butoxycarbonyl-4-t-butyldimethylsiloxy-2-mesyloxymethylpyrrolidine (5.02 g, 12.3 mmol) and p-mercaptobenzenesulfonamide (2.39 g, 12.6 mmol) in THF (60 ml) with -N,N-dimethylformamide (20 ml), 1,8-diazabicyclo[5.4.0]-7-undecene (2.46 ml, 16.4 ml) was added dropwise in a nitrogen stream at room temperature. The reaction solution was stirred at the same temperature for 7 hours and then poured into a liquid mixture of ethyl acetate with water. The organic layer was washed with saturated aqueous sodium chloride, dried over anhydrous sodium sulfate, and then concentrated in vacuo. The resulting residue was subjected to silica gel column chromatography (Wakogel™ C-300 heptane-ethyl acetate 9:1→4:1→3:2) to give (2S,4R)-N-t-butoxycarbonyl-4-t-butyldimethylsiloxy-2-(4-sulfamoylphenyl)thiomethylpyrrolidine (2.65 g, yield: 43.1%) as a colorless oily substance.

IR(KBr)cm⁻¹: 3336,3255,2929,1683,1579

¹H-NMR(CDCl₃)δ: 0.05(6 H,s),0.85(9 H,s),1.45(9 H,s), 1.85-2.15(2 H,m),2.96-3.15(1 H,m),3.28-3.60(3 H,m), 4.10-4.42(2 H,m),4.72-4.86(2 H,br s),7.38-7.58(2 H,m), 7.75-7.85(2 H,m)

(Step 2)

A solution of the compound (2.65 g, 5.28 mmol) obtained in Step 1 in 5.4N hydrogen chloride-methanol (40 ml) was stirred at room temperature for 18 hours. This reaction solution was concentrated in vacuo and the resulting residue was dissolved in a liquid mixture of dioxane (25 ml) with water (25 ml). This solution was adjusted to pH 8.0 with 5N and 1N aqueous NaOH under cooling with ice. To this solution, sodium hydrogencarbonate (1.11 g, 13.2 mmol) was added at room temperature, and then a solution of p-nitrobenzyloxycarbonyl chloride (2.28 g, 10.6 mmol) in dioxane (5 ml) was added dropwise. This reaction solution was stirred at room temperature for 2 hours and then concentrated in vacuo. The resulting residue was extracted with ethyl acetate. The organic layer was washed successively with water and saturated aqueous sodium chloride, dried over anhydrous sodium sulfate, and concentrated in vacuo. The resulting residue was subjected to silica gel column chromatography (Wakogel™ C-300 ethyl acetate) to give (2S,4R)-4-hydroxy-N-p-nitrobenzyloxycarbonyl-2-(4-sulfamoylphenyl)thiomethylpyrrolidine (2.12 g, yield: 86.0%) as a pale yellow oily substance.

IR(KBr)cm⁻¹: 3367,3264,2942,1683

¹H-NMR(DMSO-d₆)δ: 1.80-2.10(2 H,m),3.03-3.61(4 H,m),3.94-4.16(1 H,m),4.20-4.13(1 H,m),4.94-5.05(1 H,m),5.15-5.30(1 H,m),7.23-7.73(8 H,m),8.23(2 H,d,J=8.9 Hz)

(Step 3)

To a solution of the compound (2.09 g, 4.48 mmol) obtained in Step 2 and triethylamine (0.75 ml, 5.38 mmol) in THF (50 ml), mesyl chloride (0.35 ml 4.52 mmol) was added dropwise in a nitrogen stream under cooling with ice. This reaction solution was stirred at the same temperature for 40 minutes. Then, triethylamine (0.2 ml, 1.43 mmol) and mesyl chloride (0.11 ml, 1.42 mmol) were added thereto, and the resulting reaction solution was stirred under cooling with ice for 20 minutes. After addition of ethyl acetate (100 ml), the reaction solution was washed successively with water and saturated aqueous sodium chloride, dried over anhydrous sodium sulfate, and concentrated in vacuo. The resulting residue was dissolved in N,N-dimethylformamide (30 ml) and the resulting solution was stirred in a nitrogen stream under heating at 60° C. To this solution, potassium thioacetate (780 mg, 6.84 mmol) was added and this reaction solution was stirred at the same temperature for 7 hours. After addition of ethyl acetate, the reaction solution was washed successively with water, saturated sodium hydrogencarbonate, water and saturated aqueous sodium chloride, dried over anhydrous sodium sulfate, and concentrated in vacuo. The resulting residue was subjected to silica gel column chromatography (Wakogel™ C-300 heptane-ethyl acetate 4:1) to give (2S,4S)-4-acetylthio-1-p-nitrobenzyloxycarbonyl-2-(4-sulfamoylphenyl)thiomethylpyrrolidine (1.51 g, yield: 64.4%) as a pale yellow oily substance.

IR(KBr)cm⁻¹: 3365,3261,1697,1521

¹H-NMR(DMSO-d₆)δ: 1.75-1.95(1 H,m),2.33(3 H,s), 3.07-3.38(2 H,m),3.48-3.70(1 H,m),3.75-4.20(4 H,m), 5.15-5.32(2 H,m),7.32(2 H,br s),7.37-7.76(6 H,m),8.23(2 H,d,J=8.9 Hz)

Reference Example 3

(2S,4S)-1-Allyloxycarbonyl-2-[4-(2-allyloxycarbonylaminoethylthio)phenylthiomethyl]-4-tritylthiopyrrolidine

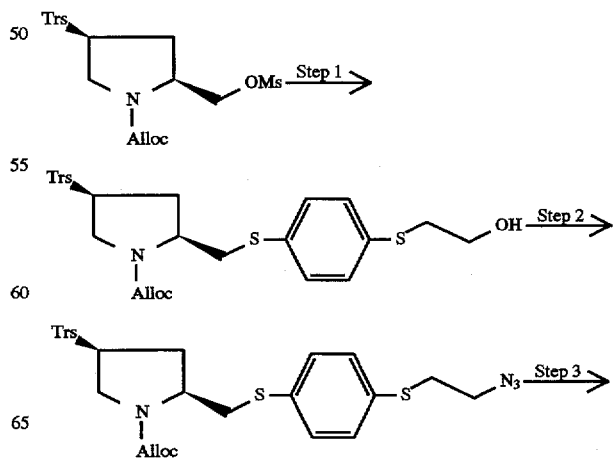

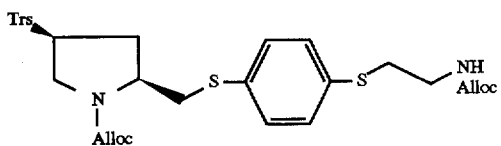

(Step 1)

To a solution of (2S,4S)-1-allyloxycarbonyl-2-mesyloxymethyl-4-tritylthiopyrrolidine (12.8 g, 23.8 mmol) and 4-(2-hydroxyethylthio)thiophenol (4.47 g, 25.6 mmol) in THF (100 ml), 1,8-diazabicyclo[5.4.0]-7-undecene (4.11 ml, 26.1 mmol) was gradually added dropwise in a nitrogen stream. This reaction solution was stirred at room temperature overnight and then the solvent was distilled off in vacuo. The residue was extracted with ethyl acetate. This ethyl acetate solution was washed successively with water, 10% aqueous citric acid and saturated aqueous sodium chloride, dried over anhydrous sodium sulfate, and concentrated in vacuo. The resulting oily residue was subjected to silica gel column chromatography (Wakogel™ C-300 heptane-ethyl acetate 2:1→1:1) to give (2S,4S)-1-allyloxyarbonyl-2-[4-(2-hydroxyethylthio)phenylthiomethyl]-4-tritylthiopyrrolidine (9.67 g, yield: 65%).

IR(KBr)cm$^{-1}$: 3428,1697,1442,1405,1353,1195,1106, 746,702

$^1$H-NMR(CDCl$_3$)δ: 1.76(1 H,m),2.18(1 H,m), 2.70–2.90(4 H,m), 3.06(2 H,t,J=6.0 Hz),3.30(1 H,m),3.72(2 H,t,J=6.0 Hz), 3.78(1 H,m),4.45(2 H,m),5.23(2 H,m),5.85(1 H,m),7.20–7.50(15 H,m)

(Step 2)

To a solution of the compound (7.53 g, 12.0 mmol) obtained in Step 1 in dichloromethane, mesyl chloride (0.975 ml, 12.6 mmol) and triethylamine (1.93 ml, 13.8 mmol) were successively added under cooling with ice. The resulting reaction solution was stirred at 0° C. for 30 minutes. The reaction solution was washed with water and saturated aqueous sodium chloride, dried over anhydrous sodium sulfate, and concentrated in vacuo to give a foamy solid (8.10 g).

This foamy solid was dissolved in dimethyl sulfoxide (40 ml). To this solution, sodium azide (purity 90%, 2.60 g, 36 mmol) was added. The resulting reaction solution was stirred for 2 hours under heating at from 50° C. to 60° C. and then poured into ethyl acetate. The organic layer was washed with water and saturated aqueous sodium chloride, dried over anhydrous sodium sulfate, and concentrated in vacuo. The resulting oily residue was subjected to silica gel column chromatography (Wakogel™ C-300 heptane-ethyl acetate 5:1→4:1→3:1) to give (2S,4S)-1-allyloxycarbonyl-2-[4-(2-azidoethylthio)phenylthiomethyl]-4-tritylthiopyrrolidine (6.65 g, yield: 85%) as a colorless oily substance.

IR(KBr)cm$^{-1}$: 2100,1697,1405,1349,1319,1197,1105, 744,702

$^1$H-NMR(CDCl$_3$)δ: 1.72(1 H,m),2.18(1 H,m), 2.70–3.00(4 H,m), 3.03(2 H,t,J=7.0 Hz),3.41(2 H,t,J=7.0 Hz),3.51(1 H,m), 3.81(1 H,m),4.45(2 H,m),5.21(2 H,m), 5.85(1 H,m),7.10–7.50(15 H,m)

(Step 3)

To a solution of the compound (3.26 g, 5.0 mmol) obtained in Step 2 in THF (50 ml), triphenylphosphine (1.38 g, 5.25 mmol) and water (135 mg, 7.5 mmol) were added and the resulting reaction solution was stirred at room temperature overnight. To this reaction solution, triethylamine (0.91 ml, 6.5 mmol) and allyl chloroformate (0.64 ml, 6.0 mmol) were added under cooling with ice and the reaction solution was stirred at the same temperature for 1 hour. The reaction solution was concentrated in vacuo and the resulting residue was extracted with ethyl acetate. This ethyl acetate solution was washed successively with water and saturated aqueous sodium chloride, dried over anhydrous sodium sulfate, and concentrated in vacuo. The resulting residue was subjected to silica gel column chromatography (Wakogel™ C-300 heptane-ethyl acetate 4:1→3:1→2:1) to give (2S,4S)-1-allyloxycarbonyl-2-[4-(2-allyloxycarbonylaminoethylthio)phenylthiomethyl]-4-tritylthiopyrrolidine (1.53 g, yield: 43%).

IR(KBr)cm$^{-1}$: 1716,1697,1405,1353,1321,1249,1197, 1141,1105, 989,929,811,744,702

$^1$H-NMR(CDCl$_{13}$)δ: 1.75(1 H,m),2.20(1 H,m), 2.70–3.00(4 H,m), 3.00(2 H,t,J=6.2 Hz),3.33(2 H,t,J=6.2 Hz),3.50(1 H,m), 3.79(1 H,m),4.40–4.60(4 H,m),5.10(1 H,br m),5.20–5.30(4 H,m),5.80–6.00(2 H,m),7.20–7.50(15 H,m)

Reference Example 4

(2S,4S)-4-Acetylthio-4-allyloxycarbonyl-2-(3-allyloxycarbonylaminomethyl-4-chlorophenyl)thiomethylpyrrolidine

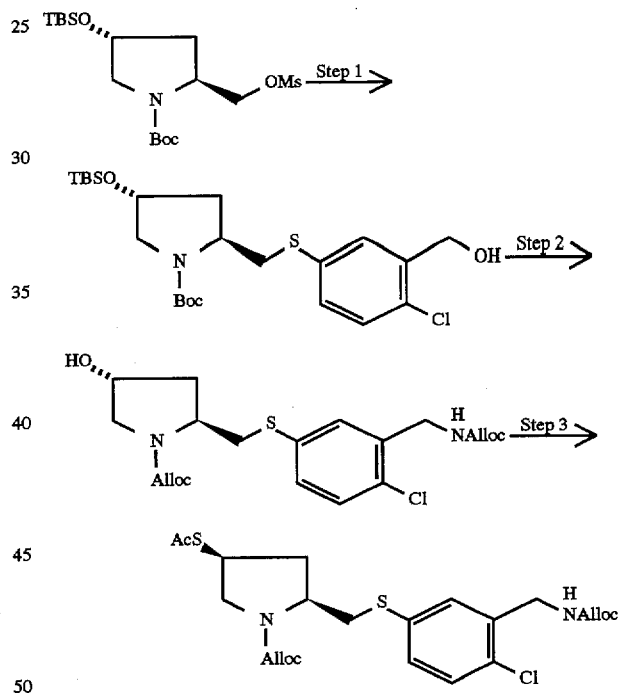

(Step 1)

To a mixed solution of (2S,4R)-N-t-butoxycarbonyl-4-t-butyldimethylsiloxy-2-mesyloxymethylpyrrolidine (6.43 g, 15.7 mmol) in a mixture of THF (50 ml) with N,N-dimethylformamide (50 ml), (4-chloro-3-hydroxy) thiophenol (2.74 g, 15.7 mmol) and 1,8-diazabicyclo[5.4.0]-7-undecene (2.82 ml, 18.8 mmol) were successively added in a nitrogen stream. The resulting reaction solution was stirred at room temperature for 14 hours and then poured into a liquid mixture of ethyl acetate with water. The organic layer was washed with saturated aqueous sodium chloride, dried over anhydrous magnesium sulfate, and concentrated in vacuo. The resulting oily residue was subjected to silica gel column chromatography (Wakogel™ C-300 heptane-ethyl acetate 8:1→4:1) to give (2S,4R)-N-t-butoxycarbonyl-4-t-butyldimethylsiloxy-2-(4-chloro-3-hydroxymethyl)

phenylthiomethylpyrrolidine (7.12 g, yield: 87.5%) as a yellow oily substance.

$^1$H-NMR(CDCl$_3$)δ: 0.05(6 H,s),0.80(9 H,s),1.20–1.30(2 H,m), 1.39(9 H,s),1.90–2.15(3 H,m),3.10–3.55(3 H,m), 4.00–4.80(3 H,m),7.10–7.50(3 H,m)

(Step 2)

To a solution of the compound (1.33 g, 2.72 mmol) obtained in Step 1 in THF (25 ml), triethylamine (417 µl, 2.99 mmol) and mesyl chloride (232 µl, 2.99 mmol) were successively added in a nitrogen stream under cooling with ice. The resulting reaction solution was stirred at the same temperature for 15 minutes. To the reaction solution, saturated aqueous ammonium chloride was added and the organic layer was washed with saturated aqueous sodium chloride and dried over anhydrous magnesium sulfate. Then the solvent was distilled off in vacuo to give a crude mesyl derivative.

To a solution of the crude mesyl derivative in dimethyl sulfoxide (10 ml), sodium azide (530 mg, 8.16 mmol) was added. The resulting reaction solution was stirred at 70° C. in a nitrogen stream for 2 hours. The reaction solution was poured into water (100 ml) and extracted with ethyl acetate (50 ml×3). The organic layers were combined, then washed with saturated aqueous sodium chloride, and dried over anhydrous magnesium sulfate. The solvent was distilled off in vacuo to obtain a yellow residue containing (2S,4R)-N-t-butoxycarbonyl-4-t-butyldimethylsiloxy-2-(3-azidomethyl-2-chloro)phenylthiomethylpyrrolidine.

To a solution of the residue in THF (10 ml), water (73 µl, 4.08 mmol) and triphenylphosphine (1.07 g, 4.08 mmol) were successively added. The resulting reaction solution was stirred at room temperature for 14 hours and concentrated in vacuo. After addition of 1.75N hydrogen chloride-methanol solution (32 ml), the reaction solution was stirred at room temperature for 14 hours and concentrated in vacuo to give a yellow residue. A solution of the residue in dioxane-water (2:1, 50 ml) was adjusted to pH 8.5 with 5N aqueous NaOH. To this solution, a solution of allyl chloroformate (787 µl, 6.53 mmol) in dioxane (5 ml) was added dropwise under cooling with ice, while the reaction solution was maintained at pH 8.0–9.0 by using 5N aqueous NaOH. The reaction solution was poured into a liquid mixture of ethyl acetate-water. The organic layer was washed with saturated aqueous sodium chloride, dried over anhydrous magnesium sulfate, and concentrated in vacuo. The resulting residue was subjected to silica gel column chromatography (Wakogel™ C-300 heptane-ethyl acetate 4:1→1:1) to give (2S,4R)-N-allyloxycarbonyl-4-hydroxy-2-[3-(N-allyloxycarbonylaminomethyl)-4-chloro]phenylthiomethylpyrrolidine (1.85 g, yield: 100%).

$^1$H-NMR(CDCl$_3$)ε: 2.80–3.90(7 H,m),4.40–4.70(5 H,m), 5.20–5.40(4 H,m),5.80–6.00(2 H,m),7.20–7.50(3 H,m)

(Step 3)

To a solution of the compound (1.85 g, 2.7 mmol) obtained in Step 2 in THF (10 ml), triethylamine (376 µl, 2.7 mmol) and mesyl chloride (209 µl, 2.7 mmol) were successively added in a nitrogen stream under cooling with ice and the resulting reaction solution was stirred at the same temperature for 15 minutes. To the reaction solution, saturated aqueous ammonium chloride was added. The organic layer was washed with saturated aqueous sodium chloride and dried over anhydrous magnesium sulfate. The solvent was distilled off in vacuo to give a crude mesyl derivative.

To a solution of the the crude mesyl derivative in N,N-dimethylformamide (10 ml), potassium thioacetate (461 mg, 4.05 mmol) was added and the resulting reaction solution was stirred at 70° C. for 3 hours. To the reaction solution, water was added and then the organic layer was washed with saturated aqueous sodium chloride, dried over anhydrous magnesium sulfate, and concentrated in vacuo. The resulting oily residue was subjected to silica gel column chromatography (Wakogel™ C-300 heptane-ethyl acetate 5:1→2:1) to give (2S,4S)-4-acetylthio-1-allyloxycarbonyl-2-(3-allyloxycarbonylaminomethyl-4-chlorophenyl)thiomethylpyrrolidine (960 mg, yield: 69.0%) as a yellow oily substance.

$^1$H-NMR(CDCl$_3$)δ: 1.90–2.20(2 H,m),2.34(3 H,s), 2.50–4.20(5 H,m),4.40–4.70(5 H,m),5.20–5.40(4 H,m), 5.80–6.00(2 H,m),7.20–7.50(3 H,m)

Reference Example 5

(2S,4S)-4-Acetylthio-2-[(4-p-nitrobenzyloxycarbonylaminomethyl-2-sulfamoyl)phenylthiomethyl]-1-p-nitrobenzyloxycarbonylpyrrolidine

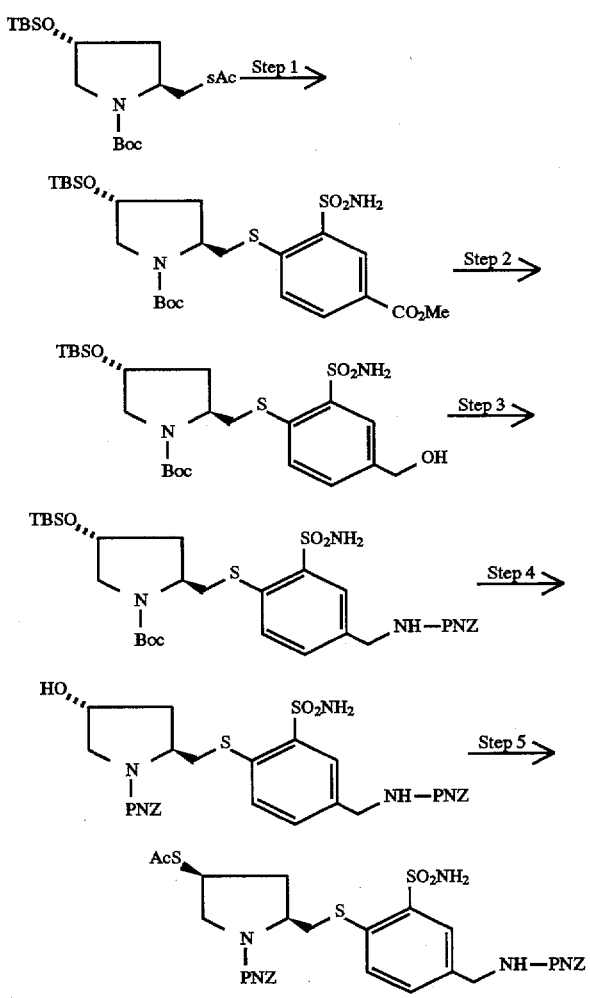

(Step 1)

To a solution of (2S,4R)-2-acetylthiomethyl-N-t-butoxycarbonyl-4-t-butyldimethylsiloxypyrrolidine (3.9 g, 10 mmol) in methanol (50 ml), 1N aqueous NaOH (11.0 ml, 11 mmol) was added in nitrogen stream under cooling with ice. The resulting solution was stirred for 30 minutes, then brought together with 1N aqueous HCl (12.0 ml, 12 mmol), and concentrated in vacuo. The resulting residue was poured into a liquid mixture of ethyl acetate with water. The organic layer was washed with saturated aqueous sodium chloride, and dried over anhydrous magnesium sulfate, and concentrated in vacuo to give a crude product of (2S,4R)-N-t-butoxycarbonyl-4-t-butyldimethylsiloxy-2-mercaptomethylpyrrolidine.

To a solution of the above crude product in hexamethylphosphoramide (20 ml), 440 mg (11 mmol) of 60% oily sodium hydride was added in a nitrogen stream under cooling with ice. To the solution which was stirred for 10 minutes, methyl 4-chloro-3-sulfamoyl-1-benzoate (2.75 g, 11 mmol) was added. The reaction solution was stirred at the same temperature overnight and poured into a liquid mixture of ethyl acetate with water. The organic layer was washed with saturated aqueous sodium chloride, dried over anhydrous magnesium sulfate, and concentrated in vacuo. The resulting residue was subjected to silica gel column chromatography (Wakogel™ C-300 ethyl acetateheptane 1:4→2:5) to give (2S,4R)-N-t-butoxycarbonyl-4-t-butyldimethylsiloxy-2-(4-methoxycarbonyl-2-sulfamoyl)phenylthiomethylpyrrolidine (3.84 g, yield: 68.4%) as a pale yellow oily substance.

IR(KBr)cm$^{-1}$: 3369,3267,2954,1724,1686

$^1$H-NMR(CDCl$_3$)δ: 0.04(6 H,s),0.84(9 H,s),1.44(9 H,s), 1.90–2.20(2 H,m),3.10–3.25(1 H,m),3.39(2 H,d,J=3.4 Hz), 3.60(1 H,dd,J=3.4 & 13.0 Hz),3.91(3 H,s),4.20–4.40(1 H,m), 4.35(1 H,t,J=3.8 Hz),5.41(2 H,s),7.26(1 H,d,J=9.0 Hz),8.09(1 H,d,J=9.0 Hz),8.59(1 H,s)

(Step 2)

To a suspension of lithium aluminum hydride (207 mg, 5.46 mmol) in ether (60 ml), a solution of the compound (1.02 g, 1.82 mmol) obtained in Step 1 in ether (20 ml) was added dropwise in a nitrogen stream under cooling with ice and the resulting reaction solution was stirred for 1 hour. To the reaction solution which was diluted with ether (30 ml) sodium sulfate decahydrate (3.52 g, 10.9 mmol) was gradually added and the reaction solution was stirred at room temperature overnight. The insolubles were filtered off and the filtrate was concentrated in vacuo. The resulting residue was subjected to silica gel column chromatography (Wakogel™ C-300 ethyl acetate-heptane 2:3) to give (2S, 4R)-N-t-butoxycarbonyl-4-t-butyldimethylsiloxy-2-(4-hydroxymethyl-2-sulfamoyl)phenylthiomethylpyrrolidine (860 mg, yield: 88.7%) as white crystals.

IR(KBr)cm$^{-1}$: 3406,2929,1676,1589

$^1$H-NMR(CDCl$_3$)δ: 0.05(6 H,s),0.86(9 H,s),1.44(9 H,s), 1.95–2.20(2 H,m),3.20(1 H,m),3.35–3.55.(3 H,m),4.20(1 H,m), 4.35(1 H,t,J=3.0 Hz),4.71(2 H,d,J=5.4 Hz),5.40(2 H,s), 7.45–7.70(2 H,m),8.01(1 H,s)

(Step 3)

To a solution of the compound (910 mg, 1.71 mmol) obtained in Step 2 in THF (40 ml), triphenylphosphine (538 mg, 2.05 mmol) and phthalimide (302 mg, 2.05 mol) were added. The resulting reaction solution was stirred at room temperature in a nitrogen stream for 1 hour and then diethyl azodicarboxylate was added dropwise to this reaction solution. Then the reaction solution was stirred at room temperature for 1 hour, concentrated in vacuo, and subjected to silica gel column chromatography (Wakogel™ C-300 ethyl acetate-heptane 1:3→1:2) to give a crude product containing (2S,4R)-N-t-butoxycarbonyl-4-t-butyldimethylsiloxy-2-(4-phthalimidomethyl-2-sulfamoyl) phenylthiomethylpyrrolidine.

To a solution of the crude product in ethanol (15 ml), hydrazine hydrate (592 mg, 11.8 mmol) was added. This solution was refluxed under heating for 4 hours and then poured into a liquid mixture of ethyl acetate with 8% aqueous ammonia. The organic layer was washed with saturated aqueous sodium chloride, dried over anhydrous magnesium sulfate, and concentrated in vacuo to give a crude powder. The crude powder is dissolved in a solvent mixture of dioxane (30 ml) with water (30 ml). To the resulting solution, 4,6-dimethyl-2-(p-nitrobenzyloxycarbonylthio)pyrimidine (655 mg, 2.05 mmol) was added while the solution was maintained at pH 8 by using saturated aqueous sodium hydrogencarbonate. Then, the solution was stirred at room temperature overnight. After completion of the reaction, ethyl acetate was added to the reaction solution. The reaction solution was washed successively with 10% aqueous citric acid, saturated aqueous sodium hydrogencarbonate and saturated aqueous sodium chloride, dried over anhydrous magnesium sulfate, and concentrated in vacuo. The resulting residue was subjected to silica gel column chromatography (Wakogel™ C-300 chloroform-methanol 100:2) to give (2S,4R)-N-t-butoxycarbonyl-4-t-butyldimethylsiloxy-2-(4-p-nitrobenzyloxycarbonylaminomethyl-2-sulfamoyl) phenylthiomethylpyrrolidine (690 mg, yield: 57.3%) as a pale yellow foamy powder.

IR(KBr)cm$^{-1}$: 3369,2933,1707,1524

$^1$H-NMR(CDCl$_3$)δ: 0.05(6 H,s),0.85(9 H,s),1.43(9 H,s), 1.90–2.10(2 H,m),3.15(1 H,m),3.30–3.55(3 H,m),4.20(1 H,m), 4.30–4.45(3 H,m),5.22(2 H,s),5.40(2 H,s), 7.40–7.55(3 H,m),7.65(1 H,m),7.95(1 H,s),8.22(2 H,d,J=8.5 Hz)

(Step 4)

To the compound (690 mg, 0.98 mmol) obtained in Step 3, 1.75N HCl-methanol solution (6 ml) was added under cooling with ice and then resulting solution was stirred at room temperature overnight. After completion of the reaction, the reaction solution was concentrated in vacuo to give a crude powder. This crude powder was dissolved in a liquid mixture of dioxane (10 ml) with water (10 ml). To the resulting solution, 4,6-dimethyl-2-(p-nitrobenzyloxycarbonylthio)pyrimidine (375 mg, 1.17 mmol) was added while the solution was maintained at pH 8 by using saturated aqueous sodium hydrogencarbonate. Then, the reaction solution was stirred at room temperature overnight. After completion of the reaction, ethyl acetate was added to the reaction solution. The organic layer was washed successively with 10% aqueous citric acid, saturated aqueous sodium hydrogencarbonate and saturated aqueous sodium chloride, dried over anhydrous magnesium sulfate, and then concentrated in vacuo. The resulting residue was subjected to silica gel column chromatography (Wakogel™ C-300 chloroform-methanol 100:3) to give (2S,4R)-4-hydroxy-N-t-nitrobenzyloxycarbonyl-2-(4-p-nitrobenzyloxycarbonylaminomethyl)-2-sulfamoyl) phenylthiomethylpyrrolidine (480 mg, yield: 41.6%) as a colorless foamy powder.

IR(KBr)cm$^{-1}$: 3390,1697,1520

$^1$H-NMR(CDCl$_3$)δ: 1.90–2.10(2 H,m),3.05(1 H,m), 3.40–3.80(3 H,m),4.05(1 H,m),4.25–4.45(3 H,m),5.22(4 H,s), 6.07(2 H,s),6.30(1 H,s),7.35–7.60(5 H,m), 7.72(1 H,d, J=9.0 Hz),7.97(1 H,d,J=2.0 Hz), 8.21(4 H,d,J=7.5 Hz)

(Step 5)

Diethyl azodicarboxylate was added to a solution of triphenylphosphine (97.8 mg, 0.37 mmol) in THF (5 ml) in a nitrogen stream under cooling with ice and the resulting reaction solution was stirred at the same temperature for 30 minutes. To this solution, a solution of the compound (210 mg, 0.31 mmol) obtained in Step 4 and thioacetic acid (0.027 ml, 0.37 mmol) in THF (5 ml) was added dropwise and the resulting reaction solution was stirred for 1 hour. After completion of the reaction, the reaction solution was concentrated in vacuo and subjected to silica gel column chromatography (Wakogel™ C-300 ethyl acetate-heptane 1:2→2:1) to give (2S,4S)-4-acetylthio-2-[(4-p-nitrobenzyloxycarbonylaminomethyl-2-sulfamoyl)phenylthiomethyl]-1-p-nitrobenzyloxycarbonylpyrrolidine (140 mg, yield: 61.4%) as a yellow oily substance.

IR(KBr)cm$^{-1}$: 3340,1697,1518

$^1$H-NMR(CDCl$_3$)δ: 2.05(1 H,m),2.35(3 H,s),2.60(2 H,m), 3.15(1 H,m),3.35(1 H,m),3.70(1 H,m),3.90(1 H,m), 4.05(1 H,m),4.50(1 H,d,J=6.0 Hz),5.22(4 H,s),5.30(2 H,s), 7.40–7.80(6 H,m),7.95(1 H,s),8.20(4 H,d,J=8–5 Hz)

In the following Reference Examples 6 to 94, the physicochemical data of compounds used in Examples as thiols or thiol precursors are shown.

Reference Example 6

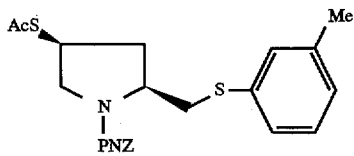

$^1$H-NMR(CDCl$_3$)δ: 1.90–2.10(2 H,m),2.20–2.38(6 H,m), 2.68–2.89(3 H,m),3.78–4.00(1 H,m),4.01–4.23(2 H,m), 5.15(2 H,s),6.90–7.53(9 H,m),8.10–8.28(2 H,m)

Reference Example 7

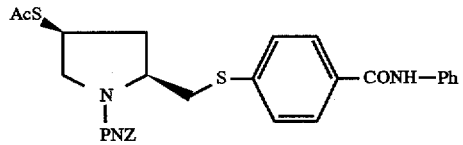

IR(KBr)cm$^{-1}$: 3245,1695,1531,1255

$^1$H-NMR(CDCl$_3$)δ: 2.35(3 H,s),3.01–4.00(4 H,m), 4.10–4.31(4 H,m),5.18(2 H,s),7.10–7.85(12 H,m), 8.13–8.25(2 H,m)

Reference Example 8

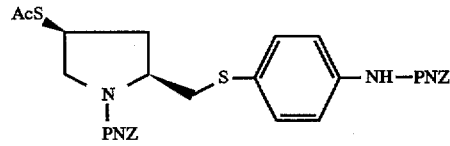

$^1$H-NMR(CDCl$_3$)δ: 1.90–2.10(1 H,m),2.34(3 H,s), 2.43–2.69(1 H,m),2.80–3.55(3 H,m),3.78–4.20(3 H,m), 5.08–5.25(2 H,m),5.25–5.34(2 H,m),6.62–6.75(1 H,m), 7.17–7.63(8 H,m),8.12–8.30(4 H,m)

Reference Example 9

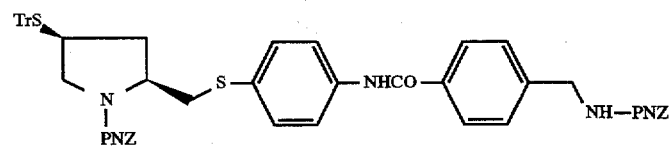

$^1$H-NMR(CDCl$_3$)δ: 2.04(2 H,s),2.85–3.00(4 H,m),3.12–3.35(2 H,m),3.73–3.91(1 H,m),4.46(2 H,d,J=5.8 Hz), 4.95–5.10(2 H,m),5.24(2 H,s),7.13–7.57(25 H,m), 7.65–7.90(3 H,m),8.05–8.25(4 H,m)

Reference Example 10

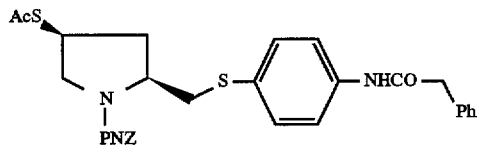

$^1$H-NMR(CDCl$_3$)δ: 1.92–2.08(1 H,m),2.34(3 H,d,J=2.0 Hz),2.85–3.53(3 H,m),3.60–4.20(41 H,m),5.13.(2 H,s), 5.28(2 H,s), 6.65–6.80(1 H,m),7.15–7.60(9 H,m), 8.10–8.30(4 H,m)

Reference Example 11

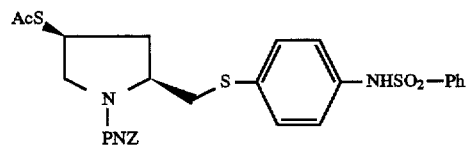

IR(KBr)cm$^{-1}$: 3425,1695,1519,1344,1162,759

$^1$H-NMR(CDCl$_3$)δ: 1.85–2.06(1 H,m),3.49(3 H,s), 2.90–3.60(4 H,m),3.80–3.95(3 H,m),5.10–5.25(2 H,m), 6.47–6.63(1 H,m),6.85–7.04(2 H,m),7.10–7.32(2 H,m), 7.40–7.59(5 H,m),7.70–7.90(2 H,m),8.15–8.26(2 H,m)

Reference Example 12

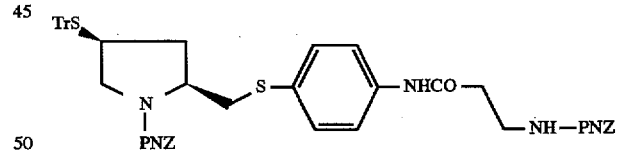

$^1$H-NMR(CDCl$_3$)δ: 2.05–2.11(2 H,m),2.51–2.70(2 H,m), 2.88– 2.95(4 H,m),3.14–3.33(2 H,m),3.45–3.68(2 H,m), 3.74–3.93(1 H,m),4.95–5.25(4 H,m),7.15–7.65(24 H,m), 7.72–7.90(4 H,m)

Reference Example 13

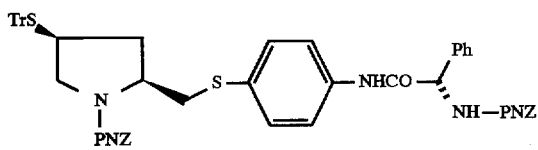

¹H-NMR(CDCl₃)δ: 1.55–1.95(2 H,m),2.01–2.15(1 H,m), 2.65–3.90(7 H,m),4.91–5.34(4 H,m),6.17–6.30(1 H,m), 7.10–7.61(28 H,m),8.05–8.28(4 H,m)

Reference Example 14

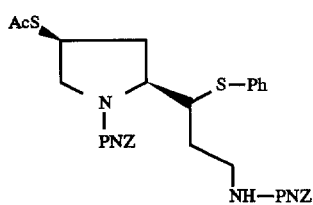

Starting material for diastereomer A

¹H-NMR(CDCl₃)δ: 1.67–2.05(2 H,m),2.25–2.40(3 H,m), 2.45–2.71(1 H,m),2.90–4.35(9 H,m),4.91–5.25(4 H,m), 7.05–7.55(5 H,m),8.05–8.26(4 H,m)

Starting material for diastereomer B

¹H-NMR(CDCl₃)δ: 1.71–2.12(2 H,m),2.20–2.48(3 H,m), 3.01–4.30(10 H,m),5.02–5.25(4 H,m),7.05–7.55(5 H,m), 8.06–8.28(4 H,m)

Reference Example 15

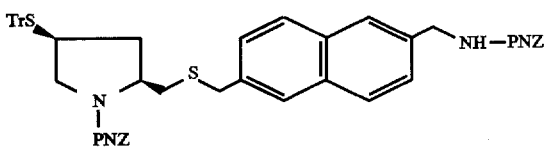

¹H-NMR(CDCl₃)δ: 1.56(1 H,s),2.50–2.95(4 H,m), 3.67–3.86(3 H,m),4.53(2 H,d,J=5.5 Hz),4.92–5.10(2 H,m), 5.15–5.25(4 H,m),7.02–7.90(26 H,m),8.12–8.25(4 H,m)

Reference Example 16

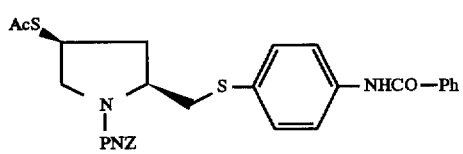

¹H-NMR(DMSO-d₆)δ: 1.80–1.95(1 H,m),2.33(3 H,d,J= 1.2 Hz),3.29–3.38(4 H,m),3.80–4.12(3 H,m),5.10–5.29(2 H,m),7.25–7.96(11 H,m),8.18(2 H,d,J=7.9 Hz),10.22(1 H,s)

Reference Example 17

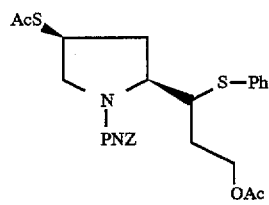

Starting material for diastereomer A

¹H-NMR(CDCl₃)δ: 1.57(2 H,s),1.80–2.10(6 H,m), 2.30–2.45(4 H,m),3.70–3.87(1 H,m),3.99–4.40(4 H,m), 4.68–4.99(2 H,m),7.10–7.40(7 H,m),8.10–8.17(2 H,m)

Starting material for diastereomer B

¹H-NMR(CDCl₃)δ: 1.60(2 H,s),1.85–2.10(6 H,m),2.33–2.47(4 H,m),3.67–3.85(1 H,m),4.01–4.43(4 H,m), 4.70–5.02(2 H,m),7.12–7.43(7 H,m),8.12–8.20(2 H,m)

Reference Example 18

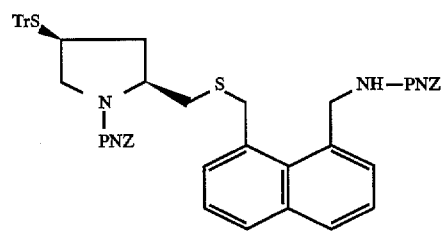

IR(KBr)cm⁻¹: 1705,1600,1520,1440,1400,1345,1105

¹H-NMR(CDCl₃)δ: 2.65–3.01(4 H,m),3.70–3.90(1 H,m), 4.05–4.21(2 H,m),4.95–5.18(4 H,m),5.18–5.28(2 H,m), 5.28–5.38(4 H,s),7.15–7.60(23 H,m),7.75–7.85(2 H,m), 8.15–8.29(4 H,m)

Reference Example 19

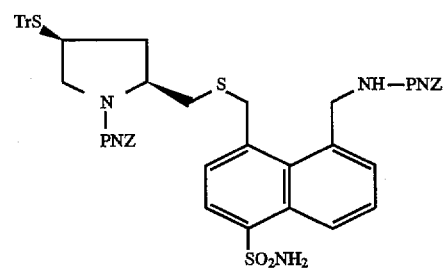

IR(KBr)cm⁻¹: 1705,1520,1345,1155,745

¹H-NMR(CDCl₃)δ: 2.43–2.94(5 H,m),3.68–3.82(1 H,m), 4.05–4.20(3 H,m),4.93–5.39(8 H,m),7.12–7.68(24 H,m), 8.05–8.24(5 H,m),8.67–8.74(1 H,m)

Reference Example 20

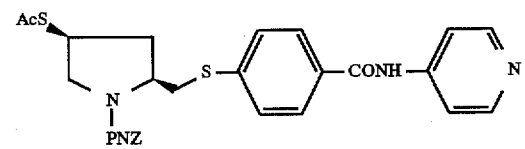

¹H-NMR(CDCl₃)δ: 2.35(3 H,s),2.57–2.72(2 H,m),3.00–3.10(1 H,m),3.27–3.43(1 H,m),3.68–3.76(1 H,m), 3.85–3.95(1 H,m),4.08–4.28(2 H,m),5.10–5.32(3 H,m), 7.47–7.50(4 H,m),7.63(2 H,d,J=5.4 Hz),7.75(2 H, d,J=8.5 Hz),8.20 (2 H,d,J=8.5 Hz),8.52(2 H,d,J=6.4 Hz)

Reference Example 21

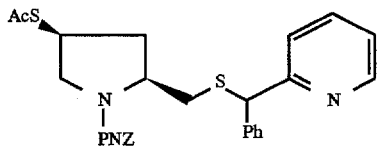

$^1$H-NMR(CDCl$_3$)δ: 1.83–2.01(2 H,m),2.30(3 H,s), 2.82–3.03(2 H,m),3.14–3.28(1 H,m),3.75–3.90(1 H,m), 3.98–4.15(2 H,m),5.07–5.28(3 H,m),7.19–7.64(7 H,m), 7.99(3 H,br s),8.16(2 H,d,J=8.9 Hz),8.45–8.60(1 H,m)

Reference Example 22

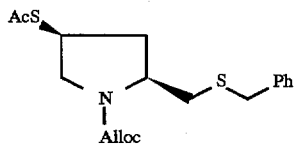

$^1$H-NMR(CDCl$_3$)δ: 1.80–1.95(1 H,m),2.32(3 H,s), 2.40–2.80(2 H,m),2.85–3.10(1 H,m),3.15–3.25(1 H,m), 3.72(2 H,s),3.80–4.15(3 H,m),4.52–4.63(2 H,m), 5.18–5.35(2 H,m),5.80–6.00(1 H,m),7.20–7.40(5 H,m)

Reference Example 23

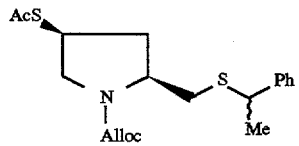

$^1$H-NMR(CDCl$_3$)δ: 1.57(3 H,d,J=6.4 Hz),1.75–1.95(1 H,m), 2.32(3 H,s),2.45–3.00(3 H,m),3.11–3.24(1 H,m), 3.70–4.12(3 H,m),4.49–4.70(2 H,m),5.16–5.40(3 H,m), 5.72–6.17(1 H,m),7.20–7.42(5 H,m)

Reference Example 24

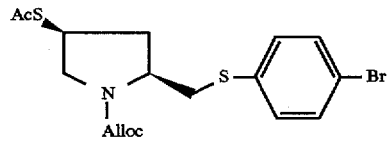

$^1$H-NMR(CDCl$_3$)δ: 1.89–2.05(1 H,m),2.33(3 H,s), 2.40–2.65(1 H,m),2.80–3.10(1 H,m),3.15–3.30(1 H,m), 3.42–3.65(1 H,m),3.75–4.15(3 H,m),4.12–4.48(2 H,m), 5.16–5.37(2 H,m),5.80–6.12(1 H,m),7.19–7.42(4 H,m)

Reference Example 25

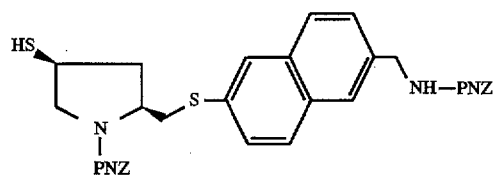

IR(KBr)cm$^{-1}$: 1700,1520,1345,1090

$^1$H-NMR(CDCl$_3$)δ: 1.71–1.79(1 H,m),1.89–2.13(1 H,m), 2.55–2.80(1 H,m),3.10–3.68(4 H,m),3.92–4.03(1 H,m), 4.10–4.28(1 H,m),4.47–4.60(2 H,m),4.92–5.15(2 H,m), 5.20–5.30(2 H,m),7.15–8.30(14 H,m)

Reference Example 26

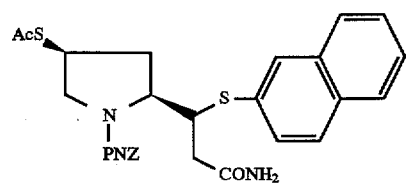

Starting material for diastereomer A

IR(KBr)cm$^{-1}$: 1695,1515,1345

$^1$H-NMR(CDCl$_3$)δ: 2.00–2.20(1 H,m),2.34(3 H,s), 3.10–3.35(1 H,m),3.60–3.85(1 H,m),4.15–4.52(3 H,m), 5.05–5.75(3 H,m),7.25–8.10(11 H,m)

Starting material for diastereomer B

IR(KBr)cm$^{-1}$: 1695,1520,1400,1345,1115

$^1$H-NMR(CDCl$_3$)δ: 1.95–2.25(1 H,m),2.34(3 H,s), 3.05–3.35(1 H,m),3.60–4.78(4 H,m),5.10–5.95(3 H,m), 6.90–7.10(1 H,m),7.35–8.05(10 H,m)

Reference Example 27

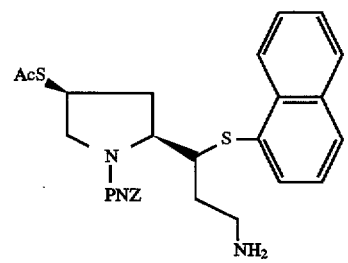

Starting material for diastereomer A $^1$H-NMR(CDCl$_3$)δ: 1.70–1.95(2 H,m),2.15–2.27(1 H,m), 2.36(3 H,s),2.91–3.04(1 H,m),3.39–3.58(2 H,m), 3.65–3.94(2 H,m),4.08–4.22(1 H,m),4.32–4.86(3 H,m), 5.00–5.25(3 H,m),6.94–7.33(4 H,m),7.40–7.70(5 H,m), 7.70–7.90(1 H,m),8.05–8.28(4 H,m),8.35–8.50(1 H,m)

Starting material for diastereomer B $^1$H-NMR(CDCl$_3$)δ: 1.70–2.05(3 H,m),2.34(3 H,s), 2.50–2.70(1 H,m),3.34–3.84(4 H,m),3.95–4.35(2 H,m), 4.55–5.28(5 H,m),6.95–7.10(1 H,m),7.35–7.63(6 H,m), 7.65–7.92(3 H,m),7.93–8.48(5 H,m)

Reference Example 28

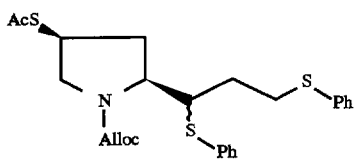

¹H-NMR(CDCl₃)δ: 1.65–2.09(3 H,m),2.31(3 H,s), 2.85–3.39(3 H,m),3.59–3.85(1 H,m),3.92–4.42(4 H,m), 4.52–4.63(1 H,m),5.07–5.35(3 H,m),5.60–6.01(1 H,m), 7.09–7.50(10 H,m)

Reference Example 29

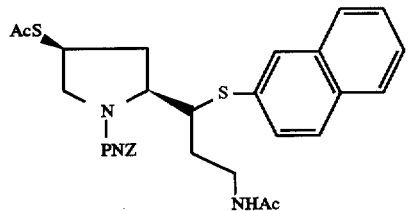

Starting material for diastereomer A
IR(KBr)cm⁻¹: 1700,1525,1405,1345,1115
¹H-NMR(CDCl₃)δ: 1.49–2.10(6 H,m),2.33(3 H,s), 2.51–2.72(1 H,m),3.04–3.23(1 H,m),3.34–3.82(3 H,m), 4.10–4.39(2 H,m),4.95–5.30(2 H,m),5.62–5.85(1 H,m), 7.05–7.19(1 H,m),7.35–7.58(5 H,m),7.60–7.85(3 H,m), 7.86–8.05(1 H,m),8.15–8.30(1 H,m)

Starting material for diastereomer B
IR(KBr)cm⁻¹: 1700,1525,1420,1345,1115
¹H-NMR(CDCl₃)δ: 1.52–1.71(1 H,m),1.75–2.20(6 H,m), 2.35(3 H,s),3.01–3.19(1 H,m),3.45–4.05(4 H,m), 4.10–4.45(3 H,m),4.60–4.72(1 H,m),5.80–5.95(1 H,m), 6.90–7.00(1 H,m),7.30–7.55(4 H,m),7.60–7.85(4 H,m), 7.90–8.05(2 H,m)

Reference Example 30

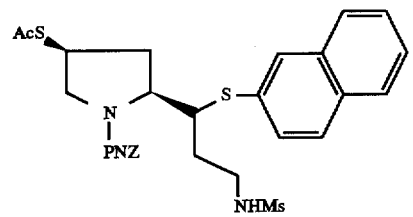

Starting material for diastereomer A
IR(KBr)cm⁻¹: 1700,1525,1410,1340,1115
¹H-NMR(CDCl₃)δ: 1.70–2.05(2 H,m),2.33(3 H,s), 2.55–2.70(1 H,m),2.92(3 H,s),3.05–3.52,(3 H,m), 3.63–4.45(5 H,m),4.52–5.30(3 H,m),6.89–7.25(2 H,m), 7.35–8.00(8 H,m),8.15–8.30(1 H,m)

Starting material for diastereomer B
IR(KBr)cm⁻¹: 1700,1520,1415,1340,1150,1115
¹H-NMR(CDCl₃)δ: 1.65–2.25(4 H,m),2.36(3 H,s),2.93(3 H,s), 3.02–3.55(3 H,m),3.65–4.05(2 H,m),4.06–4.48(2 H,m), 4.55–5.01(2 H,m),6.89–6.98(1 H,d,J=8.7 Hz), 7.15–7.55(3 H,m),7.61–7.78(3 H,m),7.82–8.05(4 H,m)

Reference Example 31

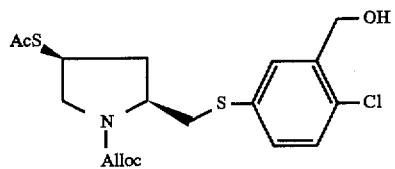

IR(KBr)cm⁻¹: 3452,1743,1699,1404,1352,1230,1113, 1045

¹H-NMR(CDCl₃)δ: 1.90–2.05(1 H,m),2.17(3 H,s),2.34(3 H,s), 2.50–2.60(1 H,m),2.90–4.20(6 H,m),4.50–4.60(2 H,m), 5.15–5.35(4 H,m),5.80–6.00(1 H,m),7.25–7.50(3 H,m)

Reference Example 32

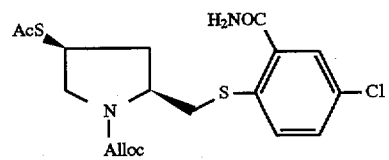

IR(KBr)cm⁻¹: 3435,1691,1406,1354,1115,606

¹H-NMR(CDCl₃)δ: 1.90–2.10(1 H,m),2.34(3 H,s), 2.60–2.75(1 H,m),3.20–4.15(4 H,m),4.50–4.65(2 H,m), 5.20–5.35(2 H,m),5.75–6.00(2 H,m),6.50–6.65(1 H,m), 7.30–7.70(3 H,m)

Reference Example 33

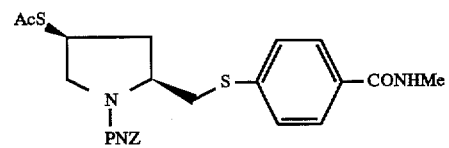

IR(KBr)cm⁻¹: 3452,1695,1647,1601,1531,1408,1346, 1113

¹H-NMR(CDCl₃)δ: 1.95–2.05(1 H,m),2.35(3 H,s), 2.50–2.65(1 H,m),3.00(3 H,s),3.05–4.20(6 H,m), 5.15–5.30(2 H,m),6.00–6.10(1 H,br s),7.40–8.25(8 H,m)

Reference Example 34

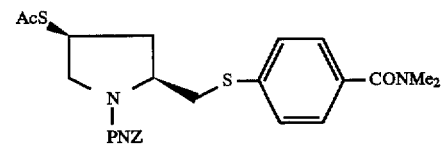

IR(KBr)cm⁻¹: 3454,1693,1593,1531,1518,1408,1346

¹H-NMR(CDCl₃)δ: 1.90–2.10(1 H,m),2.35(1 H,s), 2.50–2.60(1 H,m),2.80–3.20(8 H,m),3.20–4.20(4 H,m), 5.15–5.30(2 H,m),7.20–8.30(8 H,m)

Reference Example 35

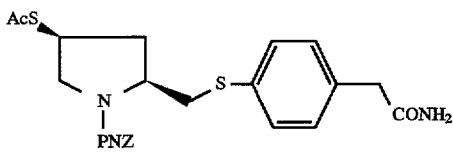

IR(KBr)cm⁻¹: 3454,1693,1601,1518,1408,1346,1113

¹H-NMR(CDCl₃)δ: 1.90–2.10(1 H,m),2.35(3 H,s), 2.50–2.65(1 H,m),3.20–3.70(4 H,m),3.80–4.20(2 H,m), 5.15–5.20(2 H,m),5.30–5.40(2 H,br),7.10–8.30(8 H,m)

Reference Example 36

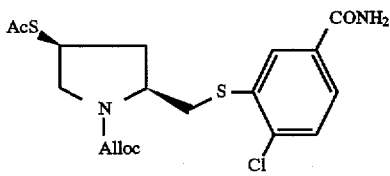

IR(KBr)cm⁻¹: 3429,1676,1554,1408,1348,1120,768,608

¹H-NMR(CDCl₃)δ: 1.90–2.10(1 H,m),2.37(3 H,s), 2.60–3.00(3 H,m),3.30–3.50(1 H,m),3.70–4.20(4 H,m), 4.55–4.70(2 H,m),5.20–5.40(2 H,m),5.50–5.60(1 H,br), 5.80–6.00(1 H,m),7.40–8.30(3 H,m)

Reference Example 37

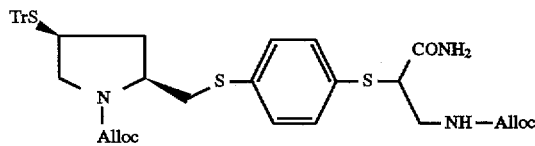

IR(KBr)cm⁻¹: 1701,1439,1406,1321,1254,1146,1103, 989

¹H-NMR(CDCl₃)δ: 1.60–1.80(1 H,m),2.15–2.25(1 H,m), 2.70–3.00(2 H,m),3.50–3.80(7 H,m),4.40–4.60(4 H,m), 5.15–5.50(5 H,m),5.80–6.00(2 H,m),6.05–6.25(1 H,br), 7.20–7.55(19 H,m)

Reference Example 38

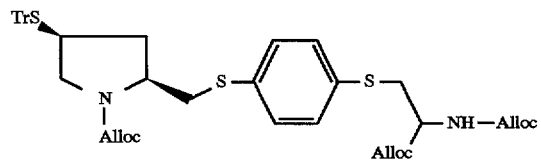

IR(KBr)cm⁻¹: 2950,2450,1701,1439,1410,1329,1178, 1103,989, 704

¹H-NMR(CDCl₃)δ: 1.70–1.85(1 H,m),2.0–2.20(1 H,m), 2.70–3.00(5 H,m),3.30–3.40(3 H,m),3.75–3.90(1 H,m), 4.20–4.70(7 H,m),5.15–5.30(4 H,m),5.50–5.60(1 H,m), 5.70–5.90(3 H,m),7.20–7.50(19 H,m)

Reference Example 39

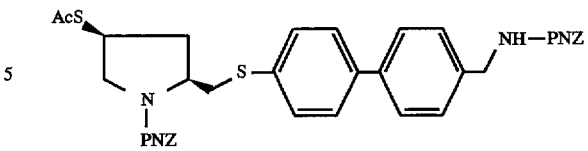

¹H-NMR(CDCl₃)δ: 2.32(3 H,s),4.42(2 H,br d),4.90–5.40(4 H,m), 7.10–7.60(12 H,m),7.90–8.30(4 H,m)

Reference Example 40

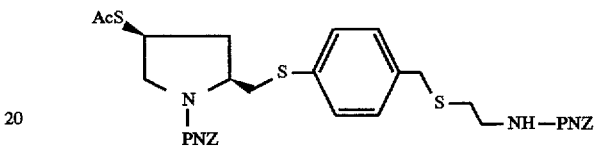

IR(KBr)cm⁻¹: 3747,2925,1700,1519,1346,1247,1114, 848,630

¹H-NMR(CDCl₃)δ: 1.59(1 H,s),2.34(3 H,s),2.56(3 H,t), 2.88–3.10(2 H,m),3.31–3.34(3 H,m),3.49(1 H,s),3.60(1 H,s), 3.65(2 H,s),3.80–4.00(1 H,m),5.18(4 H,d,J=4.7 Hz), 7.23–7.52(8 H,m),8.19–8.23(4 H,d,J=8.7 Hz)

Reference Example 41

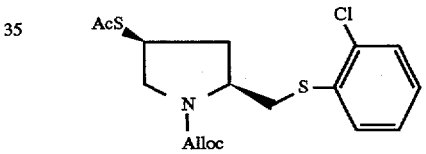

IR(KBr)cm⁻¹: 3500,2900,1695,1454,1430,1403

¹H-NMR(CDCl₃)δ: 1.92–2.12(1 H,m),2.34(3 H,s), 2.50–2.73(1 H,m),2.86–3.06(1 H,m),3.23–3.38(1 H,m), 3.49–4.25(4 H,m),4.52–4.67(2 H,m),5.18–5.41(2 H,m), 5.83–6.05(1 H,m),7.00–7.72(4 H,m)

Reference Example 42

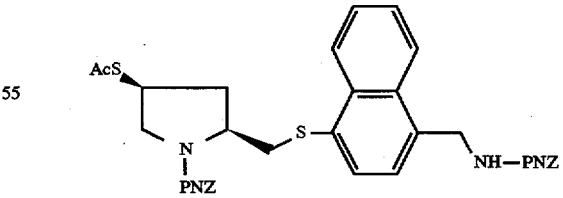

IR(KBr)cm⁻¹: 3330,3075,2925,1695,1604,1519

¹H-NMR(CDCl₃)δ: 1.95–2.20(1 H,m),2.34(3 H, s),2.46–2.73(1 H,m),3.03–3.50(2 H,m),3.62–4.28(4 H,m), 4.75–5.37(7 H,m),7.10–7.83(8 H,m),7.92–8.10(2 H,m), 8.14–8.31(3 H,m),8.37–8.53(1 H,m)

Reference Example 43

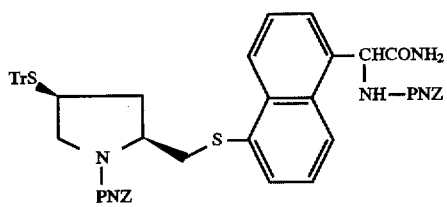

¹H-NMR(CDCl₃)δ: 1.80–1.90(1 H,m),2.70–2.90(2 H,m), 3.30–3.50(3 H,m),4.10–4.20(2 H,m),4.80–5.00(2 H,m), 5.60–5.80(3 H,m),6.10–6.20(1 H,m)

Reference Example 44

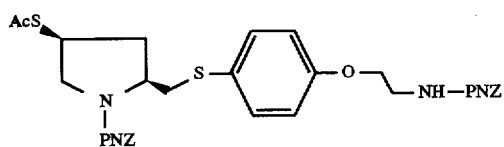

IR(KBr)cm⁻¹: 3344,2877,1695,1525,1403,1349,1238, 1110,861

¹H-NMR(CDCl₃)δ: 1.90–2.10(1 H,m),2.34(3 H,s), 2.80–4.20(5 H,m),5.10–5.30(5 H,m),6.70–6.80(2 H,m), 7.20–7.50(6 H,m),8.10–8.20(4 H,m)

Reference Example 45

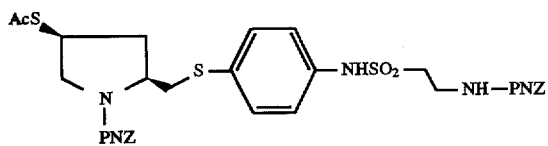

¹H-NMR(CDCl₃)δ: 1.90–2.10(1 H,m),2.35(3 H,s), 2.90–3.30(6 H,m),3.50–4.20(5 H,m),5.16(2 H,s),5.19(2 H,s), 5.50–5.70(1 H,br),7.00–7.60(8 H,m),8.20–8.30(4 H,m)

Reference Example 46

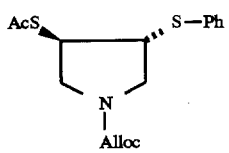

Starting material for Diastereomer A

¹H-NMR(CDCl₃)δ: 2.36(3 H,s),3.45–3.60(2 H,m),3.70–4.00(3 H,m),4.30(1 H,m),4.58(2 H,m),5.20–5.35(2 H,m), 5.91(1 H,m),7.26–7.35(3 H,m),7.40–7.55(2 H,m)

Reference Example 47

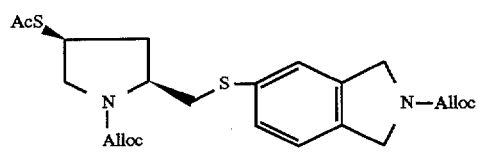

¹H-NMR(CDCl₃)δ: 1.97(1 H,m),2.33(3 H, s),2.55(1 H,m), 2.97(1 H,m),3.22(1 H,m),3.58(1 H,m),3.87(1 H,m), 4.04(2 H,m),4.45–4.75(8 H,m),5.15–5.38(4 H,m), 5.80–6.05(2 H,m),7.10–7.40(3 H,m)

Reference Example 48

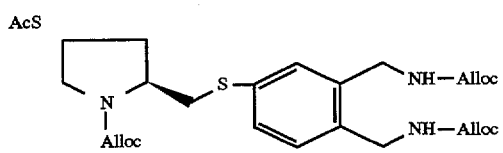

¹H-NMR(CDCl₃)δ: 1.94(1 H,m),2.33(3 H,s),2.55(1 H,m), 2.80(1 H,m),3.27(1 H,m),3.70(1 H,m),3.89(1 H,m), 4.02(2 H,m),4.30–4.60(10 H,m),5.15–5.35(6 H,m), 5.75–5.95(3 H,m),7.22(2 H,m),7.56(1 H,s)

Reference Example 49

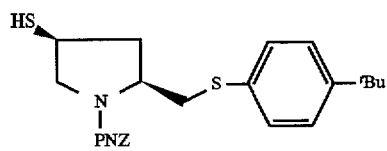

IR(KBr)cm⁻¹: 2962,1704,1606,1523,1425,1402,1346, 1199,1145, 1106,1012,854,825,765,736,549

¹H-NMR(CDCl₃)δ: 1.56(9 H,s),1.71(1 H,d,J=5.5 Hz), 1.90(1 H,m), 2.62(1 H,m),3.10–3.20(3 H,m),3.55(1 H,m), 4.00–4.20(2 H,m),5.15(2 H,s),7.24(2 H,d,J=5.5 Hz),7.33(2 H,d,J=5.5 Hz),7.49(2 H,d,J=8.3 Hz),8.21(2 H,d,J=8.3 Hz)

Reference Example 50

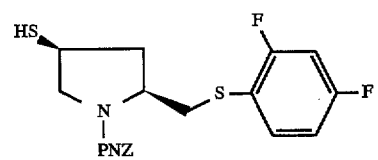

IR(KBr)cm⁻¹: 1700,1606,1591,1571,1519,1454,1427, 1402,1346, 1257,1199,1147,1106,1022,894,852,804,767, 736,599

¹H-NMR(CDCl₃)δ: 1.77(1H,d,J=5.3 Hz),1.92(1 H,m), 2.69(1 H,m), 3.10–3.30(3 H,m),3.63(1 H,dd,J=2.3 & 13.4 Hz),4.00–4.20(2 H,m),5.22(2 H,s),6.74(1 H,m),7.30–7.50(4 H,m),8.22(2 H,d,J=8.5 Hz)

Reference Example 51

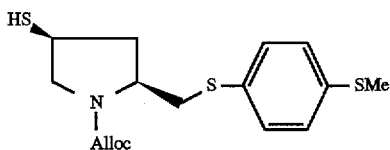

IR(KBr)cm$^{-1}$: 2921,1695,1477,1403,1322,1197,1147, 1106,987, 933,810,769,495

$^1$H-NMR(CDCl$_3$)δ: 1.69(1 H,m),1.88(1 H,m),2.46(3 H,s), 2.55(1 H,m),3.00–3.30(3 H,m),3.51(1 H,m), 3.90–4.10(2 H,m),4.52(2 H,m),5.23(2 H,m),5.87(1 H,m), 7.20–7.30(4 H,m)

Reference Example 52

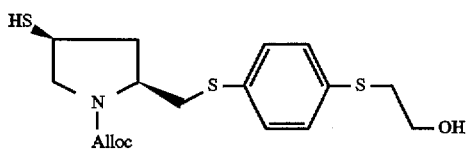

IR(KBr)cm$^{-1}$: 3448,2929,1691,1479,1421,1365,1197, 1106,1047, 1010,811,769

$^1$H-NMR(CDCl$_3$)δ: 1.71(1 H,m),1.89(1 H,m),2.57(1 H,m),3.00–3.30(6 H,m),3.73(2 H,t,J=5.9 Hz),4.05(2 H,m), 4.53(2 H,m), 5.20–5.30(2 H,m),5.91(1 H,m),7.31(4 H,s)

Reference Example 53

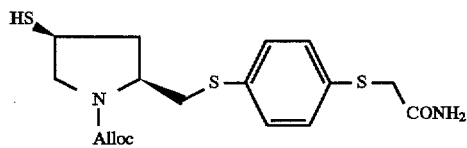

IR(KBr)cm$^{-1}$: 3380,3183,1693,1631,1407,1195,1108, 808

$^1$H-NMR(CDCl$_3$)δ: 1.71(1 H,d,J=6.3 Hz),1.85(1 H,m), 2.59(1 H,m), 3.00–3.30(3 H,m),3.58(2 H,s),3.60(1 H,m), 4.05(2 H,m), 4.53(2 H,m),5.25(2 H,m),5.45(1 H,m),5.90(1 H,m), 6.61(1 H,m),7.20–7.40(4 H,m)

Reference Example 54

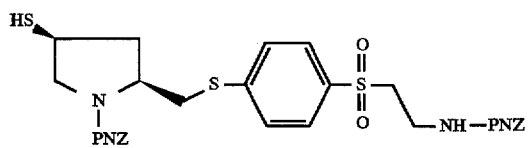

IR(KBr)cm$^{-1}$: 1700,1519,1402,1348,1253,1147,1095, 852,763, $^1$H-NMR(CDCl$_3$)δ: 1.78(1 H,d,J=6.0 Hz),1.85(1 H,m), 2.65(1 H,m), 3.10–3.40(5 H,m),3.60–3.80(3 H,m), 4.00–4.20(2 H,m), 5.18(4 H,s),5.59(1 H,m),7.50(4 H,d,J= 8.0 Hz), 7.61(2 H,d,J=8.4 Hz),7.77(2 H,d,J=8.4 Hz), 8.22(2 H,d,J=8.0 Hz)

Reference Example 55

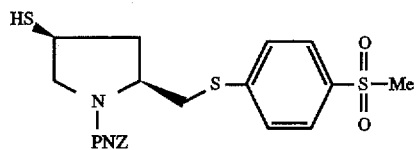

IR(KBr)cm$^{-1}$: 1700,1581,1519,1400,1348,1305,1199, 1149,1095

$^1$H-NMR(CDCl$_3$)δ: 1.77(1 H,d,J=6.3 Hz),1.87(1 H,m), 2.66(1 H,m), 3.03(3 H,s),3.20–3.40(3 H,m),3.76(1 H,dd,J= 2.8 & 13.7 Hz), 4.00–4.20(2 H,m),5.15 and 5.23(each 1 H,ABq,J=12.0 Hz), 7.51(2 H,d,J=8.7 Hz),7.58(2 H,d,J=8.5 Hz), 7.82(2 H,d,J=8.5 Hz),8.23(2 H,d,J=8.7 Hz)

Reference Example 56

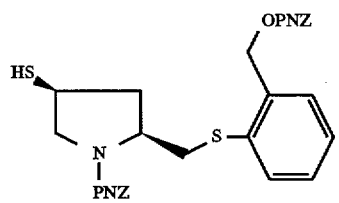

$^1$H-NMR(CDCl$_3$)δ: 1.71–1.95(2 H,m),2.55–2.69(1H,m), 3.18–4.13(5 H,m),4.86(1 H,s),5.18(2 H,s),5.29–5.33(4 H,m), 7.20–8.28(12 H,m)

Reference Example 57

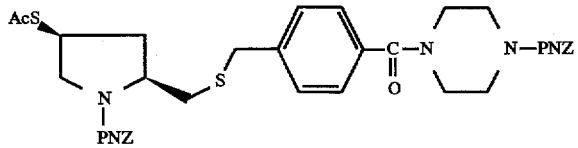

$^1$H-NMR(CDCl$_3$)δ: 1.84–1.96(2 H,m),2.33(3 H,s), 2.53–4.13(16 H,m),5.20–5.27(4 H,m),7.37–8.28(12 H,m)

Reference Example 58

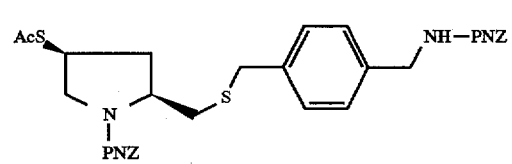

$^1$H-NMR(CDCl$_3$)δ: 1.86–2.19(2 H,m),2.35(3 H,s), 2.42–3.30(5 H,m),3.67–3.95(3 H,m),4.36–4.40(2 H,m), 5.20–5.22(4 H,m),7.21–8.26(12 H,m)

Reference Example 59

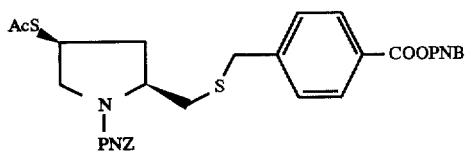

$^1$H-NMR(CDCl$_3$)δ: 1.80–1.99(2 H,m),2.31(3 H,s), 2.49–3.28(5 H,m),3.70–3.95(3 H,m),5.18(2 H,s),5.42(2 H,s), 7.39–7.62(6 H,m),7.97–8.28(6 H,m).

Reference Example 60

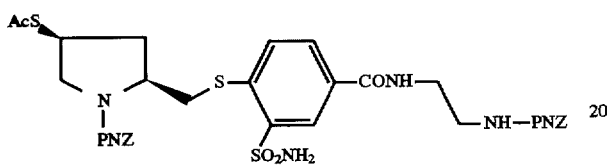

IR(KBr)cm$^{-1}$: 3429,2368,1699,1522,1346

$^1$H-NMR(CDCl$_3$)δ: 2.00(1 H,m),2.36(3 H,s),2.65(1 H,m), 3.18(1 H,m),3.35(1 H,dd,J=7.0 & 10.0 Hz),3.49(2 H,m), 3.59(2 H,m),3.75(1 H,d,J=12.0 Hz),3.94(1 H,t,J=8.0 Hz), 4.05–4.25(2 H,m),5.20(4 H,d,J=5.2 Hz),5.43(2 H,m), 5.52(1 H,m),7.20(1 H,s),7.45(2 H,d,J=8.9 Hz), 7.50(2 H,d, J=8.6 Hz),7.75(1 H,d,J=9.0 Hz), 7.88(1 H,d,J=9.0 Hz), 8.09(2 H,d,J=8.9 Hz), 8.21(2 H,d,J=8.6 Hz),8.31(1 H,s)

Reference Example 61

IR(KBr)cm$^{-1}$: 3697,1703,1524,1348,1093

$^1$H-NMR(CDCl$_3$)δ: 2.05(1 H,m),2.36(3 H, s),2.57(3 H,d, J=5.3 Hz), 3.15(1 H,m),3.35(1 H,m),3.50(2 H,m),3.62(2 H,m), 3.78(1 H,m),3.95(1 H,t,J=7.0 Hz),4.05–4.25(2 H,m), 5.23(4 H,s),5.45(1 H,br s),7.12(1 H,br s), 7.49(4 H,d,J=9.3 Hz),7.85(1 H,d,J=9.3 Hz), 7.98(1 H,d,J=9.3 Hz), 8.10–8.25(4 H,m),8.30(1 H,s)

Reference Example 62

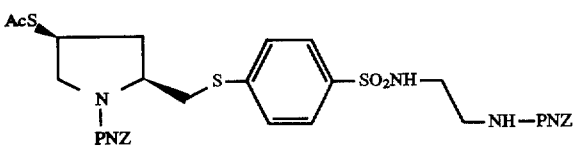

IR(KBr)cm$^{-1}$: 3388,1697,1578,1522,1346

$^1$H-NMR(CDCl$_3$)δ: 1.97(1 H,m),2.35(3 H,s),2.60(1 H,m), 3.02–3.15(3 H,m),3.25–3.40(3 H,m),3.73(1 H,dd,J= 2.7 & 13.3 Hz), 3.91(1 H,m),4.05–4.20(2 H,m),4.92(1 H,m) ,5.19(4 H,s), 5.24(1 H,m),7.45–7.55(6 H,m),7.73(1 H,d,J= 8.5 Hz), 8.22(2 H,d,J=8.8 Hz), 8.23(2 H,d,J=8.8 Hz)

Reference Example 63

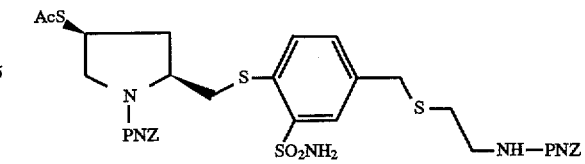

$^1$H-NMR(CDCl$_3$)δ: 2.00(1 H,m),2.35(3 H,s),2.45–2.70(3 H,m), 3.05–3.40(3 H,m),3.70(2 H,s),3.92(1 H,m), 4.03–4.25(2 H,m),5.19(4 H,d,J=8.3 Hz),5.53(2 H,s),7.47(1 H,d,J=9.0 Hz),7.52(4 H,d,J=8.9 Hz),7.75(1 H,d,J=9.0 Hz), 7.90(1 H, s),8.15–8.25(4 H,m)

Reference Example 64

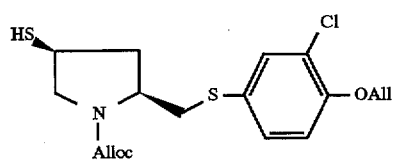

IR(KBr)cm$^{-1}$: 1772,1747,1699,1686,1650,1574,1558

$^1$H-NMR(CDCl$_3$)δ: 1.70(1 H,m),1.85(1 H,m),2.60(1 H,m),2.90–3.50(4 H,m),3.90–4.15(2 H,m),5.15–5.50(4 H,m),5.78–6.15(2 H,m),6.76(1 H,d,J=7.4 Hz),7.22(1 H,dd, J=1.6 & 7.4 Hz),7.47(1 H,d,J=1.6 Hz)

Reference Example 65

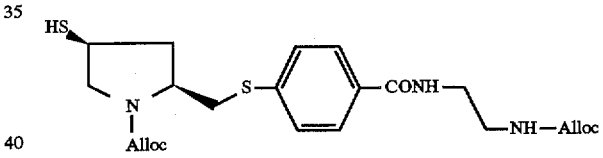

IR(KBr)cm$^{-1}$: 1695,1643,1533,1408,1092

$^1$H-NMR(CDCl$_3$)δ: 1.85(1 H,m),2.60(1 H,m), 3.00–3.35(3 H,m), 3.45(2 H,m),3.55(2 H,m),3.65(1 H,m), 3.95–4.20(2 H,m),4.50–4.65(4 H,m),5.15–5.40(4 H,m), 5.80–6.05(2 H,m),7.45(2 H,m),7.70(2 H,m)

Reference Example 66

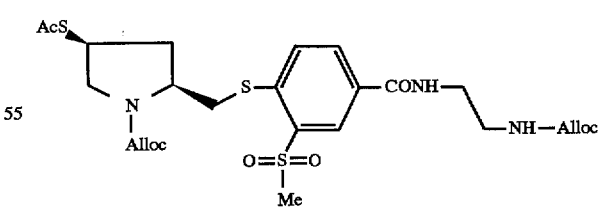

IR(KBr)cm$^{-1}$: 1695,1593,1549,1531,1408,1311,1142

$^1$H-NMR(CDCl$_3$)δ: 2.00(1 H,m),2.65(1 H,m),3.04(1 H,m), 3.22(3 H,s),3.33(1 H,m),3.46(2 H,m),3.60(2 H,m), 3.80–4.00(2 H,m),4.03–4.20(2 H,m),4.53–4.75(4 H,m), 5.15–5.45(4 H,m),5.80–6.10(2 H,m),7.65(1 H,d,J=8.2 Hz), 8.05(1 H,d,J=8.2 Hz),8.40(1 H,br s)

Reference Example 67

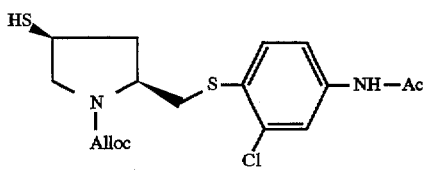

IR(KBr)cm⁻¹: 1684,1589,1520,1473,1408,1377,1117

¹H-NMR(CDCl₃)δ: 1.90(1 H,m),2.18(3 H,s),2.65(1 H,m), 3.00–3.85(4 H,m),3.90–4.20(2 H,m),4.45–4.60(2 H,m),5-15–5.35(2 H,m),5.80–6.00(1 H,m),7.20–7.40(2 H,m),7.60(1 H,m)

Reference Example 68

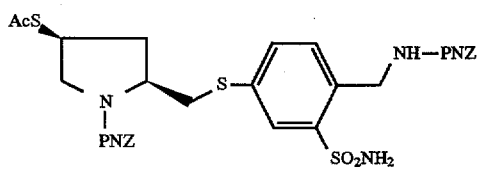

IR(KBr)cm⁻¹: 1697,1522,1346,1123

¹H-NMR(CDCl₃)δ: 1.95(1 H,m),2.60(1 H,m), 2.70–3.45(3 H,m), 3.65–4.20(3 H,m),4.65(1 H,m),4.80(1 H,m),5.05–5.25(4 H,m),7.30–7.70(6 H,m),8.10–8.30(5 H,m)

Reference Example 69

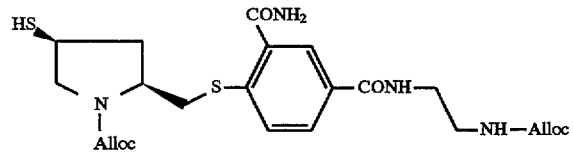

¹H-NMR(CDCl₃)δ: 1.73(1 H,d,J=6.3 Hz),1.80–1.90(1 H,m),2.60–2.70(1 H,m),3.00–3.70(8 H,m),3.90–4.10(2 H,m), 4.55(4 H,d,J=5.4 Hz),5.15(1 H,br),5.20–5.30(4 H,m), 5.77(1 H,br),5.84–5.96(2 H,m),7.03(1 H,br),7.30–7.70(3 H,m)

Reference Example 70

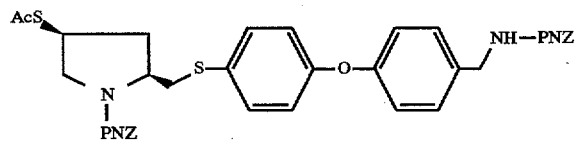

¹H-NMR(CDCl₃)δ: 2.00(1 H,m),2.34(3 H,s),2.57(1 H,m), 2.75–3.60(3 H,m),3.88(1 H,m),4.10(2 H,m),4.37(2 H,m), 5.15(2 H,s),5.20(2 H,s),5.10–5.30(1 H,m), 6.70–7.00(4 H,m),7.15–7.60(8 H,m),8.10–8-30(4 H,m)

Reference Example 71

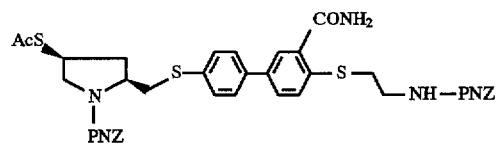

¹H-NMR(CDCl₃)δ: 2.05(1 H,m),2.35(3 H,s),2.60(1 H,m), 2.90–3.20(3 H,m),3.20–3.70(4 H,m),3.90(1 H,m), 4–10(2 H,m), 5.05–5.25(4 H,m),5.90–6.15(2 H,br), 6.35–6.70(1 H,br),7.20–7.80(11 H,m),8.15(4 H,m)

Reference Example 72

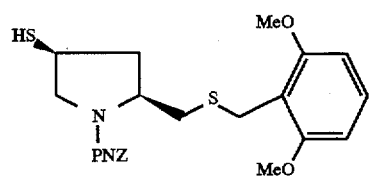

¹H-NMR(CDCl₃)δ: 1.70–2.01(1 H,m),2-38–2.70(1 H,m), 3.75–4.00(9 H,m),5.15–5.31(2 H,m),6.48–6.61(2 H,m),7.10–7.30(1 H,m),7.41–7.55(2 H,m),8.10–8.30(2 H,m)

Reference Example 73

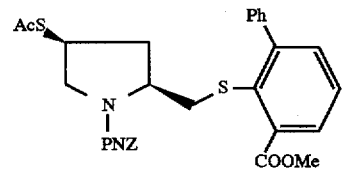

¹H-NMR(CDCl₃)δ: 2.01(1 H,m),2-30(3 H,s),2-53(1 H,m), 2.83(1 H,m),2.91(1 H,m),3.62(2 H,m),3.71(3 H,s), 3.90(2 H,m),5.10(2 H,m),7.40(8 H,m),8.19(4 H,m)

Reference Example 74

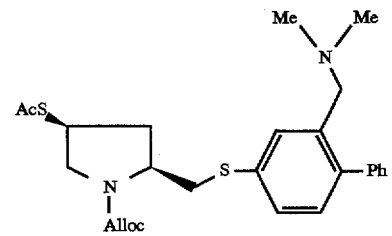

¹H-NMR(CDCl₃)δ: 2.02(1 H,m),2.16(6 H,s),2.34(3 H,s), 2.59(1 H,m),3.03(1 H,m),3.26(1 H,m),3.34(2 H,s), 3.67(1 H,m),3.86(1 H,m),4.12(2 H,m),4.51(2 H,m), 5.25(2 H,m), 5.90(1 H,m),7.19(1 H,s),7.36(6 H,m), 7.58(1 H,s)

Reference Example 75

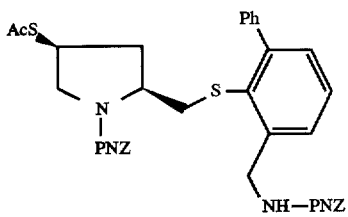

$^1$H-NMR(CDCl$_3$)δ: 1.96(2 H,m),2.03(3 H,s),2.74(2 H,m), 3.06(1 H,m),3.69(2 H,m),3.96(1 H,m),4.62(2 H,m), 5.10(2 H,s),5.23(2 H,s),5.84(1 H,s),7.40(12 H,m), 8.19(4 H,m)

Reference EXAMPLE 76

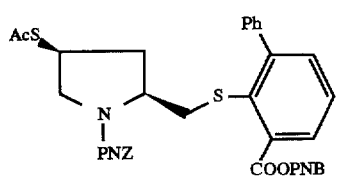

$^1$H-NMR(CDCl$_3$)δ: 1.39(1 H,m),2.02(1 H,m),2.30(3 H,s), 2.50(1 H,m),2.82(1 H,m),2.96(1 H,m),3.66(2 H,m), 3.91(1 H,m),5.08(2 H,s),5.46(2 H,s),7.46(12 H,m), 8.21(4 H,m)

Reference Example 77

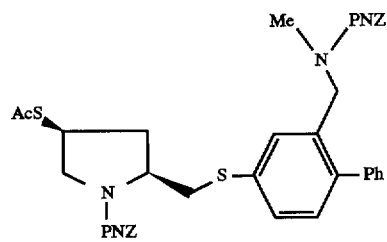

$^1$H-NMR(CDCl$_3$)δ: 2.01(1 H,m),2.36(3 H,s),2.58(1 H,m), 2.74(3 H,s),3.03(1 H,m),3.29(1 H,m),3.56(1 H,m), 3.89(1 H,m),4.12(2 H,m),4.46(2 H,m),5.19(4 H,m), 7.42(12 H,m),8.19(4 H,m)

Reference Example 78

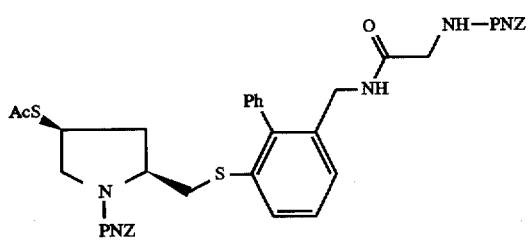

$^1$H-NMR(CDCl$_3$)δ: 1.86(1 H,m),2.01(1 H,m),2.86(1 H,m), 3.47(3 H,m),3.76(2 H,m),4.16(3 H,m),4.34(1 H,m), 5.19(4 H,s),5.52(1 H,s),5.91(1 H,s),7.40(12 H,m), 8.16(4 H,m)

Reference Example 79

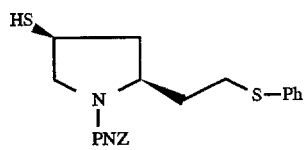

IR(KBr)cm$^{-1}$: 3650,3080,2940,2870,1700,1510,1360, 1090,960, 850,740

$^1$H-NMR(CDCl$_3$)δ: 1.68(1 H,m),1.83(1 H,m),2.25(1 H,m), 2.33(3 H,s),2.58(1 H,m),2.70–3.00(2 H,m),3.19(1 H,m),3.88(1 H,m),4.00–4.15(2 H,m),5.10–5.30(2 H,m), 7.15–7.40(5 H,m),7.40–7.60(2 H,m),8.10–8.30(2 H,m)

Reference Example 80

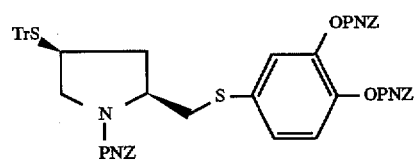

IR(KBr)cm$^{-1}$: 3750,2940,1770,1700,1520,1350,1260, 1180,1090, 850,740

$^1$H-NMR(CDCl$_3$)δ: 1.75(1 H,m),2.26(1 H,m), 2.70–3.10(3 H,m), 3.26,3.45(1 H,m),3.86(1 H,m), 5.00–5.10(3 H,m), 5.30(4 H,s),7.10–7.30(13 H,m),7.37(1 H,d,J=8.0 Hz), 7.43(6 H,d,J=7.0 Hz),7.52(4 H,d,J=8.0 Hz), 8.10–8–30(6 H,m)

Reference Example 81

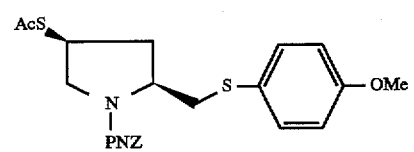

IR(KBr)cm$^{-1}$: 3650,3080,2940,1710,1510,1360,1290, 1090,960, 830,740

$^1$H-NMR(CDCl$_3$)δ: 1.95–2.10(1 H,m),2.34(3 H,s), 2.40–2.70(1 H,m),2.88,3.08(1 H,m),3.20–3.50(2 H,m), 3.75(3 H, s),3.87(1 H,m),3.95– 4.15(2 H,m),5.00–5.20(2 H,m),6.70–6.90(2 H,m),7.25–7.50(4 H,m),8.15–8.30(2 H,m)

Reference Example 82

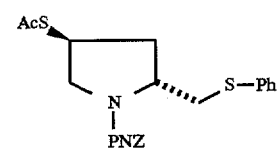

IR(KBr)cm$^{31}$ $^1$: 3750,2950,1690,1520,1340,1290,1100, 960,840, 740

$^1$H-NMR(CDCl$_3$)δ: 2.09(1 H,m),2.33(3 H,s),2.40(1 H,m), 2.92,3.07(1 H,m),3.30–3.50(2 H,m),3.87(1 H,m), 4.00–4.25(2 H,m),5.10–5.25(2 H,m),1.10–7.35(4 H,m), 7.40–7.50(3 H,m),8.15–8.25(2 H,m)

Reference Example 83

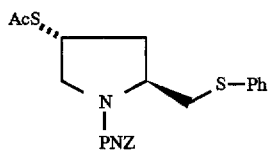

IR(KBr)cm$^{-1}$: 3650,3080,2940,1710,1510,1360,1290, 1090,960, 830,730

$^1$H-NMR(CDCl$_3$)δ: 2.09(1 H,m),2.33(3 H,s),2.41(1 H,m), 2.92,3.07(1 H,m),3.30–3.50(2 H,m),3.85(1 H,m), 4.00–4.25(2 H,m),5.10–5.25(2 H,m),7.10–7.35(4 H,m), 7.35–7.50(3 H,m),8.15–8.25(2 H,m)

Reference Example 84

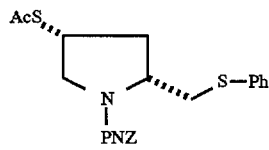

IR(KBr)cm$^{-1}$: 3650,3080,2940,1700,1510,1360,1290, 1090,950, 850,740

$^1$H-NMR(CDCl$_3$)δ: 2.01(1 H,m),2.34(3 H,s),2.56(1 H,m), 2.98,3.10(1 H,m),3.26(1 H,m),3.42,3.58(1 H,m), 3.88(1 H,m),4.00–4.20(2 H,m),5.14(2 H,s),7.10–7.35(4 H,m),7.35–7.50(3 H,m),8.15–8.25(2 H,m)

Reference Example 85

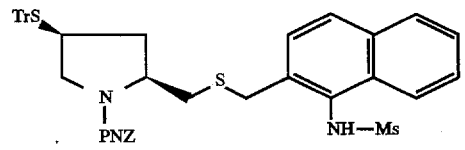

IR(KBr)cm$^{-1}$: 3750,2930,1700,1520,1440,1400,1340, 1150,1090, 750,700

$^1$H-NMR(CDCl$_3$)δ: 1.69(1 H,m),2.09(1 H,m), 2.45–2.60(2 H,m), 2.60–2.90(3 H,m),3.00(3 H,s),3.75(1 H,d,J=14.0 Hz), 3.91(1 H,m),4.49(1 H,d,J=14.0 Hz),5.04(2 H,s),7.10–7.45(17 H,m),7.45–7.65(3 H,m),7.80–7.90(2 H,m),8.10–8.25(3 H,m),8.62(1 H,s)

Reference Example 86

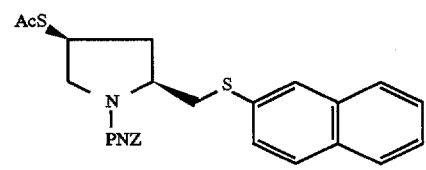

IR(KBr)cm$^{-1}$: 3750,2940,1700,1520,1400,1350,1200, 1100,960, 850,740

$^1$H-NMR(CDCl$_3$)δ: 2.08(1 H,m),2.33(3 H,m), 2.50–2.75(1 H,m), 3.00–3.40(2 H,m),3.15–3.50(1 H,m), 3.88(1 H,m),4.00– 4.30(2 H,m),4.90–5.20(2 H,m), 7.25–7.50(5 H,m), 7.64(1 H,m),7.70–7.95(3 H,m),8.00, 8.15(2 H,d,J=8.0 Hz)

Reference Example 87

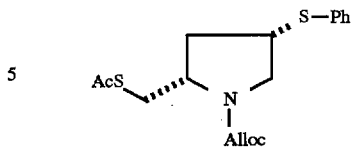

$^1$H-NMR(CDCl$_3$)δ: 1.74(1 H,m),2.30(3 H,s),2.46(1 H,m), 3.20–3.70(4 H,m),3.90–4.20(2 H,m),4.60(2 H,m), 5.15–5.40(2 H,m),5.90(1 H,m),7.20–7.50(5 H,m)

Reference Example 88

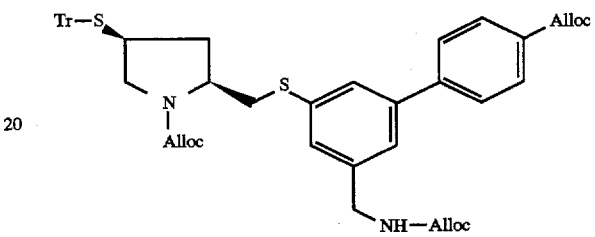

$^1$H-NMR(CDCl$_3$)δ: 1.76(1 H,m),2.04(3 H,s),2.28(1 H,m), 2.70–3.10(3 H,m),3.60(1 H,m),3.72(1H,m),4.40(3 H,m), 4.60(2 H,m),4.86(2 H,m),5.10–5.50(6 H,m), 5.60–6.15(3 H,m),7.10–7.40(10 H,m),7.40–7.70(10 H,m), 8.22(2 H,m)

Reference Example 89

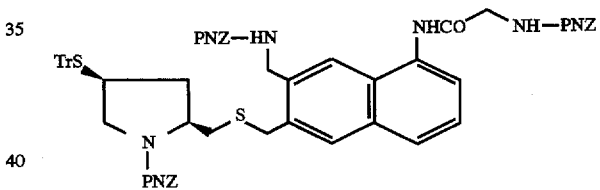

IR(KBr)cm$^-$: 3400,3330,3060,2940,1700,1520,1440, 1402,1350, 1250,1110,1050,850,740

$^1$H-NMR(CDCl$_3$)δ: 1.23(1 H,m),2.24(1 H,m),2.6–3.0(4 H,m),3.65–3.9(3 H,m),4.0–4.2(2 H,m),4.4–4.7(3 H,m), 4.8–5.3(2 H,m),5.14(2 H,s),5.20(2 H,s),5.7–6.1(2 H,m), 7.1–7.6(23 H,m),7.7–8.1(3 H,m),8.08(4 H,d,J=8 Hz), 8.16(2 H,d,J=8 Hz),8.53(1 H,m)

Reference Example 90

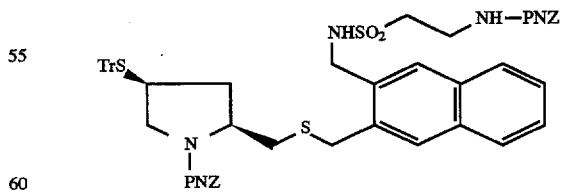

IR(KBr)cm$^{-1}$: 1706,1519,1346

$^1$H-NMR(CDCl$_3$)δ: 1.68(1 H,m),2.25(1 H,m), 2.60–3.95(4 H,m), 3.15(2 H,m),3.60(2 H,m),3.70–4.00(2 H,m),4.50(2 H,m), 4.80–5.30(4 H,m),5.60–5.80(2 H,m), 7.10–7.50(21 H,m),7.65–7.85(4 H,m),7.95–8.23(4 H,m)

Reference Example 91

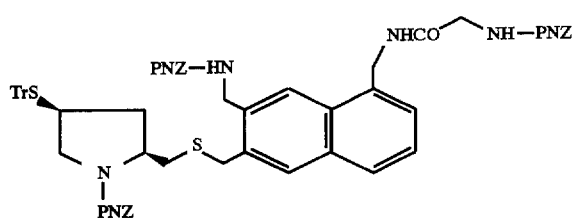

IR(KBr)cm⁻¹: 1700,1521,1346

¹H-NMR(CDCl₃)δ: 1.69(1 H,m),2.23(1 H,m), 2.65–2.98(5 H,m), 3.75–3.95(5 H,m),4.60(2 H,m),4.84(2 H,m),5.06(4 H,s), 5.22(2 H,s),7.15–7.55(23 H,m), 7.70–8.00(4 H,m),8.04–8.20(5 H,m)

Reference Example 92

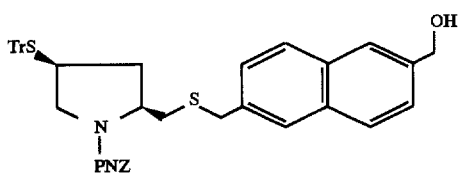

IR(KBr)cm⁻¹: 1697,1519,1403,1344,1199,1105,746,702

¹H-NMR(CDCl₃)δ: 1.75(1 H,m),2.18(1 H,m), 2.55–2.95(3 H,m), 3.65–3.90(3 H,m),4.78–5.12(6 H,m), 7.00–7.50(17 H,m),7.55–7.95(6 H,m),8.20(2 H,m)

Reference Example 93

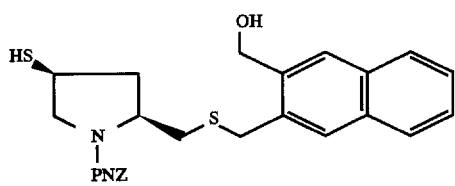

IR(KBr)cm⁻¹: 1695,1518,1404,1344,1200,1107,758,608

¹H-NMR(CDCl₃)δ: 1.74(1 H,m),2.56(1 H,m),2.84(1 H,m), 3.07(1 H,m),3.10–3.26(3 H,m),4.92–5.08(5 H,m), 5.16(2 H,s),7.47(4 H,m),7.80–7.86(4 H,m),8.19(2 H,d,J=8.5 Hz)

Reference Example 94

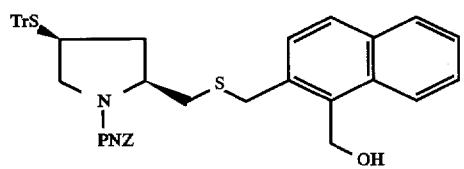

IR(KBr)cm⁻¹: 1699,1519,1408,1346,1281,1184,1107, 841, 746,706

¹H-NMR(CDCl₃)δ: 1.74(1 H,m),2.20(1 H,m), 2.54–3.00(3 H,m), 3.58–3.85(3 H,m),4.80–5.15(6 H,m), 7.10–7.55(17 H,m),7.60–7.70(6 H,m),8.08(2 H,m)

Reference Example 95

(2S,4S)-N-(p-Nitrobenzyloxycarbonyl)-2-[4-[N-P-nitrobenzyloxycarbonyl)aminomethyl]anilinomethyl]-4-tritylthiopyrrolidine

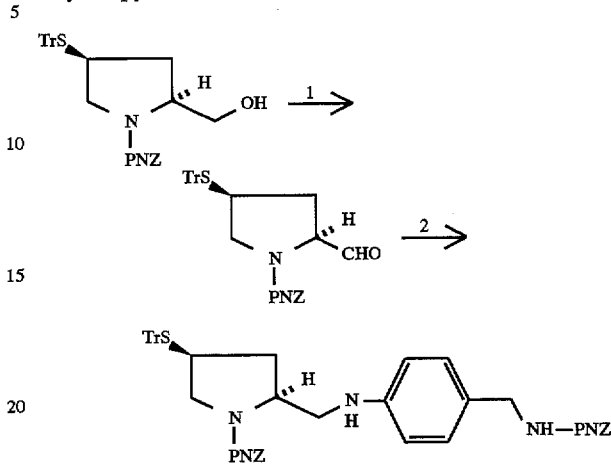

(Step 1)

Dimethyl sulfoxide (1.06 ml, 14.9 mmol) was added to a solution of oxalyl chloride (0.648 ml, 7.43 mmol) in methylene chloride (40 ml) at −78° C. in a nitrogen stream over 2 minutes. The resulting reaction solution was stirred at the same temperature for 10 minutes. To this reaction solution, a solution of (2S,4S)-2-hydroxymethyl-N-(p-nitrobenzyloxycarbonyl)-4-tritylthiopyrrolidine (2.47 g, 4.45 mmol) in methylene chloride (10 ml) was added dropwise over 5 minutes. This reaction mixed solution was stirred for 10 minutes and then triethylamine (3.11 ml, 22.3 mmol) was added dropwise over 2 minutes. This reaction solution was reverted to room temperature over 30 minutes, brought together with saturated aqueous ammonium chloride to terminate the reaction, and extracted with ethyl acetate. The organic layer was washed successively with water and saturated aqueous sodium chloride and dried over anhydrous magnesium sulfate. The solvent was distilled off in vacuo to give a crude product of (2S,4S)-N-(p-nitrobenzyloxycarbonyl)-4-tritylthioprolinal.

(Step 2)

To a solution of the compound obtained in Step 1 in tetrahydrofuran (25 ml), sodium triacetoxyborohydride (1.42 g, 668 mmol), 4-[N-(p-nitrobenzyloxycarbonyl) aminomethyl]aniline (1.61 g, 5.34 mmol) and acetic acid (0.306 ml, 5.34 mmol) were successively added at room temperature in a nitrogen stream. The reaction solution was stirred for 20 hours and then saturated aqueous sodium hydrogencarbonate was added thereto to terminate the reaction. This liquid mixture was extracted with ethyl acetate. The organic layer was washed successively with water and saturated aqueous sodium chloride, dried over anhydrous magnesium sulfate, and concentrated in vacuo. The resulting residue was subjected to silica gel column chromatography (Wakogel™ C-300 chloroform-ethyl acetate 85:15) to give the title compound (1.57 g, yield 42.1%).

¹H-NMR(CDCl₃)δ: 1.90–2.35(2 H,m),2.70–3–40(4 H,m), 3.50–3.80(1 H,m),3.84–4.04(1 H,m),4.24(2 H,d,J=5.6 Hz),⁴·⁹⁵⁻5.30(5 H,m),6.35–6.62(2 H,m),6.90–7.80(21 H,m), 8.05–8.30(4 H,m)

Reference Example 96

(2S,4S)-4-Acetylthio-N-(p-nitrobenzyloxycarbonyl)-2-[N-(p-nitrobenzyloxycarbonyl)anilinomethyl]pyrrolidine

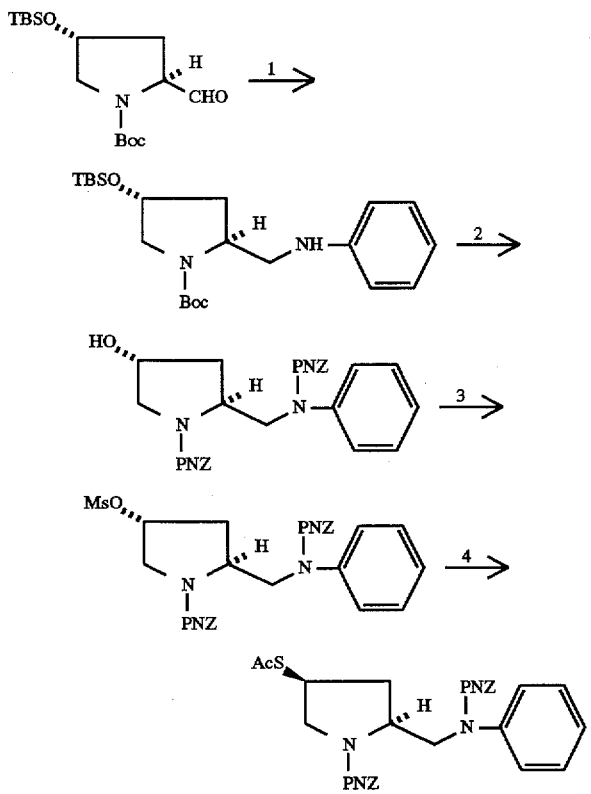

(Step 1)

(2S,4R)-2-Anilinomethyl-N-t-butoxycarbonyl-4-t-butyldimethylsiloxypyrrolidine (995 mg, yield: 82%) was prepared as a yellow oily substance, from (2S,4R)-N-t-butoxycarbonyl-4-t-butyldimethylsiloxyprolinal (990 mg, 3 mmol) and aniline (0.3 ml, 3.3 mmol), in the same manner as in Reference Example 95-2.

$^1$ H-NMR(CDCl$_3$)δ: 0.05(6 H,s),0.86(9 H,s),1.49(9 H,s), 1.70–2.11(3 H,m),3.05–3.61(4 H,m),4.07–4.40(2 H,m), 6.54–6.71(3 H,m),7.08–7.25(2 H,m)

(Step 2)

To a solution of the compound (945 mg, 2.3 mmol) obtained in Step 1 in tetrahydrofuran (8 ml), N,N-diisopropylethylamine (0.8 ml, 4.6 mmol) and then a solution of p-nitrobenzyloxycarbonyl chloride (750 mg, 3.45 mmol) in tetrahydrofuran (2 ml) were added dropwise in a nitrogen stream under cooling with ice. The reaction solution was stirred at the same temperature for 2 hours and then concentrated in vacuo. Ethyl acetate was added to the resulting residue. The organic layer was washed successively with 1N aqueous potassium hydrogensulfate and saturated aqueous sodium chloride, dried over anhydrous sodium sulfate, and concentrated in vacuo. To the resulting residue, 2N hydrogen chloride-methanol solution (4 ml) was added. The reaction solution was stirred at room temperature for 1.5 hours and then concentrated in vacuo. Methanol was added to the resulting residue and then the volatile components were distilled off in vacuo. To the resulting residue, dioxane-water solution (2:1, 9 ml) was added and the resulting solution was adjusted to pH 9.0 with 5N aqueous sodium hydroxide. While the solution was maintained at pH 8.0–9.0 by using 1N aqueous sodium hydroxide, a solution of p-nitrobenzyloxycarbonyl chloride (990 mg, 4.6 mmol) in dioxane (4 ml) was added dropwise thereto under cooling with ice. The reaction solution was poured into a liquid mixture of ethyl acetate water. The organic layer was washed with saturated aqueous sodium chloride, dried over anhydrous sodium sulfate, and concentrated in vacuo. The resulting residue was subjected to silica gel column chromatography (Wakogel™ C-300 heptane-ethyl acetate=3:1) to give (2S,4R)-4-hydroxy-N-(p-nitrobenzyloxycarbonyl)-2-[N-(p-nitrobenzyloxycarbonyl)anilinomethyl]pyrrolidine (1 g, yield: 94%) as a yellow oily substance.

$^1$H-NMR(CDCl$_3$)δ: 2.01–2.20(3 H,m),3.35–3.75(2 H,m), 3.83–4.29(3 H,m),4.40–4.55(1 H,m),5.05–5.21(4 H,m), 7.10–7.45(9 H,m),8.05–8.20(4 H,m)

(Step 3)

To a solution of the compound (1 g, 2.16 mmol) obtained in Step 2 in tetrahydrofuran (7 ml), triethylamine (0.45 ml, 3.24 mmol) and methanesulfonyl chloride (0.25 ml, 3.24 mmol) were successively added in a nitrogen stream under cooling with ice. The resulting reaction solution was stirred at the same temperature for 1.5 hours and brought together with water. The organic layer was washed with saturated aqueous sodium chloride, dried over anhydrous sodium sulfate, and concentrated in vacuo to give (2S,4R)-4-mesyloxy-N-(p-nitrobenzyloxycarbonyl)-2-[N-(p-nitrobenzyloxycarbonyl)anilinomethyl]pyrrolidine as a yellow oily substance, which was used for the next reaction without purification.

(Step 4)

To a solution of the compound obtained in Step 3 in N,N-dimethylformamide (6 ml), potassium thioacetate (428 mg, 4.32 mmol) was added. The resulting reaction solution was heated at 60° C. in a nitrogen stream for 5 hours and then poured into a liquid mixture of ethyl acetate with water. The organic layer was washed with saturated aqueous sodium chloride, dried over anhydrous sodium sulfate, and concentrated in vacuo. The resulting residue was subjected to silica gel column chromatography (Wakogel™ C-300 heptane-ethyl acetate=1:1) to give (2S,4S)-4-acetylthio-N-(p-nitrobenzyloxycarbonyl)-2-[N-(p-nitrobenzyloxycarbonyl)anilinomethyl]pyrrolidine (732 mg, yield: 65%) as a yellow oily substance.

$^1$H-NMR(CDCl$_3$)δ: 2.31(3 H,s),3.95–4.20(4 H,m),5.05(2 H,s), 5.19(2 H,s),7.19–7.45(9 H,m),8.08–8.21(4 H,m)

Reference Example 97

(2S,4S)-4-Acetylthio-N-(p-nitrobenzyloxycarbonyl)-2-[N-(p-nitrobenzyloxycarbonyl)-3-(p-nitrobenzyloxycarbonyl)anilinomethyl]pyrrolidine

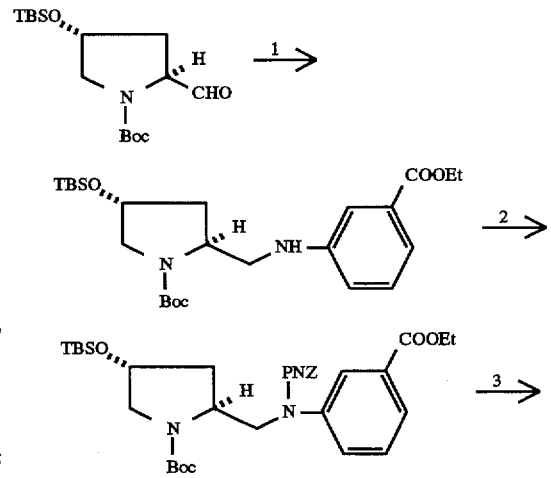

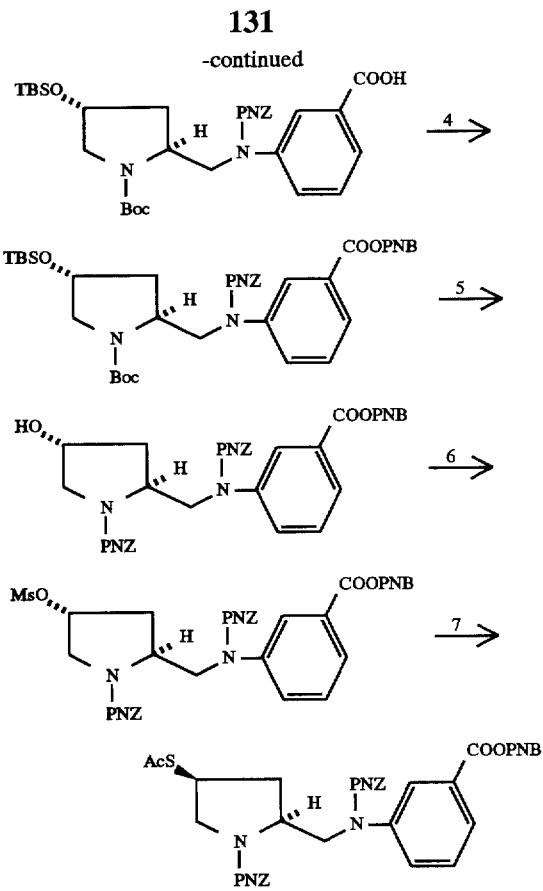

(Step 1)

(2S,4R)-N-t-Butoxycarbonyl-4-t-butyldimethylsiloxy-2-[3-(ethoxycarbonyl)anilinomethyl]pyrrolidine (1.03 g, yield: 71%) was prepared as a yellow oily substance, from (2S,4R)-N-t-butoxycarbonyl-4-t-butyldimethylsiloxy prolinal (1.0 g, 3.03 mmol) and ethyl m-aminobenzoate (550 mg, 3.33 mmol), in the same manner as in Reference Example 95-2

$^1$H-NMR(CDCl$_3$)δ: 0.01(6 H,s),0.81(9 H,s),1.32–1.41(3 H,m), 1.43(9 H,s),1.65–2.10(3 H,m),3.05–3.70(4 H,m), 4.20–4.40(4 H,m),6.70–6.78(1 H,m),7.03–7.31(3 H,m)

(Step 2)

To a solution of the compound (1.03 g, 2.15 mmol) obtained in Step 1 in tetrahydrofuran (7 ml), N,N-diisopropylethylamine (0.75 ml, 4.30 mmol) and then a solution of p-nitrobenzyloxycarbonyl chloride (694 mg, 3.22 mmol) in tetrahydrofuran (2 ml) were added dropwise in a nitrogen stream under cooling with ice. The resulting reaction solution was stirred at the same temperature for 1.5 hours, then concentrated in vacuo, and dissolved in ethyl acetate. The organic layer was washed successively with 1N aqueous potassium hydrogensulfate and saturated aqueous sodium chloride, dried over anhydrous sodium sulfate, and concentrated in vacuo. The resulting residue was subjected to silica gel column chromatography (Wakogel™ C-300, heptane-ethyl acetate=2:1) to give (2S,4R)-N-t-butoxycarbonyl-4-t-butyldimethylsiloxy- 2-[3-ethoxycarbonyl-N-(p-nitrobenzyloxycarbonyl)anilinomethyl]pyrrolidine (1.17 g, yield: 89%) as a yellow oily substance.

$^1$H-NMR(CDCl$_3$)δ: 0.03(6 H,s),0.85(9 H,s),1.22–1.50(12 H,m), 1.85–2.03(1 H,m),3.20–3.42(2 H,m),3.88–4.23(4 H,m),4.25–4.50(2 H,m),5.22(2 H,s),7.29–7.51(4 H,m), 7.85–8.02(2 H,m),8.18(2 H,d,J=8.5 Hz)

(Step 3)

To a solution of the compound (1.1 g, 1.8 mmol) obtained in Step 2 in ethanol (4.2 ml), 1N aqueous sodium hydroxide (1.8 ml, 1.8 mmol) was added. The resulting reaction solution was refluxed for 3 hours, then brought to room temperature, and acidified with 1N hydrochloric acid (2 ml, 1.98 mmol). The liquid mixture was extracted with ethyl acetate three times. The organic layer was washed with saturated aqueous sodium chloride, dried over anhydrous sodium sulfate, and concentrated in vacuo. The resulting residue was subjected to silica gel column chromatography (Wakogel™ C-300, heptane-ethyl acetate=2:1) to give (2S, 4R)-N-t-butoxycarbonyl-4-t-butyldimethylsiloxy-2-[3-carboxy-N-(p-nitrobenzyloxycarbonyl)anilinomethyl]pyrrolidine (850 mg, yield: 81%) as a yellow oily substance.

$^1$H-NMR(CDCl$_3$)δ: 0.01(6 H,s),0.81(9 H,s),1.31(9 H,s), 1.82–2.01(2 H,m),3.15–3.38(2 H,m),3.85–4.40(4 H,m), 5.20(2 H,s),7.27–7.55(4 H,m),7.90–8.05(2 H,m),8.15(2 H,d, J=8–3 Hz)

(Step 4)

To a solution of the compound (850 mg, 1.45 mmol) obtained in Step 3 in dichloromethane (4 ml), 4-(dimethylamino)pyridine (35 mg, 0.29 mmol), p-nitrobenzyl alcohol (263 mg, 1.72 mmol) and 1-ethyl-3-(3'-dimethylaminopropyl)carbodiimide hydrochloride were successively added in a nitrogen stream under cooling with ice. The resulting reaction solution was stirred at room temperature for 15 hours and then concentrated in vacuo. Ethyl acetate was added to the resulting residue and the organic layer was washed successively with 1N aqueous potassium hydrogensulfate and saturated aqueous sodium chloride, dried over anhydrous sodium sulfate, and then concentrated in vacuo. The resulting residue was subjected to silica gel column chromatography (Wakogel™ C-300, heptane-ethyl acetate=3:1) to give (2S,4R)-N-t-butoxycarbonyl-4-t-butyldimethylsiloxy-2-[N-(p-nitrobenzyloxycarbonyl)-3-(p-nitrobenzyloxycarbonyl)anilinomethyl]pyrrolidine (910 mg, yield: 87%) as a yellow oily substance.

$^1$H-NMR(CDCl$_3$)δ: 0.01(6 H,s),0.83(9 H,s),1.57(9 H,s), 1.80–2.01(2 H,m),3.20–3.40(2 H,m),3.87–4.40(4 H,m), 5.21(2 H,s),5.47(2 H,s),7.30–7.65(6 H,m),7.90–8.30(6 H,m)

(Step 5)

(2S,4R)-4-Hydroxy-N-(p-nitrobenzyloxycarbonyl)-2-[N-(p-nitrobenzyloxycarbonyl)-3-(p-nitrobenzyloxycarbonyl)anilinomethyl]pyrrolidine (775 mg, yield: 90%) was prepared as a yellow oily substance from the compound (850 mg, 1.18 mmol) obtained in Step 4 in the same manner as in Reference Example 96-2.

$^1$H-NMR(CDCl$_3$)δ: 1.45–1.70(2 H,m),3.30–3.69(2 H,m), 3.88–4.35(4 H,m),4.40–4.55(1 H,m),5.01–5.25(4 H,m), 5.40–5.49(2 H,m),7.25–7.63(8 H,m),7.85–8.28(8 H,m)

(Step 6)

(2S,4R)-4-Mesyloxy-N-(p-nitrobenzyloxycarbonyl)-2-[N-(p-nitrobenzyloxycarbonyl)-3-(p-nitrobenzyloxycarbonyl)anilinomethyl]pyrrolidine was prepared as a yellow oily substance from the compound (775 mg, 1.06 mmol) obtained in Step 5 in the same manner as in Reference Example 96-3, which was used for the next reaction without purification.

(Step 7)

(2S,4S)-4-Acetylthio-N-(p-nitrobenzyloxycarbonyl)-2-[N-(p-nitrobenzyloxycarbonyl)-3-(p-nitrobenzyloxycarbonyl)anilinomethyl]pyrrolidine (410 mg, yield: 50%) was prepared as a yellow oily substance from the compound obtained in Step 6 in the same manner as in Reference Example 96-4.

¹H-NMR(CDCl₃)δ: 2.05(3 H,s),3.08–3.22(1 H,m), 3.80–4.21(7 H,m),5.02–5.50(6 H,m),7.25–7.63(8 H,m), 7.85–8.30(8 H,m)

In the following Reference Examples 98 to 99, physicochemical data of the compounds used in Examples as thiols or thiol precursors are shown.

Reference Example 98

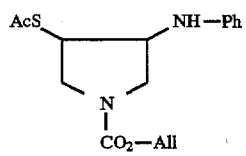

¹H-NMR(CDCl₃)δ: 2.33(3 H,s),3.36(1 H,m),3.56(1 H,m), 3.80(2 H,m),3.93(1 H,m),4.20–4.35(2 H,m),4.59(2 H,m), 5.15–5.25(2 H,m),5.91(1 H,m),6.61(2 H,d,J=7.5 Hz), 6.77(1 H,t,J=7.5 Hz),7.17(2 H,d,J=7.5 Hz)

Reference Example 99

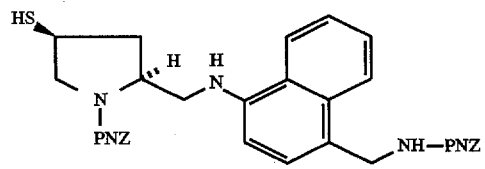

IR(KBr)cm⁻¹: 3743,1693,1517,1344

¹H-NMR(CDCl₃)δ: 1.68–1.84(1 H,m),1.81(1 H,d,J=6.6 Hz),2.70–2.85(1 H,m),3.19–3.61(4 H,m),4.12–4.25(1 H,m), 4.43–4.55(1 H,m),4.72(2 H,d,J=5.5 Hz),5.04(1 H,br s),5.19–5.36(4 H,m),6.11(1 H,br s),6.45(1 H,d,J=7.7 Hz), 7.23–7.33(1 H,m),7.40–7.57(6 H,m),7.84–7.97(2 H,m), 8.19–8.26(4 H,m)

Reference Example 100

(2S,4S)-4-Acetylthio-N-(p-nitrobenzyloxycarbonyl)-2-[4-[N-(p-nitrobenzyloxycarbonyl)aminomethyl]phenoxymethyl]-pyrrolidine

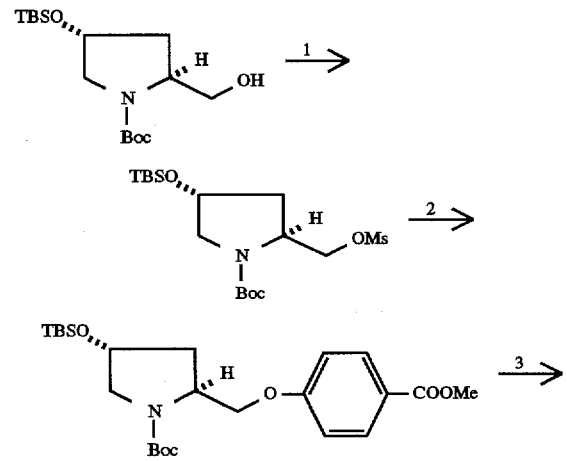

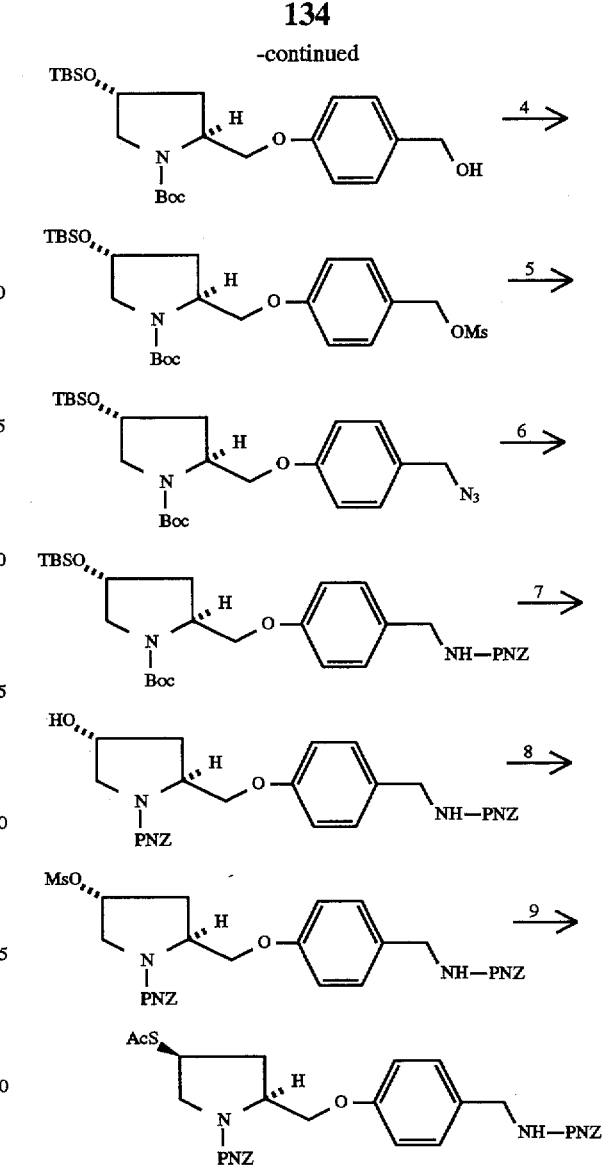

(Step 1)

N,N-Diisopropylethylamine (21.1 ml, 121 mmol) and mesyl chloride (4.67 ml, 60.3 mmol) were successively added to a solution of (2S,4R)-N-t-butoxycarbonyl-4-t-butyldimethylsiloxy-2-hydroxymethylpyrrolidine (10.2 g, 30.2 mmol; the compound of Reference Example 1–3) in European Laid Open Patent Application No. 449191) in methylene chloride (200 ml) in a nitrogen stream under cooling with ice and the resulting liquid mixture was stirred at the same temperature for 30 minutes. To this reaction solution, saturated aqueous ammonium chloride was added to terminate the reaction. The reaction mixture was extracted with ethyl acetate. The organic layer was washed successively with saturated aqueous sodium hydrogencarbonate and saturated aqueous sodium chloride and dried over anhydrous sodium sulfate. The solvent was distilled off to obtain (2S,4R)-N-t-butoxycarbonyl-4-t-butyldimethylsiloxy-2-(mesyloxymethyl)pyrrolidine as the residue.

¹H-NMR(CDCl₃)δ: 0.06(6 H,s),0.86(9 H,s),1.46(9 H,s), 1.95–2.10(2 H,m),2.99(3 H,s),3.30–3.40(2 H,m), 4.05–4.61(4 H,m)

(Step 2)

To a solution of methyl p-hydroxybenzoate (2.22 g, 1.46 mmol) in N,N-dimethylformamide (80 ml), sodium hydride (635 mg, 15.9 mmol) was added in a nitrogen stream at room temperature and then (2S,4R)-N-t-butoxycarbonyl-4-t-butyldimethylsiloxy-2-(mesyloxymethyl)pyrrolidine (5.00 g, 12.2 mmol) was added at the same temperature. The resulting reaction solution was stirred at 60° C. for 10 hours. Saturated aqueous ammonium chloride was added to the reaction solution to terminate the reaction. This liquid mixture was extracted with ethyl acetate and the organic layer was washed successively with water and saturated aqueous sodium chloride and dried over anhydrous magnesium sulfate. The solvent was distilled off in vacuo and the resulting residue was subjected to silica gel column chromatography (Wakogel™ C-300, heptane-ethyl acetate=85:15) to give (2S,4R)-N-t-butoxycarbonyl-4-t-butyldimethylsiloxy-2-[4-methoxycarbonyl)phenoxymethyl]pyrrolidine (3.62 g, yield: 63.7%).

$^1$H-NMR(CDCl$_3$)δ: 0.07(6 H,s),0.87(9 H,s),1.45(9 H,s), 1.96–2.18(2 H,m),3.26–3.50(2 H,m),3.87(3 H,s), 3.96–4.32(3 H,m),4.41–4.52(1 H,m),6.90(2 H,d,J=8.6 Hz), 7.96(2 H,d,J=8.6 Hz)

(Step 3)

To a solution of the compound (2.00 g, 3.41 mmol) obtained in the preceding step in tetrahydrofuran (40 ml), lithium aluminum hydride (388 mg, 10.2 mmol) was added in a nitrogen stream under cooling with ice. The resulting reaction solution was stirred at the same temperature for 2 hours and then sodium sulfate decahydrate (20 g) was added to terminate the reaction. The insolubles were filtered off and the filtrate was concentrated in vacuo to give a crude product of (2S,4R)-N-t-butoxycarbonyl-4-t-butyldimethylsiloxy-2-[4-hydroxymethyl)phenoxymethyl]pyrrolidine.

(Step 4)

To a solution of the crude product obtained in the preceding step in methylene chloride (40 ml), triethylamine (2.39 ml, 13.7 mmol) and mesyl chloride (0.529 ml, 6.83 mmol) were successively added in a nitrogen stream under cooling with ice and the resulting liquid mixture was stirred at the same temperature for 2 hours. Saturated aqueous sodium hydrogencarbonate was added to the reaction solution and the liquid mixture was extracted with chloroform. The organic layer was washed successively with water and saturated aqueous sodium sulfate, dried over anhydrous sodium sulfate, and then concentrated in vacuo to give a crude product of (2S,4R)-N-t-butoxycarbonyl-4-t-butyldimethylsiloxy-2-[4-mesyloxymethyl)phenoxymethyl] pyrrolidine.

(Step 5)

To a solution of the crude product obtained in the preceding step in N,N-dimethylformamide (20 ml), sodium azide (666 mg, 10.2 mmol) was added in a nitrogen stream under cooling with ice and the resulting liquid mixture was stirred for 2 hours. Saturated aqueous ammonium chloride was added to the reaction solution to terminate the reaction. This liquid mixture was extracted with ethyl acetate. The organic layer was washed successively with water and saturated aqueous sodium chloride and then dried over anhydrous magnesium sulfate. The solvent was distilled off in vacuo and the resulting residue was subjected to silica gel column chromatography (Wakogel™ C-300, heptane-ethyl acetate=9:1) to give (2S,4R)-2-(4-azidomethyl) phenoxymethyl-N-t-butoxycarbonyl-(4-t-butyldimethylsiloxy)pyrrolidine (1.01 g, yield: 50.8%).

$^1$H-NMR(CDCl$_3$)δ: 0.07(6 H,s),0.88(9 H,s),1.46(9 H,s), 1.96– 2.22(2 H,m),3.25–3.60(2 H,m),3.90–4.40(3 H,m), 4.26(2 H,s),4.45–4.57(1 H,m),6.90(2 H,d,J=8.3 Hz), 7.25(2 H,d,J=8.3 Hz)

(Step 6)

To a solution of the compound (1.02 g, 1.75 mmol) obtained in the preceding step in tetrahydrofuran (15 ml), triphenylphosphine (505 mg, 1.93 mmol) and water (0.063 ml, 3.50 mmol) were successively added in a nitrogen stream at room temperature. After 12 hours of stirring at the same temperature, to this reaction solution under cooling with ice, N,N-diisopropylethylamine (0.610 ml, 3.50 mmol) and p-nitrobenzyloxycarbonyl chloride (370 mg, 1.93 mmol) were successively added. The resulting liquid mixture was stirred at the same temperature for 15 minutes. Saturated aqueous ammonium chloride was added to this reaction solution to terminate the reaction and the liquid mixture was extracted with ethyl acetate. The organic layer was washed with saturated aqueous sodium chloride, dried over anhydrous sodium sulfate, and concentrated in vacuo. The resulting residue was subjected to silica gel column chromatography (Wakogel™ C-300, heptane-ethyl acetate= 6:4) to give (2S,4R)-N-t-butoxycarbonyl-4-t-butyldimethylsiloxy-2-[4-[N-(p-nitrobenzyloxycarbonyl) aminomethyl]phenoxymethyl]-pyrrolidine (1.02 g, yield: 75.9%).

$^1$H-NMR(CDCl$_3$)δ: 0.07(6 H,s),0.88(9 H,s),1.45(9 H,s), 1.97– 2.26(2 H,m),3.25–3.51(2 H,m),3.90–4.40(3 H,m), 4.31(2 H,d,J=5.9 Hz),4.44–4.56(1 H,m),5.09–5.20(1 H,m), 5.21(2 H,s),6.86(2 H,d,J=8.1 Hz),7.19(2 H,d,J=8.1 Hz), 7.50(2 H,d,J=8.2 Hz),8.20(2 H,d,J=8.2 Hz)

(Step 7)

To the compound obtained in the preceding step, 2.17 N hydrogen chloride-methanol solution (15 ml) was added. The resulting reaction solution was stirred in a nitrogen stream at room temperature for 10 hours and then concentrated in vacuo. The resulting residue was dissolved in dioxane-water (2:1, 30 ml) and this resulting solution was adjusted to pH 10 with 1N aqueous sodium hydroxide. While the solution was maintained at pH 9–10 by using 1N aqueous sodium hydroxide, a solution of p-nitrobenzyloxycarbonyl chloride (385 mg, 2.01 mmol) in dioxane (3 ml) was added dropwise thereto. The reaction solution was poured into a liquid mixture of ethyl acetate-water. The organic layer was washed with saturated aqueous sodium chloride, dried over anhydrous sodium sulfate, and then concentrated in vacuo. The resulting residue was subjected to silica gel column chromatography (Wakogel™ C-300, heptane-ethyl acetate=25:75) to give (2S,4R)-4-hydroxy-N-(p-nitrobenzyloxycarbonyl)-2-[4-[N-(p-nitrobenzyloxycarbonyl)aminomethyl]phenoxymethyl]-pyrrolidine (918 mg, yield 94.5%).

$^1$H-NMR(CDCl$_3$)δ: 2.00–2.40(2 H,m),3.53–3.76(2 H,m), 3.96– 4.17(1 H,m),4.32(2 H,d,J=5.9 Hz),4.25–4.45(1 H,m), 4.54–4.70(1 H,m),4.96–5.42(5 H,m),6.70–6.93(2 H,m), 7.11–7.24(2 H,m),7.35–7.60(4 H,m),8.02–8.30(4 H,m)

(Step 8)

To a solution of the compound obtained in the preceding step in methylene chloride (20 ml), N,N-diisopropylethylamine (1.09 ml, 6.23 mmol) and mesyl chloride (0.241 ml, 3.11 mmol) were successively added in a nitrogen stream under cooling with ice and the resulting liquid mixture was stirred at the same temperature for 2 hours. Saturated aqueous ammonium chloride was added to the reaction solution to terminate the reaction. This liquid mixture was extracted with ethyl acetate. The organic layer was washed successively with water and saturated aqueous sodium chloride and then dried over anhydrous magnesium sulfate. The solvent was distilled off to give a crude product of (2S,4R)-4-mesyloxy-N-(p-nitrobenzyloxycarbonyl)-2-[4-[N-(p-nitrobenzyloxycarbonyl)aminomethyl] phenoxymethyl]-pyrrolidine.

(Step 9) To a solution of the crude product obtained in the preceding step in N,N-dimethylformamide (30 ml), potassium thioacetate (534 mg, 4.67 mmol) was added in a nitrogen stream at room temperature and the resulting reaction solution was stirred at 60° C. for 3 hours. Saturated aqueous ammonium chloride was added to this reaction solution to terminate the reaction. This liquid mixture was extracted with ethyl acetate. The organic layer was washed successively with water and saturated aqueous sodium chloride, dried over anhydrous sodium sulfate, and concentrated in vacuo. The resulting residue was subjected to silica gel chromatography (Wakogel™ C-300, heptane-ethyl acetate=1:1) to give the title compound (802 mg, yield 80.6%).

$^1$H-NMR(CDCl$_3$)δ: 2.00–2.18(1 H,m),2.50–2.70(1 H,m), 3.24–3.35(1 H,m),3.80–4.40(5 H,m),4.30(2 H,d,J=5.8 Hz), 4.90–5.50(5 H,m),6.70–7.00(2 H,m),7.00–7.30(2 H,m), 7.30–7.60(4 H,m),8.00–8.30(4 H,m)

Reference Example 101

(2S,4S)-4-Acetylthio-N-(p-nitrobenzyloxycarbonyl)-4-(phenoxymethyl)pyrrolidine

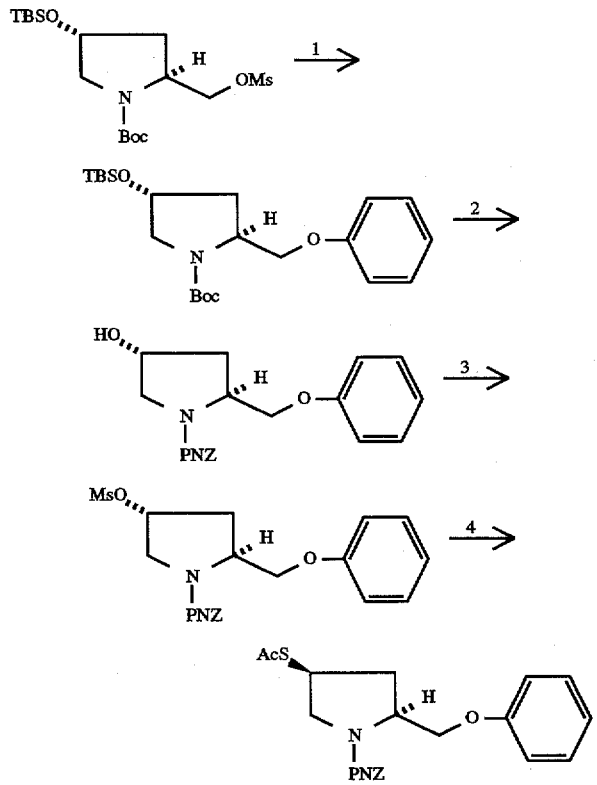

(Step 1)
Sodium hydride (60% dispersion in mineral oil, 300 mg, 7.50 mmol) was added to a solution of phenol (710 mg, 7.54 mmol) in N,N-dimethylformamide (10 ml). The resulting reaction solution was stirred at room temperature for 30 minutes and then a solution of (2S,4R)-N-t-butoxycarbonyl-4-t-butyldimethylsiloxy-2-(mesyloxymethyl)pyrrolidine (2.05 g, 5.00 mmol) in N,N-dimethylformamide (5 ml) was added thereto. The resulting liquid mixture was stirred at 70° C. overnight. The reaction solution was poured into a liquid mixture of water with ethyl acetate. The organic layer was washed with 1N aqueous potassium hydrogensulfate and saturated aqueous sodium chloride, dried over anhydrous sodium sulfate, and then concentrated in Vacuo. The resulting residue was subjected to silica gel column chromatography (Wakogel™ C-300, heptane-ethyl acetate=4:1→1:1) to give (2S,4R)-N-t-butoxycarbonyl-4-t-butyldimethylsiloxy-2-(phenoxymethyl)pyrrolidine (1.23 g, yield 60%) as a pale yellow oily substance.

$^1$H-NMR(CDCl$_3$)δ: 0.07(6 H,s),0.88(9 H,s),1.45(9 H,s), 1.95–2.20(2 H,m),3.25–3.50(2 H,m),3.90–4.30(3 H,m), 4.40–4.60(1 H,m),6.80–7.00(3 H,m),7.19–7.32(2 H,m)

(Step 2)
A solution of the compound (1.22 g, 2.97 mmol) obtained in Step 1 in 2.0N hydrogen chloride-methanol (50 ml) was stirred at room temperature for 5 hours and then this reaction solution was concentrated in vacuo. To the resulting residue, methanol was added and then the volatile components were distilled off in vacuo. A solution of the resulting residue in dioxane-water (2:1, 30 ml) was adjusted to pH 9.0 with 5N aqueous sodium hydroxide. While this solution was maintained at pH 9.0–8.0 by using 5N aqueous sodium hydroxide, a solution of p-nitrobenzyloxycarbonyl chloride (780 mg, 3.56 mmol) in dioxane (5 ml) was added dropwise under cooling with ice. The reaction solution was poured into a liquid mixture of ethyl acetate-water. The organic layer was washed with saturated aqueous sodium chloride, dried over anhydrous sodium sulfate, and then concentrated in vacuo. The resulting residue was subjected to silica gel column chromatography (Wakogel™ C-300, heptane-ethyl acetate=4:1→1:1) to give (2S,4R)-4-hydroxy-2-phenoxymethyl-N-((p-nitrobenzyloxycarbonyl)pyrrolidine (1.12 g, yield 100%) as a pale yellow oily substance.

$^1$H-NMR(CDCl$_3$)δ: 3.35–3.75(2 H,m),4.00–4.45(3 H,m) ,4.55–4.70(1 H,m),5.21(2 H,s),6.75–7.00(3 H,m), 7.20–7.30(2 H,m),7.40–7.50(2 H,m),8.05–8.20(2 H,m)

(Step 3)
To a solution of the compound (1.11 g, 2.96 mmol) obtained in Step 2 in tetrahydrofuran (20 ml), triethylamine (630 μl, 4.44 mmol) and methanesulfonyl chloride (280 μl, 3.55 mmol) were successively added in a nitrogen stream under cooling with ice and the resulting reaction solution was stirred at the same temperature for 1.5 hours. Water was added to the reaction solution and then the organic layer was washed with saturated aqueous sodium chloride, dried over anhydrous magnesium sulfate, and then concentrated in vacuo to give a crude product of (2S,4R)-4-mesyloxy-2-phenoxymethyl-N-(p-nitrobenzyloxycarbonyl)pyrrolidine (1.4 g) as a yellow oily residue, which was used for the next reaction without purification.

(Step 4)
To a solution of the crude product (1.4 g) obtained in Step 3 in N,N-dimethylformamide (15 ml), potassium thiosulfate (683 mg, 5.98 mmol) was added. The resulting reaction solution was heated at 70° C. in a nitrogen stream for 8 hours and then poured into a liquid mixture of ethyl acetate with water. The organic layer was washed with saturated aqueous sodium chloride, dried over anhydrous sodium sulfate, and then concentrated in vacuo. The resulting residue was subject to silica gel column chromatography (Wakogel™ C-300, heptane-ethyl acetate=9:1→2: 1) to give (2S,4S)-4-acetylthio-2-(phenoxymethyl)-N-(p-nitrobenzyloxycarbonyl)pyrrolidine (1.23 g, yield 96%) as a pale yellow oily substance.

$^1$H-NMR(CDCl$_3$)δ: 2.34(3 H,s),3.25–3.35(1 H,m), 3.70–4.35(7 H,m),5.21(2 H,s),6.80–7.00(2 H,m), 7.21–7.35(3 H,m),7.43–7.53(2 H,m),8.10–8.25(2 H,m)

In the following Reference Example 102, physicochemical data of a compound used in Examples as a thiol or a thiol precursor are shown.

Reference Example 102

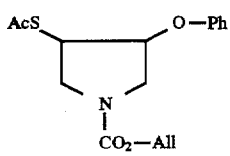

¹H-NMR(CDCl₃)δ: 2.34(3 H,s),3.52(1 H,m),3.65–3.85(2 H,m), 3.98(1 H,br t,J=8.5 Hz),4.22(1 H,m),4.58(2 H,m), 4.85(2 H,m),5.15–5.35(2 H,m),5.90(1 H,m), 6.85(2 H,m), 6.88(1 H,br t,J=7.5 Hz),7.27(2 H,m)

Reference Example 103

(2R,4S)-4-Acetylthio-N-(p-nitrobenzyloxycarbonyl)-2-[4-[N-(p-nitrobenzyloxycarbonyl)aminomethyl]phenethyl]-pyrrolidine

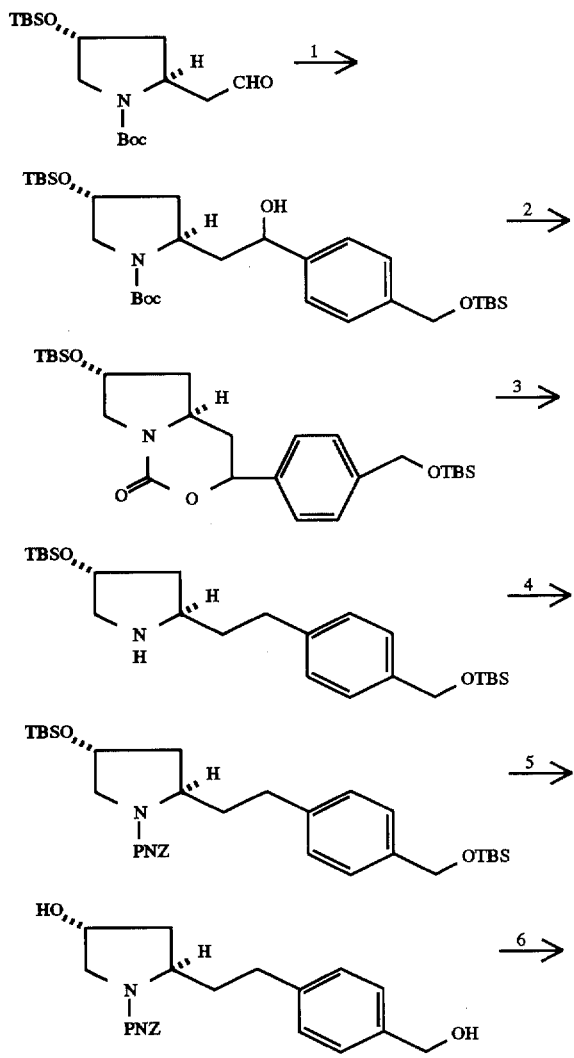

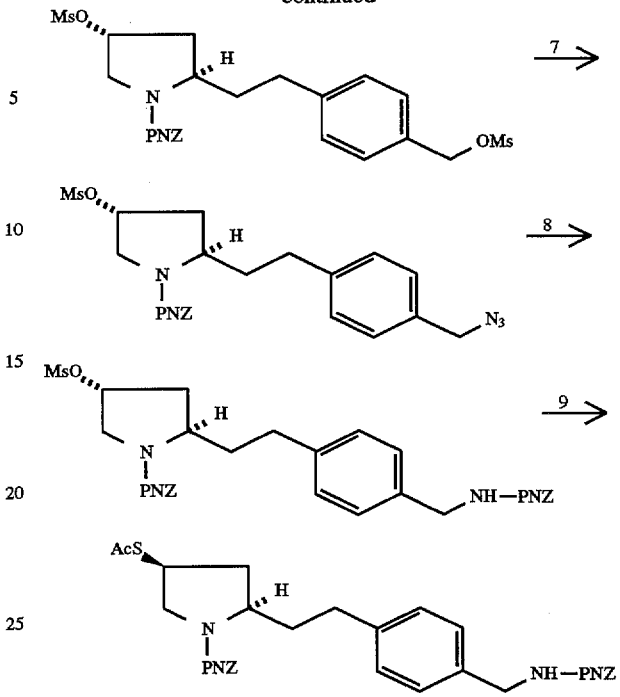

(Step 1)

1.6M Butyl lithium-hexane solution (72.5 ml, 116 mmol) was added dropwise to a solution of 4-(t-butyldimethylsiloxymethyl)bromobenzene (35.0 g, 116 mmol) in tetrahydrofuran (700 ml) in a nitrogen stream at −78° C. over 5 minutes. The resulting reaction solution was stirred for 10 minutes and then a solution of (2S,4S)-N-t-butoxycarbonyl-4-t-butyldimethylsiloxy-2-(formylmethyl) pyrrolidine (26.6 g, 77.4 mmol) in tetrahydrofuran (100 ml) was dropwise added thereto. The reaction solution was stirred for 20 minutes and saturated aqueous ammonium chloride was added thereto. The resulting liquid mixture was extracted with ethyl acetate. The organic layer was washed with saturated aqueous sodium chloride, dried over anhydrous magnesium sulfate, and concentrated in vacuo. The resulting residue was dissolved in a solvent mixture of tetrahydrofuran-methanol (10:1 220 ml) and treated with sodium boron hydride (1.46 g, 38.7 mmol) at room temperature. The reaction solution was stirred for 18 hours and then 10% aqueous citric acid was added to terminate the reaction. The liquid mixture was extracted with ethyl acetate. The organic layer was washed successively with saturated aqueous sodium hydrogencarbonate and saturated aqueous sodium chloride, dried over anhydrous magnesium sulfate, and concentrated in vacuo. The resulting residue was subjected to silica gel column chromatography (Wakogel™ C-300 heptane-ethyl acetate 92:8→85:15) to give (2R,4R)-N-t-butoxycarbonyl-4-t-butyldimethylsiloxy-2-[(2R)-2-[hydroxy-[4-(t-butyldimethylsiloxymethyl)phenyl]]ethyl] pyrrolidine diastereomer (less polar compound 13.1 g, yield: 31.5%) and diastereomer B (polar compound 13.4 g, yield: 32.2%).

Diastereomer A

¹H-NMR(CDCl₃)δ:0.06(6H,s),0.10(6H,s),0.88(9H,s), 0.94(9H,s),1.49(9H,s),1.50–1.80(3H,m),1.98–2.10(1H,m), 3.35–3.45(2H,m),4.30–4.45(2H,m),4.60–4.80(2H,m),4.72 (2H,s),5.20–5.30(1H,m), 7.28(2H,d,J=8.5Hz),7.34(2H,d,J=8.5Hz)

Diastereomer B

¹H-NMR(CDCl₃)δ:0.05(6H,s),0.09(6H,s),0.87(9H,s), 0.94(9H,s),1.46(9H,s),1.30–1.60(1H,m),1.65–1.80(2H,m), 2.00–2.20(1H,m),3.30–3.50(2H,m),4.00–4.40(2H,m), 4.60–4.85(1H,m),4.72(2H,s),7.20–7.40(4H,m)

(Step 2)

To a solution of the diastereomer A (3.00 g, 5.58 mmol) obtained in Step 1 in methylene chloride, N,N-diisopropylethylamine (2.91 ml, 16.7 mmol) and mesyl chloride (0.648 ml, 8.37 mmol) were successively added in a nitrogen stream under cooling with ice and the resulting reaction solution was stirred at the same temperature for 2 hours. Saturated aqueous ammonium chloride was added to this reaction solution to terminate the reaction and the liquid mixture was extracted with ethyl acetate. The organic layer was washed successively with water, saturated aqueous sodium hydrogencarbonate and saturated aqueous sodium chloride, dried over anhydrous sodium sulfate, and then concentrated in vacuo. The resulting residue was subjected to silica gel column chromatography (Wakogel™ C-300, heptane-ethyl acetate 75:25→65:35) to give (4S,6R,8R)-8-t-butyldimethylsiloxy-4-[4-(t-butyldimethylsiloxymethyl) phenyl]-1-aza-3-oxabicyclo[4.3.0]nonan-2-one (967 mg, yield: 37.4%).

¹H-NMR(CDCl₃)δ:0.00(12H,s),0.81(9H,s),0.84(9H,s), 1.40–1.60(2H,m),1.95–2.04(1H,m),2.28–2.37(1H,m), 3.29–3.33(1H,m),3.75(1H,dd,J=4.6&12.2Hz),3.93–4.06 (1H,m),4.37–4.42(1H,m),4.64(2H,s), 5.22(1H,dd,J= 2.2&11.7Hz),7.22(2H,d,J=8.8Hz), 7.26(2H,d,J=8.8Hz)

(Step 3)

To a solution of the compound (824 mg, 1.78 mmol) obtained in Step 2 in a mixture of tetrahydrofuran-methanol (1:1, 30 ml), 10% palladium-carbon catalyst (420 mg) was added and the resulting reaction mixture was stirred at room temperature in a hydrogen stream for 18 hours. The catalyst was separated from the reaction mixture by filtration and the filtrate was concentrated in vacuo to give a crude product of (2R,4R)-4-t-butyldimethylsiloxy-2-[4-(t-butyldimethylsiloxymethyl)phenethyl]pyrrolidine.

(Step 4)

The crude product obtained in Step 3 was dissolved in water-dioxane (1:1, 20 ml) and the resulting solution was adjusted to pH 10 with 1N aqueous sodium hydroxide. While this solution was maintained at pH 9–10 by using 1N aqueous sodium hydroxide, a solution of p-nitrobenzyloxycarbonyl chloride (374 mg, 1.95 mmol) in dioxane (5 ml) was added dropwise thereto under cooling with ice. The reaction solution was poured into a liquid mixture of ethyl acetate-water. The organic layer was washed with saturated aqueous sodium chloride and dried over anhydrous sodium sulfate. The solvent was distilled off in vacuo to give a crude product of (2R,4R)-4-t-butyldimethylsiloxy-2-[4-(t-butyldimethylsiloxymethyl) phenethyl]-N-(p-nitrobenzyloxycarbonyl)pyrrolidine.

(Step 5)

A solution of the crude product obtained in Step 4 in 2.17M hydrogen chloride-methanol (30 ml) was stirred at room temperature for 24 hours. The reaction solution was concentrated in vacuo and then diluted with ethyl acetate-water. The organic layer was washed successively with water and saturated aqueous sodium chloride, dried over anhydrous magnesium sulfate, and then concentrated in vacuo. The resulting residue was subjected to silica gel column chromatography (Wakogel™ C-300 heptane-ethyl acetate 2:8) to give (2R,4R)-4-hydroxy-2-[4-(hydroxymethyl)phenethyl]-N-(p-nitrobenzyloxycarbonyl) pyrrolidine (532 mg, yield: 74.8%).

¹H-NMR(CDCl₃)δ:1.50–1.95(4H,m),2.05–2.45(2H,m), 2.45–2.65(2H,m),3.35–3.55(1H,m),3.55–3.75(1H,m), 3.95–4.15(1H,m),4.40–4.50(1H,m),4.63(2H,s),5.05–5.30 (2H,m),6.90–7.35(4H,m),7.35–7.60(2H,m),8.05–8.30 (2H,m)

(Step 6)

To a solution of the compound (520 mg, 1.30 mmol) obtained in the preceding step in methylene chloride, N,N-diisopropylethylamine (1.36 ml, 7.79 mmol) and mesyl chloride (0.302 ml, 3.90 mmol) were successively added in a nitrogen stream under cooling with ice. This reaction solution was stirred at the same temperature for 1 hour and then saturated aqueous ammonium chloride was added thereto to terminate the reaction. This liquid mixture was extracted with ethyl acetate, washed successively with water and saturated aqueous sodium chloride, and then dried over anhydrous magnesium sulfate. The solvent was distilled off in vacuo to give a crude product of (2R,4R)-4-mesyloxy-2-[4-(mesyloxymethyl)phenethyl]-N-(p-nitrobenzyloxycarbonyl)pyrrolidine.

(Step 7)

To a solution of the crude product obtained in Step 6 in N,N-dimethylformamide (10 ml), sodium azide (101 mg, 1.56 mmol) was added in a nitrogen stream under cooling with ice and the resulting reaction mixed solution was stirred at the same temperature for 2 hours. To this reaction solution, saturated aqueous ammonium chloride was added to terminate the reaction and the liquid mixture was extracted with ethyl acetate. The organic layer was washed successively with water and saturated aqueous sodium chloride and dried over anhydrous magnesium sulfate. The solvent was distilled off to give a crude product of (2R,4R)-2-[4-(azidomethyl)phenethyl]-4-mesyloxy-N-(p-nitrobenzyloxycarbonyl)pyrrolidine.

(Step 8)

To a solution of the crude product obtained in Step 7 in tetrahydrofuran (10 ml), triphenylphosphine (375 mg, 1.43 mmol) and water (46.8 µl, 2.60 mmol) were successively added in a nitrogen stream at room temperature. The reaction solution was stirred at the same temperature for 12 hours and then N,N-diisopropylethylamine (0.679 ml, 3.89 mmol) and p-nitrobenzyloxycarbonyl chloride (273 mg, 1.43 mmol) were successively added thereto under cooling with ice. The reaction solution was stirred for another 1 hour. Saturated aqueous ammonium chloride was added to this reaction solution to terminate the reaction and the resulting liquid mixture was extracted with ethyl acetate. The organic layer was washed successively with water and saturated aqueous sodium chloride, dried over anhydrous magnesium sulfate, and then concentrated in vacuo. The resulting residue was subjected to silica gel column chromatography (Wakogel™ C-300 heptane-ethyl acetate 4:6) to give (2R, 4R)-4-mesyloxy-N-(p-nitrobenzyloxycarbonyl)-2-[4-[N-(p-nitrobenzyloxycarbonyl)aminomethyl]phenethyl]-pyrrolidine (552 mg, yield: 64.7%).

¹H-NMR(CDCl₃)δ:1.60–1.80(1H,m),1.90–2.70(5H,m), 3.02(3H,s),3.50–3.67(1H,m),3.97–4.16(2H,m), 4.34(2H,d, J=6.4Hz),5.10–5.40(6H,m),7.00–7.30(4H,m),7.40–7.60 (4H,m),8.10–8.30(4H,m)

(Step 9)

To a solution of the compound (540 mg, 0.822 mmol) obtained in Step 8 in N,N-dimethylformamide (20 ml), potassium thioacetate (235 mg, 2.06 mmol) was added in a nitrogen stream at room temperature and the resulting reaction mixed solution was stirred at 55° C. for 3 hours. Saturated aqueous ammonium chloride was added to this reaction solution to terminate the reaction. This liquid mixture was extracted with ethyl acetate. The organic layer was washed successively with water and saturated aqueous sodium chloride, dried over anhydrous magnesium sulfate, and then concentrated in vacuo. The resulting residue was subjected to silica gel column chromatography (Wakogel™ C-300 hexane-ethyl acetate 1:1) to give (2R,4S)-4-acetylthio-N-(p-nitrobenzyloxycarbonyl)-2-[4-[N-(p-nitrobenzyloxyoarbonyl)aminomethyl]phenethyl]-pyrrolidine (505 mg, yield: 96.5%).

$^1$H-NMR(CDCl$_3$)δ:1.60–1.90(2H,m),2.50(3H,s), 2.46–2.70(3H,m),3.17–3.26(1H,m),3.82–4.02(2H,m), 4.08–4.18(1H,m),4.36(2H,d,J=5.9Hz),5.07–5.32(6H,m), 7.00–7.30(4H,m),7.40–7.60(4H,m),8.12–8.34(4H,m)

REFERENCE EXAMPLE 104

(2R,4S)-4-Acetylthio-N-(p-nitrobenzyloxycarbonyl)-2-[4-[N-(p-nitrobenzyloxycarbonyl)aminomethyl]benzyl]-pyrrolidine

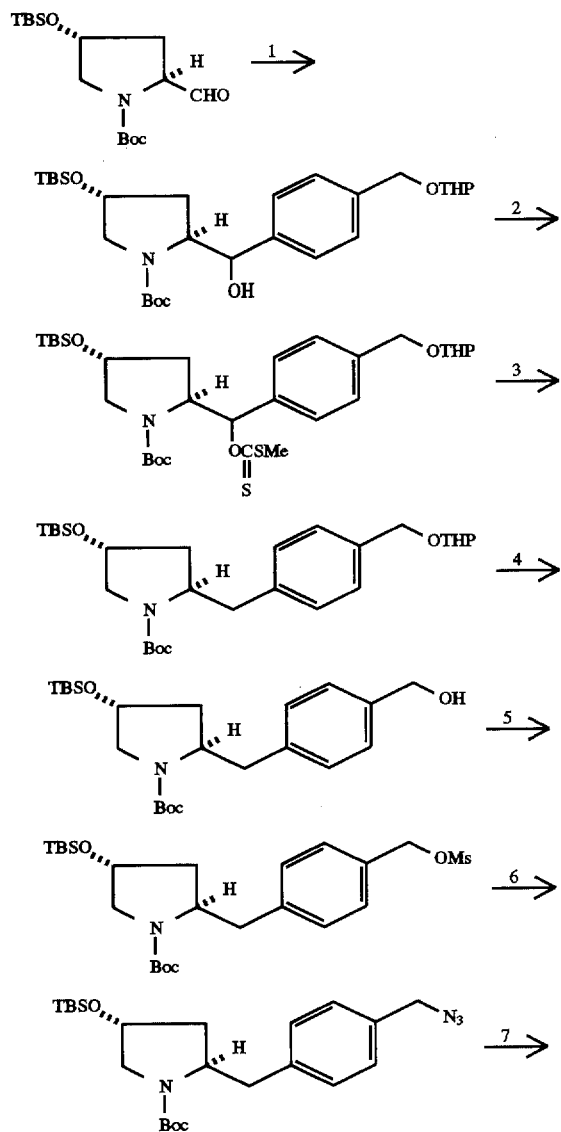

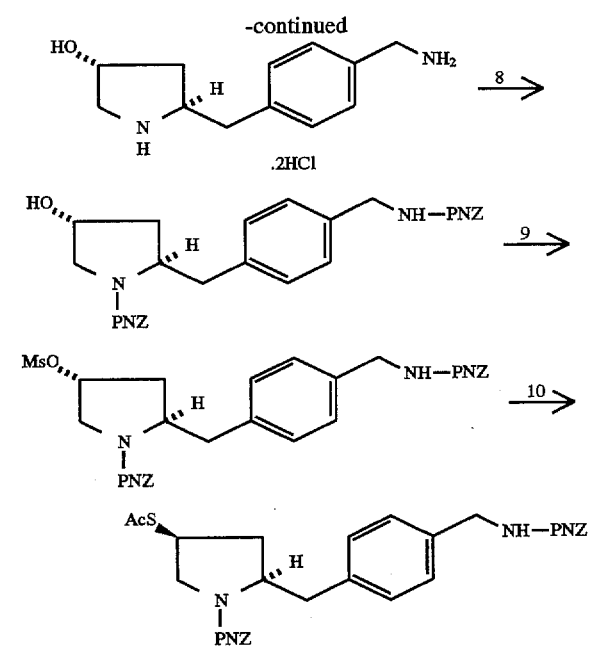

(Step 1)

(2S,4R)-N-t-Butoxycarbonyl-4-(t-butyldimethylsiloxy)-2-[α-hydroxy-4-(tetrahydropyranyloxymethyl)benzyl]-pyrrolidine (7.67 g, yield: 57.7%) was prepared as a yellow oily substance from (2S,4R)-N-t-butoxycarbonyl-4-(t-butyldimethylsiloxy)prolinal (8.37 g, 25.4 mmol) and -4-(tetrahydropyranyloxymethyl)bromobenzene (13.8 g, 50.9 mmol) in the same manner as in Reference Example 103-1.

$^1$H-NMR(CDCl$_3$)δ:0.03(6H,s),0.85(9H,s),1.28–2.11 (17H,m), 3.20–3.63(3H,m),3.78–4.59(4H,m),4.69–4.93(3H, m),7.22–7.45(4H,m)

(Step 2)

To a solution of the compound (7.67 g, 14.7 mmol) obtained in Step 1 and imidazole (10 mg, 0.15 mmol) in tetrahydrofuran (150 ml), 60% sodium hydride (825 mg, 20.6 mmol) was added in a nitrogen stream at room temperature and the reaction solution was stirred for 20 minutes. Then, carbon disulfide (2.65 g, 44 mmol) was added and the reaction solution was stirred for 30 minutes. Methyl iodide (1.84 ml, 29.6 mmol) was added to the reaction solution and the reaction solution was stirred for 30 minutes and then poured into a liquid mixture of 10% aqueous citric acid with ethyl acetate. The organic layer was washed with saturated aqueous sodium chloride, dried over anhydrous sodium sulfate, and concentrated in vacuo. The resulting residue was subjected to silica gel column chromatography (Wakogel™ C-300 heptane-ethyl acetate 8:1) to give (2S,4R)-N-t-butoxycarbonyl-4-t-butyldimethylsiloxy-2-[α-(methylthiothiocarbonyloxy)-4-(tetrahydropyranyloxymethyl)benzyl]pyrrolidine (4.01 g, yield: 44.6%) as a yellow oily substance.

$^1$H-NMR(CDCl$_3$)δ:0.07(6H,s),0.87(9H,s),1.40–2.21 (17H,m), 2.65(3H,s),3.01–4.03(5H,m),4.36–4.70(2H,m), 4.73–4.89(2H,m),7.19–7.52(4H,m)

(Step 3)

To a solution of the compound (4.01 g, 6.56 mmol) obtained in Step 2 in toluene (80 ml), catalytic amounts of 2,2'-azobisisobutyronitrile and tributyltin hydride (12.0 ml, 44.6 mmol) were successively added in an nitrogen stream and the resulting reaction solution was refluxed for 15 hours. After addition of aqueous potassium fluoride at room temperature, the reaction solution was filtered through celite and the filtrate was poured into a liquid mixture of ethyl acetate with water. The organic layer was washed with saturated aqueous sodium sulfate, dried over anhydrous sodium sulfate, and concentrated in vacuo. The resulting residue was subjected to silica gel column chromatography (Wakogel™ C-300 heptane-ethyl acetate 8:1) to give (2R, 4R)-N-t-butoxycarbonyl-4-t-butyldimethylsiloxy-2-[4-(tetrahydropyranyloxymethyl)benzyl]pyrrolidine (3.29 g, yield: 99.3%) as a yellow oily substance.

$^1$H-NMR(CDCl$_3$)δ:0.00(6H,s),0.82(9H,s),1.21–1.97 (17H,m), 2.61–2.82(1H,m),2.98–3.62(4H,m),3.89–4.25(3H, m),4.46(1H,d,J=11.9Hz),4.68–4.81(2H,m),7.06–7.37 (4H,m)

(Step 4)

To a solution of the compound (3.29 g, 6.51 mmol) obtained in Step 3 in methanol (250 ml), pyridinium p-toluenesulfonate (160 mg, 0.64 mmol) was added at room temperature in a nitrogen stream. The resulting reaction solution was stirred at 50° C. for 3.5 hours and then concentrated in vacuo. The resulting residue was poured into a liquid mixture of ethyl acetate with water. The organic layer was washed with saturated aqueous sodium chloride, dried over anhydrous sodium sulfate, and concentrated in vacuo. The residue was subjected to silica gel column chromatography (Wakogel™ C-300 heptane-ethyl acetate 4:1) to give (2R,4R)-N-t-butoxycarbonyl-4-t-butyldimethylsiloxy-2-[(4-hydroxymethyl)benzyl]pyrrolidine (2.1 g, yield: 76.6%) as a yellow oily substance.

$^1$H-NMR(CDCl$_3$)δ:0.01(6H,s),0.84(9H,S),1.53(9H,s), 1.68– 1.91(2H,m),2.60–2.82(1H,m),2.99–3.41(3H,m), 3.97–4.26(2H,m),4.69(2H,s),7.10–7.40(4H,m)

(Step 5)

To a solution of the compound (2.1 g, 4.99 mmol) obtained in Step 4 in tetrahydrofuran (30 ml), triethylamine (880 μl, 6.31 mmol) and mesyl chloride (480 μl, 6.20 mmol) were successively added a nitrogen stream under cooling with ice. The reaction solution was stirred at the same temperature for 30 minutes and then poured into a liquid mixture of ethyl acetate with water. The organic layer was washed with saturated aqueous sodium chloride, dried over anhydrous sodium sulfate and concentrated in vacuo to give (2R,4R)-N-t-butoxycarbonyl-4-t-butyldimethylsiloxy-2-(4-mesyloxymethylbenzyl)pyrrolidine as a yellow oily residue, which was used for the next reaction without purification.

(Step 6)

(2R,4R)-2-(4-Azidomethylbenzyl)-N-t-butoxycarbonyl-4-(t-butyldimethylsiloxy)pyrrolidine (2.05 g, yield: 92.1%) was prepared as a yellow oily substance from the compound obtained in Step 5 and sodium azide (405 mg, 6.23 mmol), in the same manner as in Example 103-7.

$^1$H-NMR(CDCl$_3$)δ:0.01(6H,s),0.84(9H,s),1.53(9H,s), 1.70–1.90(2H,m),2.63–2.86(1H,m),2.98–3.42(3H,m), 3.95–4.24(2H,m),4.34(2H,s),7.11–7.32(4H,m)

(Step 7)

To a solution of the compound (2.05 g, 4.6 mmol) obtained in Step 6 in tetrahydrofuran (20 ml), water (170 μl, 9.44 mmol) and triphenylphosphine (1.5 g, 5.72 mmol) were successively added at room temperature in a nitrogen stream and the resulting reaction solution was stirred at the same temperature for 17 hours. Then, the reaction solution was concentrated in vacuo and the resulting yellow oily residue was dissolved in 2.17N hydrogen chloride-methanol solution (17 ml). The resulting solution was stirred at room temperature for 3 hours and then concentrated in vacuo. Dichloromethane was added to the residue and the volatile components were distilled off in vacuo to give a yellow oily residue containing (2R,4R)-2-(4-aminomethylbenzyl)-4-hydroxypyrrolidine dihydrochloride, which was used for the next reaction without purification.

(Step 8)

A solution of the compound obtained in Step 7 in dioxane-water (1:1, 60 ml) was adjusted to pH 9.0 with 1N aqueous sodium hydroxide. While this solution was maintained at pH 8.0–9.0 by using 1N aqueous sodium hydroxide, a solution of p-nitrobenzyloxycarbonyl chloride (2.1 g, 10.4 mmol) in dioxane (5 ml) was added thereto dropwise. The reaction solution was poured into a liquid mixture of ethyl acetate-water. The organic layer was washed with saturated aqueous sodium chloride, dried over anhydrous sodium sulfate, and then concentrated in vacuo. The resulting residue was subjected to silica gel column chromatography (Wakogel™ C-300 heptane-ethyl acetate 1:4) to give (2R,4R)-4-hydroxy-2-[4-[N-(p-nitrobenzyloxycarbonyl)aminomethyl]benzyl]-N-(p-nitrobenzyloxycarbonyl)pyrrolidine (2.9 g, containing triphenylphosphine oxide) as a yellow oily substance.

$^1$H-NMR(CDCl$_3$)δ:1.60–2.00(2H,m),2.69–2.80(1H,m), 3.03–3.68(3H,m),4.20–4.32(2H,m),4.36(2H,d,j=5.9Hz), 5.23(2H,s),5.28(2H,s),7.02–7.23(4H,m),8.18–8.30(4H,m)

(Step 9)

To a solution of the compound (2.9 g) obtained in Step 8 in tetrahydrofuran (30 ml), triethylamine (670 μl, 4.81 mmol) and mesyl chloride (370 μl, 4.78 mmol) were successively added in a nitrogen stream under cooling with ice. The resulting reaction solution was stirred at the same temperature for 1 hour and then poured into a liquid mixture of ethyl acetate with water. The organic layer was washed with saturated aqueous sodium chloride, dried over anhydrous sodium sulfate, and concentrated in vacuo. The resulting residue was subjected to silica gel column chromatography (Wakogel™ C-300 heptane-ethyl acetate 1:2) to give (2R,4R)-4-mesyloxy-2-[4-[N-(p-nitrobenzyloxycarbonyl)aminomethyl]benzyl]-N-(p-nitrobenzyloxycarbonyl)pyrrolidine (2.4 g, yield: 81.1%) as a yellow oily substance.

$^1$H-NMR(CDCl$_3$)δ:1.92–2.38(2H,m),2.72–2.88(1H,m), 2.98(3H,s),3.02–3.50(2H,m),3.88–4.00(1H,m),4.25–4.43 (3H,m),4.92(1H,br s),5.23(2H,s),5.29(2H,s),7.00–7.23(4H, m),8.12–8.30(4H,m)

(Step 10)

(2R,4S)-4-Acetylthio-N-(p-nitrobenzyloxycarbonyl)-2-[4-[N-(p-nitrobenzyloxycarbonyl)aminomethyl]benzyl]-pyrrolidine (1.83 g, yield: 78.8%) was prepared as a red oily substance from the compound (2.4 g, 3.73 mmol) obtained in Step 9 and potassium thioacetate (930 mg, 8.16 mmol) in the same manner as in Reference Example 103-9.

$^1$H-NMR(CDCl$_3$)δ:1.61–1.81(1H,m),2.20–2.42(4H,m), 2.60–2.78(1H,m),3.12–3.45(2H,m),3.81–3.95(1H,m), 4.02–4.25(2H,m),4.37(2B,d,J=6.0Hz),5.12–5.32(4H,m), 7.00–7.31(4H,m),7.35–7.60(4H,m),8.11–8.32(4H,m)

REFERENCE EXAMPLE 105

(2R,4S)-4-Acetylthio-N-(p-nitrobenzyloxycarbonyl)-2-[3-[N-(p-nitrobenzyloxycarbonyl)aminomethyl]benzyl]-pyrrolidine

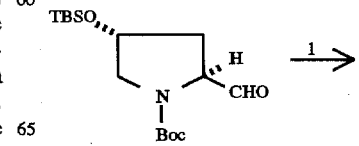

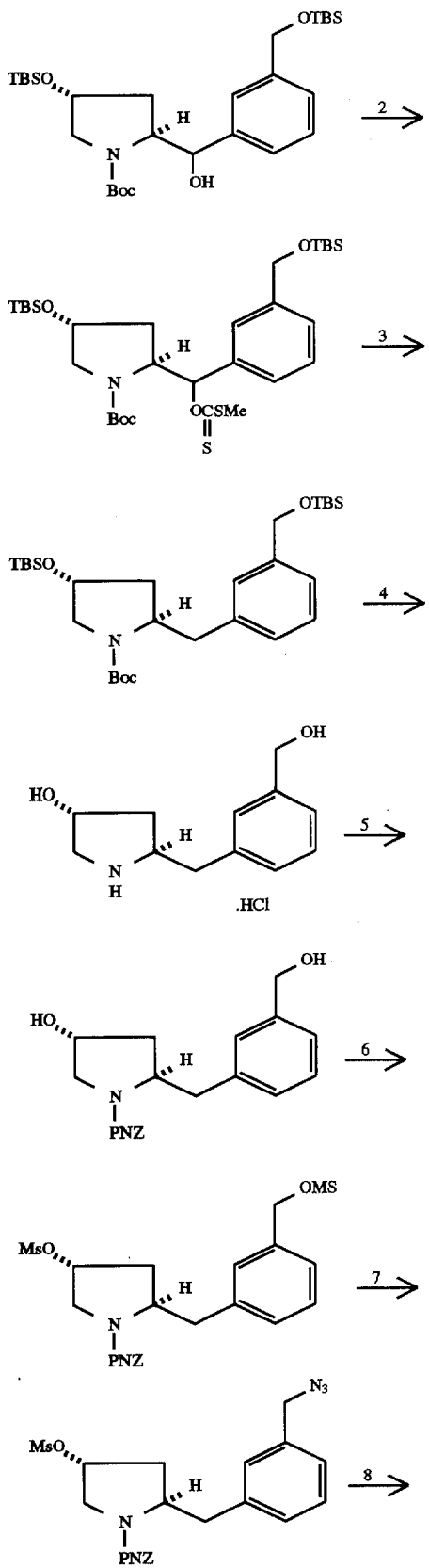

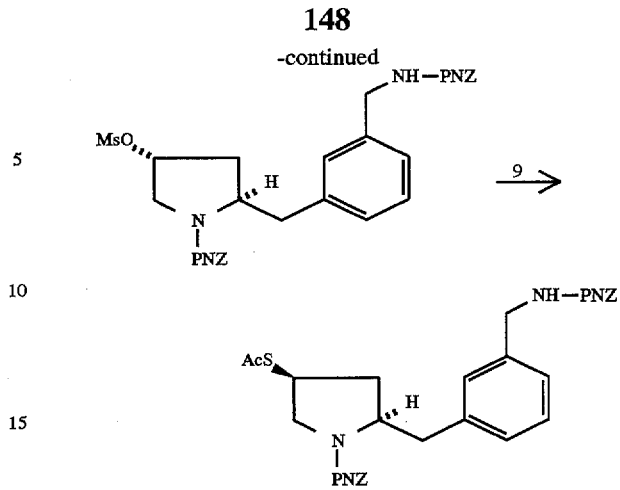

(Step 1)

(2S,4R)-N-t-Butoxycarbonyl-4-t-butyldimethylsiloxy-2-[3-(t-butyldimethylsiloxymethyl)-α-hydroxybenzyl]pyrrolidine (11.3 g, yield: 86.5%) was prepared as a yellow oily substance from (2S,4R)-N-t-butoxycarbonyl-4-(t-butyldimethylsiloxy)prolinal (7.8 g, 23.7 mmol) and 3-(t-butyldimethylsiloxymethyl)bromobenzene (13.7 g, 4.55 mmol), in the same manner as in Reference Example 103-1.

$^1$H-NMR(CDCl$_3$)δ:0.00–0.16(12H,m),0.78–1.02(18H,m), 1.42–2.12(11H,m),3.21–3.90(2H,m),4.08–4.58(2H,m), 4.78(2H,s),7.18–7.40(4H,m)

(Step 2)

(2S,4R)-N-t-Butoxycarbonyl-4-t-butyldimethylsiloxy-2-[3-(t-butyldimethylsiloxymethyl)-α-(methylthiothiocarbonyloxy)benzyl]pyrrolidine (9.8 g, yield: 74.6%) was prepared as a yellow oily substance, from the compound (11.3 g, 20.5 mmol) obtained in Step 1, 60% sodium hydride (1.1 g, 27.5 mmol), carbon disulfide (3.5 ml, 58.2 mmol) and methyl iodide (2.45 ml, 39.4 mmol), in the same manner as in Reference Example 104-2.

$^1$H-NMR(CDCl$_3$)δ:0.00–0.20(12H,m),0.82–1.10(18H,m), 1.50–1.70(10H,m),1.90–2.20(1H,m),2.66(3H,s), 4.30–4.68(2H,m),4.81(2H,s),7.10–7.50(4H,m)

(Step 3)

(2R,4R)-N-t-Butoxycarbonyl-4-t-butyldimethylsiloxy-2-[3-(t-butyldimethylsiloxymethyl)benzyl]pyrrolidine (6.53 g, yield: 79.8%) was prepared as a yellow oily substance, from the compound (9.8 g, 15.3 mmol) obtained in Step 2 and catalytic amounts of 2,2'-azobisisobutyronitrile and tributyltin hydride (27.0 ml, 100.4 mmol), in the same manner as in Reference Example 104-3.

$^1$H-NMR(CDCl$_3$)δ:0.00–0.15(12H,m),0.80–1.00(18H,m), 1.20–1.88(11H,m),2.55–3.40(4H,m),3.92–4.50(2H,m), 4.70(2H,s),6.98–7.40(4H,m)

(Step 4)

A solution of the compound (6.5 g, 12.2 mmol) obtained in Step 3 in 2.17N hydrogen chloride-methanol (40 ml) was stirred at room temperature for 15 hours and then concentrated in vacuo. Dichloromethane was added to the residue and the volatile components were distilled off in vacuo to give a yellow oily residue containing (2R,4R)-4-hydroxy-2-(hydroxybenzyl)pyrrolidine monohydrochloride, which was used for the next reaction without purification.

(Step 5)

A solution of the compound obtained in Step 4 in dioxane-water (1:1, 100 ml) was adjusted to pH 9.0 with 1N aqueous sodium hydroxide. While this solution was maintained at pH 8.0–9.0 by using 1N aqueous sodium hydroxide, a solution of p-nitrobenzyloxycarbonyl chloride (2.7 g, 13.4 mmol) in dioxane (5 ml) was added dropwise thereto. The reaction solution was poured into a liquid mixture of ethyl acetate-water. The organic layer was washed with saturated aqueous sodium chloride, dried over anhydrous sodium sulfate, and concentrated in vacuo. The resulting residue was subjected to silica gel column chromatography (Wakogel™ C-300 ethyl acetate) to give (2R,4R)-4-hydroxy-2-(3-hydroxymethylbenzyl)-N-(p-nitrobenzyloxycarbonyl) pyrrolidine (2.91 g, yield: 61.8%) as a yellow oily substance.

$^1$H-NMR(CDCl$_3$)δ:1.60–2.03(2H,m),2.58–2.80(1H,m), 3.08–3.65(3H,m),4.22–4.35(2H,br s),4.65(2H,s),5.30(2H, s), 6.98–7.30(4H,m),7.55(2H,d,J=8.6Hz),8.19–8.28(2H,m)

(step 6)

(2R,4R)-4-Mesyloxy-2-(3-mesyloxymethylbenzyl)-N-(p-nitrobenzyloxycarbonyl)pyrrolidine was prepared as a yellow oily substance from the compound (1.21 g, 3.13 mmol) obtained in Step 5, mesyl chloride (850 µl, 10.98 mmol) and triethylamine (1.53 ml, 10.98 mmol), in the same manner as in Reference Example 103-6. The product was used for the next reaction without purification.

(Step 7)

(2R,4R)-2-(3-Azidomethylbenzyl)-4-mesyloxy-N-(p-nitrobenzyloxycarbonyl)pyrrolidine (1.38 g, yield: 56.3%) was prepared as a yellow oily substance from the compound obtained in Step 6 and sodium azide (325 mg, 5.0 mmol) in the same manner as in Reference Example 103-7.

$^1$H-NMR(CDCl$_3$)δ:1.95–2.40(2H,m),2.70–3.45(6H,m), 3.89–4.02(1H,m),4.29(2H,s),5.00(1H,br s),5.30(2H,s), 7.00–7.35(4H,m),7.56(2H,d,J=8.6Hz),8.25(2H,d,J=8.4Hz)

(Step 8)

(2R,4R)-4-Mesyloxy-N-(p-nitrobenzyloxycarbonyl)-2-[3-[N-((p-nitrobenzyloxycarbonyl)aminomethyl]benzyl]-pyrrolidine (1.52 g, containing triphenylphosphine oxide) was prepared as a yellow oily substance, from the compound (1.38 g, 2.82 mmol) obtained in Step 7, triphenylphosphine (1.85 g, 7.05 mmol), water (170 µl, 9.4 mmol) and p-nitrobenzyloxycarbonyl chloride (1.04 g, 5.16 mmol), in the same manner as in Reference Example 103-8.

$^1$H-NMR(CDCl$_3$)δ:1.98–2.40(2H,m),2.72–2.86(1H,m), 2.97(3H,s),3.18–3.52(2H,m),4.25–4.40(2H,m),4.85–4.96 (1H,m),5.29(2H,s),5.30(2H,s),6.94–7.31(4H,m), 8.16–8.30 (4H,m)

(Step 9)

(2R,4S)-4-Acetylthio-N-(p-nitrobenzyloxycarbonyl)-2-[3-[N-(p-nitrobenzyloxycarbonyl)aminomethyl]benzyl]-pyrrolidine (981 mg, yield: 56.1%) was prepared as a red oily substance, from the compound (1.52 g) obtained in Step 8 and potassium thioacetate (480 mg, 4.21 mmol), in the same manner as in Reference Example 103-9.

$^1$H-NMR(CDCl$_3$)δ:1.60–1.80(1H,m),2.34(3H,s), 2.58–2.80(1H,m),3.12–3.50(2H,m),3.80–3.94(1H,m), 4.05–4.21(2H,m),4.32–4.42(2H,m),5.08–5.31(5H,m), 7.00–7.31(4H,m),7.48–7.60(4H,m),8.18–8.30(4H,m)

REFERENCE EXAMPLE 106

(2R,4S)-4-Acetylthio-2-benzyl-N-(p-nitrobenzyloxycarbonyl)pyrrolidine

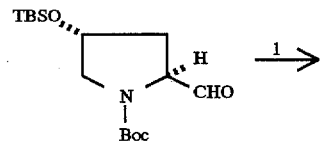

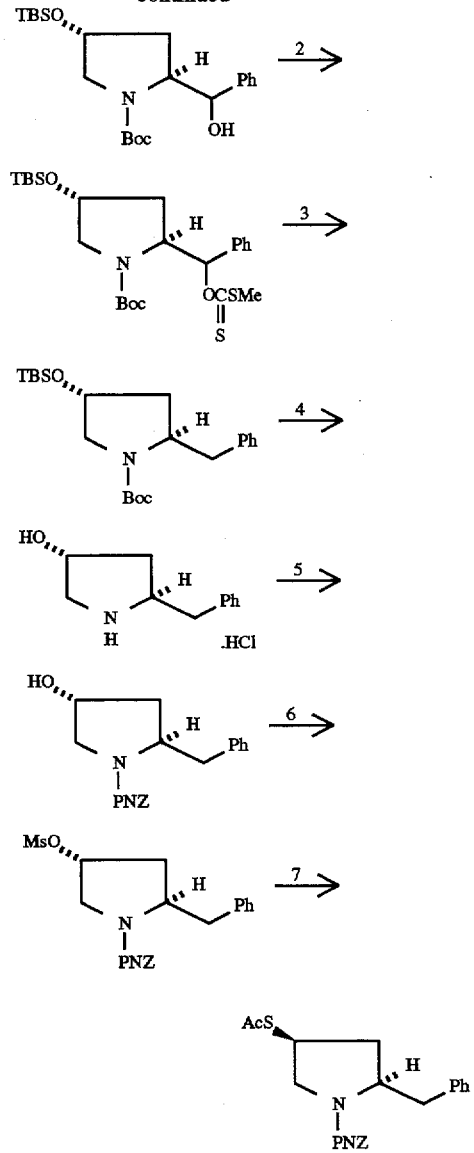

(Step 1)

2.0M Phenylmagnesium bromide-tetrahydrofuran solution (22.8 ml, 45.6 mmol) was added dropwise to a solution of (2S,4R)-N-t-butoxycarbonyl-4-(t-butyldimethylsiloxy) prolinal (10 g, 30.4 mmol) in tetrahydrofuran (200 ml) at −78° C. in a nitrogen stream. The reaction solution was allowed to gradually warm and then stirred at room temperature for 3 hours. After addition of water, this reaction solution was concentrated in vacuo. The resulting residue was poured into a liquid mixture of ethyl acetate with water. The organic layer was washed with saturated aqueous sodium chloride, dried over anhydrous sodium sulfate, and then concentrated in vacuo. The resulting oily residue was subjected to silica gel column chromatography (Wakogel™ C-300 heptane:ethyl acetate 4:1) to give (2S,4R)-N-t-butoxycarbonyl-4-t-butyldimethylsiloxy-2-(α-hydroxybenzyl)pyrrolidine (11.98 g, yield: 96.8%) as a colorless oily substance.

$^1$H-NMR(CDCl$_3$)δ:0.01(6H,s),0.83(9H,s),1.54(9H,s), 1.79–1.92(1H,m),2.83–3.84(3H,m),4.08–4.61(2H,m), 4.84–5.34(1H,m),7.34(5H,m)

(Step 2)

(2S,4R)-N-t-Butoxycarbonyl-4-t-butyldimethylsiloxy-2-[(α-methylthiothiocarbonyloxy)benzyl]pyrrolidine (8.58 g, yield: 100%) was prepared as a yellow oily substance from the compound (7.03 g, 17.3 mmol) obtained in Step 1, carbon disulfide (3.12 ml, 51.9 mmol), 60% sodium hydride (1.04 g, 26.0 mmol) and methyl iodide (5 ml, 80 mmol), in the same manner as in Reference Example 104-2.

(Step 3)

(2R,4R)-2-Benzyl-N-t-butoxycarbony-4-(t-butyldimethylsiloxy)pyrrolidine (4.81 g, yield: 71.1%) was prepared as a colorless oily substance from the compound (8.58 g, 17.3 mmol) obtained in Step 2, tributyltin hydride (18.6 ml, 69.2 mmol) and α,α'-azobisisobutyronitrile (284 mg, 1.73 mmol) in the same manner as in Reference Example 104-3.

$^1$H-NMR(CDCl$_3$)δ:0.01(6H,s),0.83(9H,s),1.52(9H,s), 1.81(2H,m),2.73(1H,m),3.06(1H,m),3.29(2H,m), 4.11(2H,m),7.22(5H,m)

(Step 4)

A crude product (1.07 g) of (2R,4R)-2-benzyl-4-hydroxypyrrolidine monohydrochloride was prepared as a yellow oily substance from the compound (2.4 g, 6.14 mmol) obtained in Step 3 and 3.7N hydrogen chloride-methanol solution in the same manner as in Reference Example 105-4. The crude product was used for the next reaction without purification.

$^1$H-NMR(D$_2$O)δ:1.88–2.19(2H,m),3.04–3.32(3H,m), 3.51–3.69(2H,m),4.17(1H,m),7.39(5H,m)

(Step 5)

(2R,4R)-2-Benzyl-4-hydroxy-N-(p-nitrobenzyloxycarbonyl)pyrrolidine (1.52 g, yield: 70.0%) was prepared as a yellow oily substance from the crude product (1.07 g) obtained in Step 4 and p-nitrobenzyloxycarbonyl chloride (1.72 g, 8.0 mmol) in the same manner as in Reference Example 105-5.

$^1$H-NMR(CDCl$_3$)δ:1.80(2H,m),2.76(1H,m),3.03–3.41 (2H,m), 3.08(1H,m),4.29(2H,m),5.29(2H,s),7.19(5H,m), 7.52(2H,m),8.23(2H,m)

(Step 6)

A crude product of (2R,4R)-2-benzyl-4-mesyloxy-N-(p-nitrobenzyloxycarbonyl)pyrrolidine (1.84 g) was prepared as a yellow oily substance from the compound (1.52 g, 4.27 mmol) obtained in Step 5, triethylamine (655 μl, 4.70 mmol) and mesyl chloride (364 μl, 4.70 mmol) in the same manner as in Reference Example 104-9. The crude product was used for the next reaction without purification.

$^1$H-NMR(CDCl$_3$)δ:2.02(1H,m),2.22(1H,m),2.83(1H,m), 2.97(3H,s),3.13(1H,m),3.40(1H,m),3.94(1H,m), 4.33(1H,m),4.97(1H,m),5.28(2H,s),7.10(2H,m), 7.26(3H,m),7.52(2H,m),8.23(2H,m)

(Step 7)

The title compound (1.02 g, yield: 57.8%) was prepared as a brown oily substance from the crude product (2.06 g, 4.23 mmol) obtained in Step 6 and potassium thioacetate (1.45 g, 12.7 mmol) in the same manner as in Reference Example 103-9.

$^1$H-NMR(CDCl$_3$)δ:1.73(1H,m),2.31(3H,s),2.36(1H,m), 2.69(1H,m),3.28(2H,m),3.88(1H,m),4.11(2H,m), 5.26(2H,m),7.21(5H,m),7.51(2H,m),8.23(2H,m)

REFERENCE EXAMPLE 107

(2R,4S)-4-Acetylthio-N-(p-nitrobenzyloxycarbonyl)-2-[4-(p-nitrobenzyloxycarbonylaminomethyl)-1-naphthylmethyl]pyrrolidine

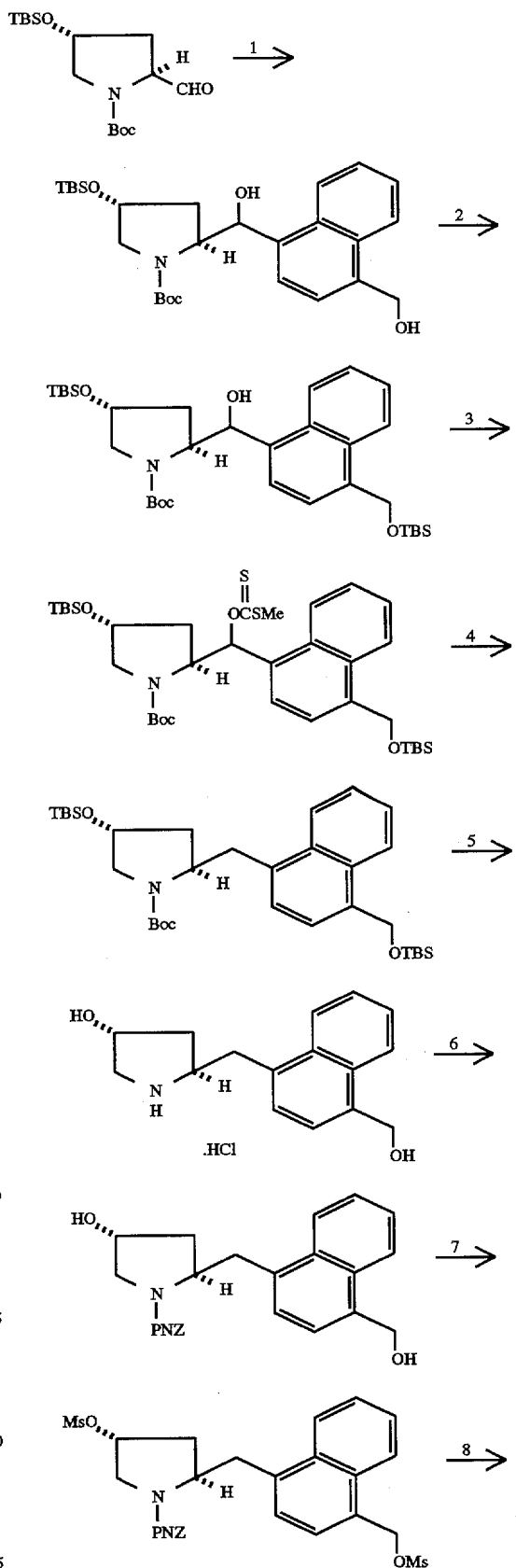

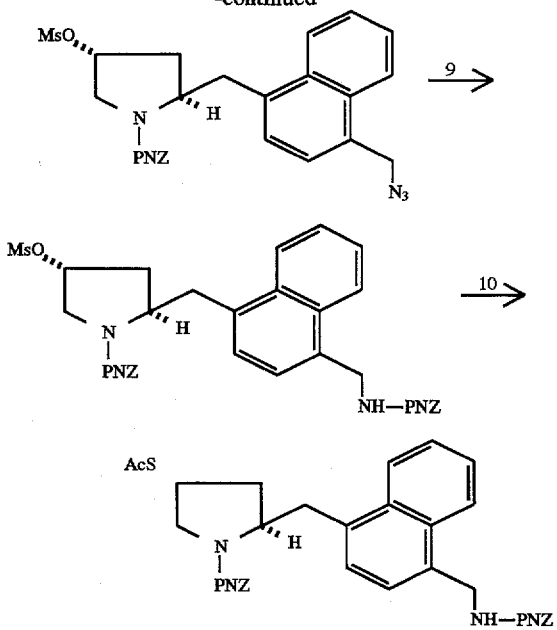

(Step 1)

A solution of 4-hydroxymethyl-1-bromonaphthalene (3 g, 12.7 mmol) in tetrahydrofuran (50 ml) was added dropwise to a solution of 1.6M butyl lithium-hexane solution (20.6 ml, 32.9 mmol) in tetrahydrofuran (100 ml) at −72° C. in a nitrogen stream over 30 minutes. The resulting reaction solution was stirred at −72° C. for 30 minutes and a solution of (2S,4R)-N-t-butoxycarbonyl-4-(t-butyldimethylsiloxy) prolinal (4.17 g, 12.7 mmol) in tetrahydrofuran (50 ml) was added dropwise over 10 minutes. Then, the reaction solution was stirred at −63° C. for 10 minutes. After addition of saturated aqueous ammonium chloride, the reaction solution was concentrated in vacuo. The resulting residue was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300 heptane-ethyl acetate 3:1→2:1) to give (2S,4R)-N-t-butoxycarbonyl-4-t-butyldimethylsiloxy-2-[hydroxy(4-hydroxymethyl-1-naphthyl)methyl]pyrrolidine (2.71 g, yield: 44.0%) as a colorless oily substance.

$^1$H-NMR(CDCl$_3$)δ:0.01(6H,s),0.79(9H,s),1.54(9H,s), 2.01(2H,m),3.26–3.52(2H,m),4.03–4.68(2H,m),5.03–5.36 (2H,m),5.94–6.29(1H,m),7.52(4H,m),8.09(1H,m), 8.38(1H, m)

(Step 2)

To a solution of the compound (1.15 g, 2.37 mmol) obtained in Step 1 in N,N-dimethylformamide (20 ml), imidazole (193 mg, 2.84 mmol) and t-butyldimethylsilyl chloride (393 mg, 2.61 mmol) were added and the resulting reaction solution was stirred at room temperature for 2 hours. The reaction solution was poured into a liquid mixture of ethyl acetate with water. The organic layer was washed with saturated aqueous sodium chloride, dried over anhydrous sodium sulfate and concentrated in vacuo to give a crude product of (2S,4R)-N-t-butoxycarbonyl-4-t-butyldimethylsiloxy-2-[(4-t-butyldimethylsiloxymethyl-1-naphthyl)hydroxymethyl]pyrrolidine as a yellow oily substance (1.45 g), which was used for the next reaction without purification.

(Step 3)

60% Sodium hydride (142 mg, 3.56 mmol) was added to a solution of the crude product (1.45 g) obtained in Step 2 in tetrahydrofuran (30 ml). The resulting reaction solution was stirred at room temperature for 30 minutes and carbon disulfide (427 μl, 7.11 mmol) was added thereto. The reaction solution was stirred at the same temperature for 30 minutes. Methyl iodide (5 ml, 80.3 mmol) was added to the reaction solution at room temperature. The reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300 heptane-ethyl acetate 10:1) to give (2S,4R)-N-t-butoxycarbonyl-4-t-butyldimethylsiloxy-2-[(4-t-butyldimethylsiloxymethyl-1-naphthyl)(methylthiothiocarbonyloxy)methyl]pyrrolidine (1.19 g, yield: 72.4%) as a yellow oily substance.

$^1$H-NMR(CDCl$_3$)δ:0.01(6H,m),0.13(6H,s),0.81(9H,m), 0.96(9H,s),1.40(9H,m),2.00(1H,m),2.30(1H,m), 2.58(3H,s), 2.80–3.13(1H,m),3.28–3.60(1H,m),3.74–4.01(1H,m), 4.51–4.88(2H,m),5.18(2H,m),7.52(4H,m), 7.84–8.36(2H, m)

(Step 4)

To a solution of the compound (1.19 g, 1.71 mmol) obtained in Step 3 in toluene (30 ml), tributyltin hydride (1.84 ml, 6.84 mmol) and α,α'-azobisisobutyronitrile (28 mg, 0.17 mmol) were added in a nitrogen stream. The resulting reaction solution was refluxed under heating for 16 hours and then poured into saturated aqueous potassium fluoride. The precipitate was filtered off and the filtrate was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300 heptane:ethyl acetate 10:1) to give (2R,4R)-N-t-butoxycarbonyl-4-t-butyldimethylsiloxy-2-(4-t-butyldimethylsiloxymethyl-1-naphthylmethyl)pyrrolidine (924 g, yield: 92.4%) as a colorless oily substance.

$^1$H-NMR(CDCl$_3$)δ:0.01(6H,m),0.12(6H,s),0.81(9H,s), 0.96(9H,s),1.54(9H,s),1.68(1H,m),1.85(1H,m), 2.82(1H,m), 3.19–3.52(2H,m),3.80(1H,m),4.09–4.42(2H,m),5.19(2H,s), 7.22(1H,m),7.51(3H,m), 7.99(1H,m),8.23–8.46(1H,m)

(Step 5)

A solution of the compound (906 mg, 1.55 mmol) obtained in Step 4 in 2.7N hydrogen chloride-dioxane (30 ml) was stirred at room temperature for 49 hours. This reaction solution was concentrated in vacuo to give a crude product of (2R,4R)-4-hydroxy-2-(4-hydroxymethyl-1-naphthylmethyl)pyrrolidine hydrochloride, which was used for the next reaction without purification.

(Step 6)

A solution of the crude product obtained in Step 5 in a mixture of dioxane-water (4:1, 50 ml) was adjusted to pH 10.0 with 1N aqueous sodium hydroxide. While this solution was maintained at pH 8.0–10.0 by using 1N aqueous sodium hydroxide, a solution of p-nitrobenzyloxycarbonyl chloride (434 mg, 2.01 mmol) in dioxane (2 ml) was added dropwise thereto under cooling with ice. This reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300 heptane-ethyl acetate 1:4) to give (2R,4R)-4-hydroxy-2-(4- hydroxymethyl-1-naphthylmethyl)-N-(p-nitrobenzyloxycarbonyl)pyrrolidine (191 mg, yield: 28.3%) as a yellow oily substance.

$^1$H-NMR(CDCl$_3$)δ:1.81(1H,m),1.93(1H,m),2.73(1H,m), 3.61(1H,m),3.75(1H,m),4.03–4.52(2H,m),5.08–5.36(3H, m), 7.20–7.64(5H,m),7.99–8.53(3H,m)

(Step 7)

To a solution of the compound (191 mg, 0.44 mmol) obtained in Step 6 in dichloromethane (5 ml), triethylamine (244 μl, 1.75 mmol) and mesyl chloride (85 μl, 1.10 mmol) were successively added in a nitrogen stream under cooling with ice and the resulting reaction solution was stirred at the same temperature for 10 minutes. The reaction solution was poured into a liquid mixture of ethyl acetate with water. The organic layer was washed with saturated aqueous sodium chloride, dried over anhydrous sodium sulfate, and concentrated in vacuo to give a crude product of (2R,4R)-4-mesyloxy-2-(4-mesyloxymethyl-1-naphthylmethyl)-N-(p-nitrobenzyloxycarbonyl)pyrrolidine as a yellow oily substance, which was used for the next reaction without purification.

(Step 8)

To a solution of the crude product obtained in Step 7 in N,N-dimethylformamide (5 ml), sodium azide (57 mg, 0.88 mmol) was added and the resulting reaction solution was stirred at room temperature for 2 hours. It was poured into a liquid mixture of ethyl acetate with water. The organic layer was washed with saturated aqueous sodium chloride, dried over anhydrous sodium sulfate, and concentrated in vacuo to give a crude product of (2R,4R)-2-(4-azidomethyl-1-naphthylmethyl)-4-mesyloxy-N-(p-nitrobenzyloxycarbonyl)pyrrolidine as a yellow oily substance, which was used for the next reaction without purification.

$^1$H-NMR(CDCl$_3$)δ:2.12(2H,m),2.79(1H,m),3.61–3.90 (1H,m), 4.01–4.12(1H,m),4.23(1H,m),4.50(1H,m),4.66(1H, m), 5.13–5.36(2H,m),7.20–7.71(5H,m),8.03(2H,m), 8.20–8.51(3H,m)

(Step 9)

To a solution of the crude product (341 mg) obtained in Step 8 in tetrahydrofuran (10 ml), triphenylphosphine (392 mg, 1.50 mmol) and water (3 ml) were successively added. After 23 hours of stirring at room temperature, the reaction solution was concentrated in vacuo. The resulting residue was dissolved in dichloromethane (10 ml) and p-nitrobenzyloxycarbonyl chloride (242 mg, 1.12 mmol) and diisopropylethylamine (391 μl, 2.25 mmol) were successively added thereto. The reaction solution was stirred at room temperature for 10 minutes and then concentrated in vacuo. The resulting residue was poured into a liquid mixture of ethyl acetate with water. The organic layer was washed successively with saturated aqueous ammonium chloride and saturated aqueous sodium chloride, dried over anhydrous sodium sulfate, and concentrated in vacuo. The resulting oily residue was subjected to silica gel column chromatography (Wakogel™ C-300 heptane-ethyl acetate 2:3) to give (2R,4R)-4-mesyloxy-N-(p-nitrobenzyloxycarbonyl)-2-[4-(p-nitrobenzyloxycarbonylaminomethyl)-1-naphthylmethyl] pyrrolidine (493 mg) containing triphenylphosphine oxide as a yellow oily substance.

(Step 10)

To a solution of the mixture (493 mg) obtained in Step 1 in N,N-dimethylformamide (10 ml), potassium thioacetate (343 mg, 3.0 mmol) was added. The resulting reaction solution was refluxed under heating for 3 hours and then poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300 heptane-ethyl acetate 1:1) to give the title compound (14.4 mg) as a yellow oily substance.

$^1$H-NMR(CDCl$_3$)δ:1.81(1H,m),2.16(1H,m),2.83(1H,m), 3.42(1H,m),3.90(1H,m),4.09–4.28(2H,m),4.36(1H,m), 4.73 (2H,m),5.16(1H,m),5.24(2H,m),5.31(2H,m), 7.31(1H,m), 7.55(6H,m),8.01(2H,m),8.23(4H,m), 8.56(1H,m)

REFERENCE EXAMPLE 108

(2R,4S)-4-Acetylthio-N-allyloxycarbonyl-2-(1-naphthylmethyl)pyrrolidine

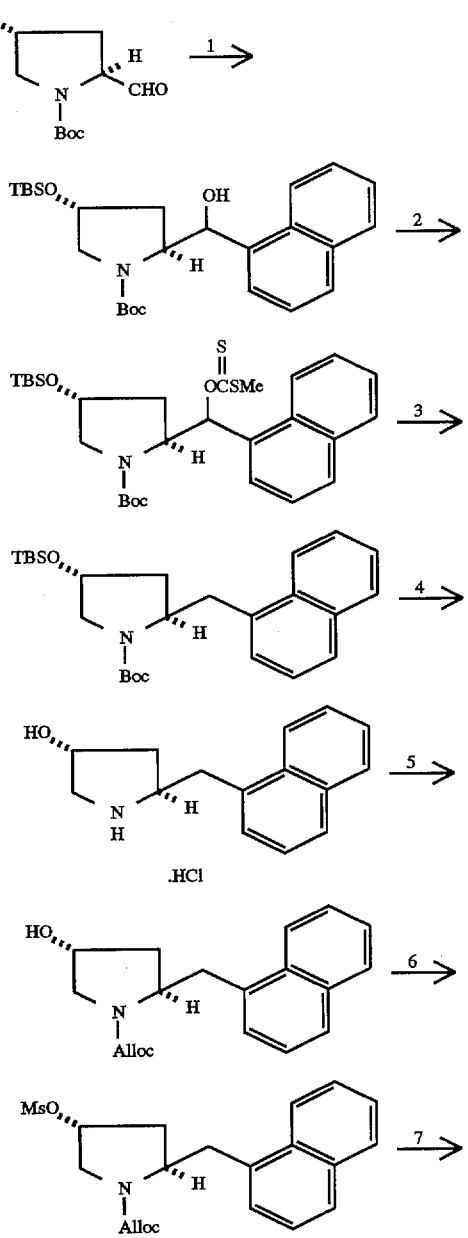

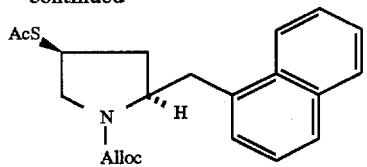

(Step 1)

Magnesium (3.4 g, 140 mmol) and a solution of 1,2-dibromoethane (5.3 ml, 60.8 mmol) in diethyl ether (40 ml) were successively added to a solution of 1-bromonaphthalene (12.6 g, 60.8 mmol) in diethyl ether (160 ml) at room temperature in a nitrogen stream and the resulting reaction solution was refluxed under heating for 3 hours. The reaction solution was gradually cooled and a solution of (2S,4R)-N-t-butoxycarbonyl-4-(t-butyldimethylsilyl)prolinal (10 g, 30.4 mmol) in tetrahydrofuran (40 ml) was added dropwise thereto under cooling with ice over 10 minutes. The reaction solution was stirred at the same temperature for 10 minutes. After addition of saturated aqueous ammonium chloride, the reaction solution was concentrated in vacuo. The resulting residue was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300 heptane:ethyl acetate 500:1→5:1) to give (2S,4R)-N-t-butoxycarbonyl-4-t-butyldimethylsiloxy-2-[hydroxy(1-naphthyl)methyl]pyrrolidine (12.36 g, yield: 89%) as a yellow oily substance.

$^1$-NMR(CDCl$_3$)δ:0.01(6H,s),0.80(9H,s),1.55(9H,s), 1.60(1H,m),2.08(1H,m),3.20–3.78(2H,m),4.03–4.71(2H,m), 6.08(1H,m),7.49(3H,m),7.81(3H,m), 8.29(1H,m)

(Step 2)

(2S,4R)-N-t-Butoxycarbonyl-4-t-butyldimethylsiloxy-2-[(methylthiothiocarbonyloxy)(1-naphthyl)methyl]pyrrolidine was prepared as a yellow oily substance (5.18 g, yield: 52.2%) from the compound (8.29 g, 18.2 mmol) obtained in Step 1, carbon disulfide (3.27 ml, 54.5 mmol), 60% sodium hydride (1.09 g, 27.2 mmol) and methyl iodide (10 ml, 159 mmol), in the same manner as in Reference Example 107-3.

(Step 3)

(2R,4R)-N-t-butoxycarbonyl-4-t-butyldimethylsiloxy-2-(1-naphthylmethyl)pyrrolidine (4.2 g, yield: 100%) was prepared as a pale yellow oily substance from the compound (5.18 g, 9.47 mmol) obtained in Step 2, tributyltin hydride (19.5 ml, 72.6 mmol) and α,α'-azobisisobutyronitrile (156 mg, 0.95 mmol), in the same manner as in Reference Example 107-4.

$^1$H-NMR(CDCl$_3$)δ:0.01(6H,s),0.80(9H,s),1.53(9H,s), 1.61(1H,m),1.83(1H,m),2.83(1H,m),3.14–3.60(2H,m),3.79(1H,m),4.03–4.46(2H,m),7.36(1H,m), 7.40(3H,m),7.80(2H,m),8.31(1H,m)

(Step 4)

A brown powder containing (2R,4R)-4-hydroxy-2-(1-naphthylmethyl)pyrrolidine monohydrochloride was prepared from the compound (4.23 g, 9.60 mmol) obtained in Step 3 and 2N hydrogen chloride-dioxane solution (100 ml) in the same manner as in Reference Example 107-5.

$^1$H-NMR(D$_2$O)δ:1.73–2.08(2H,m),3.02–3.29(2H,m), 3.49(2H,m),4.08–4.52(2H,m),7.43(4H,m), 7.80(2H,m),8.03(1H,m)

(Step 5)

To a suspension of the crude product obtained in Step 4 in dichloromethane (50 ml), triethylamine (6.7 ml, 48.0 mmol) and allyloxycarbonyl chloride (2.04 ml, 19.2 mmol) were successively added and the resulting reaction solution was stirred at room temperature for 10 minutes. The reaction solution was concentrated in vacuo and the resulting residue was poured into a liquid mixture of ethyl acetate with water. The organic layer was washed with saturated aqueous sodium chloride, dried over anhydrous sodium sulfate and concentrated in vacuo to give a crude product of (2R,4R)-N-allyloxycarbonyl-4-hydroxy-2-(1-naphthylmethyl)pyrrolidine (3.16 g) as a yellow oily substance, which was used for the next reaction without purification.

$^1$H-NMR(CDCl$_3$)δ:1.96(1H,m),2.74(2H,m),3.56(2H,m), 4.06(1H,m),4.40(2H,m),4.70(2H,m),5.31(2H,m), 6.02(1H,m),7.40(4H,m),7.79(2H,m),8.18–8.51(1H,m)

(Step 6)

(2R,4R)-N-Allyloxycarbonyl-4-mesyloxy-2-(1-naphthylmethyl)pyrrolidine (1.61 g) was prepared as a pale yellow oily substance from the crude product (3.16 g) obtained in Step 5, triethylamine (1.48 ml, 10.6 mmol) and mesyl chloride (820 μl, 10.6 mmol), in the same manner as in Reference Example 107-7.

$^1$H-NMR(CDCl$_3$)δ:2.09(1H,m),2.74(1H,m),2.92(3H,s), 3.61(1H,m),3.87–4.28(3H,m),4.47(1H,m),4.73(2H,m), 5.13(1H,m),5.21–5.51(2H,m),6.01(1H,m),7.38(4H,m), 7.76(2H,m),8.12–8.47(1H,m)

(Step 7)

The title compound (1.15 g, yield: 75.0%) was prepared as a yellow solid from the compound (1.61 g, 3.83 mmol) obtained in Step 6 and potassium thioacetate (1.31 g, 11.5 mmol), in the same manner as in Reference Example 107-10.

$^1$H-NMR(CDCl$_3$)δ:1.73(1H,m),2.16(1H,m),2.38(3H,s), 2.83(1H,m),3.40(1H,m),3.91(1H,m),4.03–4.42(3H,m),4.73(2H,m),5.19–5.52(2H,m),6.01(1H,m), 7.41(4H,m),7.73(2H,m),8.19–8.56(1H,m)

REFERENCE EXAMPLE 109

(2R,4S)-4-Acetylthio-N-(p-nitrobenzyloxycarbonyl)-2-[4'-(p-nitrobenzyloxycarbonylaminomethyl)-4-biphenylmethyl]pyrrolidine

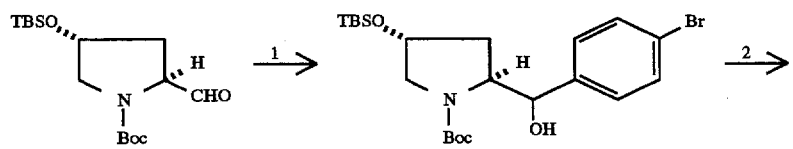

-continued
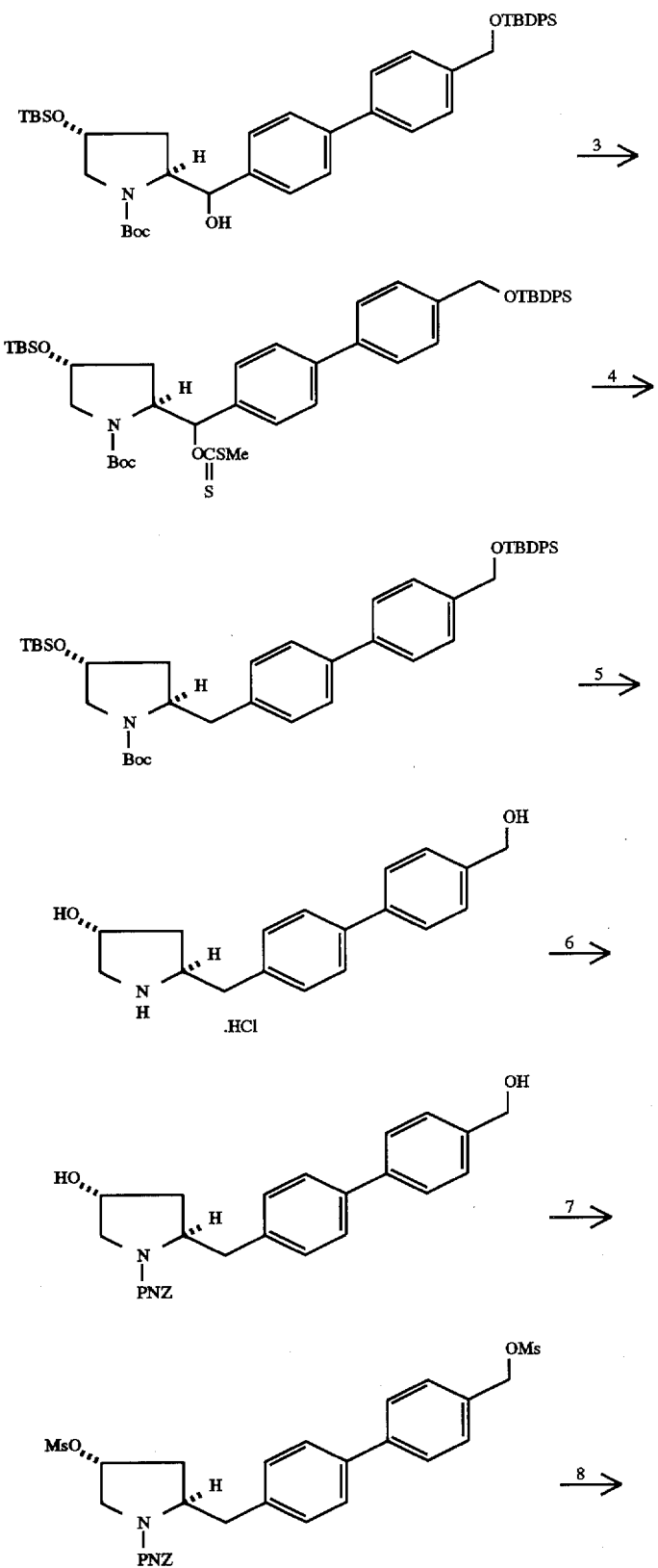

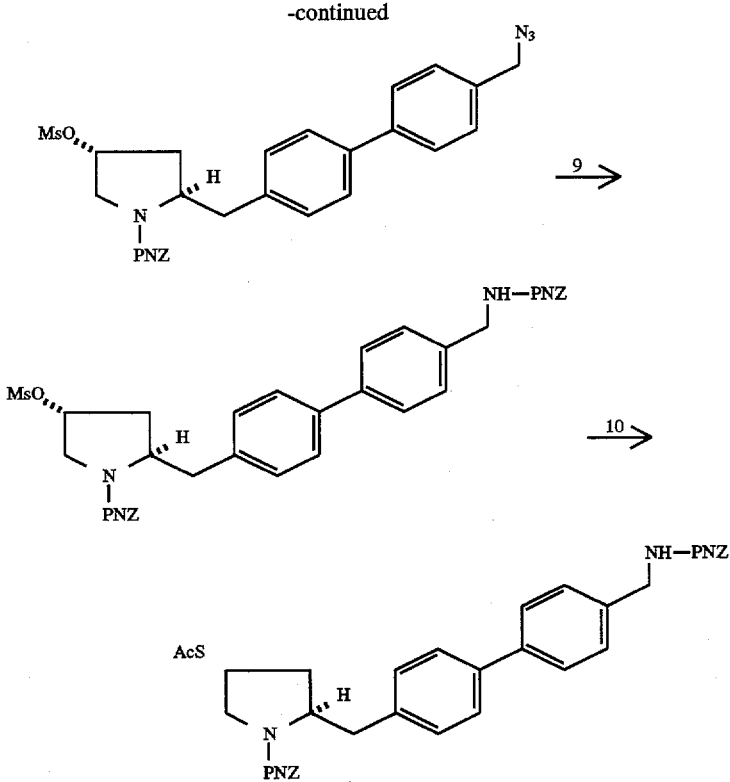

(Step 1)

A solution of p-bromoiodobenzene (9.44 g, 33.4 mmol) in tetrahydrofuran (10 ml) was added dropwise to a solution of 1.6M butyl lithium-hexane solution (19.0 ml, 30.3 mmol) in tetrahydrofuran (50 ml) at −78° C. in a nitrogen stream over 15 minutes. The resulting reaction solution was stirred at −78° C. for 40 minutes and then a solution of (2S,4R)-N-t-butoxycarbonyl-4-(t-butyldimethylsiloxy)prolinal (5.0 g, 15.2 mmol) in tetrahydrofuran (17 ml) was added dropwise thereto over 10 minutes. The reaction solution was stirred at −78° C. for 1.5 hours. After addition of saturated aqueous ammonium chloride, the reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel Column chromatography (Wakogel™ C-300, 200 ml ethyl acetate-heptane 2:3→3:2) to give (2S,4R)-N-t-butoxycarbonyl-4-t-butyldimethylsiloxy-2-[(4-bromophenyl)hydroxymethyl]pyrrolidine (6.30 g, yield: 85.3%) as a pale yellow oily substance.

¹H-NMR(CDCl₃)δ:0.01(6H,s),0.85(9H,s),1.52(9H,s), 1.76–2.08(2H,m),2.86–6.15(5H,m),7.28–7.58(4H,m)

(Step 2)

To a solution of the compound (4.46 g, 9.17 mmol) obtained in Step 1 in 1,2-dimethoxyethane (40 ml), tetrakistriphenylphosphine palladium (508.5 mg, 4.8 mol %) was added and the resulting reaction solution was stirred at 15 minutes. To the reaction solution, a solution of 4-[t-butyldiphenylsiloxymethyl]phenyl borate (4.12 g, 10.5 mmol; see U.S. Pat. No. 5,192,758) in ethanol-1,2-dimethoxyethane (1:1, 30 ml) was added. This reaction solution was stirred at 15 minutes. After addition of 2M aqueous potassium carbonate (40 ml), the reaction solution was stirred at 110° C. in a nitrogen stream for 19 hours and then was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300 200 ml ethyl acetate-heptane 2:3→3:2) to give (2S, 4R)-N-t-butoxycarbonyl-4-t-butyldimethylsiloxy-2-[[4'-(t-butyldiphenylsiloxymethyl)-4-biphenyl]hydroxymethyl]pyrrolidine (5.42 g, yield: 78.5%) as a pale yellow oily substance.

¹H-NMR(CDCl₃)δ:0.01(6H,s),0.84(9H,s),1.11(9H,s), 1.58(9H,s),1.82–1.95(2H,m),2.89–5.99(7H,m),7.34–7.75 (18H,m)

(Step 3)

(2S,4R)-N-t-Butoxycarbonyl-4-t-butyldimethylsiloxy-2-[[4'-(t-butyldiphenylsiloxymethyl)-4-biphenyl](methylthiothiocarbonyloxy)methyl]pyrrolidine was prepared as a pale yellow oily substance (1.02 g, yield: 91.1%) from the compound (1.0 g, 1.33 mmol) obtained in Step 2, sodium hydride (79.8 mg, 1.99 mmol), carbon disulfide (0.24 ml, 3.99 mmol) and methyl iodide (0.83 ml, 13.3 mmol), in the same manner as in Reference Example 107-3.

¹H-NMR(CDCl₃)δ:0.09(6H,s),0.80–0.89(9H,m),1.13 (9H,s), 1.51–1.54(9H,m),1.75–2.36(4H,m),2.62(3H,s), 3.05–3.83(2H,m),4.30–4.63(1H,m),4.72(2H,s),6.86–7.76 (18H,m)

(Step 4)

(2R,4R)-2-[4'-(t-Butyldiphenylsiloxymethyl)-4-biphenylmethyl]-N-t-butoxycarbonyl-4-(t-butyldimethylsiloxy)pyrrolidine was prepared as a pale yellow oily substance (894 mg, yield: 100%) from the compound (1.0 g, 1.19 mmol) obtained in Step 3, tributyltin hydride (2.56 ml, 9.5 mmol) and 2,2'-azobisisobutyronitrile (20 mg), in the same manner as in Reference Example 107-4.

¹H-NMR(CDCl₃)δ:0.03(6H,s),0.82(9H,s),1.11(9H,s), 1.52(9H,s),1.84–1.88(2H,m),2.71–3.41(4H,m),4.02–4.27 (1H,m),4.78–4.82(3H,m),7.22–7.76(18H,m)

(Step 5)

A crude product of (2R,4R)-4-hydroxy-2-(4'-hydroxymethyl-4-biphenylmethyl)pyrrolidine monohydrochloride was prepared as a yellow oily residue from the compound (874 mg, 1.19 mmol) obtained in Step 4 and 1.75N hydrogen chloride-methanol solution (30 ml), in the same manner as in Reference Example 107-5.

(Step 6)

(2R,4R)-4-Hydroxy-2-(4'-hydroxymethyl-4-biphenylmethyl)-N-(p-nitrobenzyloxycarbony)pyrrolidine was prepared as a pale yellow oily substance (401 mg, yield: 73.0%) from the compound obtained in Step 5, p-nitrobenzyloxycarbonyl chloride (307.2 mg, 1.42 mmol) and sodium hydrogencarbonate (1.0 g, 11.8 mmol), in the same manner as in Example 107-6.

$^1$H-NMR(CDCl$_3$)δ:1.68–1.99(2H,m),2.76–3.68(4H,m), 4.28–4.41(2H,m),4.75–4.77(2H,m),5.29(2H,s),7.15–7.58 (10H,m),8.20–8.24(2H,m)

(Step 7)

A crude product of (2R,4R)-4-mesyloxy-2-(4'-mesyloxymethyl-4-biphenylmethyl)-N-(p-nitrobenzyloxcarbonyl)pyrrolidine was prepared as a yellow oily residue from the compound (485 mg, 1.05 mmol) obtained in Step 6, mesyl chloride (0.20 ml, 2.62 mmol) and triethylamine (0.44 ml, 3.15 mmol), in the same manner as in Reference Example 107-7.

(Step 8)

(2R,4R)-2-(4'-Azidomethyl-4-biphenylmethyl)-4-mesyloxy-N-(p-nitrobenzyloxycarbony)pyrrolidine was prepared as a pale yellow oily substance (573 mg, yield: 96.6%) from the residue obtained in Step 7 and sodium azide (136.3 mg, 2.10 mmol), in the same manner as in Reference Example 107-8.

$^1$H-NMR(CDCl$_3$)δ:2.09–2.41(2H,m),2.81–3.50(4H,m), 2.99(3H,s),3.93–4.41(3H,m),5.04(1H,s),5.31(2H,s), 7.13–7.60(10H,m),8.22–8.29(2H,m)

(Step 9)

(2R,4R)-4-Mesyloxy-N-(p-nitrobenzyloxycarbony)-2-[4'-(p-nitrobenzyloxycarbonylaminomethyl)-4-biphenylmethyl]pyrrolidine was prepared as a pale yellow oily substance (557 mg, yield: 77.6%) from the compound (565 mg, 1.00 mmol) obtained in Step 8, triphenylphosphine (471.6 mg, 1.80 mmol), p-nitrobenzyloxycarbonyl chloride (247.7 mg, 1.15 mmol) and triethylamine (0.18 ml, 1.30 mmol), in the same manner as in Reference Example 107-9.

$^1$H-NMR(CDCl$_3$)δ:2.07–2.43(2H,m),2.84–2.95(1H,m), 2.99(3H,s),3.08–3.50(2H,m),3.95–4.48(4H,m),5.04–5.33 (5H,m),7.12–7.58(12H,m),8.21–8.26(4H,m)

(Step 10)

(2R,4S)-4-Acetylthio-N-(p-nitrobenzyloxycarbonyl)-2-[4'-(p-nitrobenzyloxycarbonylaminomethyl)-4-biphenylmethyl]pyrrolidine was prepared as a pale yellow oily substance (483 mg, yield: 90.3%) from the compound (550 mg, 0.77 mmol) obtained in Step 9 and potassium thioacetate (262.2 mg, 2.30 mmol), in the same manner as in Reference Example 107-10.

$^1$H-NMR(CDCl$_3$)δ:1.71–2.22(2H,m),2.35(3H,s), 2.68–3.29(4H,m),3.41–3.96(2H,m),4.10–4.47(3H,m), 5.16–5.27(5H,m),7.16–7.63(12H,m),8.19–8.24(4H,m)

In the following Reference Example 110, physicochemical data of compounds used in Examples as thiols or thiol precursors are shown.

REFERENCE EXAMPLE 110

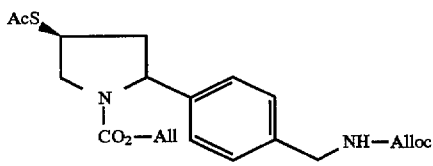

Diastereomer A $^1$H-NMR(CDCl$_3$)δ:1.86(1H,m),2.30(3H,s),2.80(1H,m), 3.42(1H,dd,J=11&8.5Hz),3.97(1H,m),4.20–4.65(7H,m), 7.15–7.30(4H,m)

MS:419(M+H)

Diastereomer B $^1$H-NMR(CDCl$_3$)δ:2.25(1H,m),2.32(3H,s),3.62(1H,m), 4.06(2H,m),4.34(2H,m),4.40–4.70(4H,m),4.85–5.40(6H, m), 7.20–7.40(2H,m)

MS:419(M+H)

REFERENCE EXAMPLE 111

(2S,4S)-4-Acetylthio-N-(p-nitrobenzyloxycarbonyl)-2-[hydroxy[4'-[(p-nitrobenzyloxycarbonylamino)methyl]-4-biphenyl]methyl]pyrrolidine diastereomer I

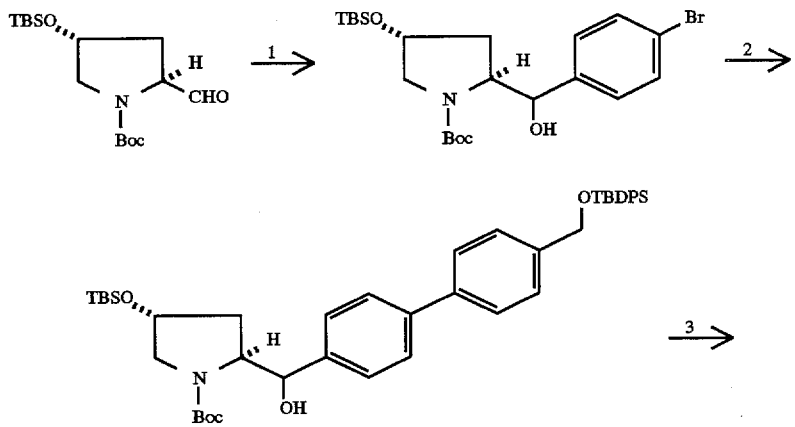

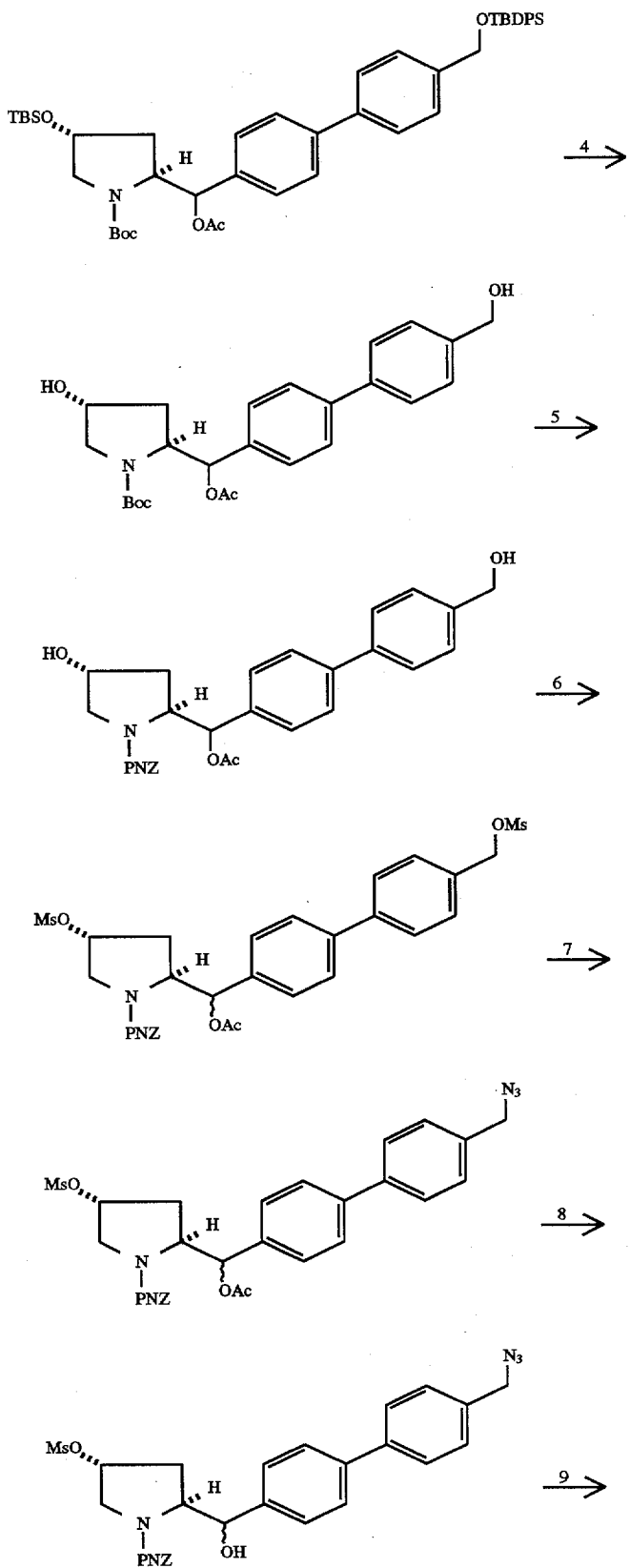

-continued

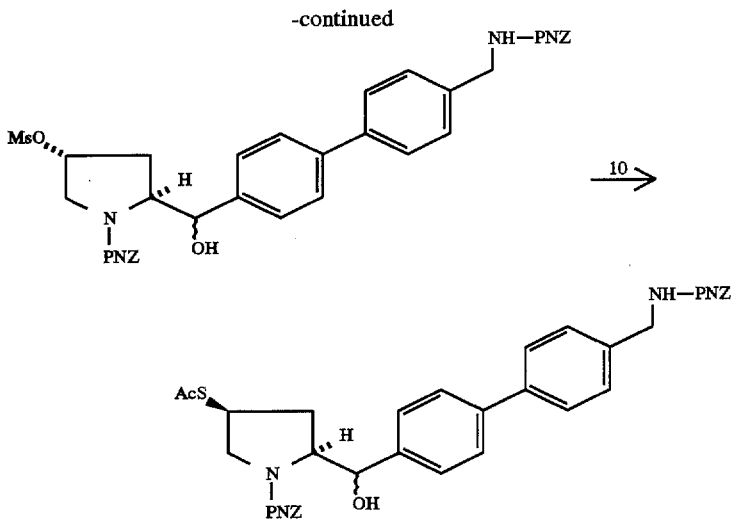

(Step 1)
A solution of 4-bromo-1-iodobenzene (9.44 g, 33.4 mmol) in tetrahydrofuran (10 ml) was added dropwise to a solution of 1.6M n-butyl lithium-hexane solution (19.0 ml, 30.3 mmol) in tetrahydrofuran (50 ml) at −78° C. for in a nitrogen stream over 15 minutes. This reaction solution was stirred −78° C. for 40 minutes and then a solution of (2S,4R)-N-t-butoxycarbonyl-4-(t-butyldimethylsiloxy) prolinal (5.0 g, 15.2 mmol) in tetrahydrofuran (17 ml) was added dropwise thereto over 10 minutes. The reaction solution was stirred at −78° C. for 1.5 hours and then saturated ammonium chloride solution was added thereto. The reaction solution was poured into a liquid mixture of ethyl acetate with water. The organic layer was washed with saturated aqueous sodium chloride and dried over anhydrous sodium sulfate. The solvent was distilled off in vacuo and the resulting oily residue was subjected to silica gel column chromatography (Wakogel™ C-300, 200 ml; ethyl acetate-heptane 2:3→3:2) to give (2S,4R)-N-t-butoxycarbonyl-4-t-butyldimethylsiloxy-2-[(4-bromophenyl)hydroxymethyl]pyrrolidine (6.30 g, yield: 85.3%) as a pale yellow oily substance.

$^1$H-NMR(CDCl$_3$)δ:0.01(6H,s),0.85(9H,s),1.52(9H,s), 1.76–2.08(2H,m),2.86–6.15(5H,m),7.28–7.58(4H,m)

(Step 2)
To a solution of the compound (4.46 g, 9.17 mmol) obtained in Step 1 in 1,2-dimethoxyethane (40 ml), tetrakistriphenylphosphinepalladium (0) (508.5 mg, 4.8 mol %) was added at room temperature and the reaction solution was stirred for 15 minutes. To the reaction solution, a solution of 4-(t-butyldiphenylsiloxymethyl)phenyl borate (4.12 g, 10.5 mmol; see U.S. Pat. No. 5,192,758) in ethanol-1,2-dimethoxyethane (1:1, 30 ml) was added. The reaction solution was stirred for 15 minutes and 2M aqueous potassium carbonate (40 ml) was added thereto. The reaction solution was stirred at 110° C. in a nitrogen stream for 19 hours and then poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, 200 ml; ethyl acetate-heptane= 2:3→3:2) to give (2S,4R)-N-t-butoxycarbonyl-4-t-butyldimethylsiloxy-2-[[4'-(t-butyldiphenylsiloxymethyl)-4-biphenyl]hydroxymethyl]pyrrolidine (5.42 g, yield: 78.5%) as a pale yellow oily substance.

$^1$H-NMR(CDCl$_3$)δ:0.01(6H,s),0.84(9H,s),1.11(9H,s), 1.58(9H,s),1.82–1.95(2H,m),2.89–5.99(7H,m),7.34–7.75 (18H,m)

(Step 3)
To a solution of the compound (2.50, 3.32 mmol) obtained in Step 2 in dichloromethane (30 ml), 4-N,N-dimethylaminopyridine (609 mg, 5.00 mmol) and acetic anhydride (0.38 ml, 4.00 mmol) were successively added in a nitrogen stream under cooling with ice and the resulting reaction solution was stirred at the same temperature for 10 minutes. It was allowed to gradually warm and then stirred at room temperature for 1.5 hours and aqueous sodium hydrogencarbonate was added thereto. The reaction solution was poured into a liquid mixture of ethyl acetate with water. The organic layer was washed with saturated aqueous sodium chloride and dried over anhydrous sodium sulfate. The solvent was distilled off in vacuo and the resulting oily residue was subjected silica gel column chromatography (Wakogel™ C-300, 100 ml; ethyl acetate-heptane= 3:17→1:4) to give (2S,4R)-2-[acetoxy[4'-(t-butyldiphenylsiloxymethyl)-4-biphenyl]methyl]-N-t-butoxycarbonyl-4-(t-butyldimethylsiloxy)pyrrolidine diastereomer I as a pale yellow substance (polar compound, 1.09 g, yield: 41.3%) and diastereomer II as a pale yellow oily substance (less polar compound, 1.38 g, yield: 52.3%).

Diastereomer I
$^1$H-NMR(CDCl$_3$)δ:0.04(6H,s),0.95(9H,s),1.11(9H,s), 1.57(9H,s),1.65–1.76(1H,m),2.16(3H,s),2.18–2.24(1H,m), 3.33–3.56(2H,m),4.27–4.50(2H,m), 4.81(2H,s),6.38(1H,s), 7.27–7.72(18H,m)

Diastereomer II
$^1$H-NMR(CDCl$_3$)δ:0.01(6H,s),0.80(9H,s),1.15(9H,s), 1.59(9H,s),1.81–2.11(2H,m),2.16–2.20(3H,m),3.05–3.71 (3H,m),4.31–4.45(1H,m),4.86(2H,s),6.12–6.23(1H,m), 7.32–7.85(18H,m)

(Step 4)
To a solution of the compound (diastereomer I: 740 mg, 0.93 mmol) obtained in Step 3 in tetrahydrofuran (13 ml), acetic acid (43 µl, 0.75 mmol) and 1.0M tetrabutylammonium fluoride-tetrahydrofuran solution (3.72 ml, 3.72 mmol) were successively added under cooling with ice. The resulting reaction solution was stirred at the same temperature for 15 minutes and then at 35° C. for 4 hours. The reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, 100 mg; ethyl acetate-heptane=9:1) to give (2S,4R)-2-[acetoxy(4'-hydroxymethyl-4-biphenyl) methyl]-N-t-butoxycarbonyl-4-hydroxypyrrolidine diastereomer I as a pale yellow oily substance (polar compound, 420 mg, yield: 99.9%). Likewise, from the compound (diastereomer II: 1.06 g, 1.33 mmol), acetic acid (0.06 ml, 1.07 mmol) and 1.0M tetrabutylammonium fluoride-tetrahydrofuran solution (5.34 ml, 5.34 mmol), (2S,4R)-2-[acetoxy(4'-hydroxymethyl-4-biphenyl)methyl]-N-t-butoxycarbonyl-4-hydroxypyrrolidine diastereomer II was prepared as a pale yellow substance (less polar compound, 593 mg, yield: 99.8%).
Diastereomer I $^1$H-NMR(CDCl$_3$)δ:1.58(9H,s),1.72–2.37(2H,m),2.18 (3H,s), 3.43–4.52(4H,m),4.74–4.79(2H,m),6.49(1H,s), 7.32–7.60(8H,m)

Diastereomer II $^1$H-NMR(CDCl$_3$)δ:1.55(9H,s),1.68–2.09(2H,m),2.15 (3H,s), 2.99–4.44(4H,m),4.75(2H,s),6.21(1H,s),7.31–7.60 (8H,m)

(Step 5)

To a solution of the compound (diastereomer I: 420 mg, 1.01 mmol) obtained in Step 4 in dichloromethane (15 ml), trifluoroacetic acid (10 ml) was added on an ice bath. The resulting reaction solution was stirred for 45 minutes and then concentrated in vacuo. To a solution of the residue in dioxane-water (4:3, 45 ml), sodium hydrogencarbonate (845 mg, 10.1 mmol) and p-nitrobenzyloxycarbonyl chloride (249.4 mg, 1.16 mmol) were successively added on an ice bath. The resulting reaction solution was stirred at the same temperature for 10 minutes. The reaction solution was allowed to gradually warm and stirred at room temperature for 1 hour. The reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300,100 ml; acetone-ethyl acetate=1:1) to give (2S,4R)-2-[acetoxy-4'-hydroxymethyl-4-biphenyl)methyl]-4-hydroxy-N-(p-nitrobenzyloxycarbonyl)pyrrolidine diastereomer I as a pale yellow oily substance (highly polar compound, 433 mg, yield: 81.4%). Likewise, from the compound (diastereomer II: 593 mg, 1.42 mmol) obtained in Step 4, sodium hydrogencarbonate (1.19 g, 14.2 mmol) and p-nitrobenzyloxycarbonyl chloride (352.1 mg, 1.63 mmol), (2S,4R)-2-[acetoxy-(4'-hydroxymethyl)-4-biphenyl]methyl]-4-hydroxy-N-(p-nitrobenzyloxycarbonyl)pyrrolidine diastereomer II was prepared as a pale yellow oily substance (slightly polar compound, 612 mg, yield: 81.5%).
Diastereomer I $^1$H-NMR(CDCl$_3$)δ:1.74–2.39(2H,m),2.16(3H,s), 3.38–4.53(4H,m),4.72–4.76(2H,m),5.30(2H,s),6.45–6.53 (1H,m),7.39–8.27(12H,m)

Diastereomer II $^1$H-NMR(CDCl$_3$)δ:1.79–2.18(2H,m),2.10(3H,s), 3.01–4.62(4H,m),4.72–4.77(2H,m),5.27–5.31(2H,m), 6.17–6.20(1H,m),7.30–8.26(12H,m)

(Step 6)

To a solution of the compound (diastereomer I: 433 mg, 0.82 mmol) obtained in Step 5 in dichloromethane-N,N-dimethylformamide (10:3, 13 ml), triethylamine (0.34 ml, 2.46 mmol) and mesyl chloride (0.16 ml, 2.05 mmol) were added successively in a nitrogen stream under cooling with ice and the resulting reaction solution was stirred at the same temperature for 15 minutes. Aqueous sodium hydrogencarbonate was added to the reaction solution and the organic layer was washed with saturated aqueous sodium chloride, dried over anhydrous sodium sulfate, and concentrated in vacuo to give a crude product of (2S,4R)-2-[acetoxy(4'-mesyloxymethyl-4-biphenyl)methyl]-4-mesyloxy-N-(p-nitrobenzyloxycarbonyl)pyrrolidine diastereomer I as a yellow oily residue, which was used for the next reaction without purification.

(Step 7)

To a solution of the compound (diastereomer I) obtained in Step 6 in N,N-dimethylformamide (11 ml), sodium azide (106.5 mg, 1.64 mmol) was added in a nitrogen stream under cooling with ice and the resulting reaction solution was stirred at the same temperature for 1 hour. The reaction solution was poured into a liquid mixture of ethyl acetate with water. The organic layer was washed with saturated aqueous sodium chloride, dried over anhydrous sodium sulfate, and concentrated in vacuo to give a crude product of (2S,4R)-2-[acetoxy(4'-azidomethyl-4-biphenyl)methyl]-4-mexyloxy-N-(p-nitrobenzyloxycarbonyl)pyrrolidine diastereomer I as a yellow oily residue, which was used for the next reaction without purification.

(Step 8)

To a solution of the compound (diastereomer I) obtained in Step 7 in dichloromethane-methanol (1:1, 30 ml), 0.2M aqueous potassium carbonate (10 ml) was added under cooling with ice and this reaction solution was stirred at the same temperature for 20 minutes. The reaction solution was allowed to gradually warm and then stirred at room temperature for 1 hour. The reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, 100 ml; ethyl acetate-heptane=4:1) to give (2S,4R)-2-[(4'-azidomethyl-4-biphenyl)hydroxymethyl]-4-mesyloxy-N-(p-nitrobenzyloxycarbonyl)pyrrolidine diastereomer I as a pale yellow oily residue (423 mg, yield: 88.8%).

$^1$H-NMR(CDCl$_3$)δ:2.28–3.02(2H,m),2.99(3H,s), 3.42–4.41(5H,m),5.20–5.42(4H,m),7.38–8.29(12H,m)

(Step 9)

To a solution of the compound (diastereomer I; 418 mg, 0.72 mmol) obtained in Step 8 in tetrahydrofuran-water (2.4:1, 17 ml), triphenylphosphine (339.3 mg, 1.29 mmol) was added at room temperature and this reaction solution was stirred for 18 hours. To the reaction solution, triethylamine (0.13 ml, 0.93 mmol) and p-nitrobenzyloxycarbonyl chloride (178.2 mg, 0.83 mmol) were successively added under cooling with ice and the reaction solution was stirred at the same temperature for 10 minutes. The reaction solution was allowed to gradually warm and then stirred at room temperature for 1 hours. The reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, 60 ml; ethyl acetate-heptane=4:1) to give (2S,4R)-2-[hydroxy[4'-[(p-nitrobenzyloxycarbonylamino)methyl]-4-biphenyl]methyl]-4-mesyloxy-N-p-nitrobenzyloxycarbonyl)pyrrolidine diastereomer I as a pale yellow oily substance (495 mg, yield: 93.7%).

$^1$H-NMR(CDCl$_3$)δ:2.17–3.04(2H,m),3.00(3H,s), 3.42–4.46(5H,m),5.21–5.39(7H,m),7.35–8.28(16H,m)

(Step 10)

To a solution of the compound (diastereomer I: 490 mg, 0.67 mmol) obtained in Step 9 in N,N-dimethylformamide (20 ml), potassium thioacetate (761.7 mg, 6.7 mmol) was added at room temperature. This reaction solution was heated at 70° C. in nitrogen stream for 3 hours and then poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, 60 ml; ethyl acetate-heptane=4:1) to give (2S,4S)-4-acetylthio-2-[hydroxy[4'-[(p-nitrobenzyloxycarbonylamino)methyl]-4-biphenyl]methyl]-N-(p-nitrobenzyloxycarbonyl) pyrrolidine diastereomer as a pale yellow oily substance (390 mg, yield: 81.8%).

$^1$H-NMR(CDCl$_3$)δ:2.10–2.20(1H,m),2.31(3H,s), 2.94–3.25(1H,m),3.70–4.31(3H,m),4.44–4.47(2H,m), 5.19–5.34(6H,m),7.37–7.62(12H,m),8.20–8.27(4H,m)

REFERENCE EXAMPLE 112

(2S,4S)-4-Actylthio-N-(p-nitrobenzyloxycarbonyl)-2-[hydroxy[5-[(p-nitrobenzyloxycarbonylamino)methyl]-3-biphenyl]methyl]pyrrolidine

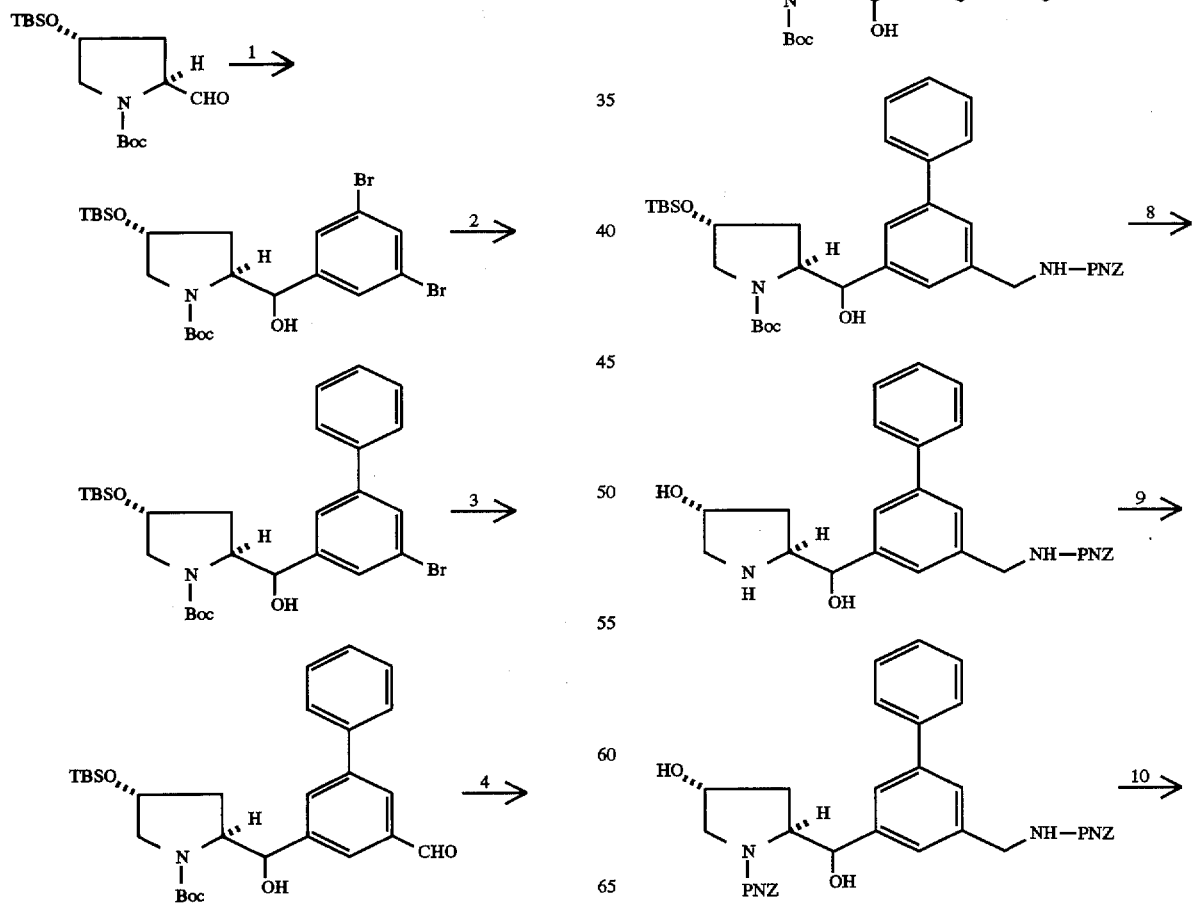

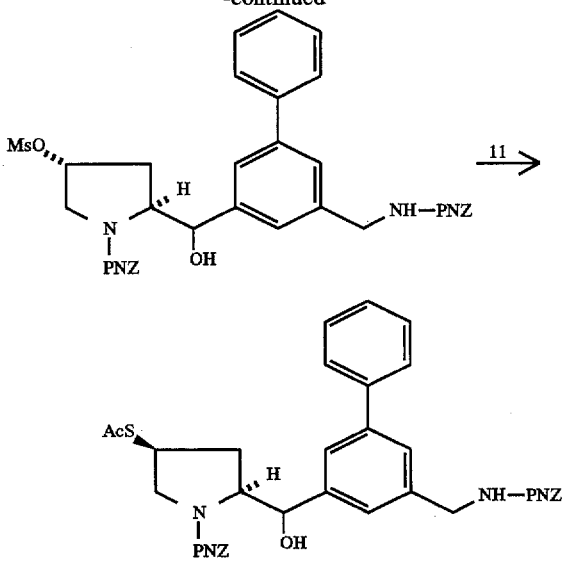

(Step 1)

(2S,4R)-N-t-Butoxycarbonyl-4-t-butyldimethylsiloxy-2-(α-hydroxy-3,5-dibromobenzyl)pyrrolidine (19.6 g, yield: 56.9%) was prepared as a yellow oily substance, from (2S,4R)-N-t-butoxycarbonyl-4-(t-butyldimethylsiloxy) prolinal (20 g, 60.8 mmol), 1,3,5-tribromobenzene (19.13 g, 60.8 mmol) and 1.6M n-butyl lithium-hexane solution (49.4 ml, 79.04 mmol), in the same manner as in Reference Example 111-1.

¹H-NMR(CDCl₃)δ:0.03(6H,s),0.86(9H,s),1.53(9H,s), 1.63–2.14(2H,m),2.88–3.64(2H,m),3.92–4.58(2H,m), 4.82–5.50(1H,m),7.56(3H,m)

(Step 2)

(2S,4R)-N-t-Butoxycarbonyl-4-t-butyldimethylsiloxy-2-[(5-bromo-3-biphenyl)hydroxymethyl]pyrrolidine (5.9 g, yield: 30.0%) was prepared from the compound (19.6 g, 34.6 mmol) obtained in Step 1, phenyl borate (2.11 g, 17.3 mmol), tetrakistriphenylphosphinepalladium(0) (1.2 g, 1.04 mmol) and sodium carbonate (3.3 g, 31.2 mmol), in the same manner as Reference Example 111-2.

¹H-NMR(CDCl₃)δ:0.01(6H,s),0.84(9H,s),1.51(9H,s), 1.85(2H,m),2.71–3.61(2H,m),3.80–4.60(2H,m),4.81–5.49 (1H,m),7.49(8H,m)

(Step 3)

To a solution of the compound (5.7 g, 10.4 mmol) obtained in Step 2 in tetrahydrofuran (30 ml), a solution of 1.6M n-butyl lithium-hexane solution (19 ml, 30.4 mmol) in tetrahydrofuran was added dropwise at −78° C. in a nitrogen stream over 30 minutes. This reaction solution was stirred at the same temperature for 30 minutes and then dimethylformamide (5 ml) was added dropwise thereto over 1 minute. The reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, heptane-ethyl acetate=5:1) to give (2S,4R)-N-t-butoxycarbonyl-4-t-butyldimethylsiloxy-2-[(5-formyl-3-biphenyl)hydroxymethyl]pyrrolidine (1.16 g, 22.3%) as a pale yellow oily substance.

¹H-NMR(CDCl₃)δ:0.01(6H,s),0.81(9H,s),1.51(9H,s), 1.82(1H,m),2.74–3.94(3H,m),4.08–4.73(2H,m),5.01–5.58 (1H,m),7.46(3H,m),7.61(2H,m),7.84(2H,m), 8.02(1H,m), 10.09(1H,s)

(Step 4)

To a solution of the compound (1.15 g, 2.25 mmol) obtained in Step 3 in tetrahydrofuran, sodium boron hydride (128 mg, 3.37 mmol) was added under cooling with ice and this reaction solution was stirred at room temperature for 30 minutes. The reaction solution was poured into a liquid mixture of ethyl acetate with water. The organic layer was washed with saturated aqueous sodium chloride, dried over anhydrous sodium sulfate, and concentrated in vacuo to give a crude product of (2S,4R)-N-t-butoxycarbonyl-4-t-butyldimethylsiloxy-2-[hydroxy(5-hydroxymethyl-3-biphenyl)methyl]pyrrolidine (1.02 g) as a yellow oily substance, which was used for the next reaction without purification.

¹H-NMR(CDCl₃)δ:0.01(6H,s),0.81(9H,s),1.52(9H,s), 1.83(1H,m),2.86–3.59(2H,m),3.81–4.80(5H,m),4.92–5.32 (1H,m),7.19–7.64(8H,m)

(Step 5)

To a solution of the compound (1.01 g, 1.97 mmol) obtained in Step 4 in dichloromethane (20 ml), triethylamine (330 µl, 2.36 mmol) and mesyl chloride (152 µl, 1.97 mmol) were successively added in a nitrogen stream under cooling with ice and this reaction solution was stirred at the same temperature for 10 minutes. The reaction solution was poured into a liquid mixture of ethyl acetate with water. The organic layer was washed with saturated aqueous sodium chloride, dried over anhydrous sodium sulfate, and concentrated in vacuo to give a crude product of (2S,4R)-N-t-butoxycarbonyl-4-t-butyldimethylsiloxy-2-[hydroxy(5-mesyloxy-3-biphenyl)methyl]pyrrolidine as a yellow oily substance, which was used for the next reaction without purification.

(Step 6)

A crude product of (2S,4R)-N-t-butoxycarbonyl-4-t-butyldimethylsiloxy-2-[(5-azidomethyl-3-biphenyl) hydroxymethyl]pyrrolidine was prepared as a yellow oily substance from the compound obtained in Step 5 and sodium azide (384 mg, 5.91 mmol), in the same manner as in Reference Example 111-7. The crude product was used for the next reaction without purification.

(Step 7)

(2S,4R)-N-t-Butoxycarbonyl-4-t-butyldimethylsiloxy-2-[hydroxy[5-[(p-nitrobenzyloxycarbonylamino)methyl]-3-biphenyl]methyl]pyrrolidine (1.06 g, yield: 78.1%) was prepared as a white oily substance from the compound obtained in Step 6, triphenylphosphine (1.03 g, 3.94 mmol) and p-nitrobenzyloxycarbonyl chloride (552 mg, 2.56 mmol), in the same manner as in Reference Example 111-8.

¹H-NMR(CDCl₃)δ:0.01(6H,s),0.80(9H,s),1.40(9H,s), 1.80(1H,m),2.84–4.31(5H,m),4.42(2H,m),4.84–5.36(3H, m), 7.40(10H,m),8.21(2H,m)

(Step 8)

A solution of the compound (1.05 g, 1.52 mmol) obtained in Step 7 in 2.6N hydrogen chloride-methanol was stirred at room temperature for 20 minutes. This reaction solution was concentrated in vacuo to give a crude product of (2S,4R)-4-hydroxy-2-[hydroxy[5-[(p-nitrobenzyloxycarbonylamino)methyl]-3-biphenyl]methyl] pyrrolidine as a yellow oily substance, which was used for the next reaction without purification.

(Step 9)

A solution of the crude product obtained in Step 8 in dioxane-water (5:1, 30 ml) was adjusted to pH 10.0 with 1N aqueous sodium hydroxide. To this solution, a solution of p-nitrobenzyloxycarbonyl chloride (426 mg, 1.96 mmol) in dioxane (2 ml) was added dropwise, while the reaction solution was maintained at pH 8.0–10.0 by using 1N aqueous sodium hydroxide. The reaction solution was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, heptane-ethyl acetate=1:3) to give (2S,4R)-2-[hydroxy[5-[(p-nitrobenzyloxycarbonylamino)methyl]-3-biphenyl]methyl]-4-hydroxy-N-(p-nitrobenzyloxycarbonyl)pyrrolidine (718 mg, yield: 72.0%) as a colorless oily substance.

$^1$H-NMR(CDCl$_3$)δ:1.77(1H,m),3.10–3.80(2H,m), 4.16–4.51(4H,m),4.63(1H,m),5.26(4H,m),5.88(1H,m), 7.36 (12H,m),8.21(4H,m)

(Step 10)

A crude product of (2S,4R)-2-[hydroxy[5-[(p-nitrobenzyloxycarbonylamino)methyl]-3-biphenyl]methyl]-4-mesyloxy-N-(p-nitrobenzyloxycarbonyl)pyrrolidine was prepared as a yellow oily substance from the compound (703 mg, 1.07 mmol) obtained in Step 9, triethylamine (178.4 μl, 1.28 mmol) and mesyl chloride (83 μl, 1.07 mmol), in the same manner as in Reference Example 112-5. The crude product was used for the next reaction without purification.

(Step 11)

The title compound (218 mg, yield: 28.3%) was prepared as a brown oily substance from the crude product obtained in Step 1 and potassium thioacetate (367 mg, 3.21 mmol), in the same manner as in Reference Example 111-10.

$^1$H-NMR(CDCl$_3$)δ:2.01(1H,m),2.30(3H,s),3.12(1H,m), 3.72(1H,m),4.21(2H,m),4.41(2H,m),5.26(5H,m), 5.78(1H,m),7.40(12H,m),8.21(4H,m)

REFERENCE EXAMPLE 113

(2S,4S)-4-Acetylthio-N-(p-nitrobenzyloxycarbonyl)-2-[hydroxy(2-naphthyl)methyl]pyrrolidine

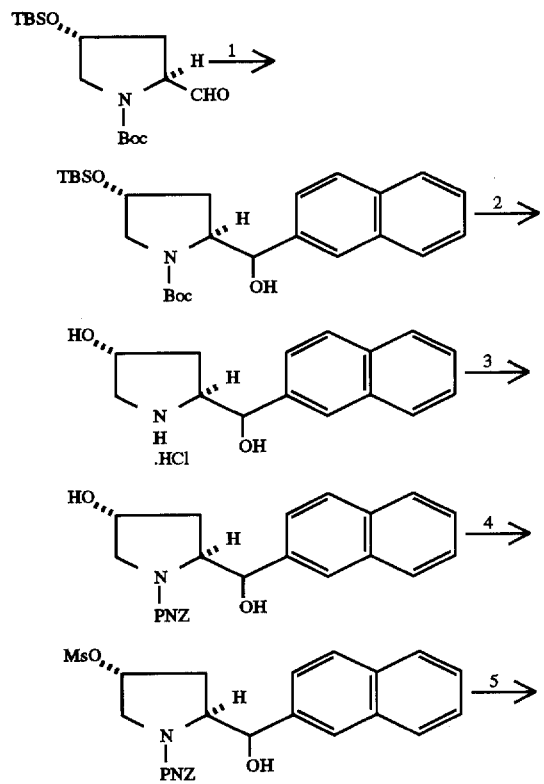

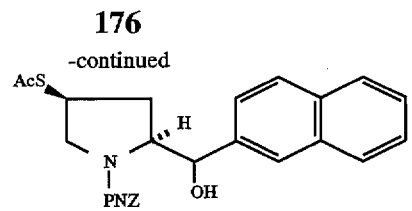

(Step 1)

Magnesium (3.4 g) and a solution of 1,2-dibromoethane (5.3 ml, 60.8 mmol) in diethyl ether (40 ml) were successively added to a solution of 2-bromonaphthalene (12.6 g, 60.8 mmol) in diethyl ether (160 ml) at room temperature in a nitrogen stream and this reaction solution was refluxed under heating for 2.5 hours. The reaction solution was gradually cooled and a solution of (2S,4R)-N-t-butoxycarbonyl-4-(t-butyldimethylsiloxy)prolinal (10 g, 30.4 mmol) in tetrahydrofuran (50 ml) was added dropwise thereto under cooling with ice. Then, the reaction solution was stirred at room temperature for 1 hour. After addition of water, the reaction solution was concentrated in vacuo and was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, heptane-ethyl acetate=4:1) to give (2S,4R)-N-t-butoxycarbonyl-4-t-butyldimethylsiloxy-2-[hydroxy(2-naphthyl)methyl]pyrrolidine (9.38 g, yield: 67.5%) as a yellow oily substance.

$^1$H-NMR(CDCl$_3$)δ:0.01(6H,s),0.76(9H,s),1.51(9H,s), 1.86(1H,m),2.83(1H,m),3.28(1H,m),3.46–3.84(1H,m), 4.03–4.44(1H,m),4.46–4.73(1H,m),5.01–5.43(1H,m),7.46 (3H,m),7.80(4H,m)

(Step 2)

A crude product of (2S,4R)-4-hydroxy-2-[hydroxy(2-naphthyl)methyl]pyrrolidine monohydrochloride was prepared as a pale red powder from the compound (2.17 g, 4.74 mmol) obtained in Step 1 and 2N hydrogen chloride-dioxane solution (50 ml), in the same manner as in Reference Example 112-8. The crude product was used for the next reaction without purification.

$^1$H-NMR(D$_2$O)δ:1.71–2.03(1H,m),2.04–2.31(1H,m), 3.33(1H,m), 3.54(1H,m),4.39(1H,m),4.62(1H,m),4.99–5.40 (1H,m), 7.62(3H,m),7.98(4H,m)

(Step 3)

(2S,4R)-4-hydroxy-2-[hydroxy(2-naphthyl)methyl]-N-(p-nitrobenzyloxycarbonyl)pyrrolidine (1.68 g, yield: 84.0%) was prepared as a white solid from the crude product obtained in Step 2 and p-nitrobenzyloxycarbonyl chloride (1.33 g, 6.16 mmol), in the same manner as in Reference Example 112-9.

$^1$H-NMR(CDCl$_3$)δ:1.51–1.96(1H,m),2.11–2.42(1H,m), 3.18–3.68(2H,m),4.28–4.61(2H,m),4.98–5.47(3H,m), 7.51 (5H,m),7.80(4H,m),8.26(2H,m)

(Step 4)

A crude product of (2S,4R)-2-[hydroxy(2-naphthyl) methyl]-4-mesyloxy-N-(p-nitrobenzyloxycarbonyl) pyrrolidine (1.57 g) was prepared as a brown powder from the compound (1.68 g, 3.98 mmol) obtained in Step 3, triethylamine (555 μl, 3.98 mmol) and mesyl chloride (308 μl, 3.98 mmol), in the same manner as in Reference Example 112-5. The crude product was used for the next reaction without purification.

$^1$H-NMR(CDCl$_3$)δ:1.91(1H,m),2.42(1H,m),2.96(3H,s), 3.03(1H,m),3.60(1H,m),4.02(1H,m),4.46(1H,m),5.16–5.53 (3H,m),7.51(5H,m),7.83(4H,m),8.26(2H,m)

(Step 5)

The title compound (615 mg, yield: 32.2%) was prepared from the crude product (1.57 g, 3.98 mmol) obtained in Step 4 and potassium thioacetate (1.36 g, 11.9 mmol), in the same manner as in Reference Example 111-10.

$^1$H-NMR(CDCl$_3$)δ:2.02(2H,m),2.31(3H,s),2.91–3.37 (1H,m), 3.75(1H,m),4.04–4.41(2H,m),4.83–5.52(3H,m), 7.46(5H,m),7.80(4H,m),8.23(2H,m)

REFERENCE EXAMPLE 114

(2S,4S)-4-Acetylthio-N-(p-nitrobenzyloxycarbonyl)-2-[hydroxy[4-[(p-nitrobenzyloxycarbonylamino)methyl]-1-naphthyl]methyl]pyrrolidine diastereomer I

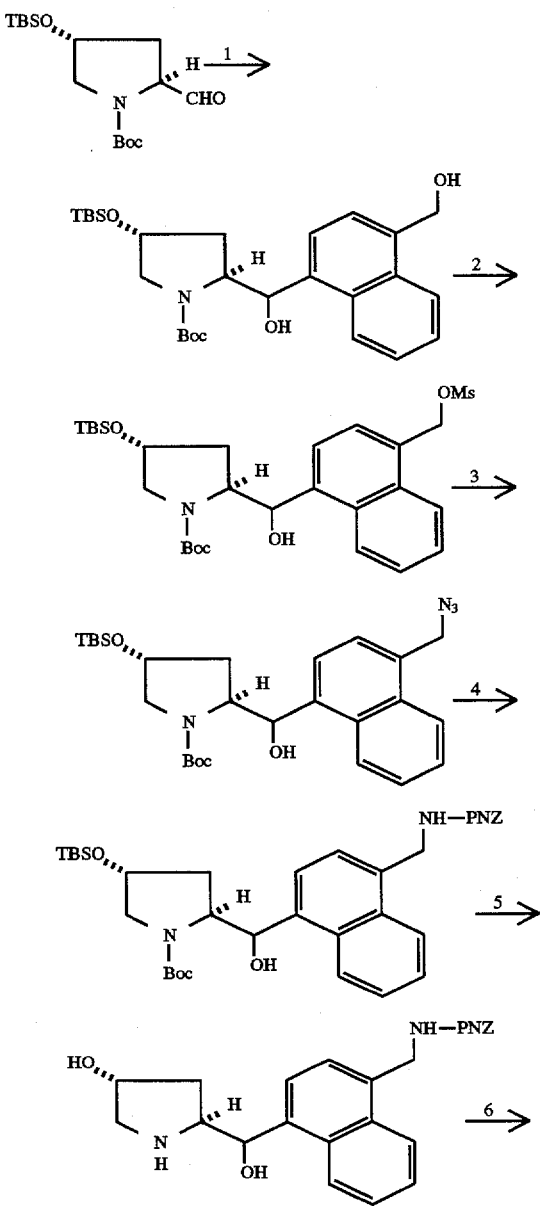

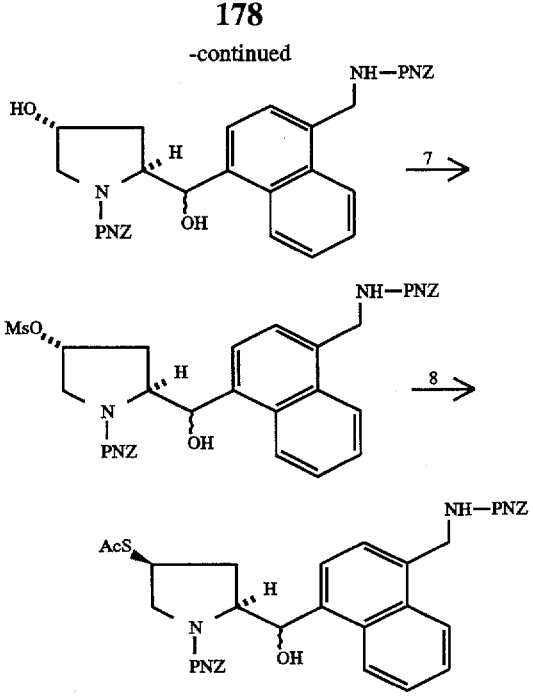

(Step 1)
(2S,4R)-N-t-Butoxycarbonyl-4-t-butyldimethylsiloxy-2-[hydroxy(4-hydroxymethyl-1-naphthyl)methyl]pyrrolidine (2.71 g, yield: 44.0%) was prepared as a colorless oily substance from (2S,4R)-N-t-butoxycarbonyl-4-(t-butyldimethylsiloxy)prolinal (4.17 g, 12.7 mmol), 4-hydroxymethyl-1-bromonaphthalene (3 g, 12.7 mmol) and 1.6M n-butyl lithium-hexane solution (20.6 ml, 39.9 mmol), in the same manner as in Reference Example 111-1.

$^1$H-NMR(CDCl$_3$)δ:0.01(6H,s),0.79(9H,s),1.54(9H,s), 2.01(2H,m),3.26–3.52(2H,m),4.03–4.68(2H,m),5.03–5.36 (2H,m),5.94–6.29(1H,m),7.52(4H,m),8.09(1H,m), 8.38(1H, m)

(Step 2)
A crude product of (2S,4R)-N-t-butoxycarbonyl-4-t-butyldimethylsiloxy-2-[hydroxy(4-mesyloxymethyl-1-naphthyl)methyl]pyrrolidine was prepared as a yellow oily substance from the compound (1.56 g, 3.20 mmol) obtained in Step 1, triethylamine (535 μl, 3.84 mmol) and mesyl chloride (248 μl, 3.20 mmol), in the same manner as in Reference Example 112-5. The crude product was used for the next reaction without purification.

(Step 3)
A crude product of (2S,4R)-N-t-butoxycarbonyl-4-t-butyldimethylsiloxy-2-[hydroxy(4-azidomethyl-1-naphthyl) methyl]pyrrolidine was prepared as a yellow oily substance from the crude product obtained in Step 2 and sodium azide (624 mg, 9.6 mmol), in the same manner as in Reference Example 111-7. This crude product was used for the next reaction without purification.

(Step 4)
(2S,4R)-N-t-Butoxycarbonyl-4-t-butyldimethylsiloxy-2-[hydroxy[4-[(p-nitrobenzyloxycarbonylamino)methyl]-1-naphthyl]methyl]pyrrolidine (570 mg) was prepared as a yellow oily substance from the compound obtained in Step 3 and p-nitrobenzyloxycarbonyl chloride (897 mg, 4.16 mmol), in the same manner as in Reference Example 111-9.

$^1$H-NMR(CDCl$_3$)δ:1.40(1H,m),2.03(1H,m),3.19–3.72 (2H,m), 4.12(1H,m),4.43(1H,m),4.82(2H,m),5.23(2H,m), 6.00(1H,m),7.51(6H,m),7.92–8.43(4H,m)

(Step 5)
A crude product of (2S,4R)-4-hydroxy-2-[hydroxy[4-[(p-nitrobenzyloxycarbonylamino)methyl]-1-naphthyl]methyl]

pyrrolidine was prepared as a yellow oily substance from the compound (570 mg, 0.857 mmol) obtained in Step 4 and 2.7N hydrogen chloride-methanol solution (20 ml), in the same manner as in Reference Example 112-8. This crude product was used for the next reaction without purification.

(Step 6)

(2S,4R)-4-Hydroxy-2-[hydroxy[4-[(p-nitrobenzyloxycarbonylamino)methyl]-1-naphthyl]methyl]-N-(p-nitrobenzyloxycarbonyl)pyrrolidine diastereomer I (265 mg, yield: 49.1%) and diastereomer II (86 mg, yield: 15.9%) were prepared as colorless oily substances from the crude product obtained in Step 5 and p-nitrobenzyloxycarbonyl chloride (240 mg, 1.11 mmol), in the same manner as in Reference Example 112-9.

Diastereomer I $^1$H-NMR(CDCl$_3$)δ:1.38(1H,m),2.33(2H,m),3.68(2H,m), 4.50(2H,m),4.82(2H,m),5.12–5.48(4H,m),7.38–7.69(8H,m) ,8.00(1H,m),8.21(4H,m),8.50(1H,m)

Diastereomer II $^1$H-NMR(CDCl$_3$)δ:1.44(1H,m),2.38(1H,m),3.50(1H,m), 3.73(1H,m),4.21(1H,m),4.70(3H,m),5.27(4H,m), 5.96(1H,m),7.54(8H,m),7.96(1H,m),8.22(4H,m), 8.40(1H,m)

(Step 7)

A crude product of (2S,4R)-2-[hydroxy[4-[(p-nitrobenzyloxycarbonylamino)methyl]-1-naphthyl]methyl]-4-mesyloxy-N-(p-nitrobenzyloxycarbonyl)pyrrolidine diastereomer I was prepared as a yellow oily substance from the compound (diastereomer I, 265 mg, 0.42 mmol) obtained in Step 6, triethylamine (70 µl, 0.51 mmol) and mesyl chloride (33 µl, 0.42 mmol) in the same manner as in Reference Example 112-5, and used for the next reaction without purification.

(Step 8)

The title compound (127 mg, yield: 43.9%) was prepared as a yellow oily substance from the compound obtained in Step 7 and potassium thioacetate (114 mg, 1.26 mmol) in the same manner as in Reference Example 111-10.

$^1$H-NMR(CDCl$_3$)δ:1.72(1H,m),2.13(1H,m),2.31(3H,s), 3.28(1H,m),3.71(2H,m),4.25(1H,m),4.38(1H,m), 4.83(2H,m),5.13–5.42(4H,m),7.36–7.72(8H,m),8.02(1H,m),8.22 (4H,m),8.42(1H,m)

REFERENCE EXAMPLE 115

(2S,4S)-4-Acetylthio-2-[α-hydroxy-3-[(D-nitrobenzyloxycarbonylamino)methyl]benzyl]-N-(p-nitrobenzyloxycarbonyl)pyrrolidine diastereomers A and B

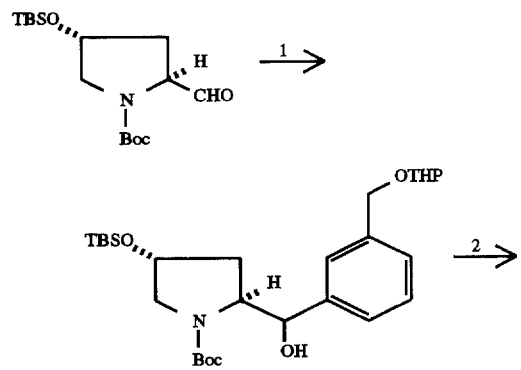

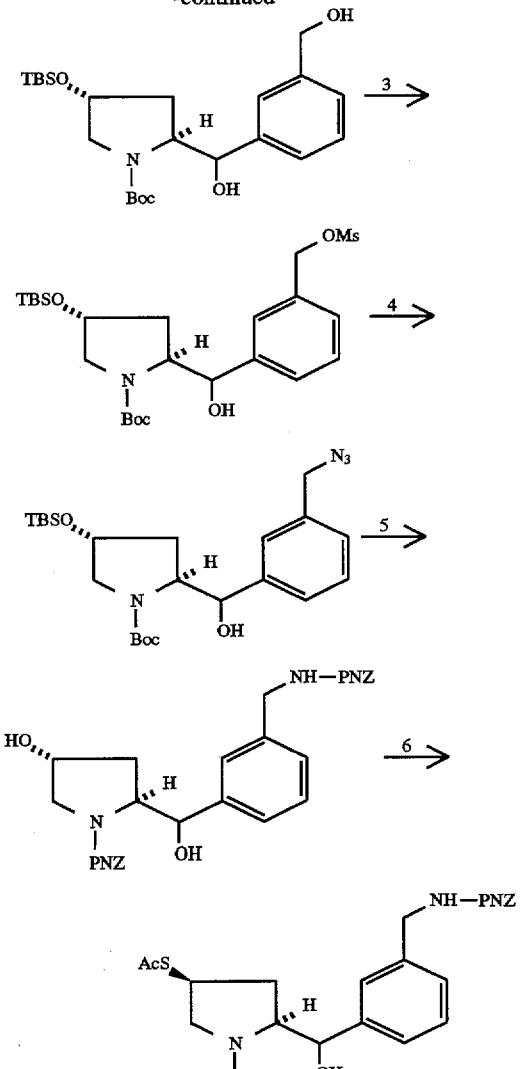

(Step 1)

A solution of 3-(tetrahydropyranyloxymethyl)bromobenzene (11.8 g, 43.5 mmol) in tetrahydrofuran (20 ml) was added dropwise to a solution of 1.6M n-butyl lithium-hexane solution (30 ml, 48 mmol) in tetrahydrofuran (100 ml) at −78° C. in a nitrogen stream over 15 minutes. This reaction solution was stirred at −78° C. for 40 minutes and then a solution of (2S,4R)-N-t-butoxycarbonyl-4-(t-butyldimethylsiloxy)prolinal (7.2 g, 21.9 mmol) in tetrahydrofuran (20 ml) was added dropwise over 20 minutes. The reaction solution was stirred at −78° C. for 30 minutes and then allowed to gradually warm and saturated aqueous ammonium chloride was added thereto. This solution was poured into a liquid mixture of ethyl acetate with water and the organic layer was washed with saturated aqueous sodium chloride, dried over anhydrous sodium sulfate, and concentrated in vacuo. The resulting oily residue was subjected to silica gel column chromatography (Wakogel™ C-300, heptane-ethyl acetate=6:1) to give (2S,4R)-N-t-butoxycarbonyl-4-t-butyldimethylsiloxy-2-[α-hydroxy-3-(tetrahydropyranyloxymethyl)benzyl]pyrrolidine (6.3 g, yield: 55.0%) as a yellow oily substance.

$^1$H-NMR(CDCl$_3$)δ:0.02(6H,s),0.82(9H,s),1.38–2.00 (17H,m), 3.19–3.98(5H,m),4.08–4.56(4H,m),4.62–5.17(3H,m)

(Step 2)

To a solution of the compound (6.3 g, 12.1 mmol) obtained in Step 1 in methanol (270 ml), pyridinium p-toluenesulfonate (275 mg, 1.09 mmol) was added at room temperature in a nitrogen stream and this reaction solution was stirred at 55° C. for 5 hours. The reaction solution was poured into a liquid mixture of ethyl acetate-water. The organic layer was washed with saturated aqueous sodium chloride, dried over anhydrous sodium sulfate, and concentrated in vacuo. The resulting residue was subjected to silica gel column chromatography (Wakogel™ C-300, heptane-ethyl acetate=1:2) to give (2S,4R)-N-t-butoxycarbonyl-4-t-butyldimethylsiloxy-2-[α-hydroxy-3-hydroxymethylbenzyl]pyrrolidine (2.0 g, yield: 35.5%) as a pale yellow oily substance.

$^1$H-NMR(CDCl$_3$)δ:0.03(6H,s),0.85(9H,s),1.38–1.92 (11H,m), 2.86–3.93(3H,m),4.09–4.62(2H,m),4.73(2H,s), 4.90–5.28(1H,m),6.10–6.20(1H,m),7.21–7.53(4H,m)

(Step 3)

To a solution of the compound (2.0 g, 4.58 mmol) obtained in Step 2 in tetrahydrofuran (20 ml), triethylamine (700 μl, 5.02 mmol)and mesyl chloride (390 μl, 5.04 mmol) were successively added in a nitrogen stream under cooling with ice and this reaction solution was stirred at the same temperature for 20 minutes. This solution was poured into a liquid mixture of ethyl acetate with water water. The organic layer was washed with saturated aqueous sodium chloride, dried over anhydrous sodium sulfate and concentrated in vacuo to give a crude product of (2S,4R)-N-t-butoxycarbonyl-4-t-butyldimethylsiloxy-2-[α-hydroxy-3-(mesyloxymethyl)benzyl]pyrrolidine as a pale yellow oily substance, which was used for the next reaction without purification.

$^1$H-NMR(CDCl$_3$)δ:0.03(6H,s),0.84(9H,s),1.42–1.68 (10H,m), 1.78–1.91(1H,m),2.95(3H,s),3.26–3.95(3H,m), 4.10–4.76(2H,m),4.92–5.31(2H,m),6.21–6.30(1H,m), 7.31–7.48(4H,m)

(Step 4)

To a solution of the compound obtained in Step 3 in N,N-dimethylformamide (20 ml), sodium azide (360 mg, 5.54 mmol) was added at room temperature in a nitrogen stream and this reaction solution was stirred at 70° C. for 2 hours. The reaction solution was poured into a liquid mixture of ethyl acetate with water. The organic layer was washed with saturated aqueous sodium chloride, dried over anhydrous sodium sulfate, and concentrated in vacuo. The resulting residue was subjected to silica gel column chromatography (Wakogel™ C-300, heptane-ethyl acetate= 10:1) to give (2S,4R)-2-(3-azidomethyl-α-hydroxybenzyl)-N-t-butoxycarbonyl-4-(t-butyldimethylsiloxy)pyrrolidine (2.0 g, yield: 94.5%) as a yellow oily substance.

$^1$H-NMR(CDCl$_3$)δ:0.01(6H,s),0.82(9H,s),1.48–1.90 (11H,m), 2.80–3.89(3H,m),4.04–4.60(4H,m),7.20–7.42(4H, m)

(Step 5)

To a solution of the compound (2.5 g, 5.41 mmol) obtained in Step 4 in tetrahydrofuran (25 ml), water (200 μl, 11.1 mmol) and triphenylphosphine (1.8 g, 6.86 mmol) were successively added at room temperature in a nitrogen stream and this reaction solution was stirred at the same temperature for 15 hours. The reaction solution was concentrated in vacuo to give a yellow oily residue. A solution of the residue in 2.17N hydrogen chloride-methanol (19 ml) was stirred at room temperature for 4 hours. This reaction solution was concentrated in vacuo and dichloromethane was added to the resulting residue. The volatile components were distilled off in vacuo to give an oily residue (4.2 g). A solution of the residue in dioxane-water (1:1, 40 ml) adjusted to pH 9.0 with 1N aqueous sodium hydroxide. To this solution, a solution of p-nitrobenzyloxycarbonyl chloride (2.4 g, 11.9 mmol) in dioxane (5 ml) was added dropwise at room temperature, while the reaction solution was maintained at pH 8.0–9.0 by using 1N aqueous sodium hydroxide. The reaction solution was poured into a liquid mixture of ethyl acetate-water. The organic layer was washed with saturated aqueous sodium chloride, dried over anhydrous sodium sulfate, and concentrated in vacuo. The resulting residue was subjected to silica gel column chromatography (Wakogel™ C-300, heptane-ethyl acetate=1:4→ethyl acetate) to give (2S,4R)-4-hydroxy-2-[α-hydroxy-3-[(p-nitrobenzyloxycarbonylamino)methyl]benzyl]-N-(p-nitrobenzyloxycarbonyl)pyrrolidine diastereomer A as a pale yellow substance (less polar compound, 807 mg, yield: 25.7%) and diastereomer B as a pale yellow oily substance (polar compound, 978 mg, yield: 31.2%).

Diastereomer A $^1$H-NMR(CDCl$_3$)δ:1.72–1.92(1H,m),2.01–2.20(1H,m), 3.28– 3.71(2H,m),4.16–4.50(4H,m),5.15–5.32(5H,m), 8.12–8.30(4H,m)

Diastereomer B $^1$H-NMR(CDCl$_3$)δ:1.47–1.70(1H,m),1.98–2.20(1H,m), 3.37–3.80(2H,m),4.10–4.66(4H,m),5.27(2H,s),5.30(2H,s), 5.82(1H,br s),8.12–8.28(4H,m)

(Step 6)

(2S,4S)-4-Acetylthio-2-[α-hydroxy-3-[(p-nitrobenzyloxycarbonylamino)methyl]benzyl]-N-(p-nitrobenzyloxycarbonyl)pyrrolidine diastereomer A (345 mg, yield: 44.3%) and diastereomer B (356 mg, yield: 38.0%) were prepared as red oily substances from the diastereomer A (807 mg, 1.39 mmol) and the diastereomer B (987 mg, 1.69 mmol) obtained in Step 5, respectively, in the same manners as in Reference Examples 112-10 and 112-11.

Diastereomer A $^1$H-NMR(CDCl$_3$)δ:1.89–2.10(1H,m),2.30(3H,s), 2.90–3.19(1H,m),3.61–3.80(1H,m),4.08–4.26(2H,m), 4.37 (2H,d,J=5.9Hz),5.07–5.38(6H,m),7.12–7.31(5H,m), 7.41–7.62(3H,m),8.12–8.30(4H,m)

Diastereomer B $^1$H-NMR(CDCl$_3$)δ:1.89–2.06(1H,m),2.32(3H,s), 3.16–3.28(1H,m),3.68–3.81(1H,m),4.08–4.31(2H,m), 4.40 (2H,d,J=6.1Hz),5.09–5.38(5H,m),5.72(1H,br s)

REFERENCE EXAMPLES 116a to 117

The following compounds were prepared in the same manner as in Reference Example 115.

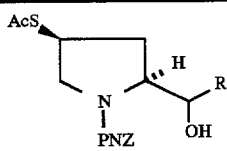

| Ex. No. | R | $^1$H-NMR (CDCl$_3$) δ | Remarks |
|---|---|---|---|
| 116a | (2-methylphenyl)-CH$_2$-NH-PNZ | 2.20–2.27(1H, m), 2.34(3H, s), 3.18–3.30 (1H, m), 3.62–3.85(1H, m), 4.02–4.63(4H, m), 5.01–5.33(5H, m), 5.71(1H, br s), 7.20–7.68(8H, m), 8.10–8.32(4H, m) | Diastereomer A (less polar) |
| 116b | (2-methylphenyl)-CH$_2$-NH-PNZ | 1.30–1.48(1H, m), 2.30(3H, s), 3.18–3.32 (1H, m), 3.55–3.90(1H, m), 4.02–4.65(3H, m), 4.86(1H, d, J=7.6Hz), 5.02–5.32(5H, m), 5.62–5.70(1H, m), 7.22–7.61 (8H, m), 8.12–8.30(4H, m) | Diastereomer B (polar) |
| 117 | (4-methylphenyl)-CH$_2$-NH-PNZ | 1.82–2.20(1H, m), 2.31 and 2.32(3H, each s), 2.88–3.31(1H, m), 3.58–3.80(1H, m), 4.08–4.30(3H, m), 4.38(2H, d, J=2.7Hz), 5.10–5.38(6H, m), 7.19–7.35(4H, m), 7.42–7.61 (4H, m), 8.13–8.32(4H, m) | — |

REFERENCE EXAMPLE 118

(2S,4S)-4-Acetylthio-2-[(S)-α-hydroxy-4-[(p-nitrobenzyloxycarbonylamino)methyl]benzyl]-N-(p-nitrobenzyloxycarbonyl)pyrrolidine

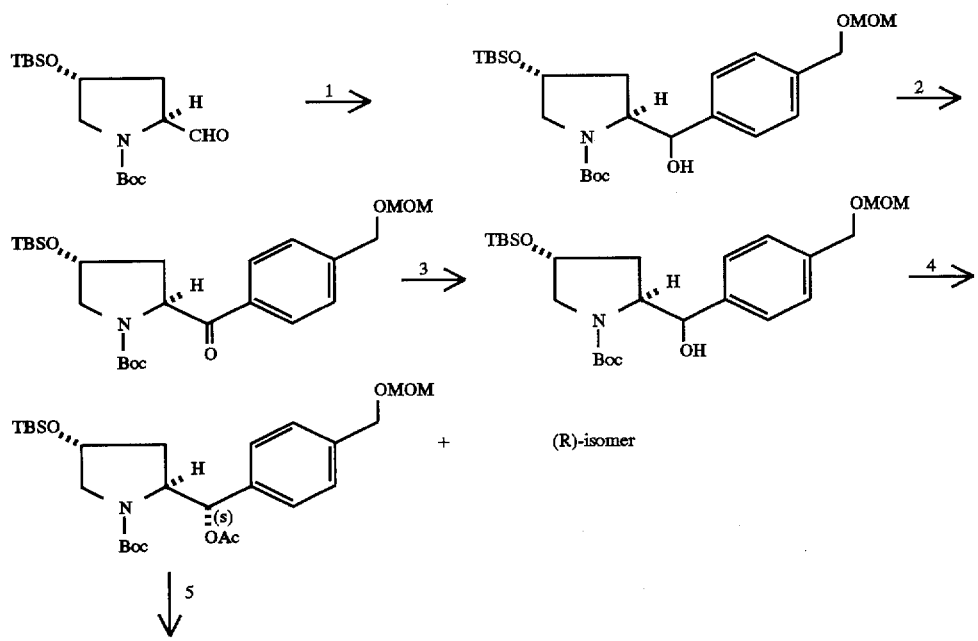

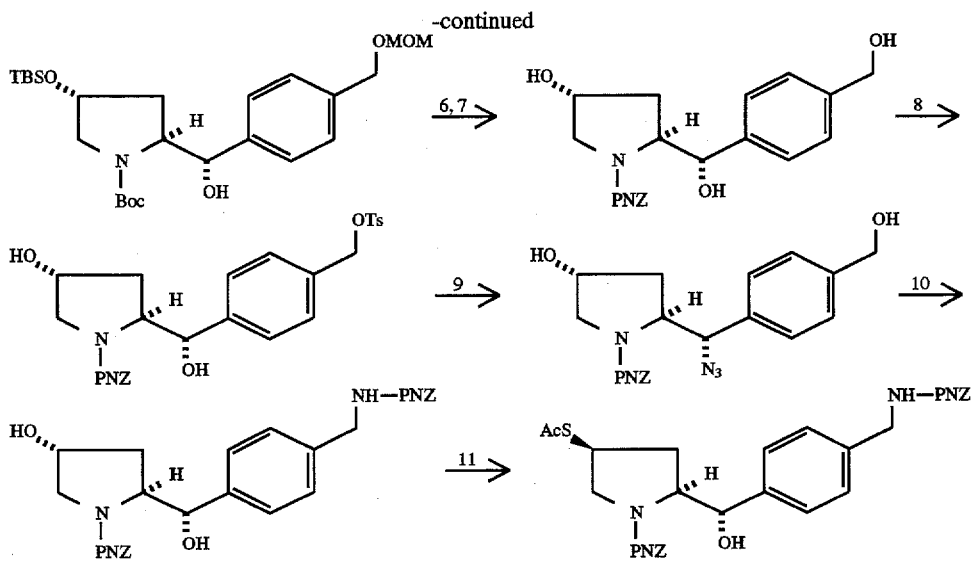

(Step 1)

1.6M n-Butyl lithium-hexane solution (104 ml, 167 mmol) was added dropwise to a solution of 1-bromo-4-(methoxymethoxymethyl)benzene (38.6 g, 167 mmol) in tetrahydrofuran (350 ml) at −78° C. in a nitrogen stream over 30 minutes. This reaction solution was stirred at −78° C. for 30 minutes and then a solution of (2S,4R)-N-t-butoxycarbonyl-4-(t-butyldimethylsiloxy)prolinal (27.5 g, 83.5 mmol) in tetrahydrofuran (300 ml) was added dropwise thereto over 1 hour. This reaction solution was stirred at −70° C. for 2 hours and then warmed and saturated aqueous ammonium chloride was added thereto at −20° C. To the reaction mixture, a liquid mixture of ethyl acetate with water was added. The organic layer was washed successively with dilute hydrochloric acid, saturated aqueous sodium hydrogencarbonate and saturated aqueous sodium chloride, then dried over anhydrous magnesium sulfate, and concentrated in vacuo. The resulting oily residue was subjected to silica gel column chromatography (Wakogel™ C-300, heptane-ethyl acetate=4:1) to give (2S,4R)-N-t-butoxycarbonyl-4-t-butyldimethylsiloxy-2-[α-hydroxy-4-(methoxymethoxymethyl)benzyl]pyrrolidine (24.1 g, yield: 59.8%) as a colorless oily substance.

$^1$H-NMR(CDCl$_3$)δ:0.00(6H,s),0.85(6H,s),1.50(9H,s), 3.40(3H,s),4.57(2H,s),4.70(2H,s),6.02(1H,s), 7.33(4H,br s)

(Step 2)

Oxalyl chloride (7.7 ml, 90 mmol) was added dropwise to a solution of dimethyl sulfoxide (12 ml, 170 mmol) in methylene chloride (300 ml) at −78° C. over 15 minutes and the resulting solution was stirred at the same temperature for 30 minutes. To this reaction solution, a solution of the compound (24.1 g, 50 mmol) obtained in Step 1 in methylene chloride (250 ml) was added dropwise at −70° C. over 30 minutes. The reaction solution was stirred at the same temperature for 30 minutes. After dropwise addition of triethylamine (48 ml, 350 mmol) at −70° C., the reaction solution was allowed to warm and water (300 ml) was added thereto at 0° C. The organic layer was washed successively with water, dilute hydrochloric acid, saturated aqueous sodium hydrogencarbonate and saturated aqueous sodium chloride, and dried over anhydrous magnesium sulfate. The solvent was distilled off in vacuo to give a crude product of (2S,4R)-N-t-butoxycarbonyl-4-t-butyldimethylsiloxy-2-[4-(methoxymethoxymethyl)benzoyl]pyrrolidine (25 g).

$^1$H-NMR(CDCl$_3$)δ:0.08(6H,s),0.90(9H,s),1.25(5H,s), 1.47(4H,s),1.98(1H,m),2.23(1H,m),3.43(3H,s),3.66–3.82 (1H,m),4.43(1H,m),4.66(2H,s),4.73(2H,s),5.26–5.48(1H, m),7.45(1H,d,J=8.3Hz),7.48(1H,d,J=8.3Hz),7.92 (1H,d,J= 8.3Hz),7.95(1H,d,J=8.3Hz)

(Step 3)

To a solution of the compound (10.08 g, 21 mmol) obtained in Step 2 in tetrahydrofuran (200 mg), 1.0M L-Selectride™-tetrahydrofuran (32.7 ml, 32.7 mmol) was added at −78° C. This reaction solution was stirred at the same temperature for 4 hours and then warmed. To the reaction solution, saturated aqueous ammonium chloride was added at −20° C. and then a liquid mixture of ethyl acetate with water was added. The organic layer was washed successively with dilute hydrochloric acid, saturated aqueous sodium hydrogencarbonate and saturated aqueous sodium chloride, and dried over anhydrous sodium sulfate. The solvent was distilled off in vacuo to give a crude product of (2S,4R)-N-t-butoxycarbonyl-4-t-butyldimethylsiloxy-2-[α-hydroxy-4-(methoxymethoxymethyl)benzyl]pyrrolidine (13.0 g) as a colorless oily substance.

$^1$H-NMR(CDCl$_3$)δ:0.00(6H,s),9.85(6H,s),1.49(9H,s), 3.40(3H,s),4.57(2H,s),4.70(2H,s),6.02(1H,s), 7.33(4H,br s)

(Step 4)

To a solution of the compound (13.0 g) obtained in Step 3 in pyridine (100 ml), acetic anhydride (20 ml) and 4-N,N-dimethylaminopyridine (800 mg, 6.5 mmol) were added. This reaction solution was stirred at room temperature overnight and then the solvent was distilled off in vacuo. To the resulting residue, ethyl acetate and 3N hydrochloric acid were added. The organic layer was washed successively with dilute hydrochloric acid, water and saturated aqueous sodium chloride, dried over anhydrous magnesium sulfate, and concentrated in vacuo. The resulting oily substance was subjected to silica gel column chromatography (Lobar™ LiChroprep™ Si60, heptane-ethyl acetate=4:1) to give (2S,4R)-2-[(S)-α-acetoxy-4-(methoxymethoxymethyl)benzyl]-N-t-butoxycarbonyl-4-(t-butyldimethylsiloxy)pyrrolidine (less polar compound, 5.11 g, yield: 46%) as a colorless oily substance.

$^1$H-NMR(CDCl$_3$)δ:−0.08(6H,br s),0.80(9H,br s), 1.58 (9H,br s),2.14(3H,br s),3.42(3H,s),4.59(2H,s), 4.71(2H,s), 7.20–7.41(4H,m)

(Step 5)

To a solution of the compound (4.81 g, 9.18 mmol) obtained in Step 4 in methanol (40 ml), aqueous potassium carbonate (30 ml) (4.0 g, 28.9 mmol) was added at room temperature. To this reaction mixture, methanol (40 ml) was added. This reaction solution was stirred at room temperature for 40 minutes and then concentrated in vacuo. The residue was extracted with ethyl acetate. The organic layer was washed successively with water and saturated aqueous sodium chloride, dried over anhydrous magnesium sulfate, and concentrated in vacuo. The resulting oily substance was subjected to silica gel column chromatography (Wakogel™ C-300, heptane-ethyl acetate=4:1) to give (2S,4R)-N-t-butoxycarbonyl-4-t-butyldimethylsiloxy-2-[(S)-α-hydroxy-4-(methoxymethoxymethyl)benzyl]pyrrolidine (4.3 g, yield: 97%).

$^1$H-NMR(CDCl$_3$)δ:0.05(6H,s),0.87(9H,s),1.56(9H,s), 3.36(1H,m),3.46(3H,s),3.57(1H,m),4.13(1H,m), 4.29(1H,m),4.58(1H,m),4.64(2H,s),4.76(2H,s), 6.07(1H,br s),7.39 (4H,br s)

(Step 6)

To a solution of the compound (1.72 g, 3.57 mmol) obtained in Step 5 in methanol (40 ml), 2N hydrogen chloride-methanol solution (20 ml) was added. After stirring at room temperature overnight, this reaction solution was concentrated in vacuo to give (2S,4R)-4-hydroxy-2-[(S)-α-hydroxy-4-(hydroxymethyl)benzyl]pyrrolidine monohydrochloride as a solid residue, which was used for the next step without purification.

(Step 7)

A solution of the residue obtained in Step 6 in dioxane (50 ml) and water (30 ml) was brought to pH 10.0 by adding 1N aqueous sodium hydroxide. To this solution, a solution of p-nitrobenzyloxycarbonyl chloride (856 mg, 4.0 mmol) in dioxane (30 ml) was added dropwise under cooling with ice, while the reaction solution was maintained at pH 9.0–10.0 by using 1N aqueous sodium hydroxide. This reaction solution was poured into a liquid mixture of ethyl acetate-water. The organic layer was washed with saturated aqueous sodium chloride, dried over anhydrous magnesium sulfate, and concentrated in vacuo. The resulting residue was subjected to silica gel column chromatography (Wakogel™ C-300, heptane-ethyl acetate=1:1→ethyl acetate) to give (2S,4R)-4-hydroxy-2-[(S)-α-hydroxy-4-(hydroxymethyl)benzyl]-N-(p-nitrobenzyloxycarbonyl)pyrrolidine (1.11 g, yield: 77%).

$^1$H-NMR(CDCl$_3$)δ:3.44(1H,m),3.71(1H,m),4.21(1H,m), 4.37(1H,m),4.62(1H,m),4.68(2H,s),5.30(2H,s), 5.57(1H,br s),7.32(4H,br s),7.54(2H,d,J=8.8Hz), 8.24(2H,d,J=8.8Hz)

(Step 8)

To a solution of the compound (990 mg, 2.46 mmol) obtained in Step 7 in methylene chloride (15 ml)—acetone (5 ml), p-toluenesulfonyl chloride (495 mg, 2.6 mmol) and triethylamine (0.36 ml, 2.6 mmol) were added at 0° C. This reaction solution was stirred at 5° C. for 2 days and then concentrated in vacuo and a liquid mixture of ethyl acetate with water was added to the resulting residue. The organic layer was washed successively with dilute hydrochloric acid, water and saturated aqueous sodium chloride, dried over anhydrous magnesium sulfate, and concentrated in vacuo. The resulting oily substance was subjected to silica gel column chromatography (Wakogel™ C-300, heptane-ethyl acetate=1:1→1:4) to give (2S,4R)-4-hydroxy-2-[(S)-α-hydroxy-4-(p-toluenesulfonyloxymethyl)benzyl]-N-(p-nitrobenzyloxycarbonyl)pyrrolidine (362 mg, yield: 26%).

$^1$H-NMR(CDCl$_3$)δ:2.08(3H,s),4.51(2H,s),5.32(2H,s), 7.35(4H,br s),7.57(2H,d,J=8.0Hz),8.26(2H,d,J=8.0Hz)

(Step 9)

To a solution of the compound obtained in Step 8 in dimethyl sulfoxide (5 ml), sodium azide (143 mg, 2.2 mmol) was added. This reaction solution was stirred at 60° C. for 15 minutes, then cooled in an ice bath, and poured into a liquid mixture of ethyl acetate with water. The organic layer was washed successively with water and saturated aqueous sodium chloride, dried over anhydrous magnesium sulfate, and concentrated in vacuo to give a crude product of (2S,4R)-4-hydroxy-2-[(S)-α-hydroxy-4-(azidomethyl)benzyl]-N-(p-nitrobenzyloxycarbonyl)pyrrolidine (300 mg).

$^1$H-NMR(CDCl$_3$)δ:3.47(1H,m),3.76(1H,m),4.25(1H,m), 4.35(2H,s),4.70(1H,m),5.33(2H,s),5.62(1H,br s),7.34(4H,m),7.57(2H,d,J=8.8Hz),8.27(2H,d,J=8.8Hz)

(Step 10)

To a solution of the compound (300 mg) obtained in Step 9 in tetrahydrofuran (5 ml), triphenylphosphine (275 mg, 1.05 mmol) and water (40 μl, 2.1 mmol) were added at room temperature and this reaction solution was stirred at the same temperature overnight. To the reaction mixture, triethylamine (0.18 ml, 1.3 mmol) and p-nitrobenzyloxycarbonyl chloride (153 mg, 0.71 mmol) were added at room temperature. The reaction solution was stirred at the same temperature for 30 minutes and then concentrated. A liquid mixture of ethyl acetate with water was added thereto. The organic layer was washed successively with water and saturated aqueous sodium chloride, dried over anhydrous sodium sulfate, and concentrated in vacuo. The resulting residue was subjected to silica gel column chromatography (Wakogel™ C-300, heptane-ethyl acetate=1:2→ethyl acetate) to give (2S,4R)-4-hydroxy-2-[(S)-α-hydroxy-4-[(p-nitrobenzyloxycarbonylamino)methyl]benzyl]-N-(p-nitrobenzyloxycarbonyl)pyrrolidine (328 mg, yield: 87%).

$^1$H-NMR(CDCl$_3$)δ:3.45(1H,m),3.74(1H,m),4.23(1H,m), 4.37(2H,d,J=5.9Hz),4.62(1H,m),5.23(2H,s), 5.30(2H,s), 5.65(1H,m),7.27(4H,m), 7.53(4H,d,J=8.0Hz),8.22(4H,d,J=8.0Hz)

(Step 11)

(2S,4S)-4-Acetylthio-2-[(S)-α-hydroxy-4-[(p-nitrobenzyloxycarbonylamino)methyl]benzyl]-N-(p-nitrobenzyloxycarbonyl)pyrrolidine (110 mg, yield: 29%) was prepared from the compound (325 mg, 0.57 mmol) obtained in Step 10, in the same manners as in Reference Examples 112-10 and 112-11.

$^1$H-NMR(CDCl$_3$)δ:2.01(1H,m),2.32(3H,s),3.22(1H,m), 3.76(1H,m),4.21(2H,m),4.38(2H,d,J=6.0Hz), 4.70(1H,m), 5.15(1H,m),5.23(2H,s), 5.28(2H,d,J=2.7Hz),5.62(1H,m), 7.20–7.35(4H,m), 7.53(4H,d,J=8.0Hz),8.23(4H,d,J=8.6Hz)

REFERENCE EXAMPLE 119

(2S,4S)-4-Acetylthio-2-(α-hydroxybenzyl)-N-(p-nitrobenzyloxycarbonyl)pyrrolidine

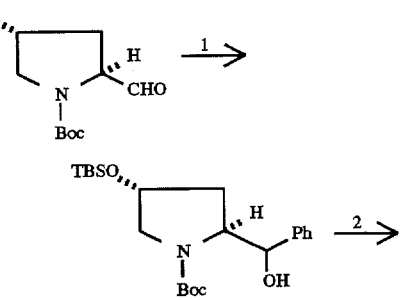

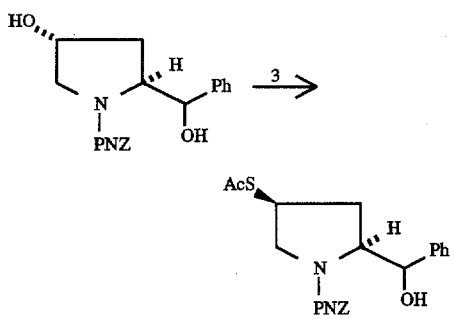

(Step 1)
2.0M Phenylmagnesium bromide-tetrahydrofuran solution (22.8 ml, 45.6 mmol) was added dropwise to a solution of (2S,4R)-N-t-butoxycarbonyl-4-(t-butyldimethylsiloxy) prolinal (10 g, 30.4 mmol) in tetrahydrofuran (200 ml) at −78° C. in a nitrogen stream over 15 minutes. This reaction solution was gradually warmed and stirred at room temperature for 3 hours. After addition of water, the reaction solution was concentrated in vacuo. The resulting residue was poured into a liquid mixture of ethyl acetate with water. The organic layer was washed with saturated aqueous sodium chloride, dried over anhydrous sodium sulfate, and concentrated in vacuo. The resulting oily residue was subjected to silica gel column chromatography (Wakogel™ C-300, heptane-ethyl acetate=4:1) to give (2S,4R)-N-t-butoxycarbonyl-4-t-butyldimethylsiloxy-2-(α-hydroxybenzyl)pyrrolidine (12.0 g, yield: 96.8%) as a colorless oily substance.

$^1$H-NMR(CDCl$_3$)δ:0.01(6H,s),0.83(9H,s),1.54(9H,s), 1.79–1.92(1H,m),2.83–3.84(3H,m),4.08–4.61(2H,m), 4.84–5.34(1H,m)

(Steps 2 and 3)
(2S,4S)-4-Acetylthio-2-(α-hydroxybenzyl)-N-(p-nitrobenzyloxycarbonyl)pyrrolidine was prepared in the same manners as in Reference Examples 112-8, 112-10 and 112-11.

$^1$H-NMR(CDCl$_3$)δ:1.86(1H,m),2.32(3H,s),2.71(1H,m), 3.38–3.39(1H,m),4.01–4.33(2H,m),4.66–4.83(1H,m), 5.13–5.37(3H,m),7.32(5H,m),7.54(2H,m),8.26(2H,m)

In the following Reference Example 120, physicochemical data of a compound used in Examples as a thiol or a thiol derivative are shown.

REFERENCE EXAMPLE 120

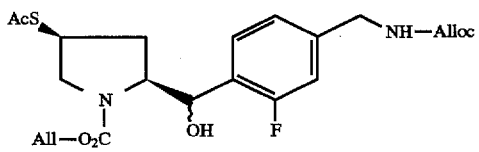

$^1$H-NMR(CDCl$_3$)δ:1.52(1H,m),2.05(1H,m),2.31(3H,s), 3.22(1H,m),3.75(1H,m),4.17(1H,m),4.20–4.40(3H,m), 4.55–4.70(4H,m),5.01(1H,br d,J=8Hz),5.10–5.40(4H,m), 5.85–6.15(2H,m),6.98(1H,t,J=8.5Hz),7.20(1H,m),7.42 (1H,m)

INDUSTRIAL APPLICABILITY

The compounds of the present invention are novel compounds not disclosed in any literatures and are useful as antibacterial agents by virtue of their strong antibacterial activities against gram positive bacterial including MRSA and against gram negative bacteria and their excellent stability against β-lactamase and against DHP-I. Particularly, they are expected to make a great contribution to treatment for hardly curable infectious deceases caused by MRSA.

We claim:
1. A compound of the formula:

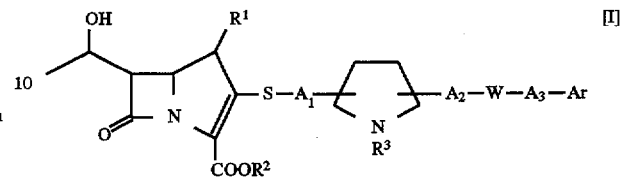

wherein R$^1$ is a hydrogen atom or a lower alkyl group, R$^2$ is a hydrogen atom or a negative charge, R$^3$ is a hydrogen atom or a lower alkyl group, Ar is a phenyl group, a naphthyl group or a group of:

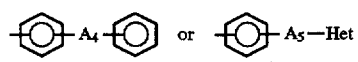

(wherein each of A$_4$ and A$_5$, which may be the same or different, is a single bond, a methylene group, an ethylene group, an oxygen atom, an imino group, a sulfur atom, a sulfonyl group, —CONH— or —NHSO$_2$—, and Het is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents, selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonyl amino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group, each of $A_1$, $A_2$ and $A_3$, which may be same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and W is a sulfur atom, a group of N-X (wherein X is a hydrogen atom, a lower alkyl group, a formyl group, a lower alkanoyl group or a sulfamoyl group), an oxygen atom, a group of CH(OH) or a single bond; or a pharmaceutically acceptable salt or ester thereof.

2. The compound according to claim 1, wherein W is a sulfur atom; or a pharmaceutically acceptable salt or ester thereof.

3. The compound according to claim 1, wherein W is a group of N-X (wherein X is a hydrogen atom, a lower alkyl group, a formyl group, a lower alkanoyl group or a sulfamoyl group), an oxygen atom, a group of CH(OH) or a single bond; or a pharmaceutically acceptable salt or ester thereof.

4. The compound according to claim 3, wherein W is a group of N-X (wherein X is a hydrogen atom, a lower alkyl group, a formyl group, a lower alkanoyl group or a sulfamoyl group); or a pharmaceutically acceptable salt or ester thereof.

5. The compound according to claim 3, wherein W is an oxygen atom; or a pharmaceutically acceptable salt or ester thereof.

6. The compound according to claim 3, wherein W is a group of CH(OH); or a pharmaceutically acceptable salt or ester thereof.

7. The compound according to claim 3, wherein W is a single bond; or a pharmaceutically acceptable salt or ester thereof.

8. The compound according to claim 1, which is represented by the formula:

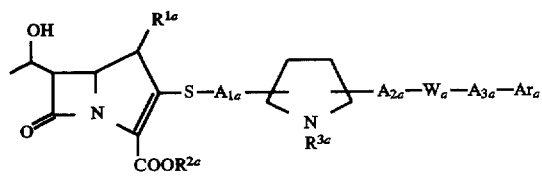

[I-a]

wherein $R^{1a}$ is a lower alkyl group, $R^{2a}$ is a hydrogen atom or a negative charge, $R^{3a}$ is a hydrogen atom, $Ar_a$ is a phenyl group, a naphthyl group or a group of:

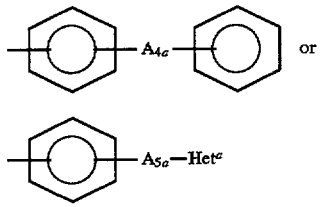

(wherein each of $A_{4a}$ and $A_{5a}$, which may be the same or different, is a single bond, a methylene group or an ethylene group, and $Het^a$ is an imidazolio group, a pyridinio group, a morpholinyl group, a quinuclidinio group or a 1,4-diazabicyclo[2.2.2]octanyl group which may be substituted with the same or different one to three substituents selected from the group consisting of a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, a lower alkylthio group, a lower alkylsulfonyl group and a lower alkylsulfamoyl group which may be substituted with the same or different one to three substituents selected from the group consisting of a hydroxyl group, a carboxyl group, a carbamoyl group, an amino group and a lower alkylamino group, and a hydroxyl group, a halogen atom, a carboxyl group, a carbamoyl group, an amino group and a sulfamoyl group, each of $A_{1a}$, $A_{2a}$ and $A_{3a}$, which may be the same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a carbamoyl group, an amino group, a lower alkylamino group and a lower alkylthio group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and $W_a$ is a sulfur atom, a group of N-$X_a$ (wherein $X_a$ is a hydrogen atom, a lower alkyl group, a formyl group, a lower alkanoyl group or a sulfamoyl group), an oxygen atom, a group of CH(OH) or a single bond; or a pharmaceutical acceptable salt or ester thereof.

9. The compound according to claim 8, wherein $W_a$ is a sulfur atom; or a pharmaceutically acceptable salt or ester thereof.

10. The compound according to claim 8, wherein $W_a$ is a group of N-$X_a$ (wherein $X_a$ is a hydrogen atom, a lower alkyl group, a formyl group, a lower alkanoyl group or a sulfamoyl group), an oxygen atom, a group of CH(OH) or a single bond; or a pharmaceutically acceptable salt or ester thereof.

11. The compound according to claim 10, wherein $W_a$ is a group of N-$X_a$ (wherein $X_a$ is a hydrogen atom, a lower alkyl group, a formyl group, a lower alkanoyl group or a sulfamoyl group); or a pharmaceutically acceptable salt or ester thereof.

12. The compound according to claim 10, wherein $W_a$ is an oxygen atom; or a pharmaceutically acceptable salt or ester thereof.

13. The compound according to claim 10, wherein $W_a$ is a group of CH(OH); or a pharmaceutically acceptable salt or ester thereof.

14. The compound according to claim 10, wherein $W_a$ is a single bond; or a pharmaceutically acceptable salt or ester thereof.

15. The compound according to claim 8, which is represented by the formula:

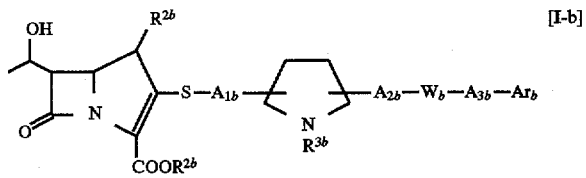

[I-b]

wherein $R^{1b}$ is a lower alkyl group, $R^{2b}$ is a hydrogen atom or a negative charge, $R^{3b}$ is a hydrogen atom, $Ar_b$ is a phenyl group, a naphthyl group or a group of:

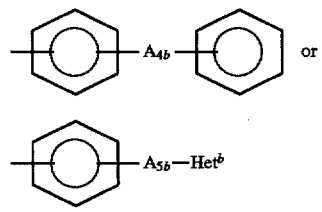

(wherein each of $A_{4b}$ and $A_{5b}$, which may be the same or different, is a single bond, a methylene group or an ethylene group, and $Het^b$ is an imidazolio group or a 1,4-diazabicyclo[2,2,2]octanyl group which may be substituted with the same or different one to three substituents selected from the group consisting of a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylthio group, a lower alkylsulfonyl group and a lower alkylsulfamoyl group which may be substituted with the same or different one to three substituents selected from the group consisting of an amino group and a lower alkylamino group, and a halogen atom, a carbamoyl group and a sulfamoyl group, each of $A_{1b}$, $A_{2b}$ and $A_{3b}$, which may be the same or different, is a single bond or a lower alkylene group which may be substituted with a substituent selected from the group consisting of a lower alkyl group which may be substituted with the same or different one to three substituents selected from the group consisting of a carbamoyl group, an amino group and a lower alkylamino group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and $W_b$ is a sulfur atom, a group of N-$X_b$ (wherein $X_b$ is a hydrogen atom, a lower alkyl group, a formyl group, a lower alkanoyl group or a sulfamoyl group), an oxygen atom, a group of CH(OH) or a single bond; or a pharmaceutical acceptable salt or ester thereof.

16. The compound according to claim 15, wherein $W_b$ is a sulfur atom; or a pharmaceutically acceptable salt or ester thereof.

17. The compound according to claim 15, wherein $W_b$ is a group of N-$X_b$ (wherein $X_b$ is a hydrogen atom, a lower alkyl group, a formyl group, a lower alkanoyl group or a sulfamoyl group), an oxygen atom, a group of CH(OH) or a single bond; or a pharmaceutically acceptable salt or ester thereof.

18. The compound according to claim 17, wherein $W_b$ is a group of N-$X_b$ (wherein $X_b$ is a hydrogen atom, a lower alkyl group, a formyl group, a lower alkanoyl group or a sulfamoyl group); or a pharmaceutically acceptable salt or ester thereof.

19. The compound according to claim 17, wherein $W_b$ is an oxygen atom; or a pharmaceutically acceptable salt or ester thereof.

20. The compound according to claim 17, wherein $W_b$ is a group of CH(OH); or a pharmaceutically acceptable salt or ester thereof.

21. The compound according to claim 17, wherein $W_b$ is a single bond; or a pharmaceutically acceptable salt or ester thereof.

22. The compound according to claim 1, which is represented by the formula:

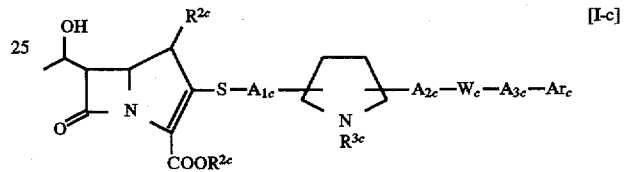

[I-c]

wherein $R^{1c}$ is a hydrogen atom or a lower alkyl group, $R^{2c}$ is a hydrogen atom or a negative charge, $R^{3c}$ is a hydrogen atom or a lower alkyl group, $Ar_c$ is a phenyl group, a naphthyl group or a group of:

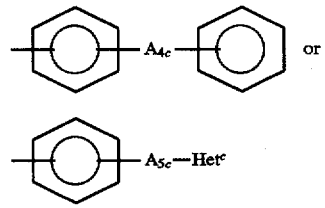

(wherein each of $A_{4c}$ and $A_{5c}$, which may be the same or different, is a single bond, a methylene group, an oxygen atom, an imino group, a sulfur atom, a sulfonyl group, —CONH— or —NHSO$_2$—, and $Het^c$ is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group) which may be substituted with the same or different one to five substituents selected from the group consisting of a lower alkyl group, a lower alkylcarbamoyl group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonylamino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group, each of $A_{1c}$, $A_{2c}$ and $A_{3c}$, which may be same or different, is a single bond or a lower alkylene group which may be substituted with a substituent selected from the group consisting of a lower alkyl group, a lower alkylcarbamoyl group, a lower consisting of a lower alkyl group, a carboxy lower alkyl group and a carbamoyl lower alkyl group), and $W_c$ is a sulfur atom; or a pharmaceutically acceptable salt or ester thereof.

23. The compound according to claim 1, which is represented by the formula:

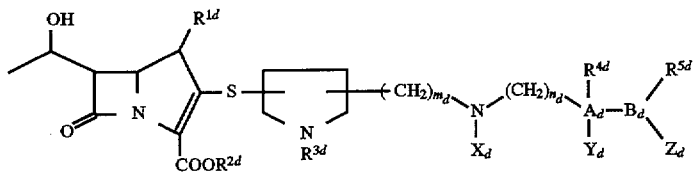

[I-d]

wherein $R^{1d}$ is a hydrogen atom or a lower alkyl group, $R^{2d}$ is a hydrogen atom, $R^{3d}$ is a hydrogen atom or a lower alkyl group, each of $R^{4d}$ and $R^{5d}$, which may be the same or different, is a hydrogen atom, a halogen atom, a hydroxyl group, a carbamoyl group or a sulfamoyl group, $X_d$ is a hydrogen atom, a lower alkyl group, a formyl group or a lower alkanoyl group, either either $Y_d$ or $Z_d$ is a hydrogen atom, the other is a group (d):

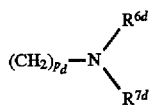

(d)

(wherein each of $R^{6d}$ and $R^{7d}$, which may be the same or different, is a hydrogen atom or a lower alkyl group, or $R^{6d}$ and $R^{7d}$ form a $C_{2-6}$ alkylene group, and $P_d$ is an integer of from 0 to 3), each of $A_d$ and $B_d$, which may be the same or different, is a phenyl group or a naphthyl group (provided that $R^{5d}$, $B_d$ and $Z_d$ may form a hydrogen atom), $m_d$ is 1 or 2, and $n_d$ is 0 or 1 (provided that when $Y_d$ or $Z_d$ is a hydrogen atom, $Z_d$ and $R^{5d}$, or $Y_d$ and $R^{4d}$ may form a nitrogen-containing 5 to 7-membered heterocyclic ring); or a pharmaceutically acceptable salt or ester thereof.

24. The compound according to claim 1, which is represented by the formula:

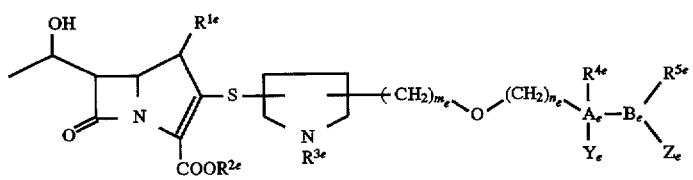

[I-e]

alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group (wherein the pyridyl group may be substituted with a substituent selected from the group wherein $R^{1e}$ is a hydrogen atom or a lower alkyl group, $R^{2e}$ is a hydrogen atom, $R^{3e}$ is a hydrogen atom or a lower alkyl group, each of $R^{4e}$ and $R^{5e}$, which may be the same or different, is a hydrogen atom, a carbamoyl group or a sulfamoyl group, either $Y_e$ or $Z_e$ is a hydrogen atom, the other is a group (e):

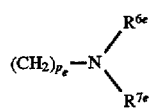

(e)

(wherein each of $R^{6e}$ and $R^{7e}$, which may be the same or different, is a hydrogen atom or a lower alkyl group, or $R^{6e}$ and $R^{7e}$ form a $C_{2-6}$ alkylene group, and $p_e$ is an integer of from 0 to 3), each of $A_e$ and $B_e$, which may be the same or different, is a phenyl group or a naphthyl group (provided that $R^{5e}$, $B_e$ and $Z_e$ may form a hydrogen atom), $m_e$ is 1 or 2, and $n_e$ is 0 or 1 (provided that when $Y_e$ or $Z_e$ is a hydrogen atom, $Z_e$ and $R^{5e}$, or $Y_e$ and $R^{4e}$ may form a nitrogen-containing 5 to 7-membered heterocyclic ring); or a pharmaceutically acceptable salt or ester thereof.

25. The compound according to claim 1, which is represented by the formula:

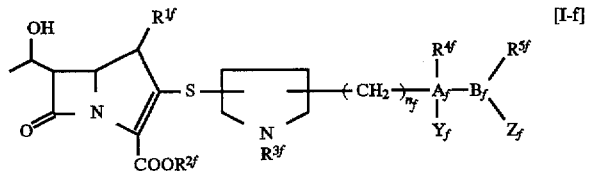

wherein $R^{1f}$ is a hydrogen atom or a lower alkyl group, $R^{2f}$ is a hydrogen atom, $R^{3f}$ is a hydrogen atom, a lower alkyl group or a lower alkenyl group, each of $R^{4f}$ and $R^{5f}$, which may be the same or different, is a hydrogen atom, a halogen atom, a hydroxyl group, a lower alkyl group, a carbamoyl group or a sulfamoyl group, either $Y_f$ or $Z_f$ is a hydrogen atom, the other is a group (f):

(wherein each of $R^{6f}$ and $R^{7f}$, which may be the same or different, is a hydrogen atom or a lower alkyl group, or $R^{6f}$ and $R^{7f}$ form a $C_{2-6}$ alkylene group, and $p_f$ is an integer of from 0 to 3), each of $A_f$ and $B_f$, which may be the same or different, is a phenyl group or a naphthyl group (provided that $R^{5f}$, $B_f$ and $Z_f$ may form a hydrogen atom), and $n_f$ is an integer of from 1 to 3 (provided that when $Y_f$ or $Z_f$ is a hydrogen atom, $Z_f$ and $R^{5f}$, or $Y_f$ and $R^{4f}$ may form a nitrogen-containing 5 to 7-membered heterocyclic ring); or a pharmaceutically acceptable salt or ester thereof.

26. The compound according to claim 1, which is represented by the formula:

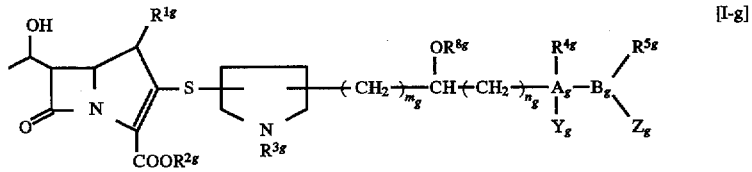

wherein $R^{1g}$ is a hydrogen atom or a lower alkyl group, $R^{2g}$ is a hydrogen atom, $R^{3g}$ is a hydrogen atom or a lower alkyl group, each of $R^{4g}$ and $R^{5g}$, which may be the same or different, is a hydrogen atom, a halogen atom, a hydroxyl group, a lower alkyl group, a carbamoyl group or a sulfamoyl group, either $Y_g$ or $Z_g$ is a hydrogen atom, the other is a group (g):

(wherein each of $R^{6g}$ and $R^{7g}$, which may be the same or different, is a hydrogen atom or a lower alkyl group, or $R^{6g}$ and $R^{7g}$ may form a $C_{2-6}$ alkylene group, and $p_g$ is an integer of from 0 to 3), $R^{8g}$ is a hydrogen atom, each of $A_g$ and $B_g$, which may be the same or different, is a phenyl group or a naphthyl group (provided that $R^{5g}$, $B_g$ and $Z_g$ may form a hydrogen atom), mg is an integer of 1 or 2, and $n_g$ is an integer of 0 or 1 (provided that when $Y_g$ or $Z_g$ is a hydrogen atom, $Z_g$ and $R^{5g}$, or $Y_g$ and $R^{4g}$ may form a nitrogen-containing 5 to 7-membered heterocyclic ring); or a pharmaceutically acceptable salt or ester thereof.

27. The compound according to claim 1, which is:

(1R,5S,6S)-2-[(3S,5S)-5-[4-(2-aminoethylthio) phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(3-aminomethyl-4-chlorophenyl) thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethyl-2-sulfamoylphenyl)thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylcarbamoyl) phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[[4-(2-aminoethylcarbamoyl)-2-sulfamoylphenyl]thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethyloxy) phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(3-aminopropionylamino) phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfonylamino) phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-aminomethylphenylthiomethyl] pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfamoyl) phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(8-aminomethyl-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(3-aminomethyl-5-glycylamino-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-[(3-aminoethylsulfonylaminoethyl)-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(3-aminomethyl-5-glycylaminomethyl-2-naphthylmethylthiomethyl)

pyrrolidin-3-ylthio]-6-[(1R)-hydroxyethyl]-1-methyl-1-carbapen-2-em-3-carboxylic acid, (1R,5S,6S)-2-[(3S,5S)-5-[6-(4-carbamoylmethyl-1,4-diazabicyclo[2.2.2]octanedium-1-ylmethyl)-2-naphthylmethylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[3-(4-carbamoylmethyl-1,4-diazabicyclo[2.2.2]octanedium-1-ylmethyl)-2-naphthylmethylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenylaminomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethyl-1-naphthylaminomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenoxymethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenylethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylbenzyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethyl-1-naphthylmethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenyl)pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethyl-5-phenylphenyl)hydroxymethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethyl-1-naphthylmethyl)hydroxymethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[(4-aminomethylphenyl)hydroxymethyl]pyrrolidin-3-ylthio]-6-[(1R)-hydroxyethyl]-1-methyl-1-carbapen-2-em-3-carboxylic acid or (1R,5S,6S)-2-[(3S,5S)-5-[(5-aminomethyl-2-fluorophenyl)hydroxymethyl]pyrrolidin-3-ylthio]-6-[(1R)-hydroxyethyl]-1-methyl-1-carbapen-2-em-3-carboxylic acid;

or a pharmaceutically acceptable salt or ester thereof.

28. The compound according to claim 1, which is:

(1R,5S,6S)-2-[(3S,5S)-5-[4-(2-aminoethylthio)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-aminomethyl-2-sulfamoylphenyl)thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylcarbamoyl)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[[4-(2-aminoethylcarbamoyl)-2-sulfamoylphenyl]thiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[[4-(3-aminopropionylamino)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfonylamino)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-aminomethylphenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-[4-(2-aminoethylsulfamoyl)phenylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(8-aminomethyl-2-naphthylmethylthiomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-[6-(4-carbamoylmethyl-1,4-diazobicyclo[2.2.2]octanedium-1-ylmethyl)-2-naphthylmethylthiomethyl]pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenylaminomethyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylbenzyl)pyrrolidin-3-ylthio]-6-[(1R)-hydroxyethyl]-1-methyl-1-carbapen-2-em-3-carboxylic acid, (1R,5S,6S)-2-[(3S,5S)-5-(4-aminomethylphenyl)pyrrolidin-3-ylthio]-6-[(1R)-hydroxyethyl]-1-methyl-1-carbapen-2-em-3-carboxylic acid or (1R,5S,6S)-2-[(3S,5S)-5-(4-aminomethylphenyl)hydroxymethyl]pyrrolidin-3-ylthio]-6-[(1R)-hydroxyethyl]-1-methyl-1-carbapen-2-em-3-carboxylic acid; or a pharmaceutically acceptable salt or ester thereof.

29. A process for producing a compound of the formula:

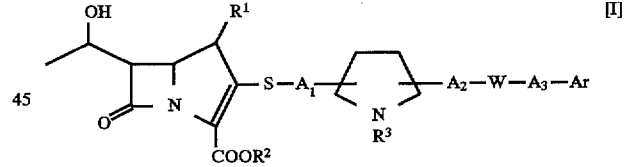

wherein $R^1$ is a hydrogen atom or a lower alkyl group, $R^2$ is a hydrogen atom or a negative charge, $R^3$ is a hydrogen atom or a lower alkyl group, Ar is a phenyl group, a naphthyl group or a group of:

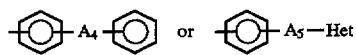

(wherein each of $A_4$ and $A_5$, which may be the same or different, is a single bond, a methylene group, an ethylene group, an oxygen atom, an imino group, a sulfur atom, a sulfonyl group, —CONH— or —NHSO$_2$—, and Het is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents, selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonylamino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group, each of $A_1$, $A_2$ and $A_3$, which may be same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a halogen atom, a cyano group, a carboxyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and W is a sulfur atom, a group of N-X (wherein X is a hydrogen atom, a lower alkyl group, a formyl group, a lower alkanoyl group or a sulfamoyl group), an oxygen atom, a group of CH(OH) or a single bond; or a pharmaceutically acceptable salt or ester thereof, which comprises reacting a compound of the formula:

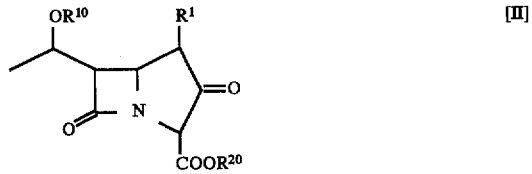

wherein $R^1$ is as defined above, $R^{10}$ is a hydrogen atom or a hydroxyl-protecting group, and $R^{20}$ is a hydrogen atom or a carboxyl-protecting group, or a reactive derivative thereof, with a compound of the formula:

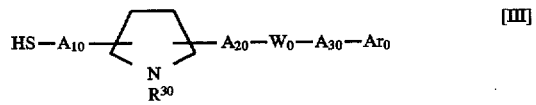

wherein $R^{30}$ is a hydrogen atom, a lower alkyl group or an imino-protecting group, $Ar_0$ is a phenyl group, a naphthyl group or a group of:

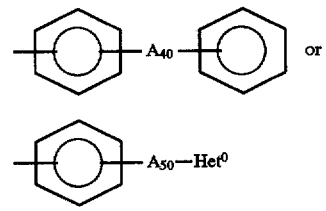

(wherein each of $A_{40}$ and $A_{50}$, which may be the same or different, is a single bond, a methylene group, an ethylene group, an oxygen atom, an imino group which may be protected, a sulfur atom, a sulfonyl group, —CONH— or —NHSO$_2$—, and Het$^0$ is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, piperazinyl group, a morpholinyl group, a benzothiazolyl group, an isoindolyl group, a quinuclidinyl group, a quinuclidinio group, a benzthiazol-1,1-dioxo-6-yl group or a 1,4-diazabicyclo[2.2.2]octanyl group which may be substituted with the same or different one to three substituents selected from the group consisting of a hydroxyl group which may be protected, a halogen atom, a cyano group, a carboxyl group which may be protected, a lower alkoxycarbonyl group, a carbamoyl group, a lower alkylcarbamoyl group, a di-lower alkylcarbamoyl group, a carbamoyloxy group, an amino group which may be protected, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group which may be protected and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group which may be protected, a halogen atom, a cyano group, a carboxyl group which may be protected, a lower alkoxycarbonyl group, a carbamoyl group, a lower alkylcarbamoyl group, a di-lower alkylcarbamoyl group, a carbamoyloxy group, an amino group which may be protected, a lower alkylamino group, a di-lower alkylamino group, a tri-lower alkylammonio group, a carbamoyl lower alkylamino group, an aroylamino group, an amino lower alkyl group which may be protected, an amino lower alkylcarbonylamino group which may be protected, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group which may be protected, a halogen atom, a cyano group, a carboxyl group which may be protected, a lower alkoxycarbonyl group, a carbamoyl group, a di-lower alkylcarbamoyl group, an arylcarbamoyl group, a piperazinocarbonyl group, an amino group which may be protected, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group which may be protected, a sulfamoyl group and a di-lower alkylsulfamoyl group, each of $A_{10}$, $A_{20}$ and $A_{30}$, which may be the same or different, is a single bond or a lower alkylene group which may be substituted with a substituent selected from the group consisting a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxy group which may be protected, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group which may be protected, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group and pyridinio group (wherein the pyridyl group and the pyridinio group may be substituted with a substituent selected from the group consisting of a lower alkyl group, a carboxy lower alkyl group which may be protected and a carbamoyl lower alkyl group), and $W_0$ is a sulfur atom, a group of N-$X_0$ (wherein $X_0$ is a hydrogen atom, an amino-protecting group, a lower alkyl group, a formyl group, a lower alkanoyl group or a sulfamoyl group), an oxygen atom, a group of CH(OR$^8$) (wherein R$^8$ is a hydrogen atom or a hydroxyl-protecting group) or a single bond, to obtain a compound of the formula:

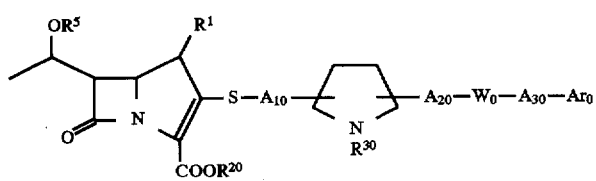

wherein $R^1$, $R^5$, $R^{20}$, $R^{30}$, $A_{10}$, $A_{20}$, $A_{30}$, $Ar_0$ and $W_0$ are as defined above, then if necessary, removing any protecting groups of the compound of the formula [IV], and if necessary, converting the compound thus obtained into a pharmaceutically acceptable salt or non-toxic ester thereof.

30. An antibacterial agent containing, as an active ingredient, a compound of the formula:

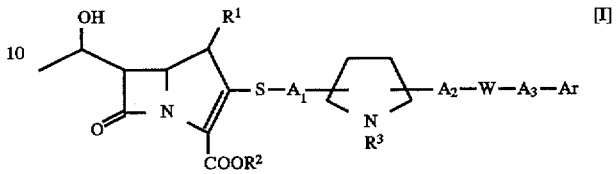

wherein $R^1$ is a hydrogen atom or a lower alkyl group, $R^2$ is a hydrogen atom or a negative charge, $R^3$ is a hydrogen atom or a lower alkyl group, Ar is a phenyl group, a naphthyl group or a group of:

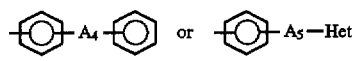

(wherein each of $A_4$ and $A_5$, which may be the same or different, is a single bond, a methylene group, an ethylene group, an oxygen atom, an imino group, a sulfur atom, a sulfonyl group, —CONH— or —NHSO$_2$—, and Het is a pyrrolinyl group, a pyrrolyl group, an imidazolyl group, an imidazolio group, a pyrazolyl group, a thiazolyl group, a pyridyl group, a pyridinio group, a pyrazinyl group, a quinolyl group, an isoquinolyl group, a pyrrolidinyl group, a piperidyl group, a piperazinyl group, a morpholinyl group, a benzothiazolyl group, an isoindolyl group, a quinuclidinyl group, a quinuclidinio group, a benzothiazol-1,1-dioxo-6-yl group or a 1,4-diazabicyclo[2.2.2]octanyl group which may be substituted with the same or different one to three substituents, selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group, a di-lower alkylsulfamoyl group, a lower alkyl group, a hydroxy lower alkyl group and a carbamoyl lower alkyl group) which may be substituted with the same or different one to five substituents selected from the group consisting of a lower alkyl group, a lower alkylcarbamoyl group, a lower alkylsulfonylamino group, a lower alkylamino group, a lower alkoxy group, an aryloxy group, a lower alkylthio group, a lower alkylsulfonyl group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a carbamoyl lower alkylamino group, an aroylamino group, an amino lower alkyl group, an amino lower alkylcarbonylamino group, a pyridyl group, a pyridylcarbonylamino group, a pyridiniocarbonylamino group, a formimidoylamino group, an acetimidoylamino group, a lower alkoxy group, a lower alkylthio group, a sulfo group, an aminosulfonyl group, a lower alkylsulfonyl group and a di-lower alkylsulfonyl group, and a hydroxyl group, a halogen atom, a cyano group, a carboxyl group, a lower alkoxycarbonyl group, a carbamoyl group, a di-lower alkylcarbamoyl group, an arylcarbamoyl group, a piperazinocarbonyl group, an amino group, a di-lower alkylamino group, a tri-lower alkylammonio group, a sulfamino group, a lower alkanoylamino group, an aralkylamino group, an aroylamino group, an arylsulfonylamino group, an amino lower alkylcarbonylamino group, a sulfamoyl group and a di-lower alkylsulfamoyl group, each of $A_1$, $A_2$ and $A_3$, which may be same or different, is a single bond or a lower alkylene group which may be substituted with a substituent selected from the group consisting of a lower alkyl group, a lower alkylcarbamoyl group, a lower alkylamino group, a lower alkoxy group, a lower alkylthio group, a lower alkylsulfonyl group, a lower alkylsulfonylamino group and a lower alkylsulfamoyl group which may be substituted with the same or different one to three substituents selected from the group consisting of a hydroxyl group, a halogen atom, a cyano group, a carboxyl group, a lower alkoxycarbonyl group, a carbamoyl group, a lower alkylcarbamoyl group, a di-lower alkylcarbamoyl group, a carbamoyloxy group, an amino group, a lower alkylamino group, a di-lower alkylamino group, a tri-lower alkylammonio group, a formimidoylamino group, an acetimidoylamino group, a lower alkoxy group, a lower alkylthio group, a lower alkylsulfonyl group, a sulfo group, a sulfamoyl group, a lower alkylsulfamoyl group and a di-lower alkylsulfamoyl group, and a pyridyl group and a pyridinio group (wherein the pyridyl group and the pyridinio group may be substituted with a substituent selected from the group consisting of a lower alkyl group, a carboxy lower alkyl group and a carbamoyl lower alkyl group), and W is a sulfur atom, a group of N-X (wherein X is a hydrogen atom, a lower alkyl group, a formyl group, a lower alkanoyl group or a sulfamoyl group), an oxygen atom, a group of CH(OH) or a single bond; or a pharmaceutically acceptable salt or ester thereof.

\* \* \* \* \*